US007993921B2

(12) United States Patent
Dugas et al.

(10) Patent No.: US 7,993,921 B2
(45) Date of Patent: Aug. 9, 2011

(54) CELL CYCLE REGULATION AND DIFFERENTIATION

(75) Inventors: Jason Dugas, Stanford, CA (US); Ben A. Barres, Palo Alto, CA (US)

(73) Assignees: National Institutes of Health (NIH), Bethesda, MD (US); The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 12/892,760

(22) Filed: Sep. 28, 2010

(65) Prior Publication Data

US 2011/0085980 A1  Apr. 14, 2011

Related U.S. Application Data

(60) Division of application No. 12/321,952, filed on Jan. 26, 2009, now Pat. No. 7,897,359, which is a continuation-in-part of application No. PCT/US2007/016858, filed on Jul. 26, 2007.

(51) Int. Cl.
*C12N 5/00* (2006.01)
(52) U.S. Cl. ...................................... 435/377
(58) Field of Classification Search .................. None
See application file for complete search history.

(56) References Cited

U.S. PATENT DOCUMENTS

| | | | |
|---|---|---|---|
| 4,485,045 A | 11/1984 | Regen | |
| 4,544,545 A | 10/1985 | Ryan et al. | |
| 5,013,556 A | 5/1991 | Woodle et al. | |
| 5,143,854 A | 9/1992 | Pirrung et al. | |
| 5,175,384 A | 12/1992 | Krimpenfort et al. | |
| 5,175,385 A | 12/1992 | Wagner et al. | |
| 5,298,422 A | 3/1994 | Schwartz et al. | |
| 5,445,934 A | 8/1995 | Fodor et al. | |
| 5,484,892 A | 1/1996 | Tedder et al. | |
| 5,585,097 A | 12/1996 | Bolt et al. | |
| 5,631,146 A | 5/1997 | Szostak et al. | |
| 5,691,145 A | 11/1997 | Pitner et al. | |
| 5,756,264 A | 5/1998 | Schwartz et al. | |
| 5,800,992 A | 9/1998 | Fodor et al. | |
| 5,837,832 A | 11/1998 | Chee et al. | |
| 5,846,534 A | 12/1998 | Waldmann et al. | |
| 6,033,884 A | 3/2000 | Woo et al. | |
| 6,465,246 B1 | 10/2002 | Mueller et al. | |
| 6,491,916 B1 | 12/2002 | Bluestone et al. | |
| 6,670,147 B1 | 12/2003 | Heidtmann et al. | |
| 6,839,586 B2 | 1/2005 | Webb | |
| 6,846,625 B1 | 1/2005 | Tally et al. | |
| 6,855,504 B2 | 2/2005 | Fogarty | |
| 6,902,881 B2 | 6/2005 | Falchuk | |
| 6,962,980 B2 | 11/2005 | Mitcham et al. | |
| 6,966,424 B2 | 11/2005 | Cram | |
| 6,972,195 B2 | 12/2005 | Xu | |
| 6,977,733 B2 | 12/2005 | Denk et al. | |
| 6,982,168 B1 | 1/2006 | Topalian et al. | |
| 6,982,321 B2 | 1/2006 | Winter | |
| 6,998,118 B2 | 2/2006 | Kasper et al. | |
| 7,008,634 B2 | 3/2006 | Cima et al. | |
| 2003/0108548 A1 | 6/2003 | Bluestone et al. | |
| 2004/0006216 A1 | 1/2004 | Waldmann et al. | |
| 2004/0092448 A1 | 5/2004 | Ohta et al. | |
| 2004/0166099 A1 | 8/2004 | Rao | |
| 2004/0265276 A1 | 12/2004 | Perricaudet et al. | |
| 2005/0002906 A1 | 1/2005 | Gregory et al. | |
| 2005/0014166 A1 | 1/2005 | Trono et al. | |
| 2005/0048031 A1 | 3/2005 | Haddada et al. | |
| 2005/0054832 A1 | 3/2005 | Lazar et al. | |
| 2005/0063953 A1 | 3/2005 | Falck-Pedersen et al. | |
| 2005/0101559 A1 | 5/2005 | Lawrence et al. | |
| 2005/0106731 A1 | 5/2005 | Davidson et al. | |
| 2005/0196751 A1 | 9/2005 | Burcin et al. | |
| 2006/0002921 A1 | 1/2006 | Winsor-Hines et al. | |

FOREIGN PATENT DOCUMENTS

| | | |
|---|---|---|
| WO | WO 92/10092 A1 | 6/1992 |
| WO | WO 93/09668 A1 | 5/1993 |
| WO | WO 93/18759 A1 | 9/1993 |
| WO | WO 97/10365 A1 | 3/1997 |
| WO | WO 97/38731 A1 | 10/1997 |

OTHER PUBLICATIONS

U.S. Appl. No. 07/855,389, filed Mar. 20, 1992, Woo, et al.
Adang, et al. The reconstruction and expression of a *Bacillus thuringiensis* cryIIIA gene in protoplasts and potato plants. Plant Molec. Biol. 1993; 21: 1131-1145.
Alheim, et al. Identification of a functional glucocorticoid response element in the promoter of the cyclin-dependent kinase inhibitor p57Kip2. J. Mol. Endocrinol. 2003; 30:359-368.
Appleman, et al. CD28 costimulation mediates down-regulation of p27kip1 and cell cycle progression by activation of the PI3K/PKB signaling pathway in primary human T cells. J. Immunol. 2002; 168:2729-2736.
Ausubel, et al. eds. Current Protocols in Molecular Biology. Wiley, John & Sons, Inc 1987 (Table of Contents).
Ausubel, et al. eds. Short Protocols in Molecular Biology. 4th edition. Wiley, John & Sons, Inc 1999 (Table of Contents).
Baas, et al. Oligodendrocyte maturation and progenitor cell proliferation are independently regulated by thyroid hormone. Glia. 1997; 19:324-332.
Baines, et al. "Purification of Immunoglobulin G (IgG)" in Methods In Molecular Biology. The Humana Press, Inc. 1992; 10:79-104.
Balint, et al. Induction of p57(KIP2) expression by p73beta. Proc. Natl. Acad. Sci. USA 2002; 99: 3529-3534.
Bambot, et al. Efficient total gene synthesis of 1.35-kb hybrid alpha-lytic protease gene using the polymerase chain reaction. PCR Methods and Applications. 1993; 2:266-271.
Barres, et al. Control of oligodendrocyte number in the developing rat optic nerve. Neuron. 1994; 12;935-942.
Barres, et al. A novel role for thyroid hormone, glucocorticoids and retinoic acid in timing oligodendrocyte development. Development. 1994; 120:1097-1108.

(Continued)

*Primary Examiner* — Michael Pak
(74) *Attorney, Agent, or Firm* — Wilson Sonsini Goodrich & Rosati

(57) ABSTRACT

The present invention provides compositions and methods for regulating neural cell proliferation or differentiation. The present invention also provides methods for selecting for bioactive agents effective in regulating proliferation or differentiation.

6 Claims, 104 Drawing Sheets

OTHER PUBLICATIONS

Barres, et al. Cell death and control of cell survival in the oligodendrocyte lineage. Cell. 1992; 70: 31-46.

Barres, et al, Multiple extracellular signals are required for long-term oligodendrocyte survival. Development. May 1993;118(1):283-295.

Baumann, et al. Biology of oligodendrocyte and myelin in the mammalian central nervous system. Physiol Rev. 2001; 81: 871-927.

Billon, et al. Roles for p53 and p73 during oligodendrocyte development. Development. 2004; 131:1211-1220.

Bitter, et al. Expression and secretion vectors for yeast. Methods in Enzymol. 1987; 153:516-544.

Boussiotis, et al. p27kip1 functions as an anergy factor inhibiting interleukin 2 transcription and clonal expansion of alloreactive human and mouse helper T lymphocytes. Nat. Med. 2000; 6:290-297.

Brody, et al. Aptamers as therapeutic and diagnostic agents. J. Biotechnol. 2000; 74:5-13.

Bruck, et al. Remyelination in multiple sclerosis. J. Neurol. Sci. 2003; 206: 181-185.

Calver, et al. Oligodendrocyte population dynamics and the role of PDGF in vivo. Neuron. 1998; 20:869-882.

Casaccia-Bonnefil, et al. Loss of p27Kip1 function results in increased proliferative capacity of oligodendrocyte progenitors but unaltered timing of differentiation. Development. 1999; 126;4027-4037.

Chu, et al. Efficiency of cytoplasmic delivery by pH-sensitive liposomes to cells in culture. Pharm. Res. 1990; 7:824-834.

Coligan, et al. eds. Current Protocol in Immunology. Wiley, John & Sons, Inc. 1991. (Table of Contents).

Compston, et al. Multiple sclerosis, Lancet. 2002; 359:1221-1231.

Cunningham, et al. Cyclin-dependent kinase inhibitors in the development of the central nervous system. Cell Growth Differ. 2001; 12:387-396.

Dillon, et al. Use of the Polymerase Chain Reaction of the Rapid Construction of Synthetic Genes. In Methods In Molecular Biology. The Humana Press, Inc. 1993; 15:263-268.

Dubois-Dalcq, et al. Enhancing central nervous system remyelination in multiple sclerosis. Neuron. 2005; 48:9-12.

Dugas, et al. A crucial role for p57(Kip2) in the intracellular timer that controls oligodendrocyte differentiation. J Neurosci. Jun. 6, 2007;27(23):6185-6196.

Dugas, et al. Functional genomic analysis of oligodendrocyte differentiation. J. Neurosci. 2006; 26:10967-10983.

Dussault, et al. Thyroid hormones and brain development. Ann. Rev. Physiol. 1987; 49:321-334.

Eglitis, et al. Retroviral vectors for introduction of genes into mammalian cells. BioTechniques. 1988; 6(7):608-614.

Elbashir, et al. Duplexes of 21-nucleotide RNAs mediate RNA interference in cultured mammalian cells. Nature. 2001: 411;494-498.

Elbashir, et al. RNA interference is mediated by 21- and 22-nucleotide RNAs. Genes Dev. 2001; 15:188-200.

Eppstein, et al. Biological activity of liposome-encapsulated murine interferon gamma is mediated by a cell mem3brane receptor. Proc. Natl. Acad. Sci. USA 1985; 82: 3688-3692.

Flusberg, et al. Fiber-optic fluorescence imaging. Nat. Methods. 2005; 2:941-950.

Freshney, ed. Animal Cell Culture. Wiley, John & Sons, Inc. 1986. (Cover and table of contents pages only).

Gabizon, et al. Pharmacokinetics and tissue distribution of doxorubicin encapsulated in stable liposomes with long circulation times. J. National Cancer Inst. 1989; 81:1484-1488.

Georgia, et al. p57 and Hes1 coordinate cell cycle exit with self-renewal of pancreatic progenitors. Dev. Biol. 2006; 298:22-31.

Ghiani, et al. Inhibition of cyclin E-cyclin-dependent kinase 2 complex formation and activity is associated with cell cycle arrest and withdrawal in oligodendrocyte progenitor cells. J. Neurosci. 2001; 21:1274-1282.

Gold, et al. Diversity of oligonucleotide functions. Ann. Rev. Biochem, 1995; 64:763-797.

Haller, et al. In vitro selection of a 7-methyl-guanosine binding RNA that inhibits translation of capped mRNA molecules. Proc. Natl. Acad. Sci. USA 1997; 94:8521-8526.

Hardy, R. Dorsoventral patterning and oligodendroglial specification in the developing central nervous system. J. Neurosci. Res. 1997; 50: 139-145.

Harlow, et al. eds. Antibodies, A Laboratory Manual. Cold Spring Harbor Laboratory Press 1988.

Hermann, et al. Adaptive recognition by nucleic acid aptamers. Science. 2000; 287:820-825.

Hsu, et al. Green tea polyphenols induce differentiation and proliferation in epidermal keratinocytes. J. Pharmacol. Exp. Ther. 2003; 306:29-34.

Hwang, et al. Hepatic uptake and degradation of unilamellar sphingomyelin/cholesterol liposomes: a kinetic study. Proc. Natl. Acad. Sci. USA 1980; 77: 4030-4034.

International search report dated Oct. 15, 2008 for PCT Application No. US2007/16858.

Jackson, et al. Induction of anergy in Th1 cells associated with increased levels of cyclin-dependent kinase inhibitors p21Cip1 and p27Kip1. J. Immunol. 2001; 166:952-958.

Jayasena. Aptamers: an emerging class of molecules that rival antibodies in diagnostics. Clinical Chemistry. 1999; 45: 1628-1650.

Joseph, et al. p57(Kip2) cooperates with Nurr1 in developing dopamine cells. Proc. Natl. Acad. Sci. USA. 2003; 100:15619-15236.

Jung, et al. In vivo mammalian brain imaging using one- and two-photon fluorescence microendoscopy. J. Neurophysiol. 2004; 92:3121-3133.

Kaufman, et al. Amplification and expression of sequences cotransfected with a modular dihydrofolate reductase complementary dna gene. J. Mol. Biol. 1982; 159:601-621.

Kimura, et al. Inhibition of leukemic cell growth by a novel anti-cancer drug (GUT-70) from calophyllum brasiliense that acts by induction of apoptosis. Int. J. Cancer. 2005; 113:158-165.

Kondo, et al. The Id4 HLH protein and the timing of oligodendrocyte differentiation. EMBO J. 2000; 19:1998-2007.

Kovalev, et al. An important role of CDK inhibitor p18(INK4c) in modulating antigen receptor-mediated T cell proliferation. J. Immunol. 2001; 167:3285-3292.

Kusser, W. Chemically modified nucleic acid aptamers for in vitro selections: evolving evolution. Reviews in Molecular Biotechnology. 2000; 74:27-38.

Legendre, et al. Cyclic amphipathic peptide-DNA complexes mediate high-efficiency transfection of adherent mammalian cells. Proc. Natl. Acad. Sci. USA 1993; 90:893-897.

Legendre, et al. Delivery of plasmid DNA into mammalian cell lines using pH-sensitive liposomes: comparison with cationic liposomes. Pharm. Res. 1992; 9:1235-1242.

Logan, et al. Adenovirus tripartite leader sequence enhances translation of mRNAs late after infection. Proc. Natl. Acad. Sci. USA 1984; 81:3655-3659.

Mack Publishing ed. Remington's Pharmaceutical Sciences, 19th edition. Mack Publishing Company, 1995.

Maclean, et al. The cyclin-dependent kinase inhibitor p57(Kip2) mediates proliferative actions of PTHrP in chondrocytes. J. Clin. Investig. 2004; 113:1334-1343.

Mansfield, et al. Autofluorescence removal, multiplexing, and automated analysis methods for in-vivo fluorescence imaging. J. Biomed. Opt. 2005; 10:41207.

Matsushima, et al. The neurotoxicant, cuprizone, as a model to study demyelination and remyelination in the central nervous system, Brain Pathol. 2001; 11:107-116.

McPherson, et al. eds. The series Methods in Enzymology (Academic Press, Inc.): PCR 2: A practical approach. Oxford University Press. New York. 1995.

Mehta, et al. Fiber optic in vivo imaging in the mammalian nervous system. Curr. Opin. Neurobiol. 2004; 14:617-628.

Miskimins, et al. p27(Kip1) enhances myelin basic protein gene promoter activity. J. Neurosci. Res. 2002; 67:100-105.

Mohapatra, et al. p27Kip1 regulates T cell proliferation. J. Biol. Chem. 2001; 276:21976-21983.

Morita, et al. Functional analysis of basic transcription element binding protein by gene targeting technology. Mol Cell Biol. Apr. 2003;23(7):2489-2500.

Nygard, et al. Hormone-dependent repression of the E2F-1 gene by thyroid hormone receptors. Mol. Endocrin. 2003; 17:79-92.

Osol, A. ed. Remington's Pharmaceutical Sciences. 16th edition. Mack Publishing Company. 1980. (Cover and table of contents pages only).

Park, et al. Oligodendrocyte specification in zebrafish requires notch-regulated cyclin-dependent kinase inhibitor function. J. Neurosci. 2005; 25: 6836-6844.

Raff, et al. A glial progenitor cell that develops in vitro into an astrocyte or an oligodendrocyte depending on culture medium. Nature. 1983; 303:390-396.

Riechmann, et al. The expression pattern of Id4, a novel dominant negative helix-loop-helix protein, is distinct from Id1, Id2 and Id3. Nucl. Acids Res. 1994; 22:749-755.

Rothschild, et al. E Proteins and Id2 converge on p57Kip2 to regulate cell cycle in neural cells. Mol. Cell. Biol. 2006; 26:4351-4361.

Salleh, et al. A comparison of gene expression changes in response to diethylstilbestrol treatment in wild-type and p53+/-hemizygous knockout mice using focussed arrays. Toxicology. 2003; 185:49-57.

Saltzman, et al. Transport rates of proteins in porous materials with known microgeometry. Biophys. J. 1989; 55:163-171.

Sambrook, et al. Molecular Cloning: A Laboratory Manual. 2nd edition Cold Spring Harbor Laboratory Press. 1989.

Scahill, et al. Expression and characterization of the product of a human immune interferon cDNA gene in Chinese hamster ovary cells. Proc. Natl. Acad. Sci. USA 1983; 80:4654-4659.

Scandura, et al. Transforming growth factor beta-induced cell cycle arrest of human hematopoietic cells requires p57KIP2 up-regulation. Proc. Natl. Acad. Sci. USA 2004: 101:15231-15236.

Sherman, et al. Mechanisms of axon ensheathment and myelin growth. Nat. Rev. Neurosci. 2005; 6:683-690.

Sherwood, et al. Controlled Antibody Delivery Systems. Bio/Technology. 1992; 10:1446-1449.

Southern, et al. Transformation of mammalian cells to antibiotic resistance with a bacterial gene under control of the SV40 early region promoter. J. Mol. Appl. Genet. 1982; 1:327-341.

Subramini, et al. Expression of the mouse dihydrofolate reductase complementary deoxyribonucleic acid in simian virus 40 vectors. Mol. Cell. Biol. 1981; 1:854-864.

Sullenger, et al. Overexpression of TAR sequences renders cells resistant to human immunodeficiency virus replication. Cell. 1990; 63:601-608.

Sun, et al. Id proteins Id1 and Id2 selectively inhibit DNA binding by one class of helix-loop-helix proteins. Mol. Cell. Biol. 1991; 11:5603-5611.

Sun, S. Technology evaluation: SELEX, Gilead Sciences Inc. Curr. Opin. Mol. Ther. 2000; 2: 100-105.

Szoka, et al. Synthesis and characterization of a trigalactosylated bisacridine compound to target DNA to hepatocytes, Bioconjug. Chem. 1993; 4:85-93.

Takahashi, et al. Mice lacking a CDK inhibitor, p57Kip2, exhibit skeletal abnormalities and growth retardation. J. Biochem. 2000; 127:73-83.

Tang, et al. Cell cycle arrest induced by ectopic expression of p27 is not sufficient to promote oligodendrocyte differentiation. J. Cell. Biochem. 1999; 76:270-279.

Tang, et al. Long-term culture of purified postnatal oligodendrocyte precursor cells. Evidence for an intrinsic maturation program that plays out over months. J. Cell Biol. 2000; 148:971-984.

Temple, et al. Clonal analysis of oligodendrocyte development in culture: evidence for a developmental clock that counts cell divisions. Cell. 1986; 44:773-779.

Tokumoto, et al. Posttranscriptional regulation of p18 and p27 Cdk inhibitor proteins and the timing of oligodendrocyte differentiation. Dev. Biol. 2002; 245:224-234.

Tokumoto, et al. Two molecularly distinct intracellular pathways to oligodendrocyte differentiation: role of a p53 family protein. EMBO J. 2001; 20: 5261-5268.

Tsai, et al. Netrin-1 is required for the normal development of spinal cord oligodendrocytes.B J. Neurosci. 2006; 26:1913-1922.

Tsai, et al. The chemokine receptor CXCR2 controls positioning of oligodendrocyte precursors in developing spinal cord by arresting their migration. Cell. 2002; 110:373-383.

Tsukiyama, et al. Down-regulation of p27Kip1 expression is required for development and function of T cells. J. Immunol. 2001; 166:304-312.

Urlaub, et al. Isolation of Chinese hamster cell mutants deficient in dihydrofolate reductase activity. Proc. Natl. Acad. Sci. USA 1980. 77:4216-4220.

Vaccarello, et al. p57Kip2 is induced by MyoD through a p73-dependent pathway. J. Mol. Biol. 2006; 356:578-588.

Walters, et al. Effects of altered thyroid states on myelinogenesis. J. Neurochemistry. 1981; 36:1792-1801.

Wang, et al. A DNA aptamer which binds to and inhibits thrombin exhibits a new structural motif for DNA. Biochemistry. 1993; 32: 1899-1904.

Wang, et al. A role for the helix-loop-helix protein Id2 in the control of oligodendrocyte development. Neuron. 2001; 29:603-614.

Wei, et al. Sox10 acts as a tissue-specific transcription factor enhancing activation of the myelin basic protein gene promoter by p27Kip1 and Sp1. J. Neurosci. Res. 2004; 78:796-802.

Wei, et al. The Sp1 family of transcription factors is involved in p. 27(Kip1)-mediated activation of myelin basic protein gene expression. Mol. Cell. Biol. 2003; 23:4035-4045.

Wilson, et al. Genomic structure and chromosomal mapping of the human CD22 gene. J. Immunol. 1993; 150:5013-5024.

Wilson, et al. cDNA cloning of the B cell membrane protein CD22: a mediator of B-B cell interactions. J. Exp. Med. 1991; 173:137-146.

Wosnick, et al. Rapid construction of large synthetic genes: total chemical synthesis of two different versions of the bovine prochymosin gene. Gene. 1987; 60:115-127.

Zezula, et al. p21cip1 is required for the differentiation of oligodendrocytes independently of cell cycle withdrawal. EMBO Rep. 2001; 2:27-34.

Zhang, et al. A transgenic mouse model with a luciferase reporter for studying in vivo transcriptional regulation of the human CYP3A4 gene. Drug Met. Disp. 2003; 31:1054-1064.

Zhang, et al. Cooperation between the Cdk inhibitors p. 27(KIP1) and p. 57(KIP2) in the control of tissue growth and development. Genes & Dev. 1998; 12:3162-3167.

Zhang, et al. Cytokine-stimulated T lymphocyte proliferation is regulated by p27Kip1. J. Immunol. 2000; 165:6270-6277.

Zhang, et al. p. 21(CIP1) and p. 57(KIP2) control muscle differentiation at the myogenin step, Genes & Dev. 1999; 13:213-224.

FIG. 3 Oligodendrocyte development

FIG. 4

Regulation of OL differentiation

- Novel genes regulated during OL differentiation
- Regulated genes linked to MS loci
- OL differentiation in distinct temporal stages
- Transcription factors that intrinsically direct OL differentiation

FIG. 7A
Most highly induced /expressed genes in OLs

| Top 50 OL upregulated genes | | |
|---|---|---|
| Fold Change | Gene Name | Gene Symbol |
| 119.43 | Myelin-assoc oligodendrocyte basic protein | MOBP |
| 98.36 | Myelin basic protein | MBP |
| 97.68 | Myelin oligodendrocyte glycoprotein | MOG |
| 93.05 | ESTs, no homologies found | |
| 77.71 | Proteolipid protein | PLP |
| 71.01 | Apolipoprotein D | APOD |
| 66.72 | Ectonucleotide pyrophos./phosphodiesterase 6** | ENPP6** |
| 60.55 | Pancreatic lipase | PNLIP |
| 49.87 | Claudin 11 / OL specific protein | OSP |
| 44.63 | Transferrin | Tf |
| 38.59 | ESTs, no homologies found | |
| 38.32 | Myelin-associated glycoprotein | MAG |
| 36.00 | Tumor protein D52 | TPD52 |
| 31.34 | Carboxypeptidase M | CPM |
| 29.86 | Mannosidase 1, alpha | MAN1A1 |
| 29.04 | Septin 5 | SEPT5 |
| 26.91 | UDP-glucuronosyltransferase 8 | UGT8 |
| 25.81 | Glycerol 3-phosphate dehydrogenase | GPD1 |
| 25.63 | Thyroid hormone-response protein-1 | APXL |
| 24.93 | Cathepsin L** | CTSL** |
| 23.75 | Transmembrane protein TMP10** | TMEM10** |
| 22.32 | Selenoprotein P** | SEPP1** |
| 21.71 | Hypothetical protein DKFZp506N034 | |
| 21.41 | Chimerin 2 | CHN2 |
| 21.11 | Ectonucleotide pyrophos./phosphodiesterase 2 | ENPP2 |
| 20.82 | Semaphorin 5A | SEMA5A |
| 19.84 | Synaptotagmin-like 2 | SYTL2 |
| 19.70 | N-acetylgalactosaminyltransferase 5 | GALNT5 |
| 19.70 | similar - ADP-ribosylation guan. nuc. factor 6a | |
| 19.56 | Protein phosphatase 1, regulatory subunit 14a** | PPP1R14A** |
| 19.03 | Cysteine and glycine-rich protein 1** | CSRP1** |
| 18.77 | Endothelial diff., LPA G-protein-coupled-R, 2 | EDG2 |
| 18.25 | Fibroblast growth factor receptor 2 | FGFR2 |
| 18.13 | Kallikrein 6 | KLK6 |
| 18.00 | Plastin 1 | PLS1 |
| 17.75 | Erythrocyte membrane protein band 4.1-like 2** | EPB41L2** |
| 17.03 | Protease, serine, 11 (IGF binding) | HTRA1 |
| 17.03 | Bone morphogenetic protein 4 | BMP4 |
| 16.91 | Dedicator of cytokinesis 9 | DOCK9 |
| 16.91 | Aspartoacylase | ASPA |
| 16.91 | Tetraspanin 2 | TSPAN2 |
| 16.91 | Lipoma HMGIC fusion partner-like 2 | LHFPL2 |
| 16.68 | HCV NS3-transactivated protein 2** | GRAMD3** |
| 16.00 | Spermatogenesis assoc. glu-rich protein 4f | SPEER4F |
| 15.78 | Chemokine-like factor super family 7 | CMTM7 |
| 15.56 | Protein tyrosine phosphatase, receptor type, D | PTPRD |
| 15.45 | Growth arrest specific 7 | GAS7 |
| 15.45 | Gelsolin | GSN |
| 15.35 | Putative phosphatase subunit | |
| 15.14 | Brevican | BCAN |

Genes on both lists (16)

▒ Genes *not previously cited as expressed in OLs (52)*

** Genes *not previously cited as expressed in OLs with white-matter enriched expression patterns (13)*

FIG. 7B
Most highly induced / expressed genes in OLs

| Top 50 OL-specific expressed genes | | |
|---|---|---|
| OL Level | Gene Name | Gene Symbol |
| 18758 | *Pancreatic lipase* | *PNLIP* |
| 14359 | *Myelin basic protein* | *MBP* |
| 13729 | *Proteolipid protein* | *PLP* |
| 12541 | CD9 antigen (p24) | CD9 |
| 10833 | ESTs, no homologies found | |
| 10533 | Sirtuin 2** | SIRT2** |
| 10485 | Farnesyltransferase, CAAX box, alpha | FNTA |
| 9064 | Deleted in polyposis 1 | REEP5 |
| 9059 | 2',3'- Cyclic nucleotide 3'-phosphodiesterase | CNP1 |
| 8588 | Lysosomal associated membrane protein 1 | LAMP1 |
| 7707 | *UDP-glucuronosyltransferase 8* | *UGT8* |
| 7334 | *Claudin 11 / OL specific protein* | *OSP* |
| 7274 | Amyloid beta precursor-like protein 1 | APLP1 |
| 7174 | *Cathepsin L*** | *CTSL*** |
| 7016 | *Septin 5* | *SEPT5* |
| 6896 | Glycolipid transfer protein** | GLTP** |
| 6808 | *Hypothetical protein DKFZp566N034* | |
| 6444 | *Brevican* | *BCAN* |
| 6141 | CD81 antigen | CD81 |
| 6043 | *Myelin-associated glycoprotein* | *MAG* |
| 5945 | Guanidinoacetate methyltransferase | GAMT |
| 5859 | Bridging integrator 1 | BIN1 |
| 5842 | Phytanoyl-CoA hydroxylase interacting protein | PHYHIP |
| 5828 | Thyroid hormone receptor alpha | THRA |
| 5638 | Prion protein (p27-30) | PRNP |
| 5574 | SH3 domain protein 2 C1 | SH3D2C1 |
| 5321 | *Chemokine-like factor super family 7* | *CMTM7* |
| 5317 | Protein phosphatase 1, regulatory subunit 16B** | PPP1R16B** |
| 5316 | Myelin protein zero-like 1** | MPZL1** |
| 5316 | *Myelin-assoc oligodendrocyte basic protein* | *MOBP* |
| 5230 | *Apolipoprotein D* | *APOD* |
| 5087 | ESTs, no homologies found | |
| 4956 | Protein tyrosine phosphatase, receptor type, O | PTPRO |
| 4944 | Dynein light chain-2 | DLC2 |
| 4838 | *Erythrocyte membrane protein band 4.1-like 2*** | *EPB41L2*** |
| 4822 | *Transferrin* | *Tf* |
| 4792 | Dihydropyrimidinase-like 4 | DPYSL4 |
| 4782 | C1q-related factor precursor | C1QL1 |
| 4765 | Pleckstrin homology domain-containing A-1 | PLEKHA1 |
| 4642 | *Chimerin 2* | *CHN2* |
| 4605 | ESTs, no homologies found | |
| 4484 | ESTs, no homologies found | |
| 4463 | Amyloid beta precursor protein | APP |
| 4418 | Striatin, calmodulin binding protein | STRN |
| 4284 | Guanine nucleotide binding protein, alpha 12** | GNA12** |
| 4266 | Ras homolog gene family, member G | RHOG |
| 4254 | BCL2/adenovirus E1B 19 kDa-interac. prot. 3 | BNIP3L |
| 4149 | Junction cell adhesion molecule 3 | JAM3 |
| 4076 | Stathmin-like 4 | STMN4 |
| 4011 | EGF receptor pathway substrate 15 | EPS15 |

Genes on both lists (16)

 Genes *not* previously cited as expressed in OLs (52)

**** Genes *not* previously cited as expressed in OLs with *white-matter enriched* expression patterns (13)

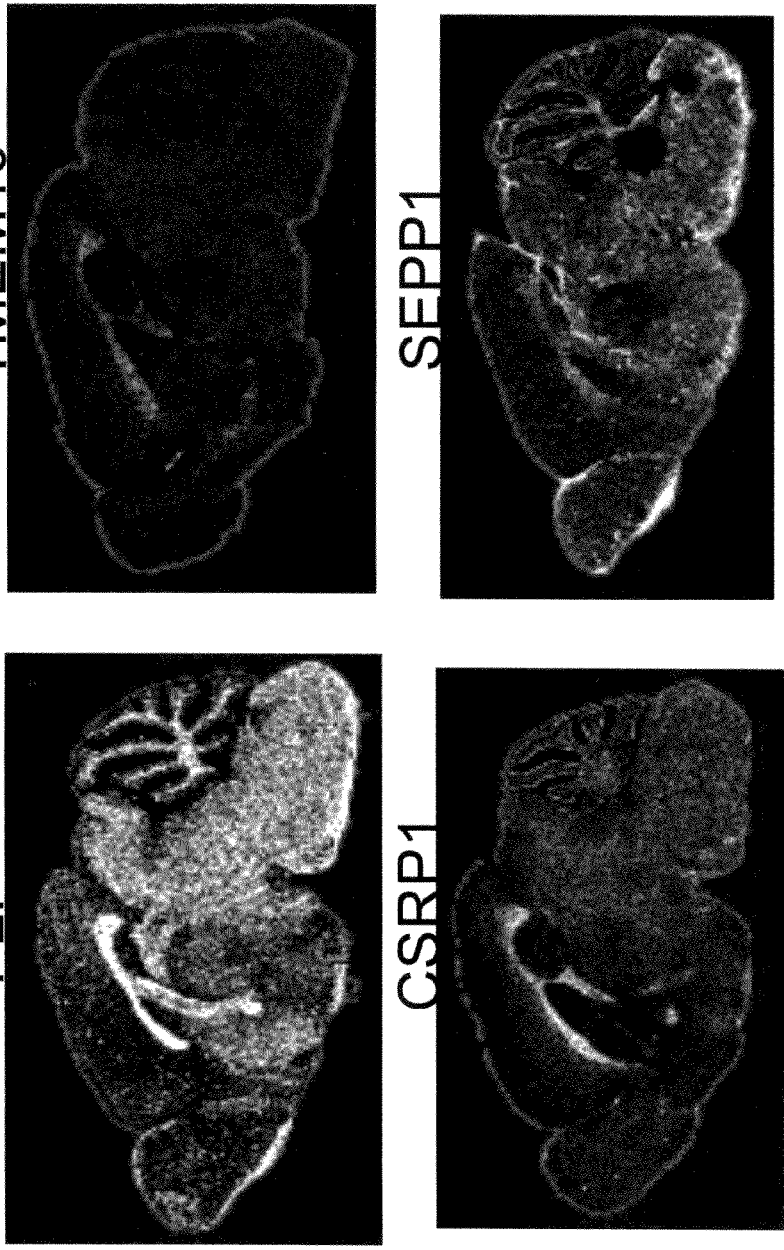

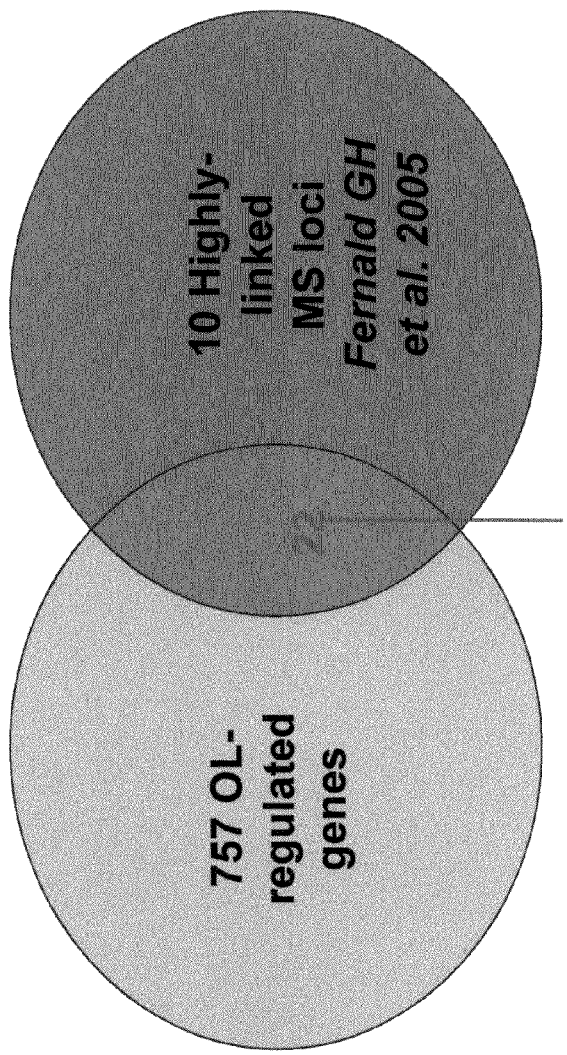

FIG. 10     OL-regulated genes linked to MS loci

| Fold Change | h-Chromosome | Gene Name | Gene Symbol |
|---|---|---|---|
| 97.68 | 6p22.1; 30 Mb | Myelin oligodendrocyte glycoprotein | MOG |
| 22.32 | 5p12; 43 Mb | Selenoprotein P, plasma, 1 | SEPP1 |
| 13.74 | 17q24.2; 64 Mb | ATP-binding cassette transporter 8a | ABCA8 |
| 12.13 | 17q25.1; 70 Mb | Tweety homolog 2 | TTYH2 |
| 7.62 | 11q23.1; 111 Mb | DIX domain containing 1 | DIXDC1 |
| 7.46 | 7p12.3; 47 Mb | Tensin-like SH2 domain containing 1 | TENS1 |
| 7.46 | 17q24.2; 64 Mb | WD40 repeat protein Interacting with PI | WIPI49 |
| 5.46 | 16q22.2; 70 Mb | Hydrocephalus inducing | HYDIN |
| 5.13 | 11q23.1; 111 Mb | Crystallin, alpha B | CRYAB |
| 4.26 | 5p13.1; 39 Mb | TORC2-specific protein AVO3 | RICTOR |
| 3.68 | 17q24.2; 62 Mb | Protein kinase C, alpha | PRKCA |
| -3.76 | 17q24.2; 63 Mb | PI transfer protein, cytoplasmic 1 | PITPNC1 |
| -3.78 | 6p22.3; 18 Mb | DEK oncogene (DNA binding) | DEK |
| -3.86 | 2q33.3; 206 Mb | Neuropilin 2 | NRP2 |
| -4.47 | 6p21.31; 34 Mb | High mobility group AT-hook 1 | HMGa1 |
| -4.99 | 19p13.3; 3 Mb | Bruno-like 5, RNA binding protein | BRUNOL5 |
| -5.13 | 17q25.1; 71 Mb | Hematological and neurological EST 1 | HN1 |
| -6.11 | 6p21.33; 31 Mb | Tubulin beta 5 chain | TUBB |
| -6.28 | 7q21.2; 92 Mb | Cyclin-dependent kinase 6 | CDK6 |
| -10.48 | 6p22.2; 25 Mb | Geminin | GMNN |
| -11.16 | 6p21.33; 32 Mb | Chloride intracellular channel 1 | CLIC1 |
| -11.31 | 17q24.2; 63 Mb | Karyopherin alpha 2 | KPNA2 |

SEPP1

- One of the most strongly induced OL genes, has white matter specific expression (*in situ*)
- Maintains normal Se$^+$ levels, including CNS
- Low Se$^+$ levels have been implicated as potential MS risk factors
- Deficiencies in SEPP1 lead to ataxia

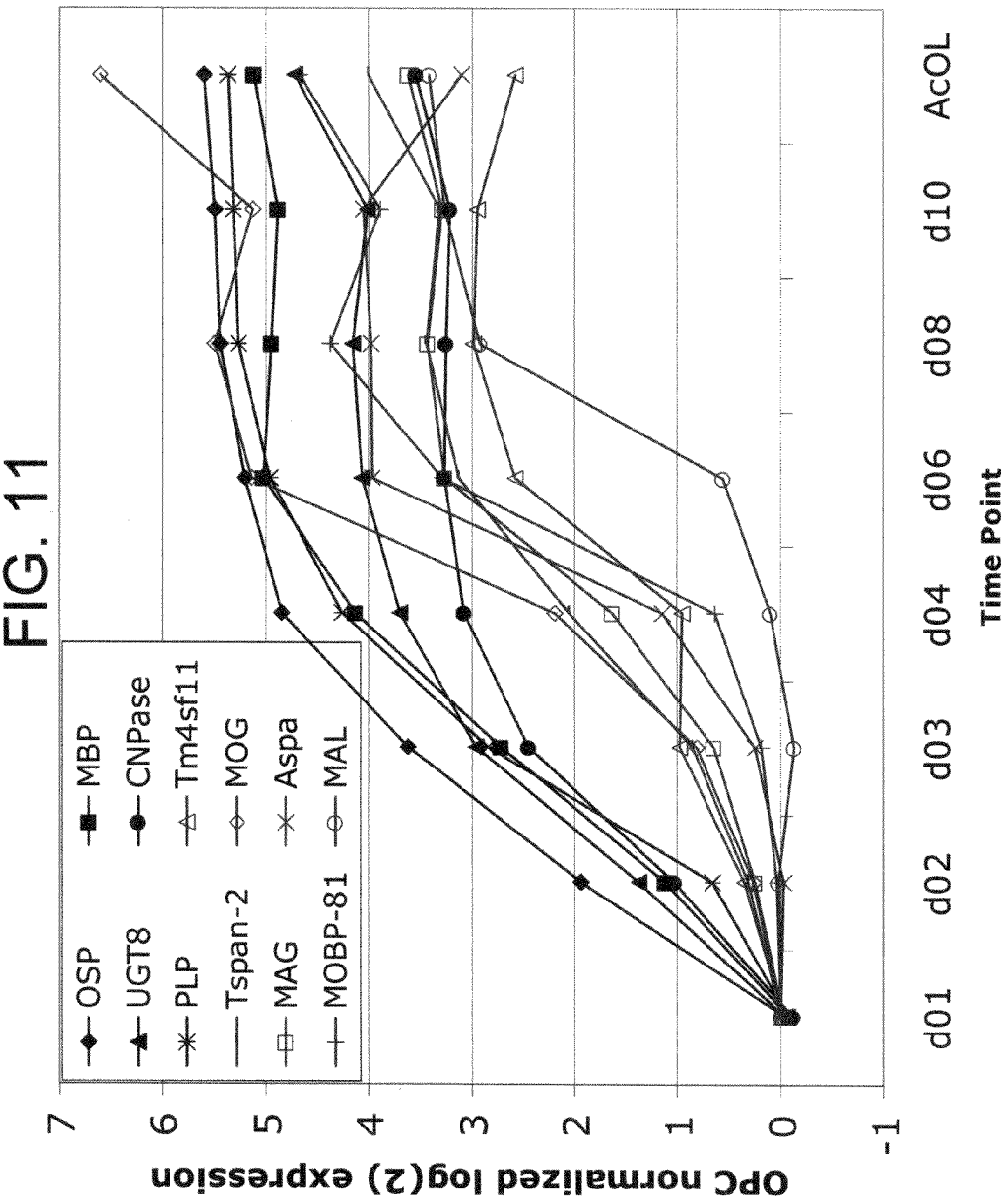

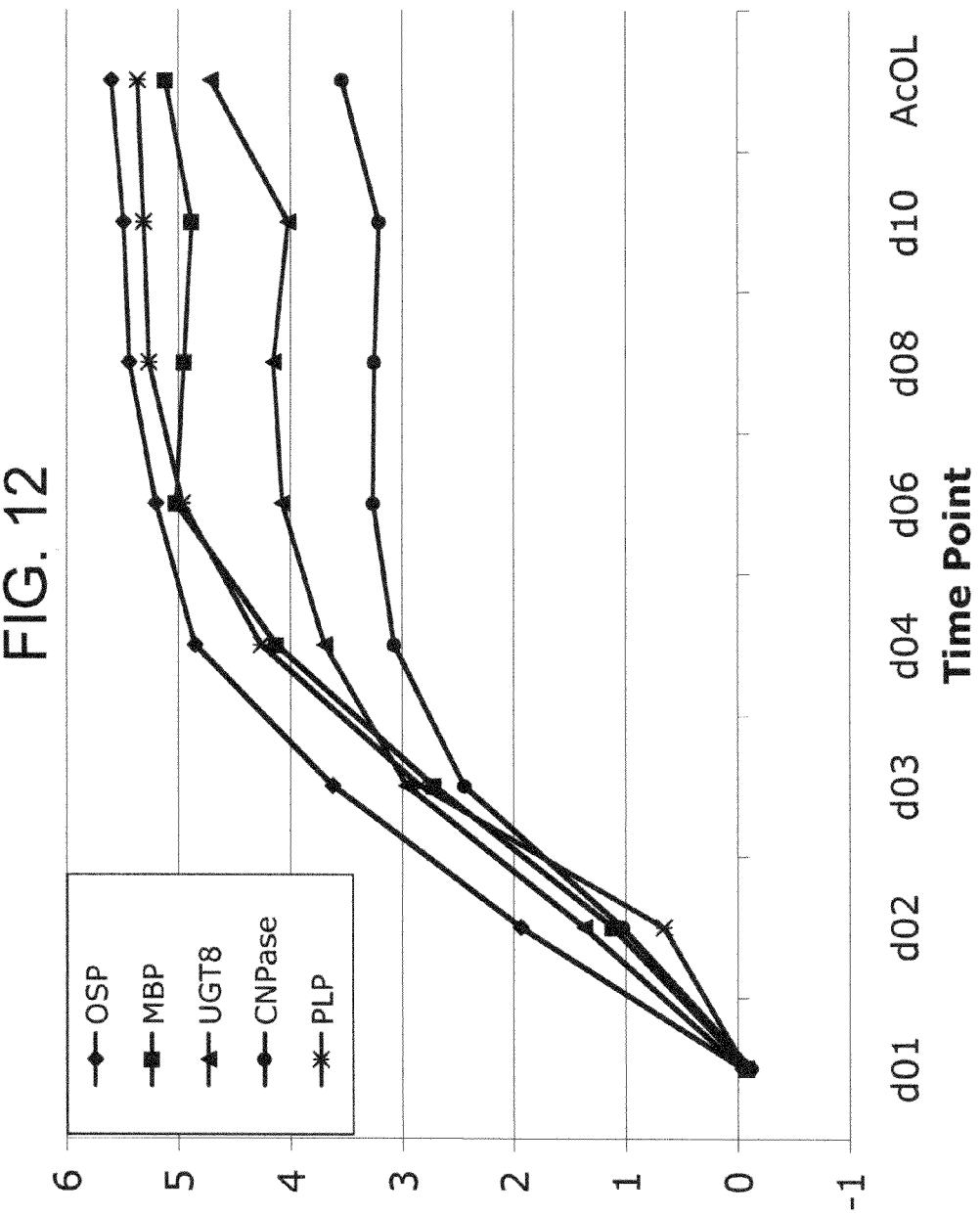

*Terminal OL differentiation proceeds in distinct temporal stages*

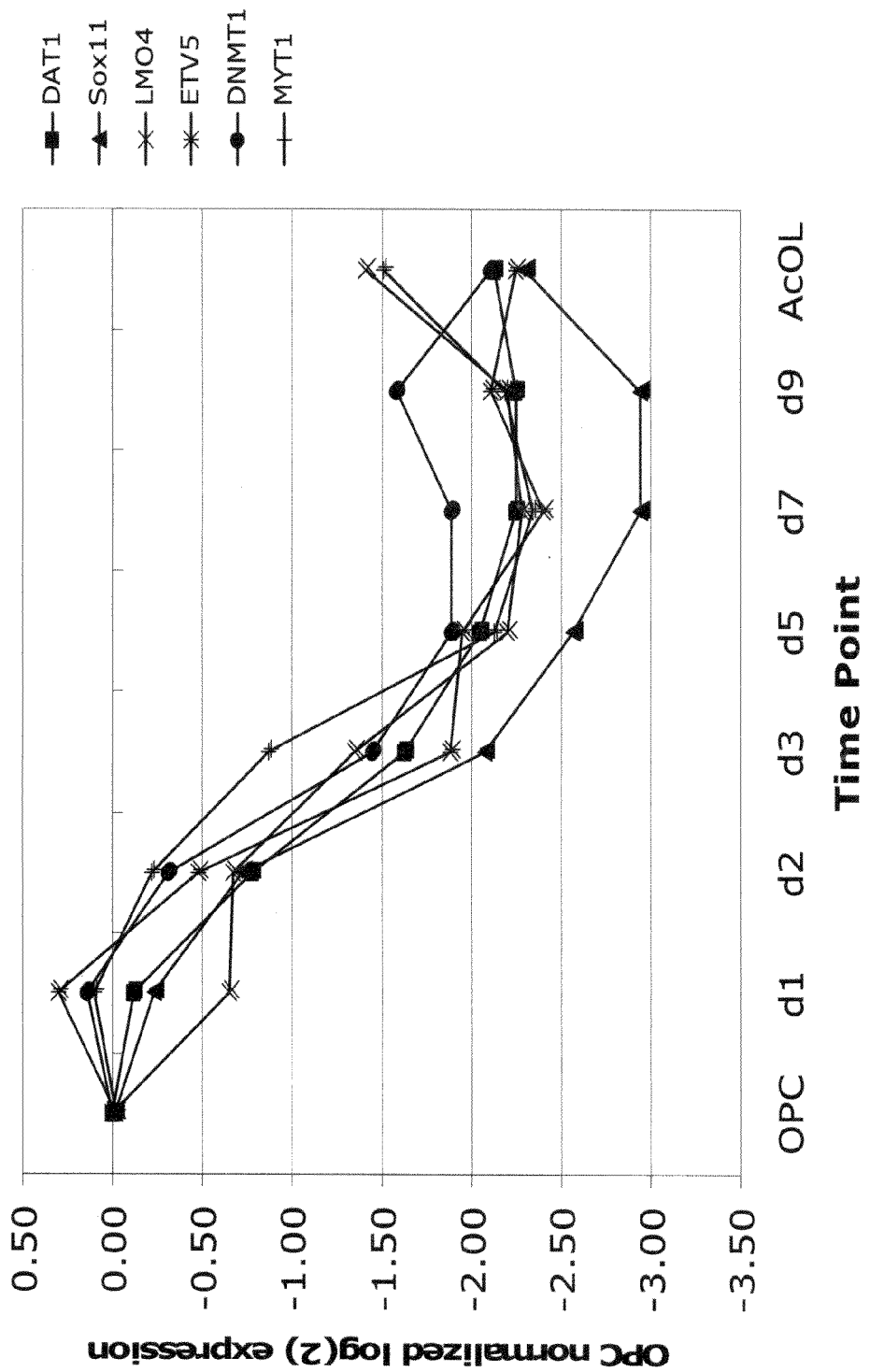

FIG. 21A

| Gene | OPC | Oligo - Immature | Oligo - Mature | Astro - Immature | Astro - Mature | Neuron - Immature |
|---|---|---|---|---|---|---|
| HMGa2 | xx | x | | | | |
| MLR1 | x | xx | x | | | |
| TCF7L2 | | xx | x | | | |
| P57 | x | xx | xx | | | |
| CARHSP1 | | xx | xx | | | |
| CREB3L2 | | xx | xx | | | |
| CHES1 | | x | xx | | | |
| ZFP536 | | x | xx | | | |
| PCAF | | x | xx | | | |
| LITAF | | | xx | | | |
| LRRFIP1 | xx | x | | | | |
| CDY1 | | xx | x | | | |
| NFKBIB | x | xx | xx | x | x | x |
| ELF1 | x | xx | xx | x | x | x |
| PRICKLE1 | | xx | xx | | | |
| RNF141 | x | x | xx | x | x | x |
| APLP1 | | x | xx | | x | x |
| APP | | x | xx | | | x |
| KUA | | x | xx | | x | |
| KLF13 | | x | xx | | | |

FIG. 21B

| Gene | OPC | Oligo - Immature | Oligo - Mature | Astro - Immature | Astro - Mature | Neuron - Immature |
|---|---|---|---|---|---|---|
| ETV5 | XX | | | | | |
| CEBPb | XX | | | XX | XX | X |
| UHRF1 | XX | X | | XX | | |
| HMGb2 | XX | X | | XX | X | XX |
| DNMT1 | XX | X | | X | | XX |
| HMGb3 | XX | X | | XX | X | XX |
| TRIP13 | XX | X | | X | | XX |
| LMO1 | XX | | | | | XX |
| LMO4 | XX | X | | XX | XX | XXX |
| FOSL2 | XX | X | | XX | XX | XXX |
| MYC | XX | X | | XX | XX | XX |
| CITED2 | XX | X | X | XX | XX | XX |
| HMGa1 | XX | X | X | X | X | XX |
| RUVBL1 | XX | X | X | X | X | XX |
| TAF9 | XX | XX | X | X | X | XX |
| TSC22d4 | X | XX | XX | | | XX |
| KLF9 | X | X | XX | XX | XXX | X |
| PBX3 | X | X | XX | XX | X | XX |
| TLE1 | | X | XX | XX | XX | X |
| CSRP1 | | X | XX | X | XXX | |
| NFE2L2 | | | XX | XX | XXX | |
| ETV1 | XX | X | XX | | | X |

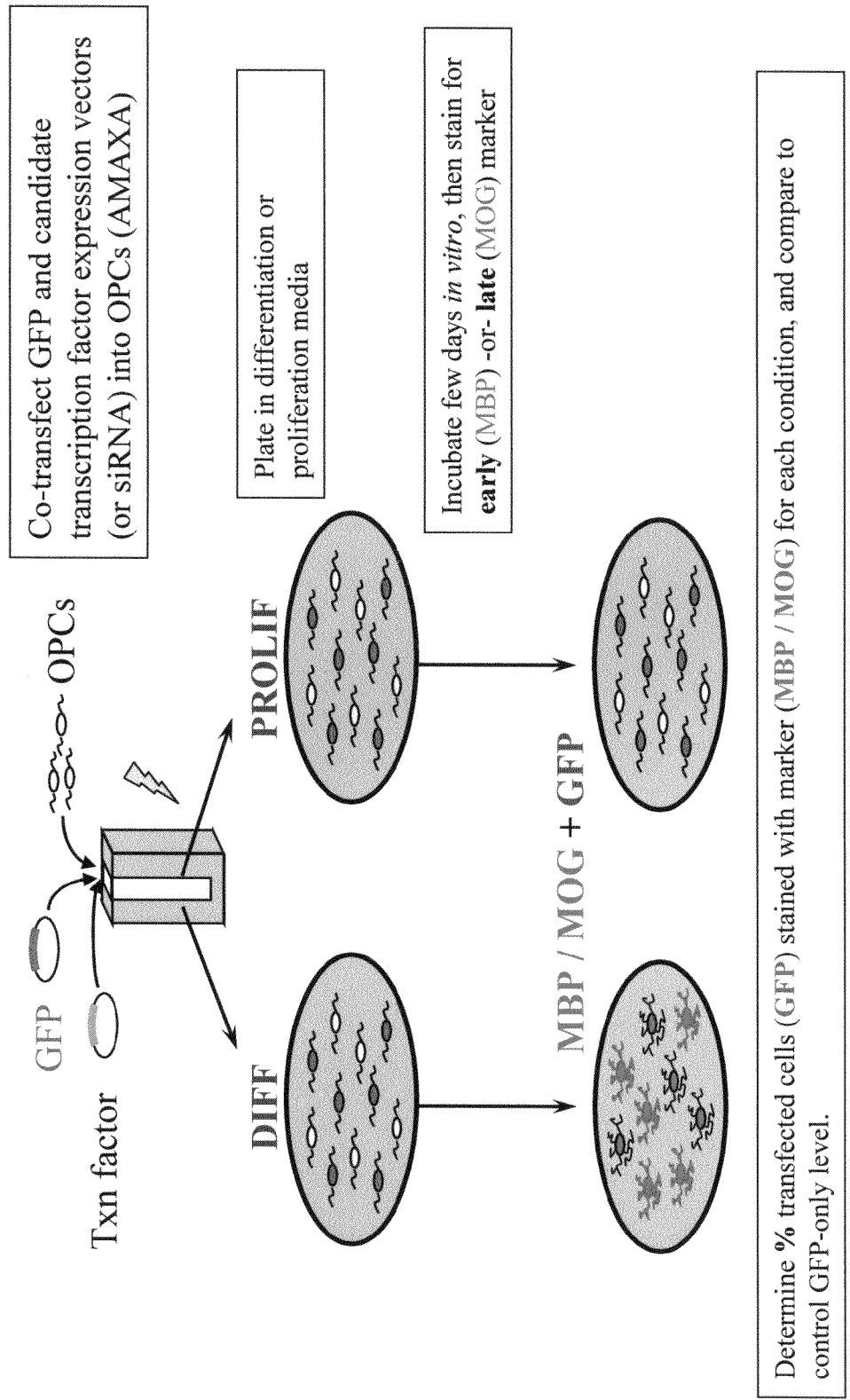

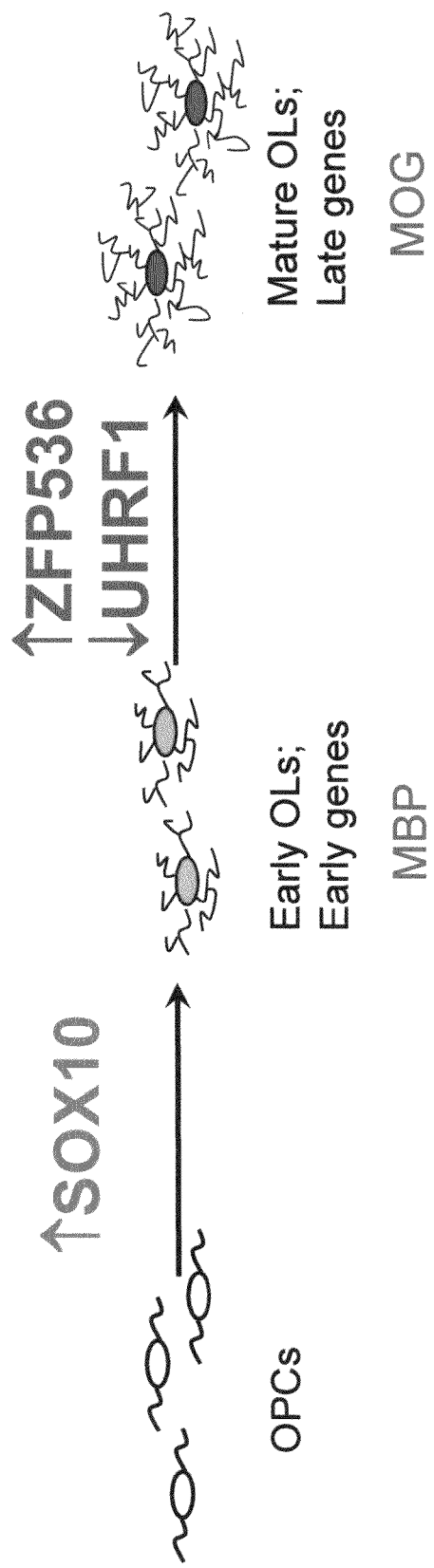

FIG. 30A
OL-regulated transcription factors

| Gene | OPC | Oligo - Immature | Oligo - Mature | Astro - Immature | Astro - Mature | Neuron - Immature | Neuron - Mature |
|---|---|---|---|---|---|---|---|
| HMGa2 | XX | X | | | | | |
| MLR1 | X | XX | X | | | | |
| TCF7L2 | | XX | X | | | | |
| P57 | X | XX | XX | | | | |
| CARHSP1 | | XX | XX | | | | |
| CREB3L2 | | XX | XX | | | | |
| CHES1 | | X | XX | | | | |
| ZFP536 | | X | XX | | | | |
| PCAF | | X | XX | | | | |
| LITAF | | | XX | | | | |
| LRRFIP1 | XX | X | | | | X | X |
| CDY1 | | XX | X | | | X | X |
| NFKBIB | X | XX | XX | X | X | X | X |
| ELF1 | X | XX | XX | X | X | | |
| PRICKLE1 | | XX | XX | | | | X |
| RNF141 | X | X | XX | X | X | X | X |
| APLP1 | | X | XX | | X | X | X |
| APP | | X | XX | | X | X | X |
| KUA | | X | XX | | X | | |
| KLF13 | | X | XX | | | | X |

FIG. 30B

OL-regulated transcription factors

| Gene | OPC | Oligo - Immature | Oligo - Mature | Astro - Immature | Astro - Mature | Neuron - Immature | Neuron - Mature |
|---|---|---|---|---|---|---|---|
| ZFP276 | xx | xx | | | | | |
| LMO1 | xx | | | | | xx | x |
| ETV5 | xx | | | xx | xx | | x |
| CEBPb | xx | | | xx | xx | x | x |
| UHRF1 | xx | | | xx | | | |
| HMGb2 | | x | | x | x | | |
| DNMT1 | xx | x | | x | x | xx | x |
| HMGb3 | xx | x | | xx | | xx | x |
| TRIP13 | xx | x | | x | | xx | |
| LMO4 | xx | x | | xx | xx | xxx | xxx |
| FOSL2 | xx | x | | xxx | xxx | xx | xxx |
| MYC | xx | x | | xx | xx | x | x |
| CITED2 | xx | x | x | xx | xx | xx | xx |
| HMGa1 | xx | x | xx | x | x | xx | xx |
| RUVBL1 | xx | x | x | x | x | xx | xx |
| TAF9 | xx | xx | x | x | x | xx | xx |
| TSC22d4 | x | xx | xx | | | xx | xx |
| KLF9 | xx | xx | xx | xx | xxx | x | xx |
| PBX3 | x | x | xx | xx | x | xx | x |
| TLE1 | xx | x | xx | x | xx | x | x |
| CSRP1 | xx | x | xx | xx | xxx | | |
| NFE2L2 | | | xx | xx | xxx | | |
| ETV1 | xx | x | xx | | | x | xx |
| BHLHB5 | x | xx | xx | xxx | xx | xx | x |
| Hr | x | xx | xx | | x | | |
| DBP | x | xx | xx | xx | xxx | x | xx |

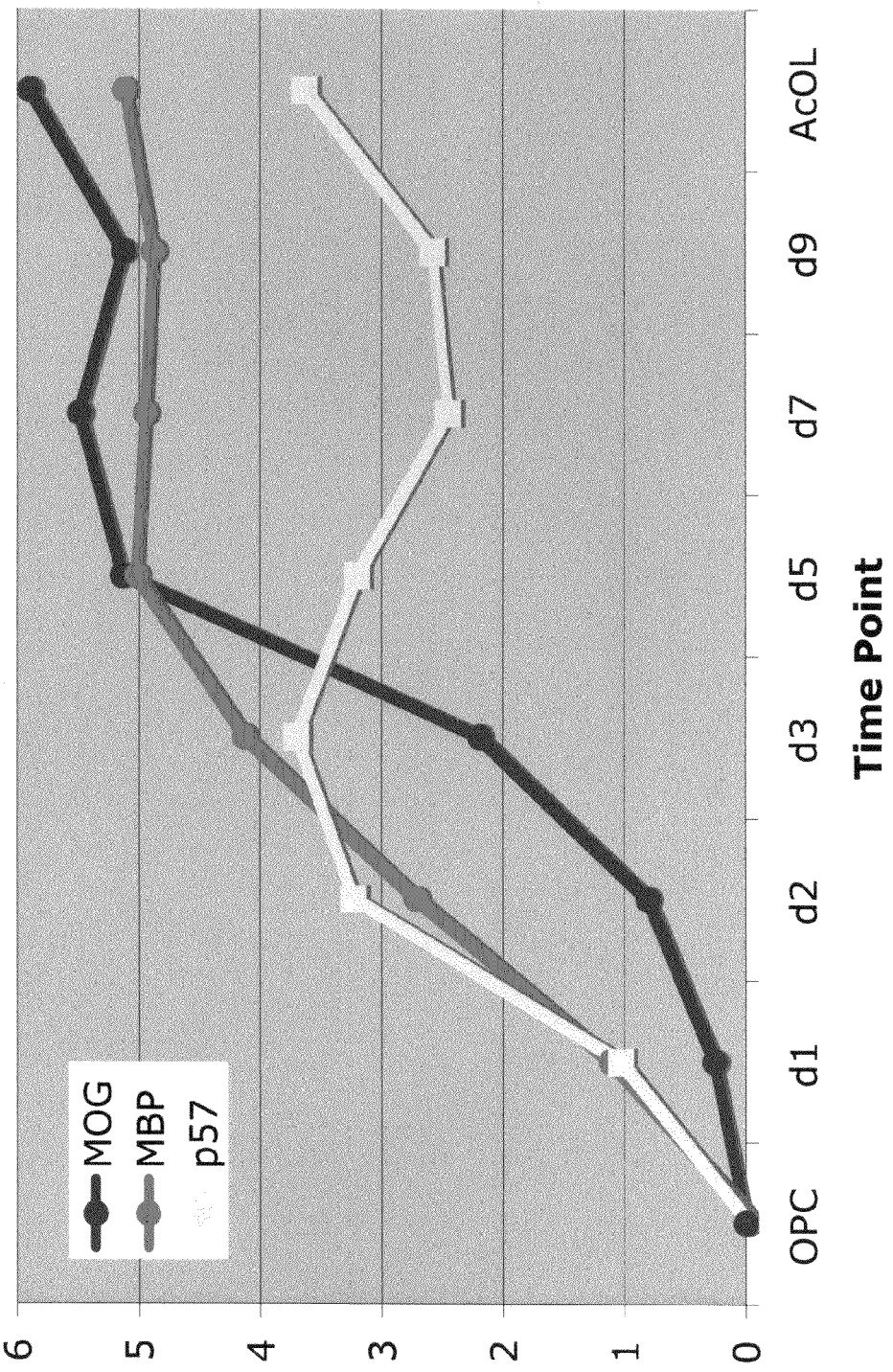

*p57KIP2 is expressed in adult white matter*

NCBI GENSAT image

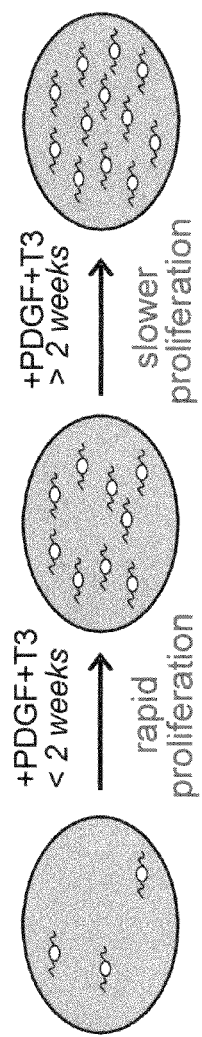
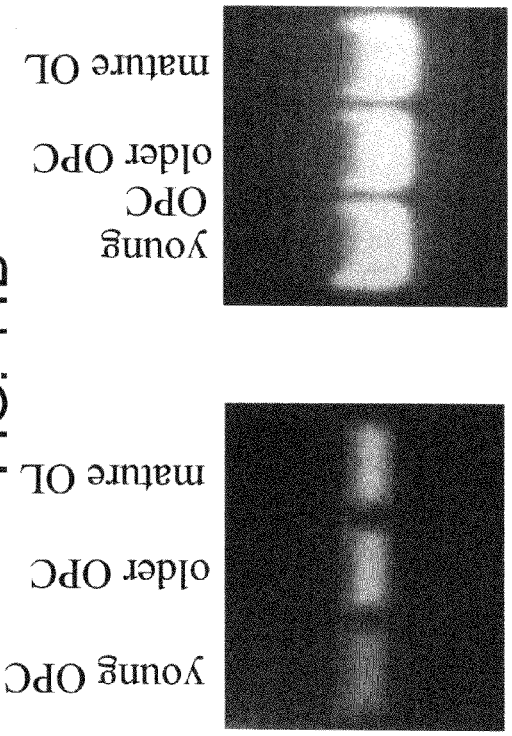
FIG. 44A
FIG. 44B

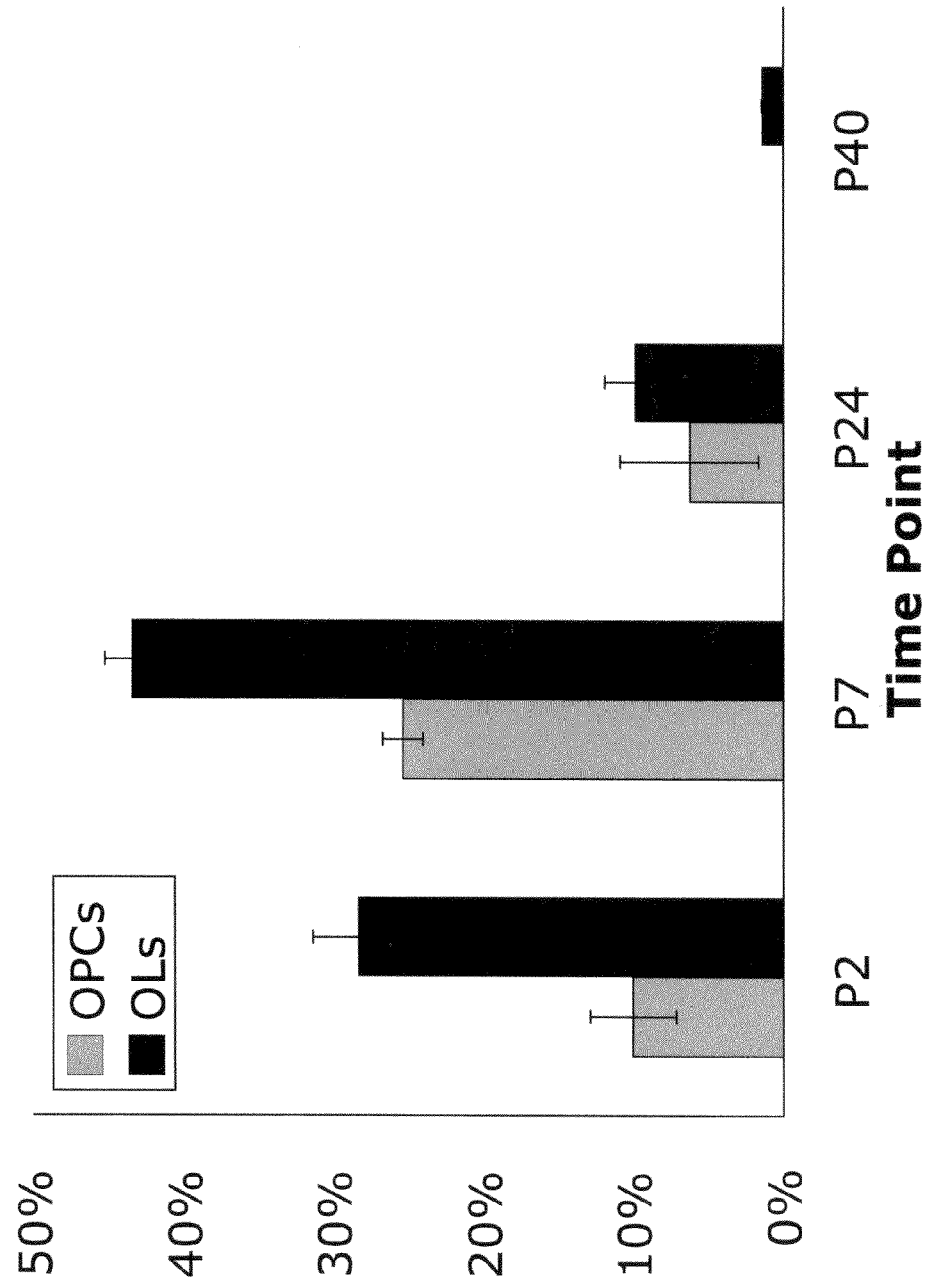

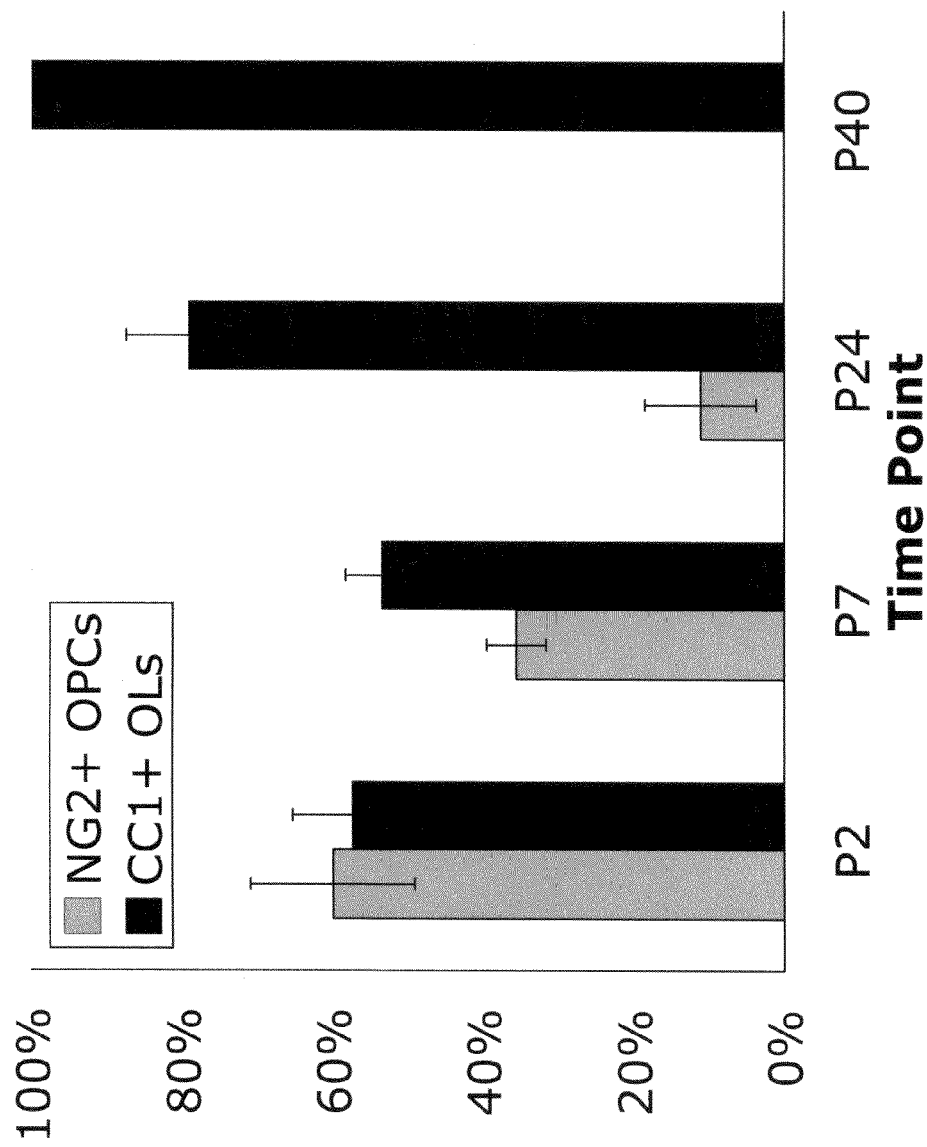

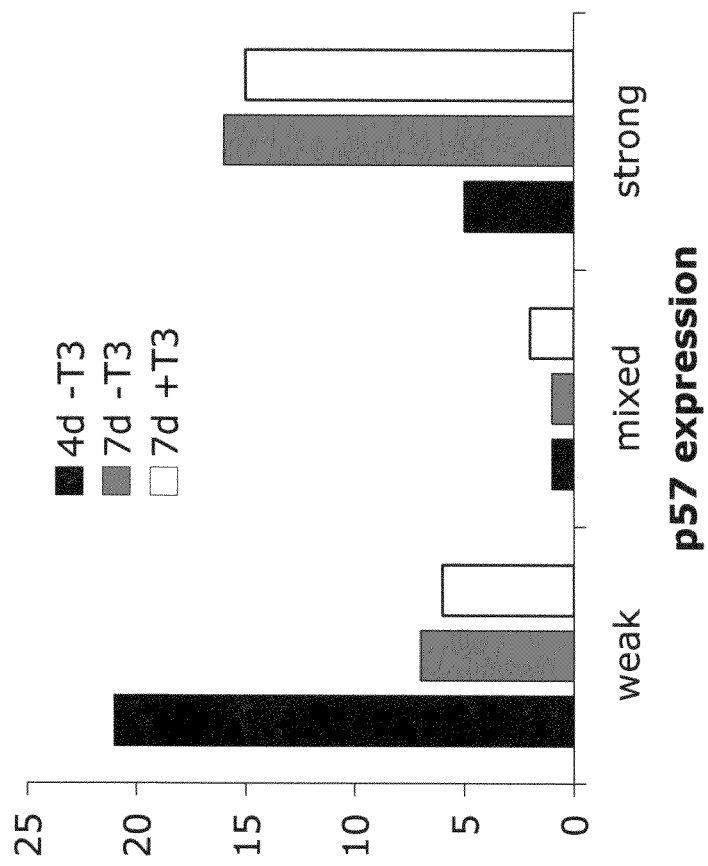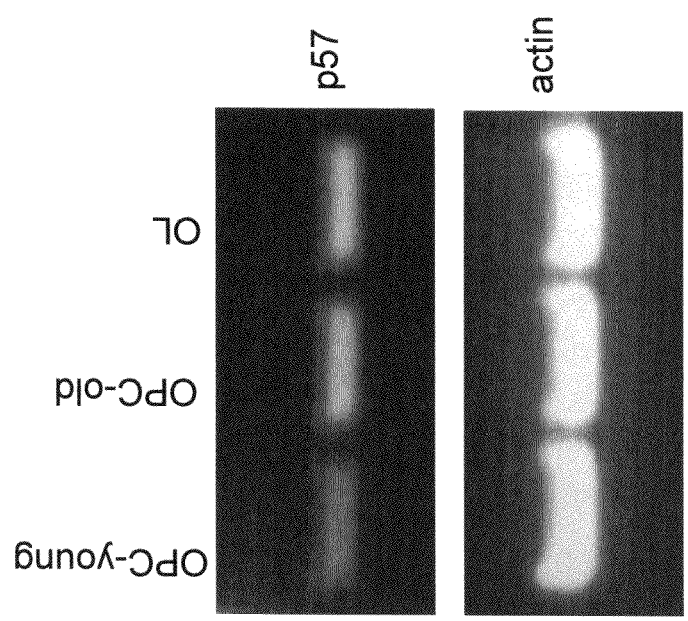
FIG. 49A
FIG. 49B

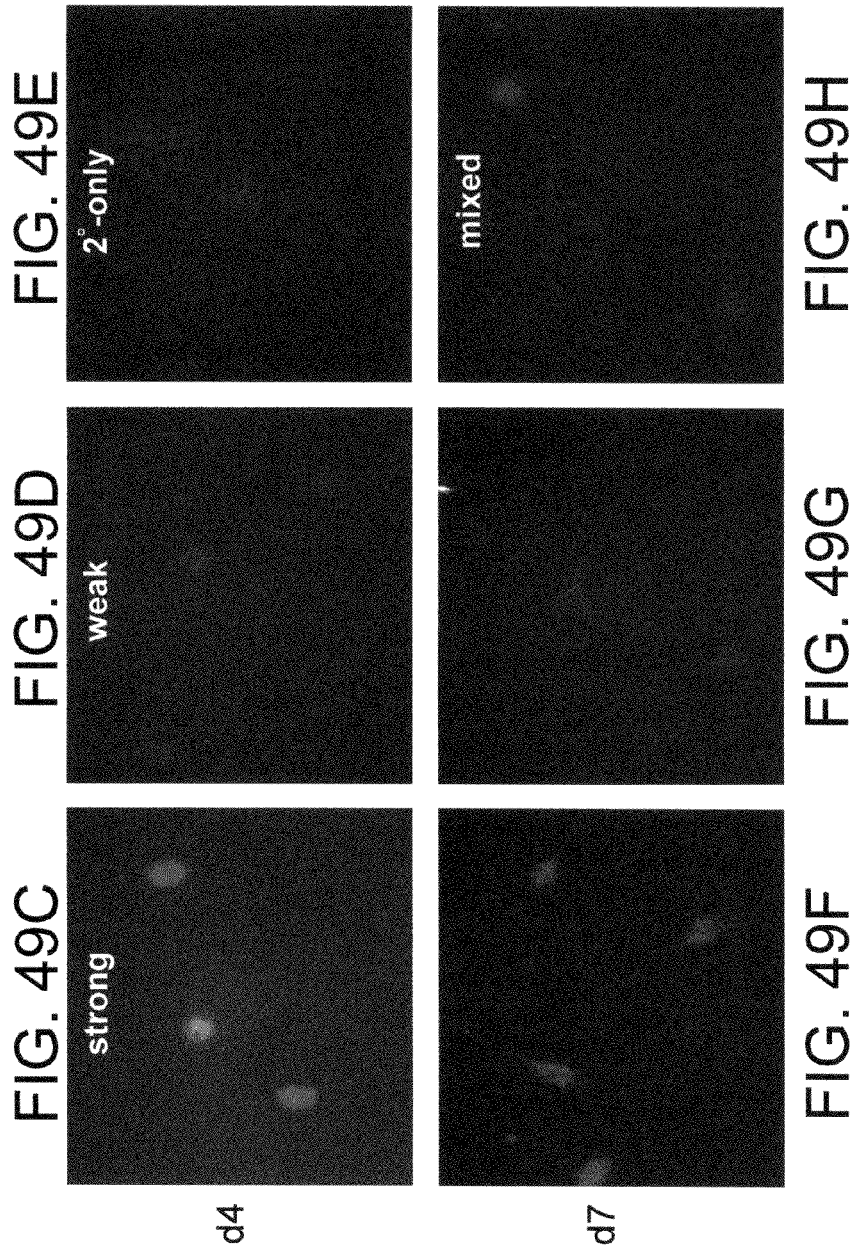

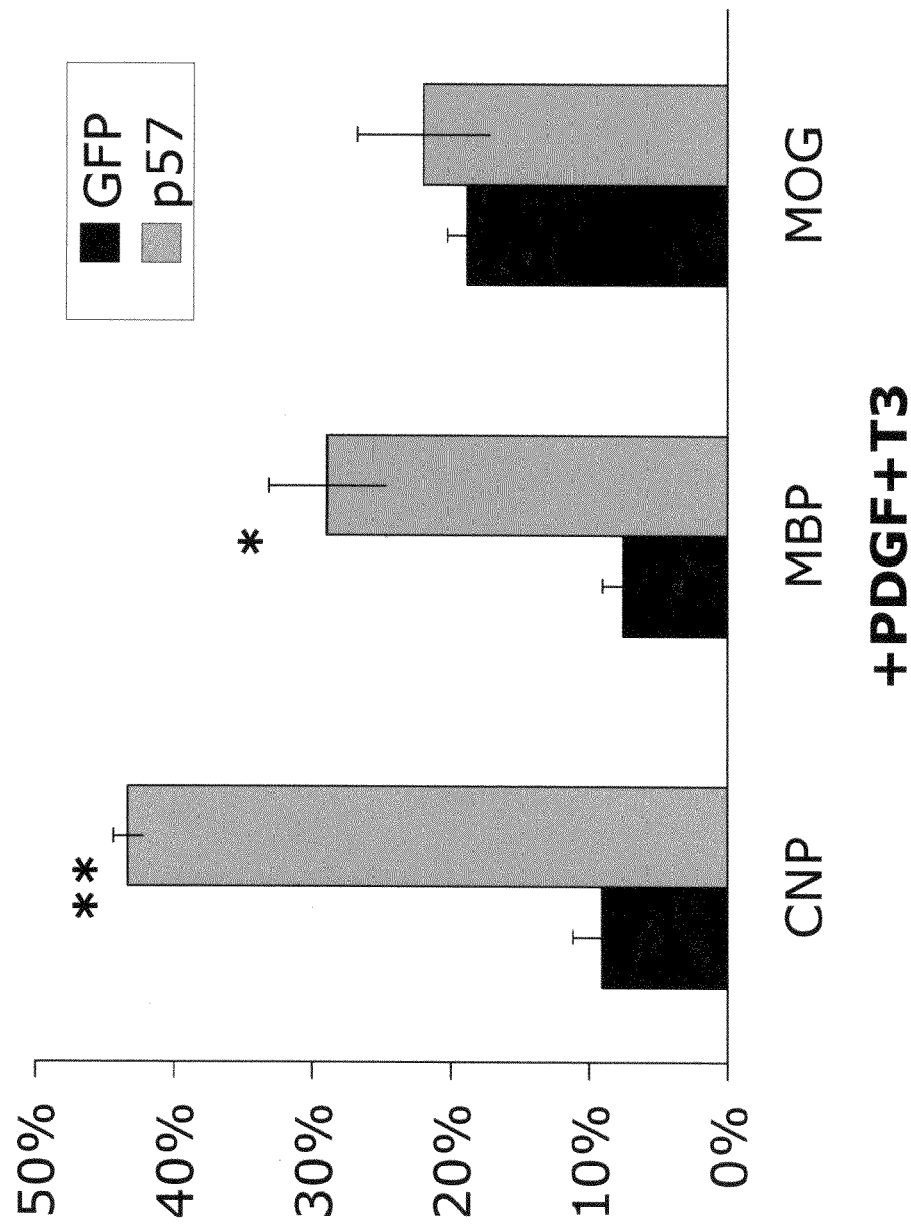

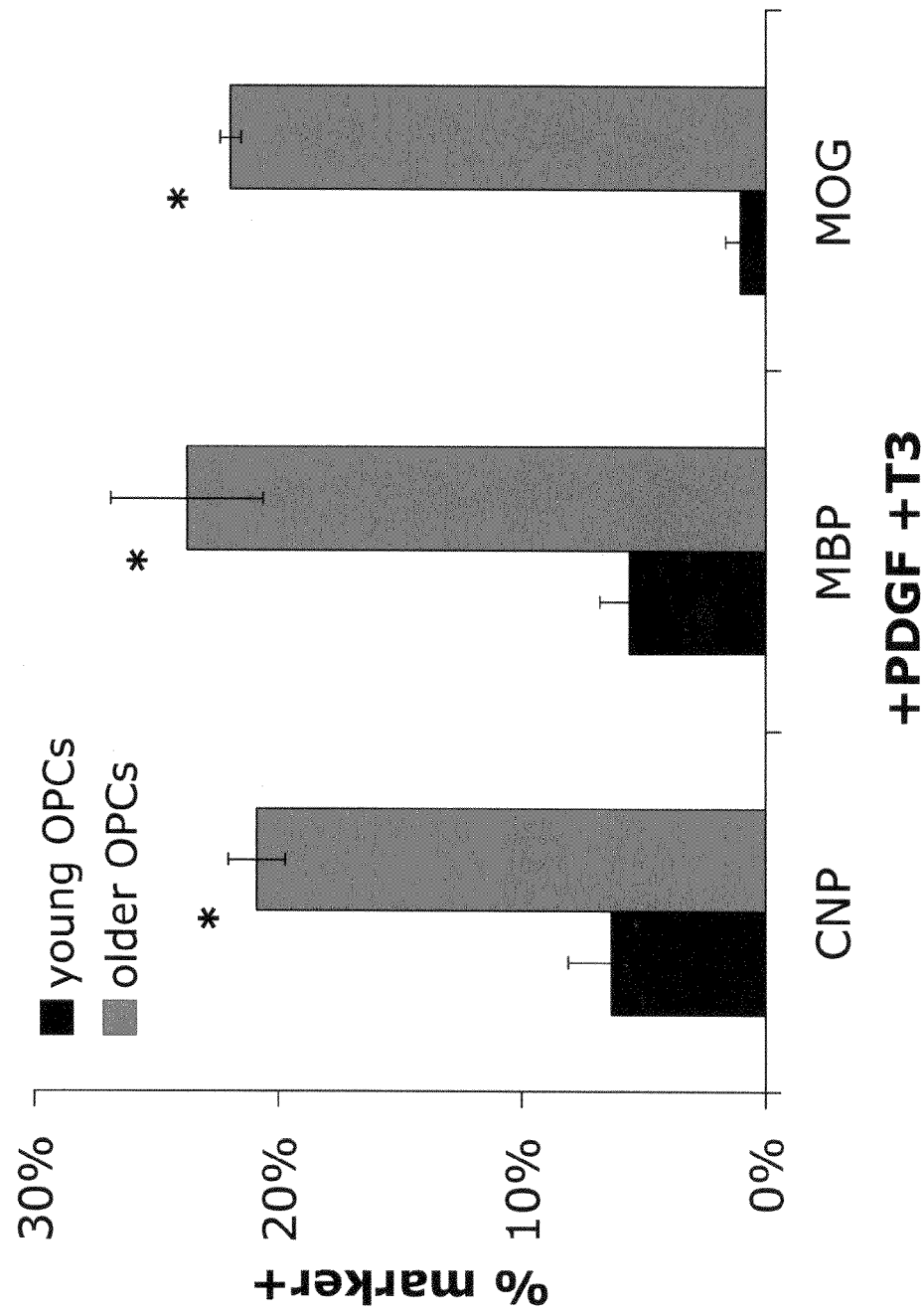

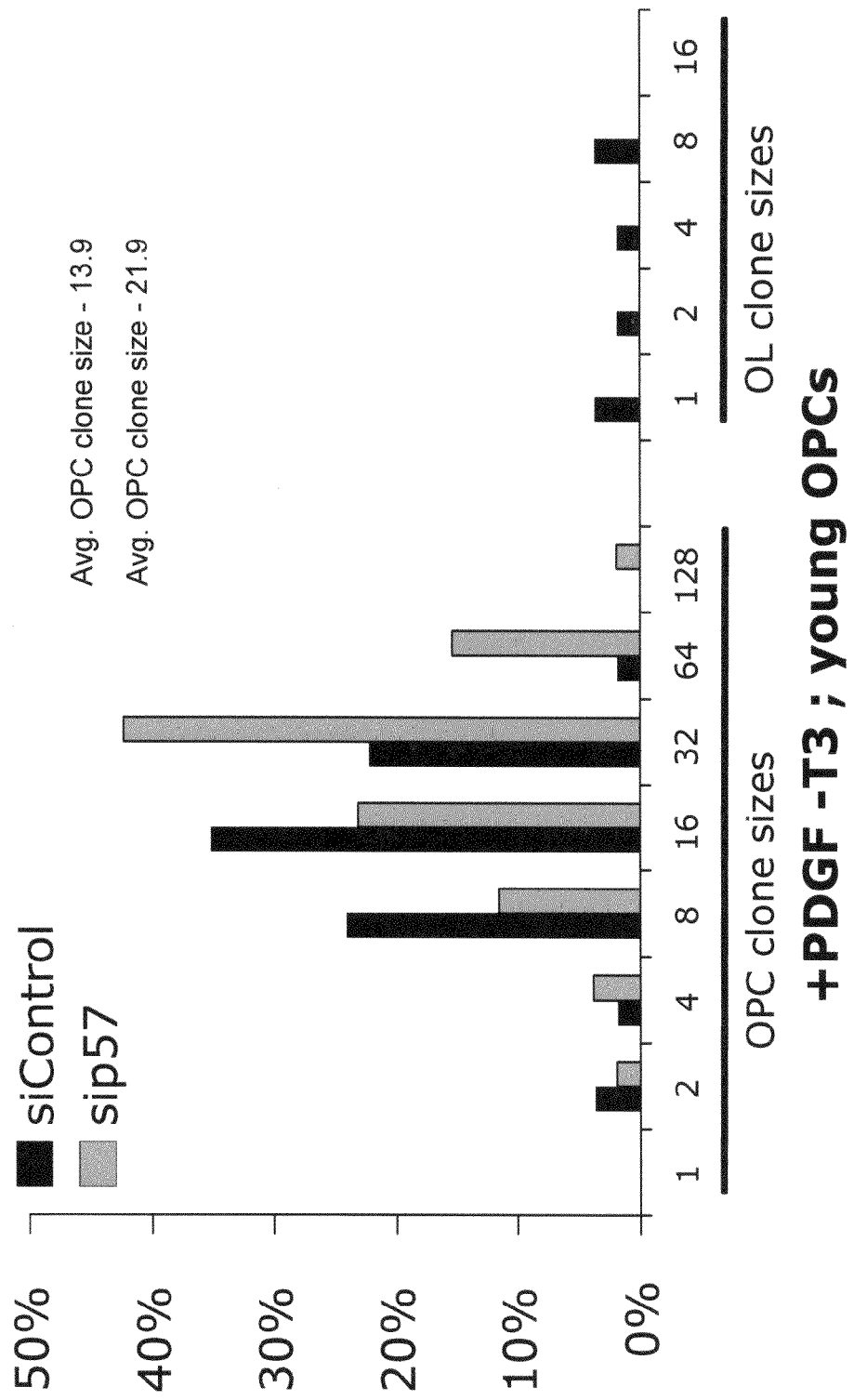

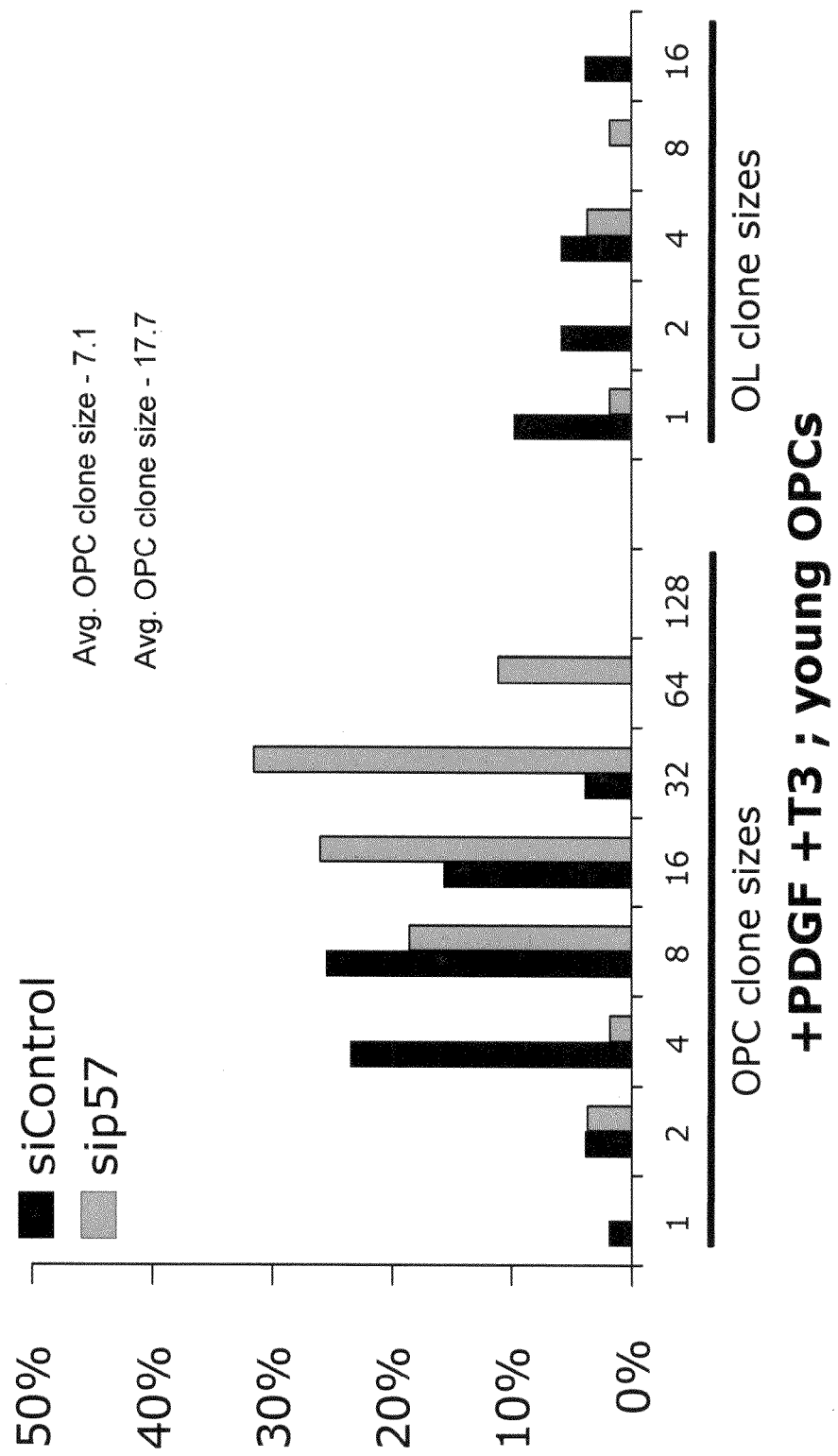

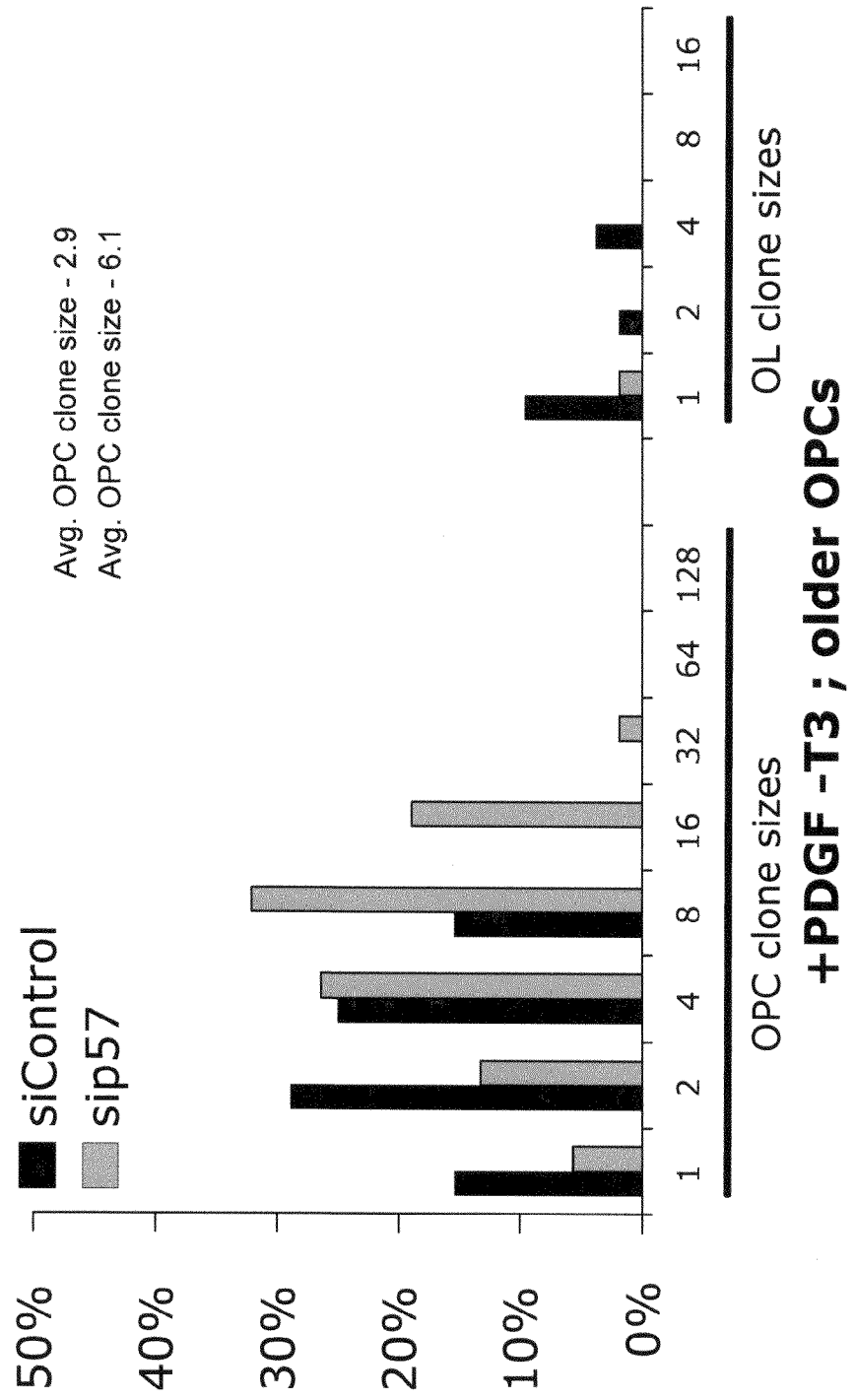

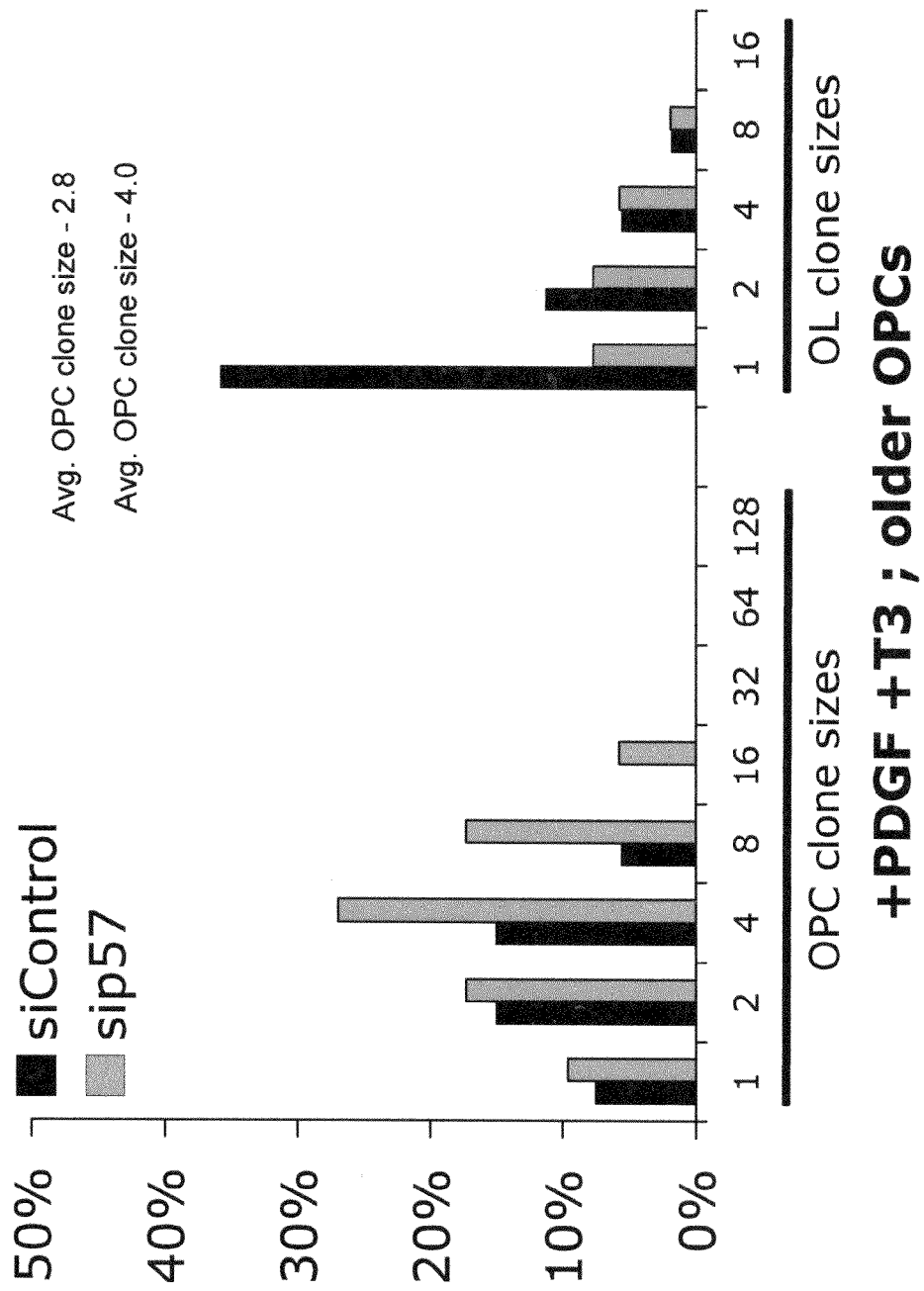

FIG. 52A
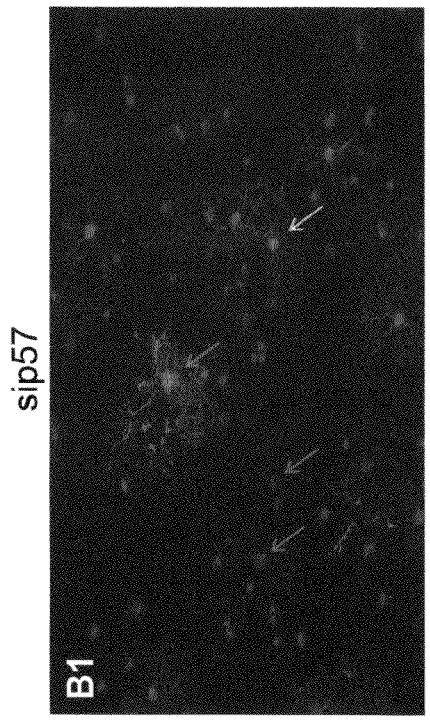
FIG. 52B
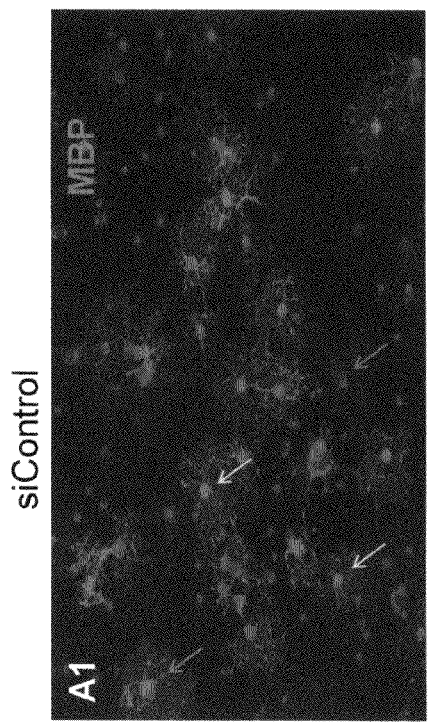
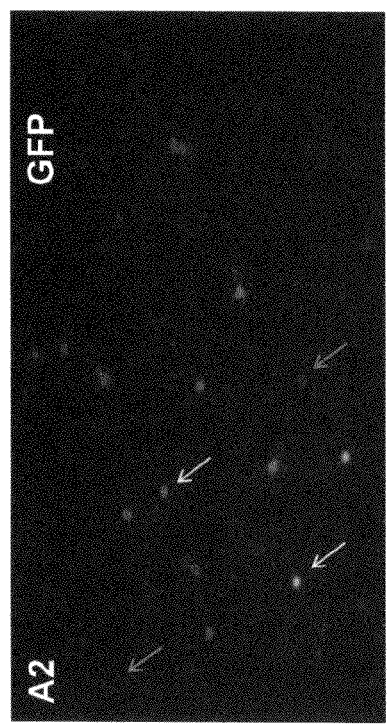

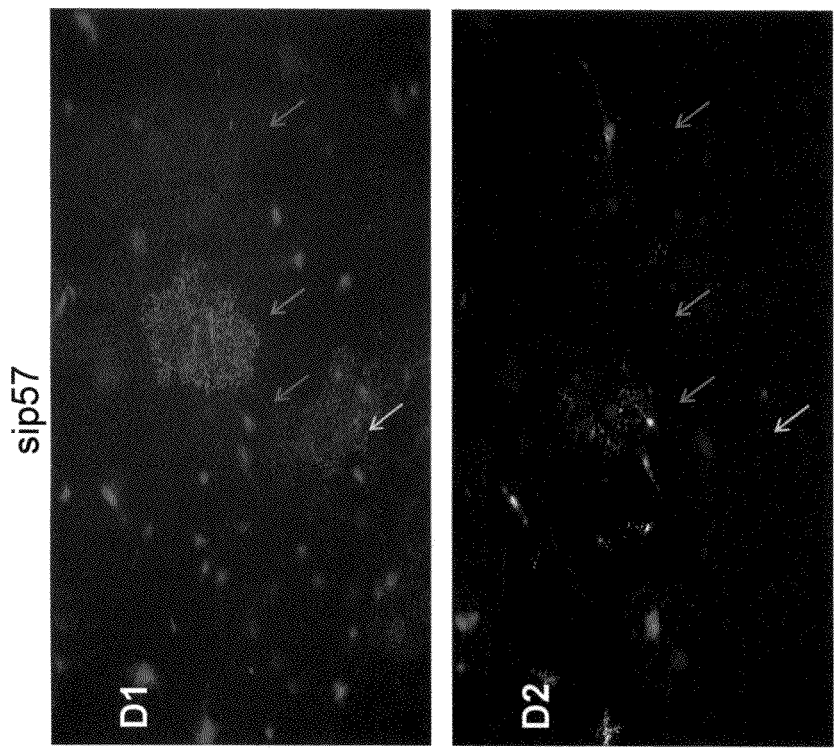
FIG. 52C
FIG. 52D
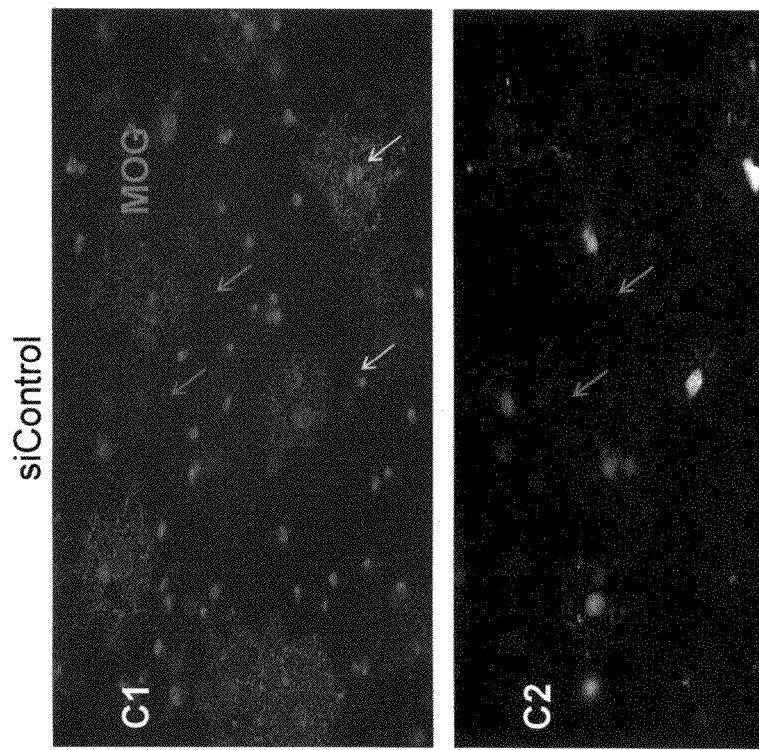

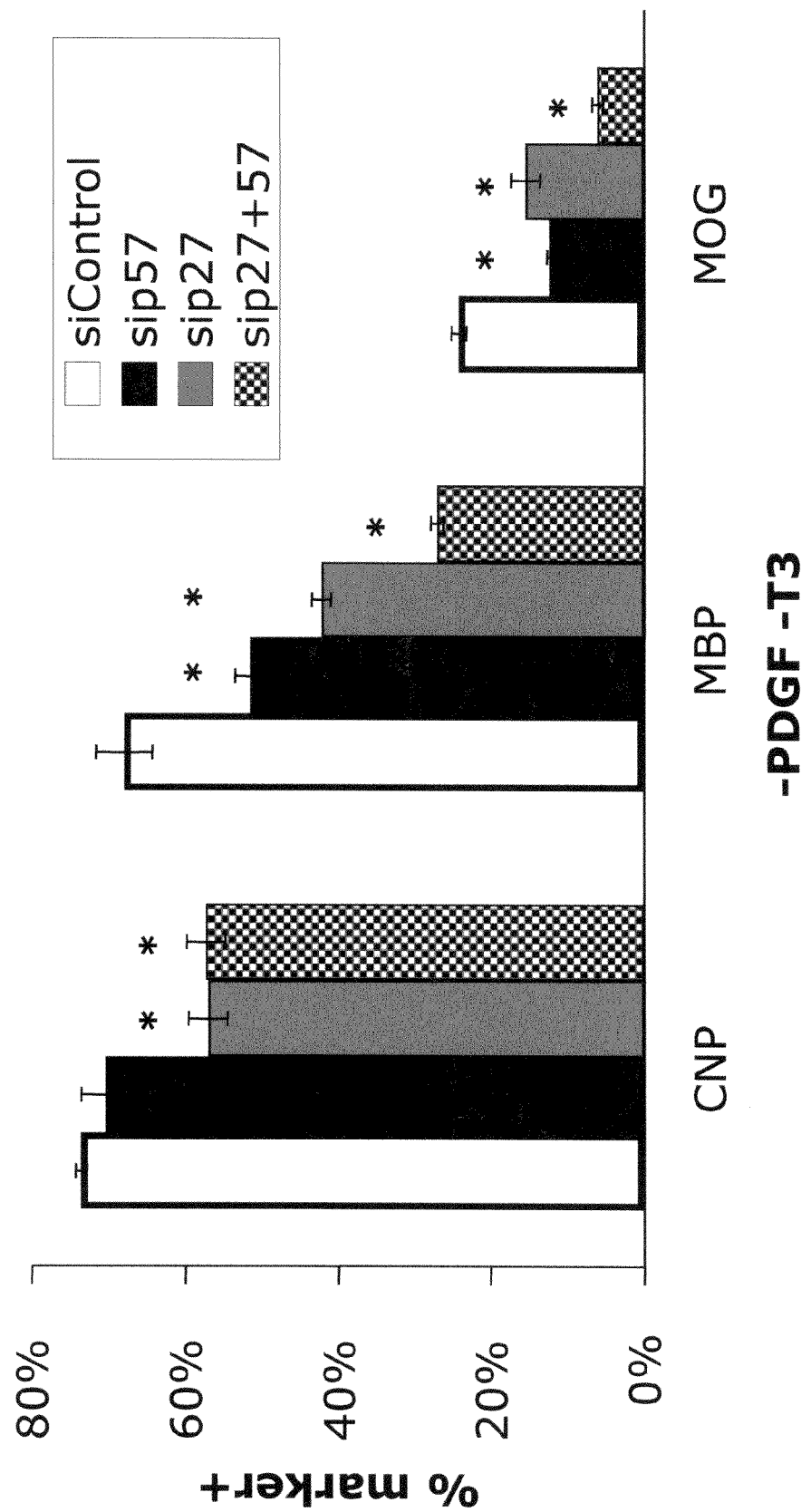

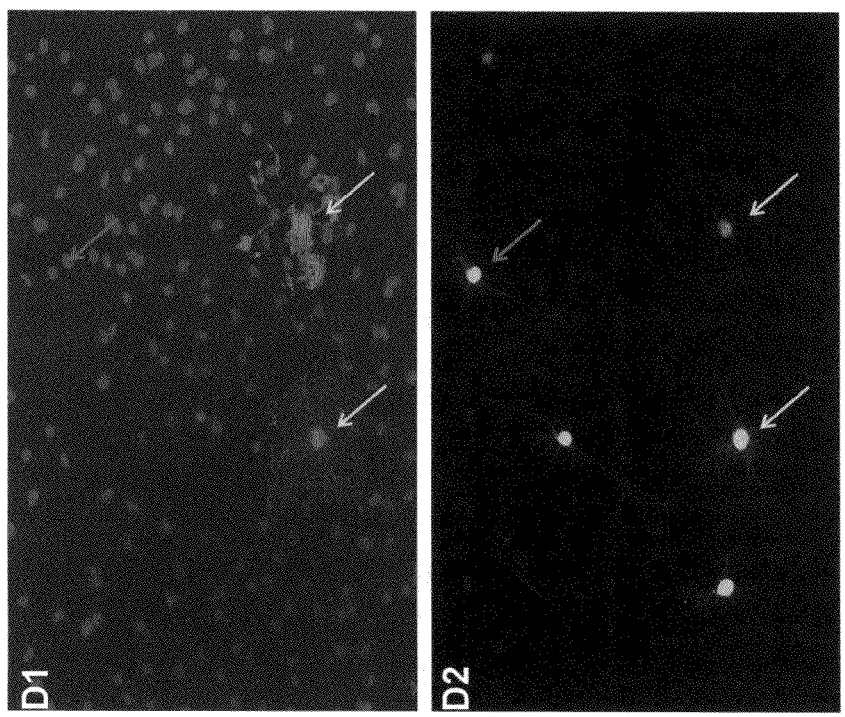
FIG. 53D p57+ZFP536
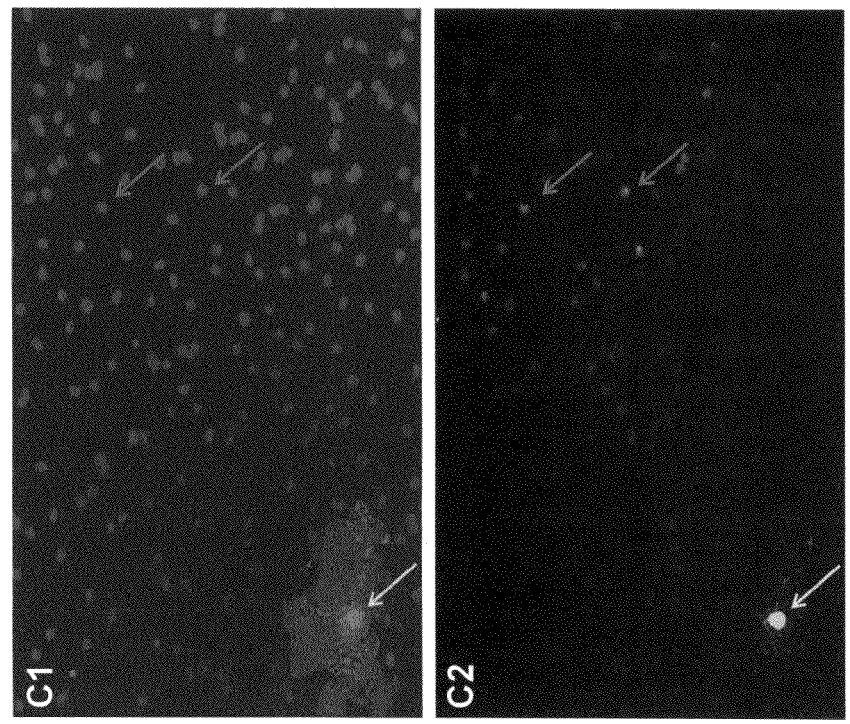
FIG. 53C ZFP536

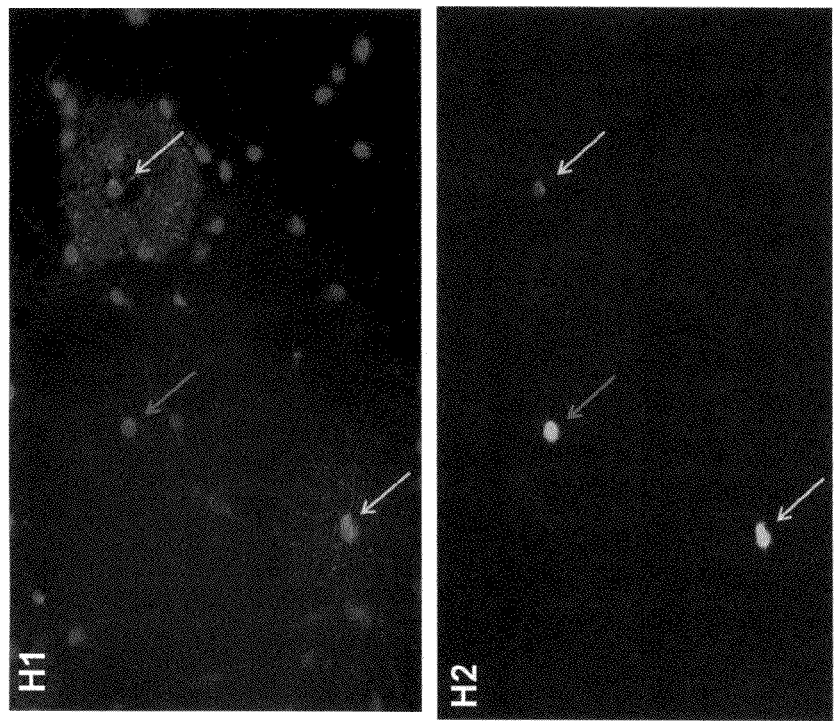
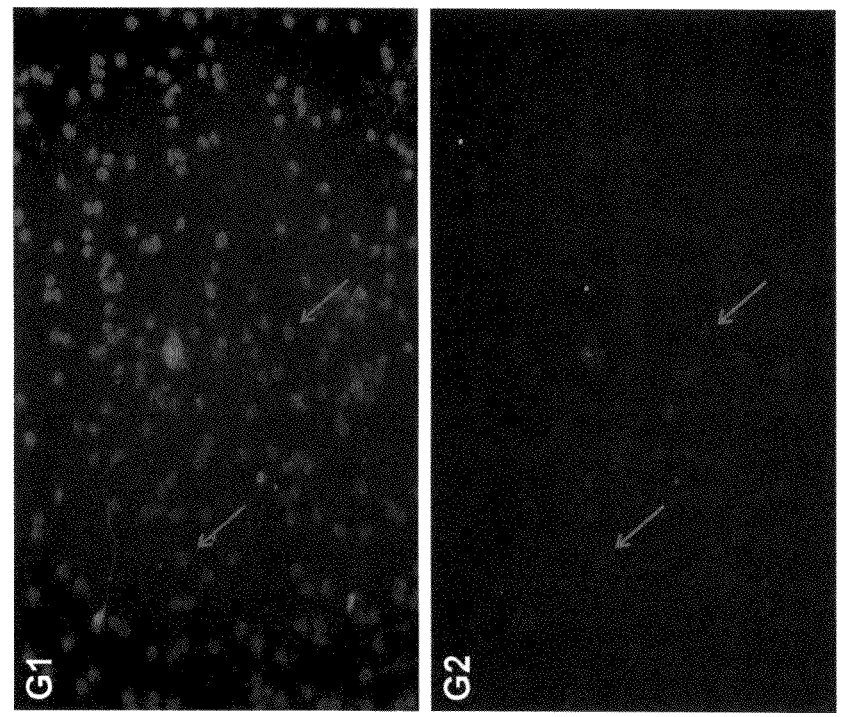
FIG. 53H p57+ZFP536
FIG. 53G ZFP536

FIG. 57

| Probe Set ID | d1-3hr/cont | d1-T3/cont | d6-3hr/cont | d6-T3/cont | Gene Symbol |
|---|---|---|---|---|---|
| 1456341_a_at | 3.60 | 4.04 | 5.60 | 6.26 | Klf9 |
| 1428288_at | 4.05 | 4.22 | 5.12 | 5.26 | Klf9 |
| 1428289_a_t | 2.77 | 3.31 | 4.89 | 5.03 | Klf9 |
| 1435950_at | 3.18 | 4.56 | 1.45 | 2.21 | Hr |
| 1438211_s_at | 1.72 | 2.13 | 2.75 | 3.92 | Dbp |
| 1418271_at | 0.60 | 0.55 | 2.55 | 7.71 | Bhlhb5 |
| 1418174_at | 1.92 | 1.95 | 2.10 | 2.18 | Dbp |

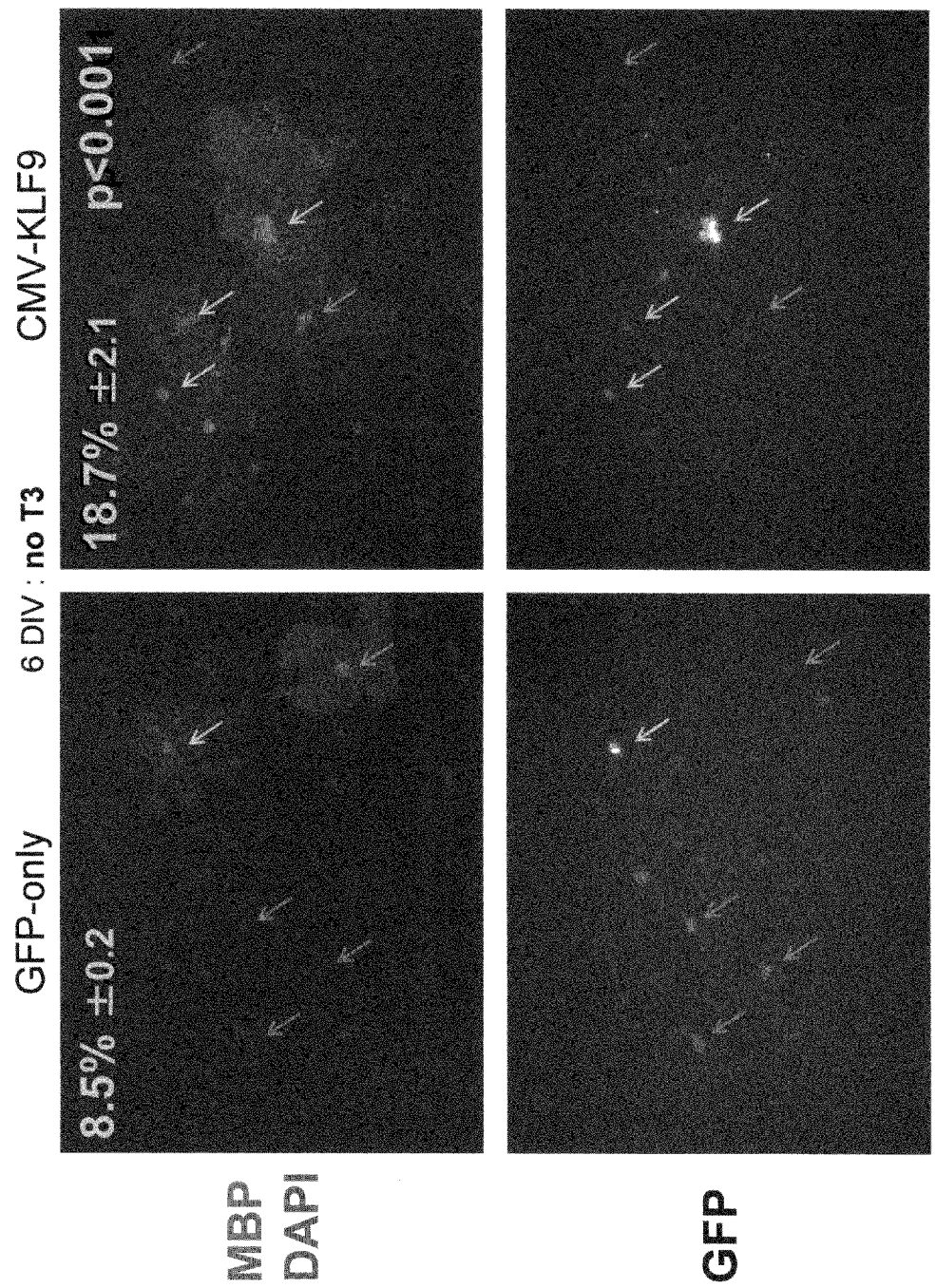

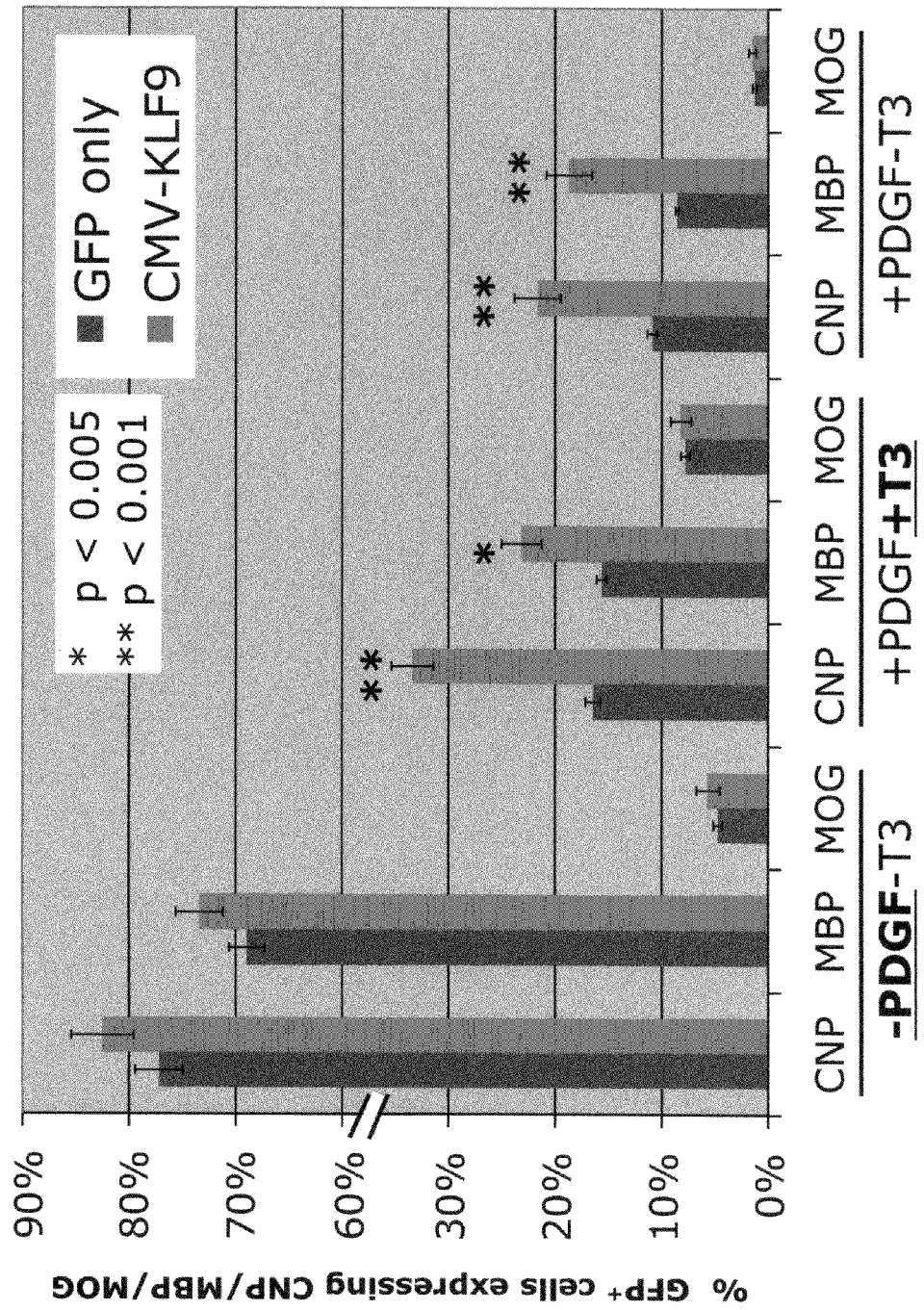

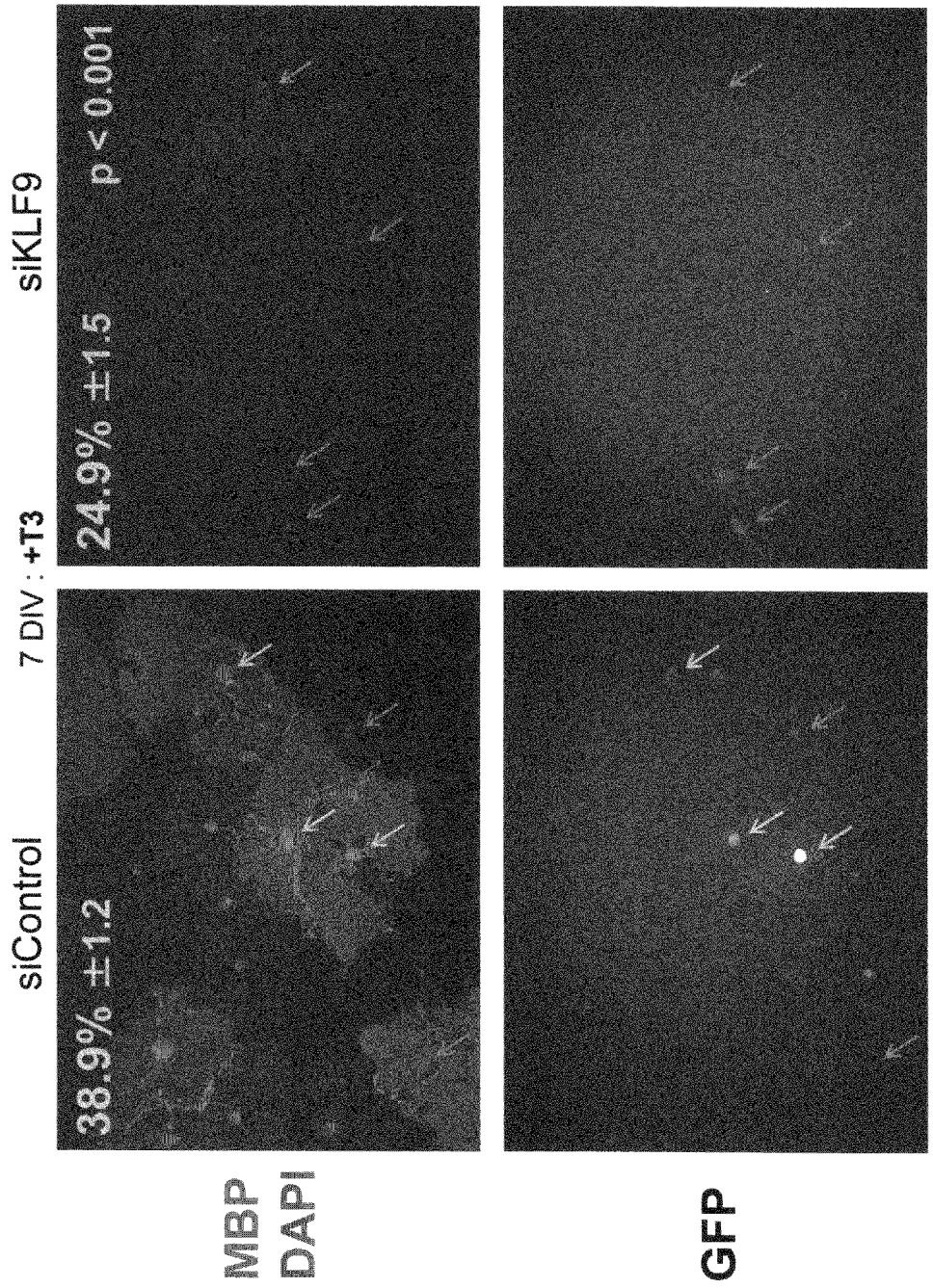

CELL CYCLE REGULATION AND DIFFERENTIATION

CROSS REFERENCE

This application is a divisional of U.S. patent application Ser. No. 12/321,952, filed on Jan. 26, 2009, which is a continuation-in-part of International Patent Application PCT/US/07/16858 with an international filing date of Jul. 26, 2007, which in turn claims priority to U.S. Provisional Application No. 60/833,744 filed on Jul. 26, 2006 and U.S. Provisional Application No. 60/933,633 filed Jun. 6, 2007, all of which are incorporated herein by reference in their entirety.

STATEMENT OF FEDERALLY SPONSORED RESEARCH

This invention was made with Government support under contract EY010257 awarded by the National Eye Institute, NIH. The Government has certain rights in this invention.

BACKGROUND OF THE INVENTION

Multiple sclerosis (MS) is an inflammatory demyelinating disease of the central nervous system (CNS) with clinical deficits ranging from relapsing-remitting to chronic-progressive patterns of expression. Although the etiology of MS is unknown, autoreactive CD4+ T cell responses mediate inflammatory damage against myelin and oligodendrocytes. (Bruck et al., *J. Neurol. Sci.* 206, 181-185 (2003)). CNS lesions have focal areas of myelin damage and are also associated with axonal pathology, neural distress, and astroglial scar formation (Compston et al., *Lancet* 359, 1221-1231 (2002)). Clinical presentation includes various neurological dysfunctions including blindness, paralysis, loss of sensation, as well as coordination and cognitive deficits.

Damage or injury to myelin has severe consequences on conduction velocity and the vulnerability of neurons to axonal destruction. There is a correlation between axon loss and progressive clinical disability and intact myelin is important in the maintenance of axonal integrity (Dubois-Dalcq et al., *Neuron* 48, 9-12 (2005)). Spontaneous remyelination occurs during the early phases of human MS, however, persistent CNS inflammation and the failure of myelin repair during later stages of the disease ultimately lead to permanent debilitation.

It is well accepted that adult oligodendrocyte progenitor cells are responsible for remyelination, and thus, the failure of remyelination is most likely associated with deficiencies in the generation of mature oligodendrocytes, their ability to myelinate, and/or neurodegeneration and axons that are not receptive to myelination.

Myelination relies on the coordination of multiple signals including those that precisely localize oligodendrocytes and their precursors (Tsai et al., *Cell* 110:373-383 (2002); Tsai et al., *J. Neurosci.* 26: 1913-22. (2006)), regulate appropriate cell numbers (Barres et al., *Cell* 70:31-46 (1992); Calver et al., *Neuron* 20:869-882 (1998)), and mediate interactions between oligodendrocytes and their target axons (Sherman and Brophy, *Nat Rev Neurosci.* 6:683-690 (2005)). Cell cycle exit is required for terminal differentiation of many cell types. By targeting components of cell cycle for neural cells involved in myelination, new strategies can be developed that enhance remyelination in myelin related disorders.

For example, by understanding what regulates the generation of oligodendrocytes (OLs), the myelin forming cells of the CNS can be regulated to promote differentiation or proliferation of progenitor cells. In other words, a "clock" that times precursor cells can be regulated to timing of OL differentiation and/or proliferation. While extrinsic cues that trigger such a clock with respect to oligodendrocyte progenitor cells (OPCs) may have been characterized, the components of the intracellular timer that intrinsically regulate when an OPC will differentiate remain largely uncharacterized.

There remains a need to develop effective methods for enhancing myelination. The present invention provides compositions and methods directed to promoting or regulating neural cell proliferation and differentiation thus promoting myelin repair. The findings disclosed herein will show a novel aspect of the mechanism by which OPCs keep time, which can be extended to similar clocks in many other precursor cell types.

SUMMARY OF THE INVENTION

One aspect of the invention is that CDK inhibitors (e.g., $p57^{Kip2}$) play a central role in the time clock mechanism that regulates progenitor cell proliferation and differentiation. Additional discoveries demonstrate that particular genes are modulated (upregulated/downregulated) differentially based on the age/maturity of cells, thus affecting differentiation. Therefore, various aspects of the invention are directed to modulation of $p57^{Kip2}$ activity or expression, which is demonstrated herein to be an important component for regulating the OPC "clock". Additional aspects of the invention are directed to modulating cell proliferation and differentiation to effect remyelination in an animal. Such modulation can be conducted by utilizing bioactive agents that modulate the activity or expression of the genes identified herein, implicated in neural cell proliferation and differentiation. With respect to methods and compositions disclosed herein, cells are neural cells, preferably glial cells and more preferably OLs and OPCs.

Accordingly, the present invention provides a method of regulating proliferation or differentiation of a neural cell. In one embodiment, the method comprises contacting a neural cell with a bioactive agent resulting in enhancement of neural cell proliferation. Such proliferation can be concurrent or subsequent to migration of such cells in the central nervous system (or peripheral nervous system). In other embodiments, the method comprises contacting a neural cell with a bioactive agent resulting in enhancement of neural cell differentiation.

In the present invention, the method typically comprises the step of contacting said neural cell with a bioactive agent effective in modulating the activity or expression level of transcription factor ZFP536, thereby regulating proliferation or differentiation of said neural cell. In some embodiments, the method comprises the step of contacting said neural cell with a bioactive agent effective in modulating the activity or expression level of transcription factor KLF9, thereby regulating proliferation or differentiation of said neural cell. The present invention further provides a method of promoting myelination comprising contacting a neural cell with a bioactive agent effective in promoting the activity or expression level of KLF9, thereby regulating said myelination of said neural cell.

In some embodiments, the present invention provides a method of regulating proliferation or differentiation of a neural cell comprising contacting the neural cell with a bioactive agent effective in modulating the activity or expression level of $p57^{Kip2}$ in the neural cell, thereby regulating said proliferation or differentiation of the neural cell.

In another related yet separate embodiment the present invention provides, a method of regulating proliferation or differentiation of a neural cell. The method involves the step of contacting said neural cell with a bioactive agent effective in modulating the activity or expression level of one or more oligodendrocyte-regulated transcription factors or myelin-enriched genes implicated in a discrete phase of differentiation of said neural cell. In a preferred embodiment, such OL-regulated gene encodes a transcription factor, a myelin protein, that is as highly upregulated as myelin genes during OL differentiation, such as, but not limited to KLF9. Non-limiting exemplary genes are listed in FIGS. 7, 10, or 21. In a preferred embodiment, the exemplary genes are those highlighted in FIG. 30. In other embodiments, an exemplary gene is linked to MS-implicated loci as identified in FIG. 10.

In yet another aspect of the invention, a method is utilized to screen a candidate agent to determine whether such an agent induces or reduces neural cell-specific gene expression. In some embodiments, a candidate agent is screened to determine whether it modulates expression of OL-specific genes and MS loci related genes. In another embodiment, a candidate agent is screened to determine whether it modulates most highly-induced OL genes and OL-specific genes disclosed herein. Such candidate compounds if found to modulate such genes upward or downward can be used to modulate OL differentiation or OPC proliferation.

In preferred embodiments, a method of screening for a candidate bioactive agent effective in regulating proliferation or differentiation of a test neural cell comprises (a) contacting the test neural cell with said candidate bioactive agent; and (b) assaying for a change in $p57^{Kip2}$ activity or $p57^{Kip2}$ expression level in the test neural cell as compared to a control neural cell, wherein the change in $p57^{Kip2}$ activity or $p57^{Kip2}$ expression level is indicative of a bioactive agent effective in regulating proliferation or differentiation of the test neural cell.

In yet another related but separate aspect, the present invention provides a method for screening a candidate bioactive agent effective in regulating proliferation or differentiation of a test neural cell comprising (a) contacting the test neural cell with the candidate bioactive agent; and (b) assaying for a change in the activity or expression level of one or more OL-regulated transcription factors or myelin-enriched genes in the test neural cell as compared to a control neural cell; wherein the change in the activity or expression level of one or more OL-regulated transcription factors or myelin-enriched genes is indicative of a bioactive agent effective in regulating proliferation or differentiation of the test neural cell.

The step of assaying further comprises analyzing data indicative of a change in the activity or expression level. Optionally, the data obtained from the assaying may be transmitted over a network. Furthermore, data relating to the bioactive agent in the methods described herein may be transmitted over a network.

In another aspect of the present invention, a method of assessing the ability of a test immature OL or a test OPC to differentiate comprising: (a) assaying an expression level of one or more OL-regulated transcription factors or myelin-enriched genes present in the test immature OL or the test OPC, wherein said one or more oligodendrocyte-regulated transcription factors or myelin-enriched genes are implicated in a discrete phase of OL differentiation, the phase being selected from an early phase of differentiation and a late phase of differentiation; and (b) comparing the expression level of (a) to that of a control immature OL or a control OPC, wherein a statistically significant increase in expression of said one or more OL-regulated transcription factors or myelin-enriched genes of said early and/or late phase implicates the ability of said test immature OL or said test OPC to differentiate. In some aspects, the assaying step is performed in vitro. In another aspect of the method, the assaying step is performed in vivo.

Bioactive agents contacting a cell in any one or more methods disclosed herein include without limitation peptides, proteins, peptidomimetics, antibodies, aptamers, siRNA, antisense or small organic molecules. In various embodiments, bioactive agents can bind a target molecule to neutralize it, block a target molecule's function or activity, or function as an antagonist to such a target molecule. In another aspect of the invention, nucleic acid expression constructs or vectors contacting a cell provide expression of a bioactive agent that modulates neural cell proliferation or differentiation.

In practicing any of the subject methods disclosed herein, neural cells include SCs, NSCs, astrocytes, and microglial cells. In preferred embodiments, suitable neural cells comprise glial cells. Where desired, the glial cells utilized in the subject methods have undergone no more than ten, nine, eight, seven, six, five, four, three or two divisions. In some instances, the glial cells utilized in subject methods are immature oligodendrocytes (OLs). In other embodiments, the glial cells are oligodendrocyte precursor cells (OPCs). In some embodiments, such cells can be transplanted into a subject to effect neural cell proliferation or differentiation, where desired. In yet other embodiments, such cells can be transfected with one or more genes implicated in regulation of neural cell proliferation and differentiation. In yet further embodiments, such cells can be transfected with one or more expression cassettes or vectors.

Also provided within the methods disclosed herein, the discrete phase of differentiation is an early phase of oligodendrocyte (OL) differentiation characterized by differential expression of one or more genes depicted in FIG. 12, 16, or 19, or a late phase of OL differentiation characterized by differential expression of one or more genes depicted in FIG. 13, 17, or 20.

The practice of any of the subject methods reduces proliferation or promotes differentiation of the neural cell, if so desired. Where desired, the practice of any of the subject methods promotes proliferation or reduces differentiation of the neural cell.

Further provided in the present invention is a microarray comprising, immobilized thereon, a plurality of probes corresponding to oligodendrocyte-regulated genes implicated in regulating oligodendrocyte proliferation or differentiation. In one aspect, the plurality of probes correspond to myelin-enriched genes and/or transcription factors including, but not limited to those implicated in a discrete phase of oligodendrocyte differentiation. Such probes may correspond to transcription factors or myelin-enriched genes implicated in the early or late phase differentiation of OLs. In some aspects, bioactive agents of the invention are administered to a subject to induce neural cell proliferation or differentiation. By promoting such proliferation or differentiation the overall amount of myelinating neural cells may be increased in the CNS thus promoting myelin repair.

BRIEF DESCRIPTION OF THE DRAWINGS

FIG. 4. Illustrates 4 aspects contributing to OL differentiation.

FIG. 7. Presents two lists: A. the top 50 OL upregulated genes, most strongly induced in mature OLs relative to their expression levels in OPCs, and B. the top 50 OL-specific expressed genes, representing the 50 genes that are expressed at the highest levels specifically in mature OLs. Sixteen genes occur on both lists, 52 genes on both lists were not previously known to be expressed in OLs, and 13 genes not previously known to be expressed in OLs and that show white matter enriched expression patterns.

FIG. 8. Depicts the in situ expression pattern in white matter of a well known myelin gene, PLP, and novel OL-expressed genes.

FIG. 9. Depicts a Venn diagram of identified genes that are OL-regulated and mapped to highly-linked MS loci.

FIG. 10. Presents the list of the 22 genes that are OL-regulated and are highly linked to MS loci, SEPP1 being one of the most strongly induced.

FIG. 11. Depicts graph of myelin-enriched genes up-regulated in OLs.

FIG. 12. Depicts myelin-enriched genes that are induced immediately upon initiation of differentiation.

FIG. 20. Depicts a graph of transcription factors that are downregulated with a delay upon initiation of differentiation.

FIG. 21. Presents a table listing OL-regulated transcription factors and type of neural cell. A. The first group of shaded genes are potentially specific to the OL lineage. B. The second group of shaded genes may be more specific to immature neural cells. The "X" represents relative levels of expression: blank=no expression, X=weaker expression than maximal OPC/OL level; XX=maximal OPC/OL level; XXX=higher expression than maximal OPC/OL level (i.e. if a gene is more strongly expressed in a cell type other than OPC/OL)

FIG. 22. Depicts a schematic representation for screening different transcription factors for their role in OL differentiation (See also, FIG. 42)

FIG. 29. Depicts a schematic representation for independently regulated myelin gene expression in two phases.

FIG. 30. Presents a table listing OL-regulated transcription factors highlighting the 10 transcription factors that demonstrate the ability to affect OL differentiation.

FIG. 31. Depicts a graph illustrating that $p57^{kip2}$ is robustly induced early in OL differentiation. Purified P7 rat OPCs were cultured for 24 hours in proliferation-promoting media (+PDGF −T3; OPC time point), then shifted into differentiation-promoting media (−PDGF +T3) and cultured for a number of days in vitro. Time points represent days on which RNA samples were collected; AcOL is RNA from acutely-isolated P12 OLs. Gene expression assayed on Affymetrix rat U34A-C gene chips; expression level changes relative to OPC expression plotted on a $\log^2$ scale.

FIG. 49. Shows p57$^{Kip2}$ expression increases synchronously over time in proliferating OPCs. A. RT-PCR (25 cycles) to detect p57$^{Kip2}$ or beta-actin expression in purified OPCs cultured for 7 DIV (OPC-young) or 28 DIV (OPC-old) in +PDGF −T3 medium, or for 4 DIV in −PDGF +T3 medium (OL). B. Quantification of clones uniformly expressing a low level of p57$^{Kip2}$ (weak), uniformly expressing a high level of p57$^{Kip2}$ (strong), or showing mixed levels of p57$^{Kip2}$ expression (mixed) as assayed by immunostaining after 4 DIV in +PDGF −T3 medium (black bars), 7 DIV in +PDGF −T3 medium (grey bars), or 7 DIV in +PDGF +T3 medium (white bars). Clones containing <2 healthy cells were not counted; >20 clones scored/condition. C-H. Generally uniform expression of p57$^{Kip2}$ in clones of OPCs. OPCs cultured for 7 DIV in +PDGF −T3 medium, then plated at clonal density and cultured for 4 DIV (C-E) or 7 DIV (F-H) in +PDGF −T3 medium were immunostained for p57$^{Kip2}$ expression (C-D, E-H), or only stained with secondary antibody (E); pictures of representative cells from within larger clones (8->50 cells/clone). C,F. Cells from clones p57$^{Kip2}$ uniformly expressing a high level of p57$^{Kip2}$. D,G. Cells from clones uniformly expressing a lower level of Cells from the one mixed intensity p57$^{Kip2}$ clone observed at 7 DIV in +PDGF −T3 (weaker expression lower left).

Figure 1:
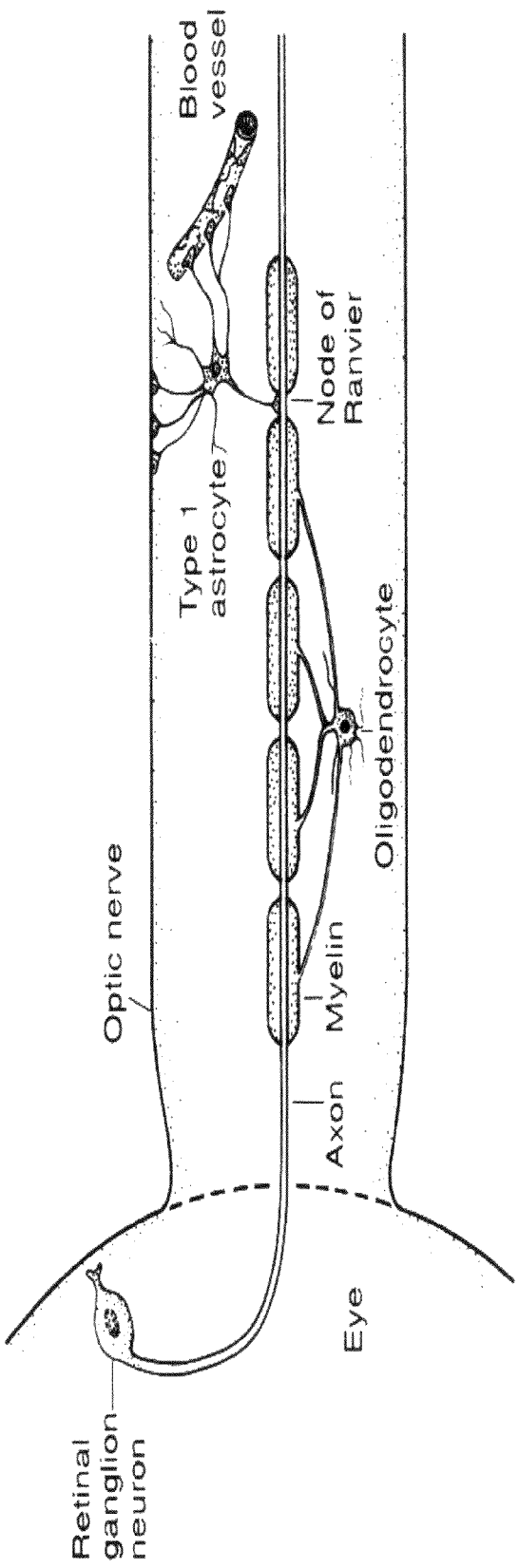
FIG. 1. Schematic drawing of a nerve, axon and oligodendrocyte.
Figure 2:
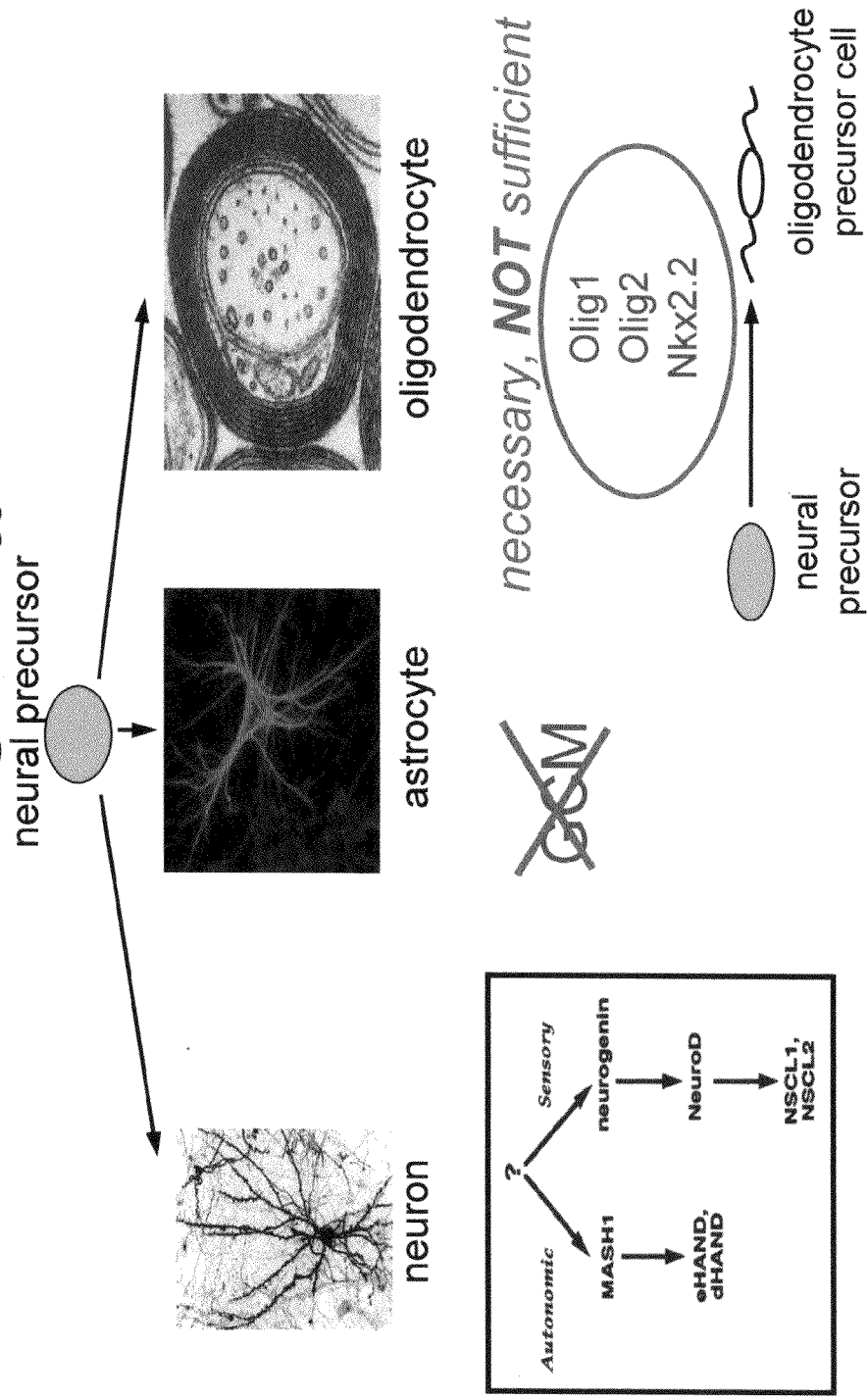
FIG. 2. Illustrates possible terminal differentiation from neural precursor cells.
Figure 3:
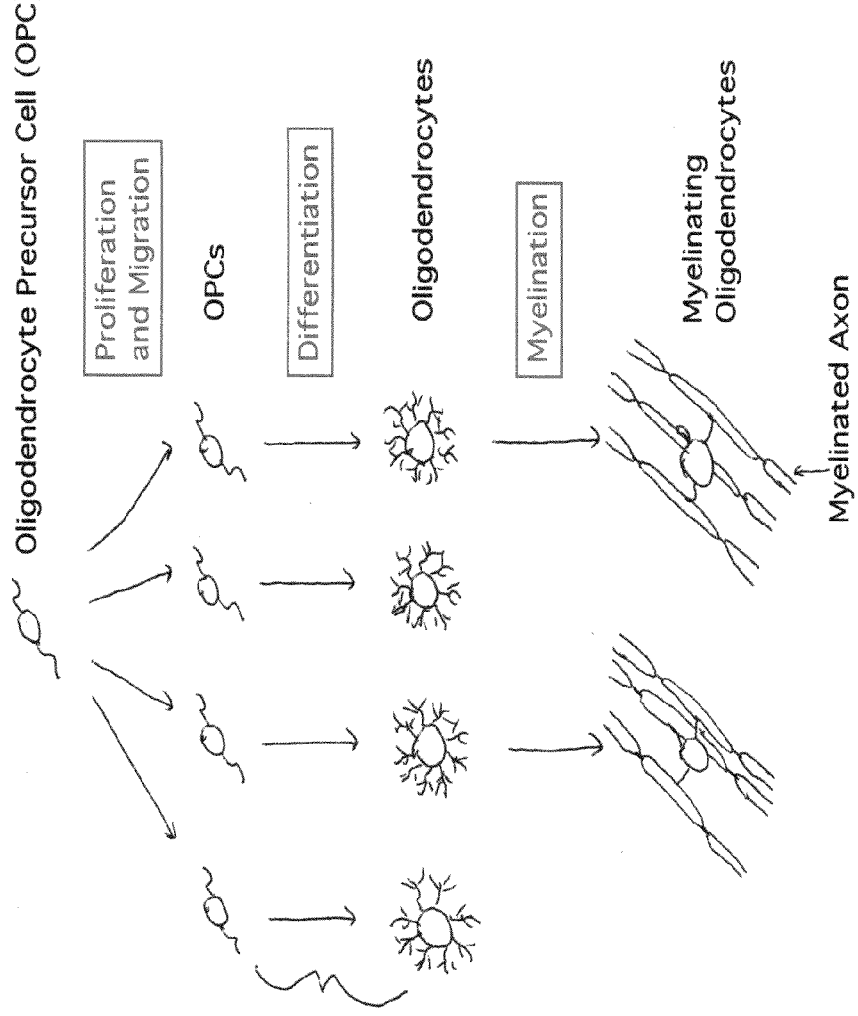
FIG. 3. Provides a schematic representation of the process of OPC cell proliferation, migration and differentiation into OLs.

Student's t-test. D-E. Purified OPCs initially cultured for 7 DIV (black bars) or 28 DIV (grey bars) in +PDGF −T3 medium were transfected with CMV-GFP and non-targeting siRNA and cultured for either: (D) an additional 7 DIV in +PDGF +T3 medium before immunostaining, p<0.006 Student's t-test, or (E) an additional 3 (CNP, MBP) or 4 (MOG) DIV in −PDGF −T3 medium before immunostaining, *=p<0.001 Student's t-test.

FIG. 51. Shows decreasing $p57^{Kip2}$ expression accelerates OPC proliferation and decreases OPC responsiveness to T3. A-D. OPCs initially cultured for 7 DIV (A-B) or 28 DIV (CD) in +PDGF −T3 medium were transfected with a CMV-GFP vector plus non-targeting siRNA (black bars) or siRNA targeting $p57^{Kip2}$ (grey bars), then plated at clonal density (A-B: 250 cells/well; C-D: 500 cells/well) and cultured for 4 DIV in PDGF/NT3 containing medium without (A, C) or with (B, D) added T3 (+PDGF ±T3). Only clones containing GFP+ cells were scored. Clones containing ≧50% OLs (by morphology) were scored as OL clones, <50% OLs as OPC clones, and both OPC and OL clone sizes were binned and plotted as histograms. In each condition >50 clones were scored. In A-D OPC clone sizes are significantly increased by $p57^{Kip2}$ knockdown (A: p<0.005, B: p<0.0001, C: p<0.0001, D: p<0.05 Student's t-test). E-F. Purified OPCs initially cultured for 7 DIV (E) or 28 DIV (F) in +PDGF −T3 medium were transfected as described in AD, then cultured for an additional 7 days in +PDGF +T3 medium. The proportions of transfected (GFP+) cells expressing CNP, MBP, or MOG were subsequently determined by immunostaining; ±S.E.M., n=3 each condition, *=p<0.05, **=p<0.01 Student's t-test.

FIG. 52. Shows reducing $p57^{Kip2}$ expression retards OPC response to mitogen withdrawal. A-D. Purified OPCs co-transfected with a CMV-GFP vector and either siRNA targeting $p57^{Kip2}$ (sip57; B, D) or control non-targeting siRNA (siControl; A, C) were plated in −PDGF −T3 medium for 3 DIV and stained for MBP (red) and GFP (white) expression (AB), or 4 DIV and stained for MOG (red) and GFP (white) expression (C-D); blue—DAPI nuclear stain. Yellow arrows indicate transfected cells (GFP+) expressing MBP (A-B) or MOG (C-D), green arrows indicate transfected cells not expressing MBP or MOG, and red arrows indicate untransfected cells (GFP−) expressing MBP or MOG. E. Proportion of siControl (white bars), sip57 (black bars), sip27 (grey bars) transfected, or sip57 +sip27 co-transfected (hatched bars) cells expressing CNP, MBP, or MOG after 3 (CNP, MBP) or 4 (MOG) DIV in −PDGF −T3 medium; ±S.E.M., n=3 each condition, *=p<0.01 Holm-Sidak post-hoc test vs. control. All sip57, sip27, and sip57+sip27 co-transfections not significantly different from each other except: CNP—sip57 vs. sip27 and sip27+sip57, MBP: sip27+sip57 vs. sip57 and sip27, MOG: sip27+sip57 vs. sip57 and sip27; all exceptions listed p<0.01 Holm-Sidak all pairwise post-hoc test.

FIG. 53. Shows increasing $p57^{Kip2}$ and ZFP536 expression promotes OL differentiation. Increasing $p57^{Kip2}$ expression initiates OL differentiation, and $p57^{Kip2}$+ZFP536 together cooperatively enhance late-stage OL differentiation in the absence of differentiation promoting stimuli. A-H. Purified OPCs transfected with a CMV-GFP vector (GFP only; A, E), or co-transfected with CMV-GFP+CMV-$p57^{Kip2}$ (p57; B, F), +CMV-ZFP536 (ZFP536; C, G), or both CMV-$p57^{Kip2}$+ CMV-ZFP536 (p57+ZFP536; D, H) were cultured for 7 DIV in +PDGF −T3 medium. Cells were then co-stained for MBP (red) and GFP (white) expression (A-D) or MOG (red) and GFP (white) expression (E-H); blue—DAPI nuclear stain. Yellow arrows indicate transfected cells (GFP+) expressing MBP (A-D) or MOG (E-H), green arrows indicate transfected cells not expressing MBP or MOG.

Figure 54:
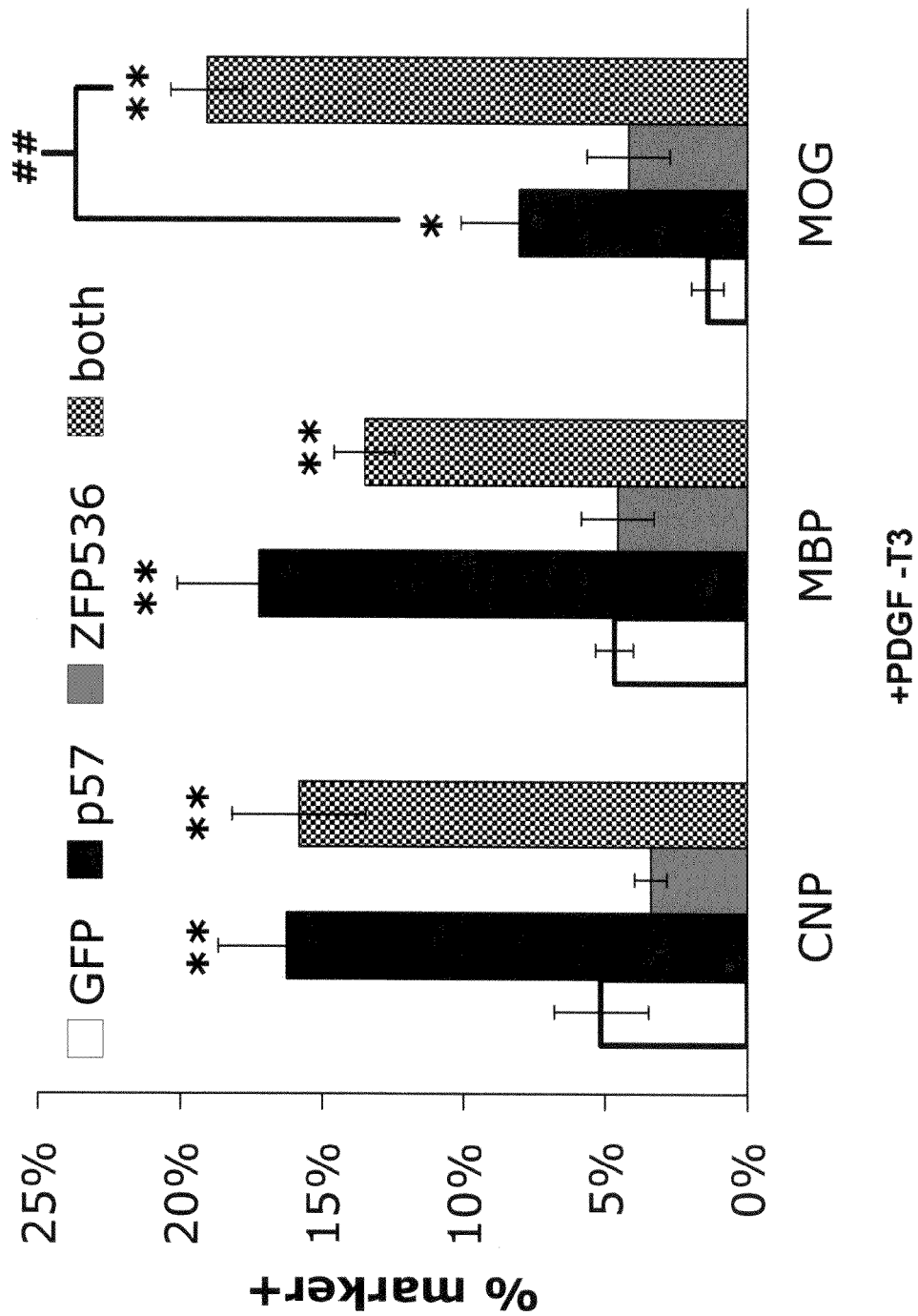

FIG. 54. Shows proportion of control (white bars), $p57^{Kip2}$ (black bars), ZFP536 (light grey bars), or $p57^{Kip2}$30 ZFP536 (dark grey bars) transfected cells expressing CNP, MBP, or MOG after 7 DIV in +PDGF −T3 medium; ±S.E.M., n=6 all conditions except CNP—both condition n=3. *=p<0.05, **=p<0.01 vs. control Holm-Sidak post-hoc test; in all cases control vs. ZFP536 p>0.05 and p57 vs. both p>0.05, except ##=p<0.01 Holm-Sidak posthoc test.

Figure 55A:
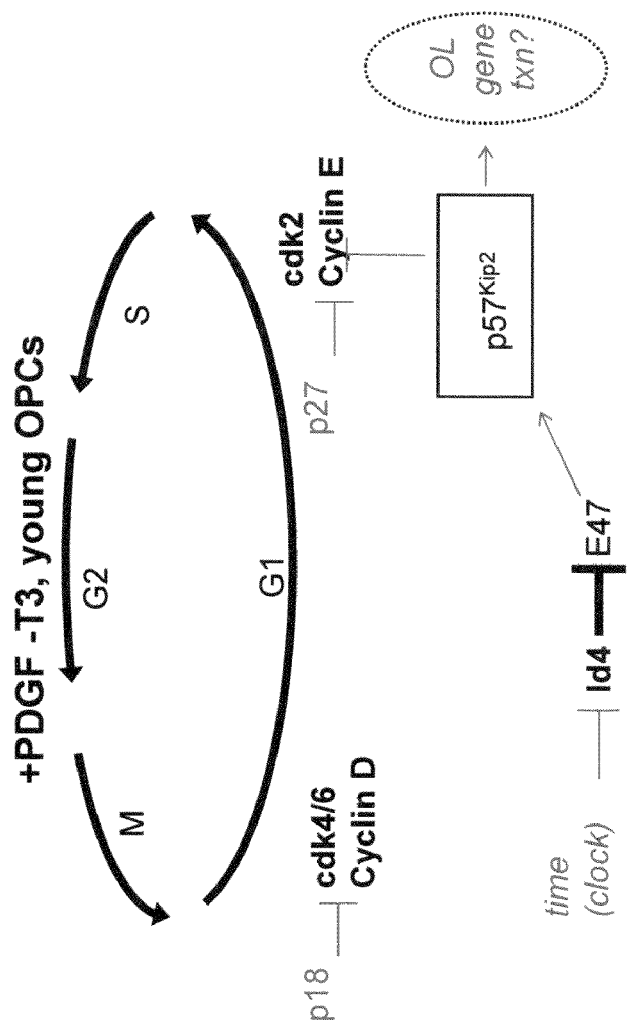

FIG. 55. Depicts a model for the role of $p57^{Kip2}$ in OL differentiation. A. In the presence of mitogens and the absence of T3 early in development, $p57^{Kip2}$ levels are kept low by inhibition of E47 by Id2 and Id4, resulting in dis-inhibition of CyclinE-cdk2 complexes and progression of the cell cycle. B. When mitogens become limiting (e.g. PDGF, "−P" in figure), CyclinD levels are reduced, eventually resulting in a reduction of 1d2. Mitogen withdrawal also results in a rapid reduction in Id4 levels. Cumulatively, this would result in an immediate dis-inhibition of E47 and increase in $p57^{Kip2}$ production, leading to the inhibition of CyclinE-cdk2 and promotion of cell cycle arrest. C. When exposed to T3 ("T3" in figure), several Ink4 cell cycle inhibitor proteins are induced, which inhibits CyclinD-cdk4/6 complex activity. CyclinE levels may also gradually be reduced by T3 inhibition of E2F1 activity. In older OPCs, Id4 levels are reduced via an unknown mechanism independent of T3 activity ("time" in figure). The resulting activation of E47 leads to an increase in $p57^{Kip2}$ which, coupled with the actions of T3, promotes cell cycle arrest in older OPCs. Both $p57^{Kip2}$ and T3 may also promote OL differentiation via more direct stimulation of OL gene transcription. In all conditions p73 likely promotes a basal level of $p57^{Kip2}$ transcription. $p27^{Kip1}$ and $p21^{Cip1}$, which are not included in the diagram, act similarly to $p57^{Kip2}$ by inhibiting CyclinE-cdk2 complex formation.

FIG. 56. Shows verification of $p57^{Kip2}$ knockdown. A. RT-PCR demonstrating knockdown of $p57^{Kip2}$ expression by siRNA. Purified OPCs were transfected with CMVGFP vector and a non-targeting siRNA pool (siCont), individual siRNAs targeting nonoverlapping regions of the rat $p57^{Kip2}$ gene (sip57-1, -2, -3, -4), or a pool of all 4 siRNAs targeting $p57^{Kip2}$ (sip57-P), and then cultured for 4 DIV in −PDGF −T3 medium. RT-PCR was performed to detect levels of $p57^{Kip2}$ (24, 26 cycles) or beta-actin (control, 24 cycles) expression. B-C. Non-overlapping siRNAs similarly inhibit OL differentiation. Purified OPCs transfected as in (A) with siControl, sip57-P, sip57-1, or sip57-4 were cultured for 3 (CNP, MBP) or 4 (MOG) DIV in −PDGF −T3 medium (B), or 7 DIV in +PDGF +T3 medium (C), and the proportions of transfected (GFP+) cells expressing CNP, MBP, or MOG were subsequently determined by immunostaining; ±S.E.M., n=3 each condition, *=p<0.01 vs. siControl Holm-Sidak post-hoc test.

FIG. 57. KLF9, Hr, DBP, and BHLHB5 are induced in OPCs by T3. Transcription factor probe sets were induced >2-fold by T3 at early time points relative to untreated (+PDGF −T3) controls. OPCs were treated with T3 for either 1 day or 6 days in vitro with T3 (+PDGF +T3), or for only 3 hours with T3 following 1 day or 6 days in vitro in media lacking T3 (+PDGF −T3, then 3 hours +PDGF +T3). All samples were labeled and hybridized to Affymetrix Mouse Genomic 430 2.0 chips.

Figure 58:
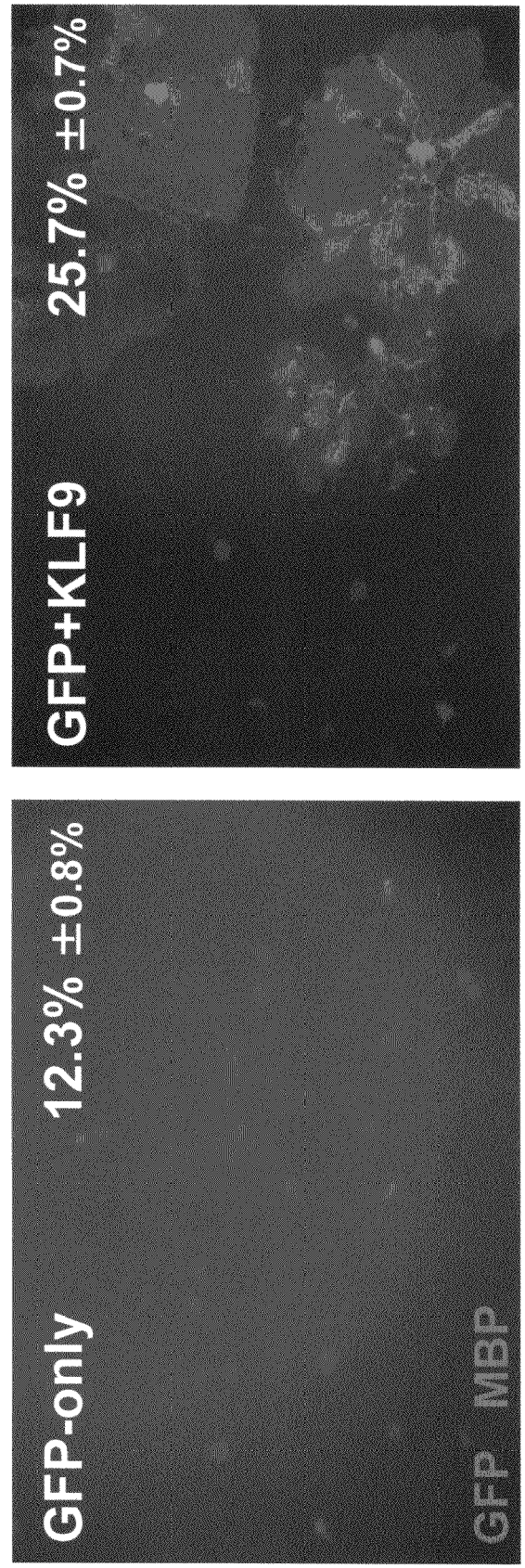

FIG. 58. Shows effect of KLF9 overexpression on MBP expression in OPCs. OPCs were transfected with CMV-GFP alone or CMV-GFP plus CMV-KLF9. Transfected OPCs were cultured for 6 DIV and then immunostained for GFP and MBP expression. The average percentages of transfected cells that express MBP in each condition (±S.E.M.) are shown (p<0.0005, two-tailed T-test).

Figure 59:
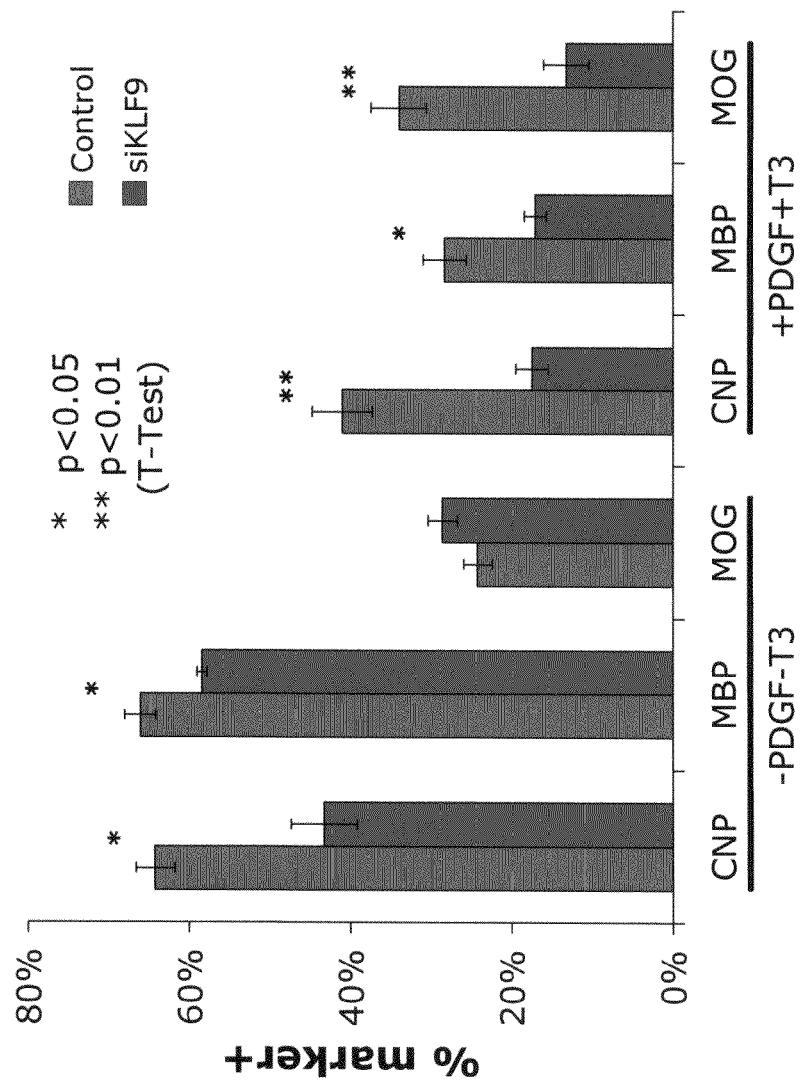

FIG. 59. Shows effect of KLF9 knockdown on T3-mediated OL differentiation. OPCs were transfected with either control non-targeting siRNA (Control) or siRNA targeting KLF9 (siKLF9). Transfected OPCs were cultured for 3 or 7 DIV in the media indicated, and then immunostained to detect CNP1, MBP, or MOG expression. The average percentages of healthy transfected cells expression indicated myelin genes (±S.E.M) are shown.

Figure 60:
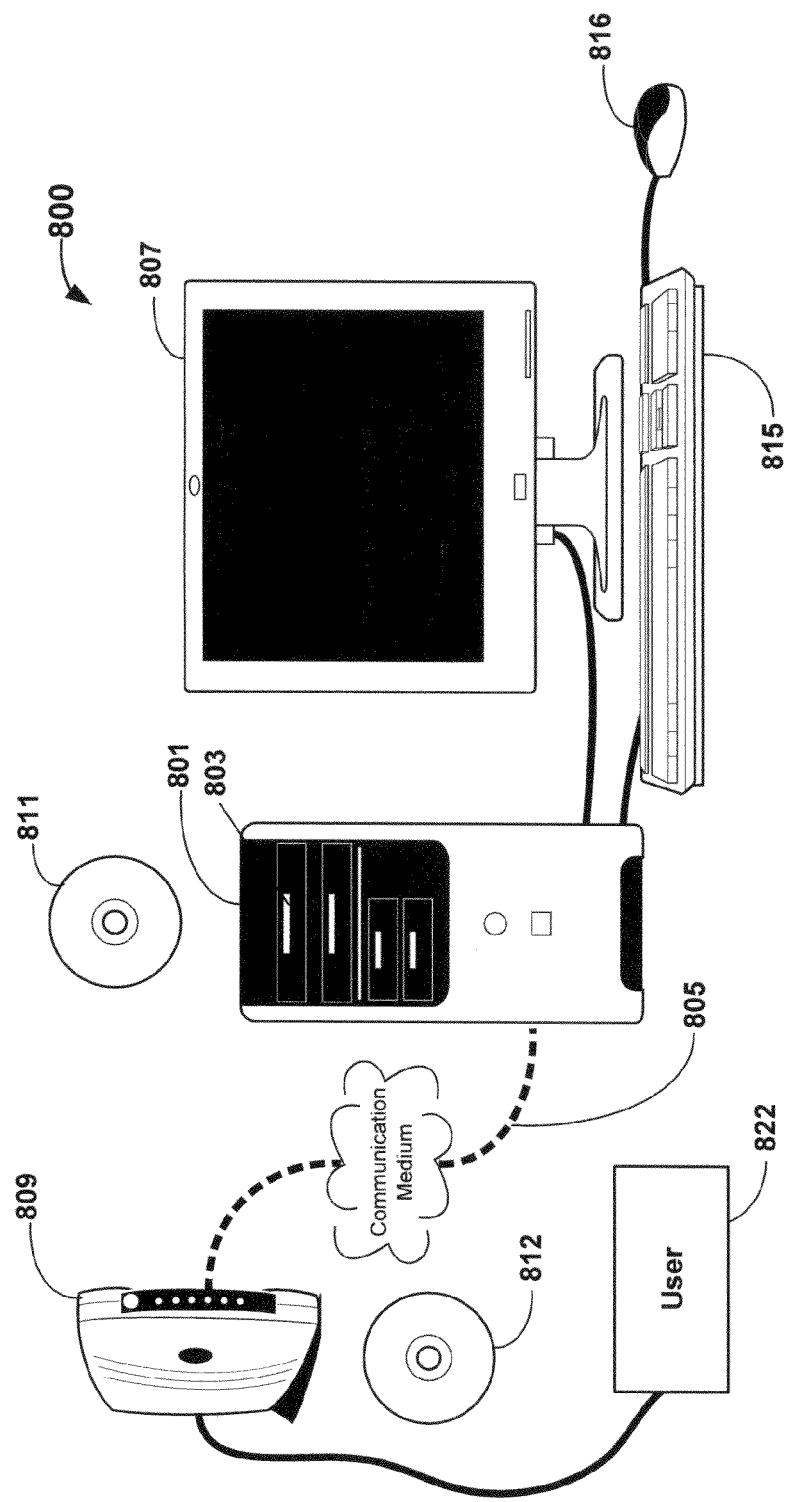

FIG. 60. Depicts a diagram of a system for analyzing data from assaying gene expressions and transmission of data from the analysis or data relating to a candidate bioactive agent over a network.

Figure 61:
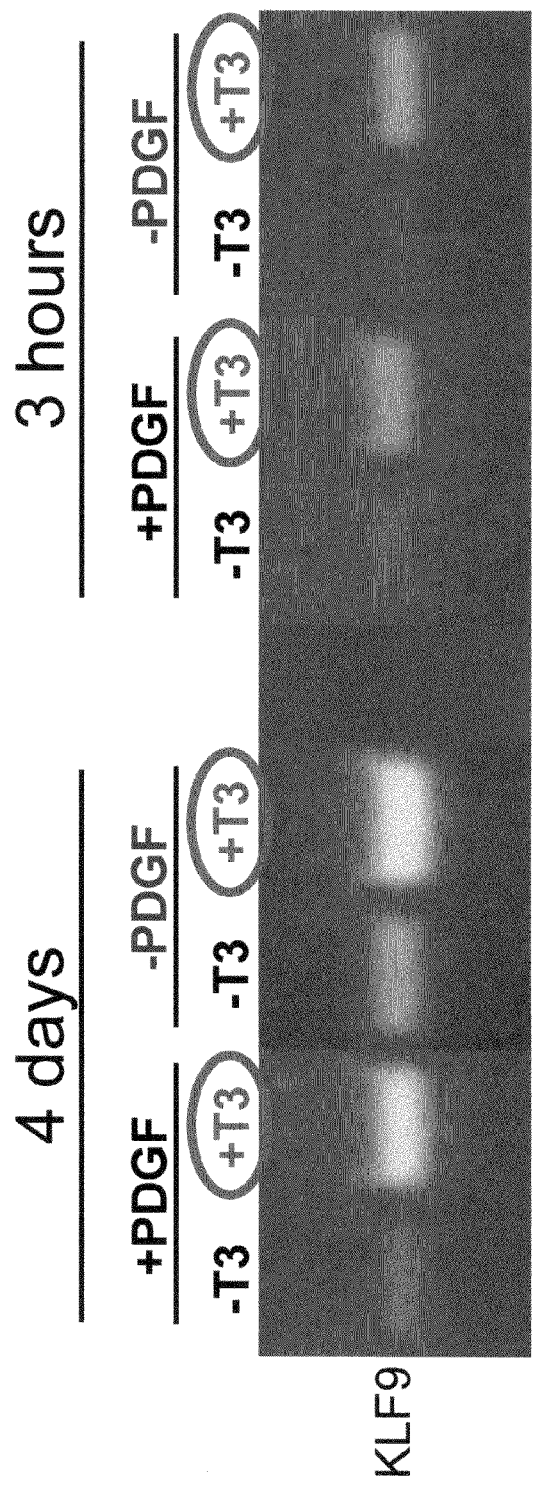

FIG. 61. Depicts RT-PCR results from OPCs incubated in short or long term in media that either contains or lacks saturating amounts of mitogens, and either contains or lacks T3. KLF9 is the most strongly induced by exposure to T3, regardless of the presence or absence of mitogens.

FIG. 62. Illustrates KLF9 overexpression induces myelin gene expression. OPCs were transfected with constructs to overexpress KLF9 and cultured them for 6 days in saturating amounts of mitogens without thyroid hormone. A) In the absence of T3, the majority of transfected GFP+ cells remain OPCs, with only a few cells differentiating into MBP+ OLs. In contrast, overexpression of KLF9 doubles the number of OPCs that differentiate in the absence of any differentiation-promoting stimuli. B) Cells were immunostained to detect CNP1, MBP, or MOG expression. The average percentages of healthy transfected cells expression indicated myelin genes (±S.E.M) are shown.

Figure 63B:
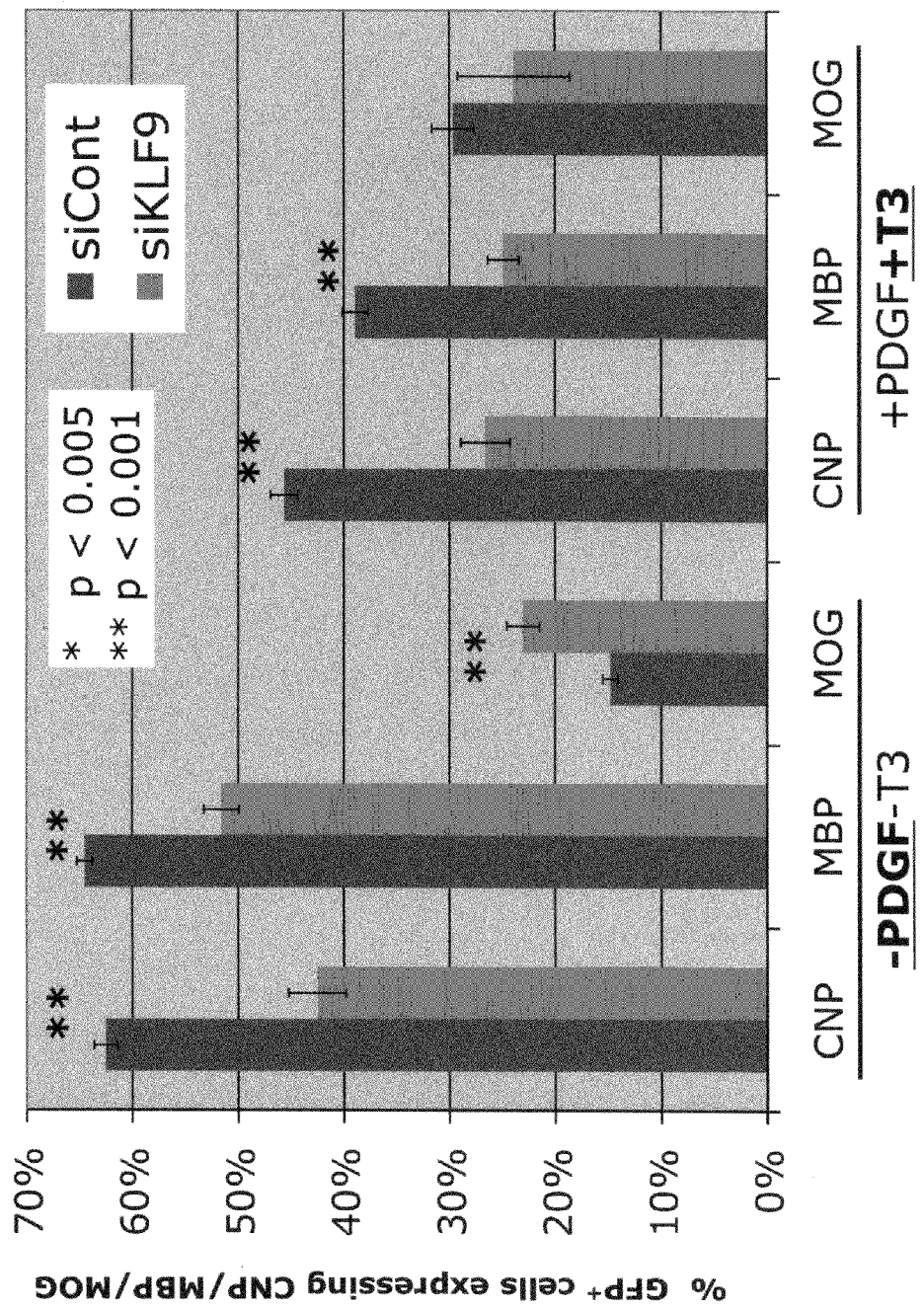

FIG. 63. Illustrates KLF9 knockdown represses T3-induced myelin gene expression. SiRNA was used to knockdown KLF9 expression and clock-mediated differentiation was stimulated by adding T3 to the media. In control cells, by 7 days T3 has triggered the differentiation of a large portion of transfected OPCs. Knocking down KLF9 in these OPCs greatly reduced the number of cells that differentiate in response to T3, indicating a slowing down in the normal rate of T3-mediated differentiation. A) Cells were immunostained to detect CNP1, MBP, or MOG expression. B) The average percentages of healthy transfected cells expression indicated myelin genes (±S.E.M) are shown.

Figure 64:
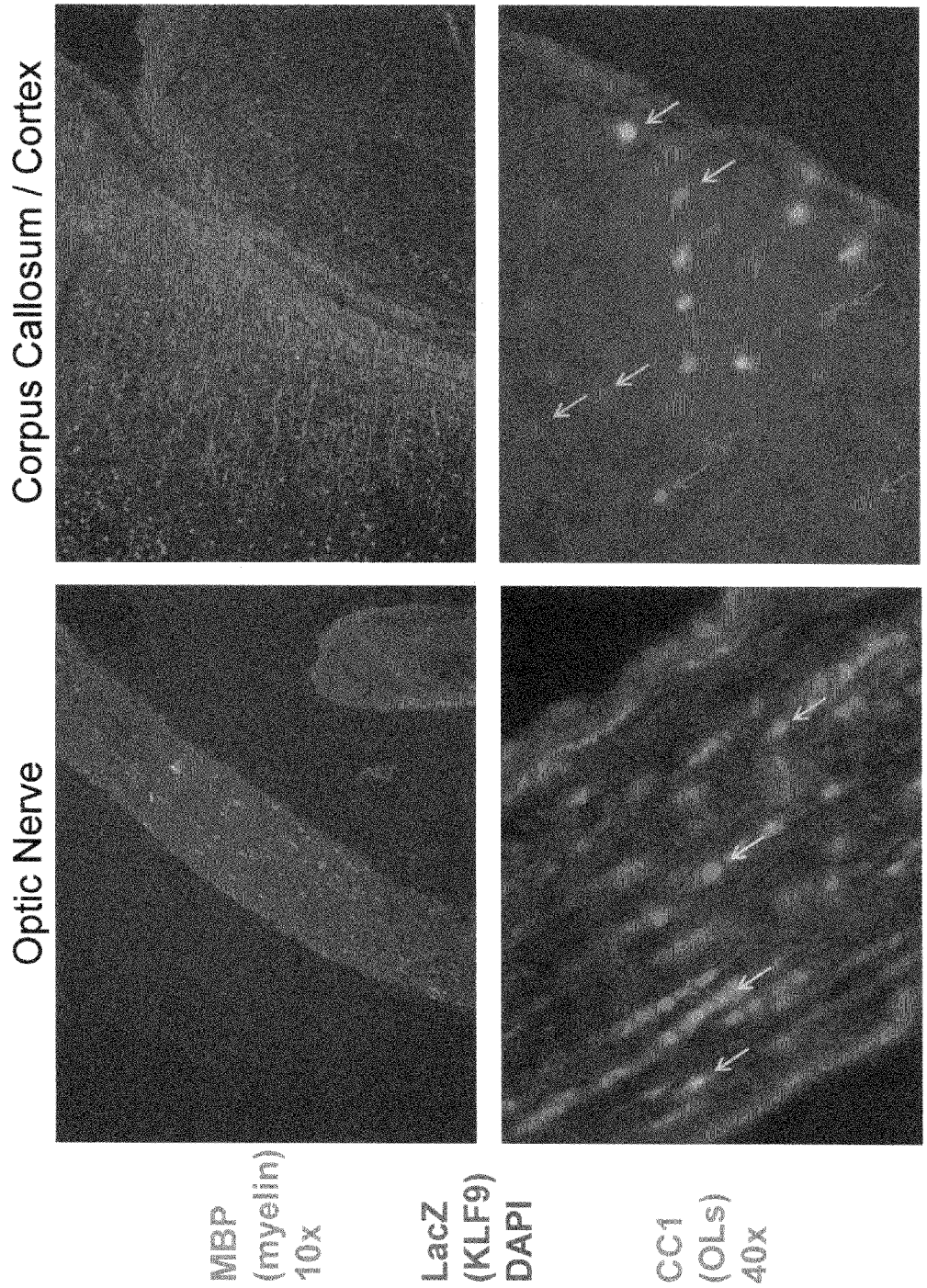

FIG. 64. Illustrates KLF9 is expressed in OLs in vivo (P17 KLF9+/−). The KLF9 promoter is active in myelinated regions of the optic nerve and basal cortex as indicated by LacZ staining. To determine whether individual OLs express KLF9, sections were costained with CC-1, which marks the cell bodies of mature OLs. In several mature OLs (labeled in green), KLF9 is being actively transcribed, as indicated by LacZ expression in red.

Figure 65:
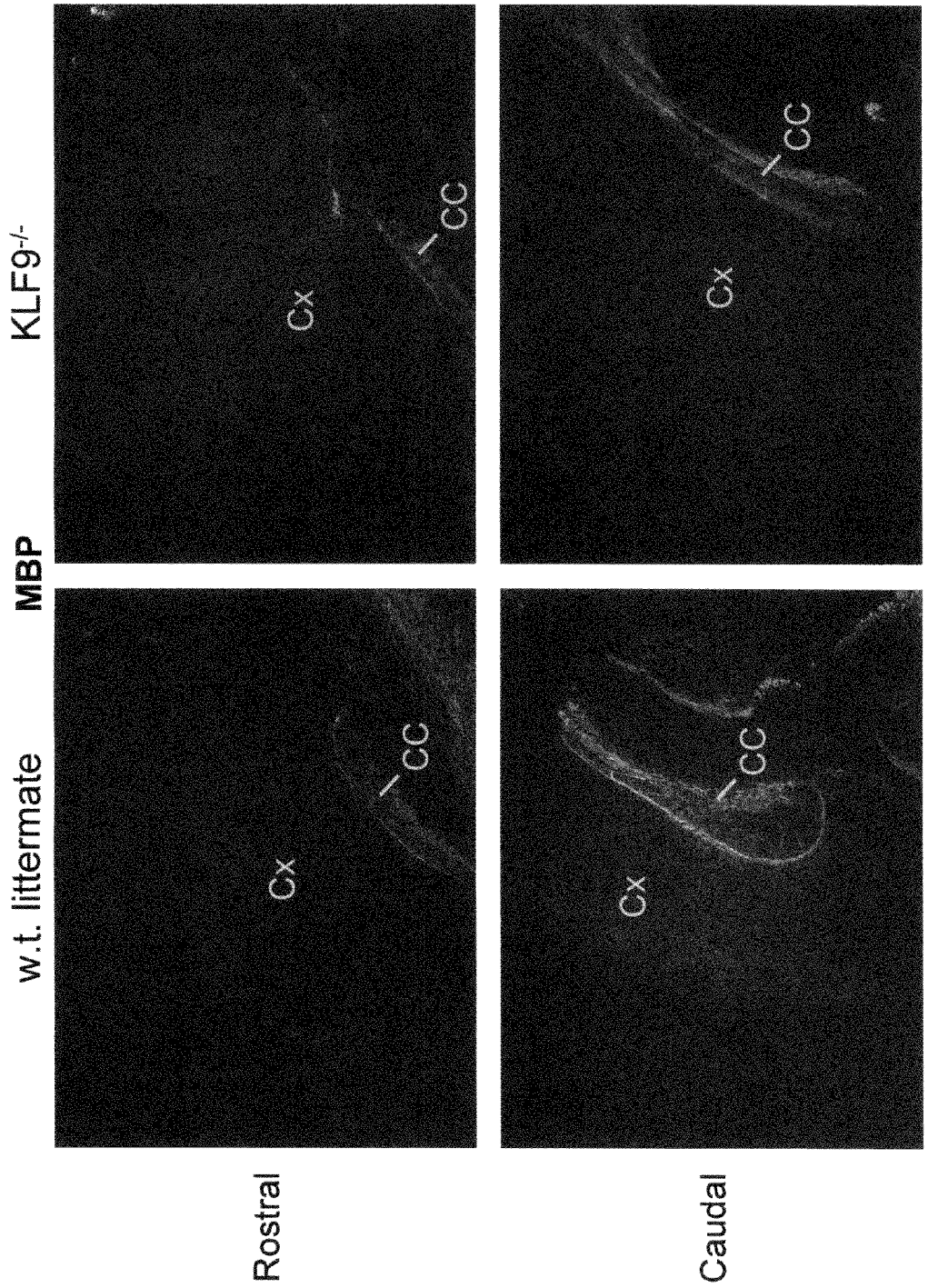

FIG. 65. Shows myelination is delayed in KLF9−/− cortex (P12-sagital). A sagital section of a P12 mouse brain shows myelination proceeding in the corpus callosum, and also is commencing in the caudal, but not yet rostral cortex, which is consistent with a caudal to rostral progression of cortical myelination. In the mutant, although myelination is proceeding in the CC, it is lacking in the cortex.

Figure 66:
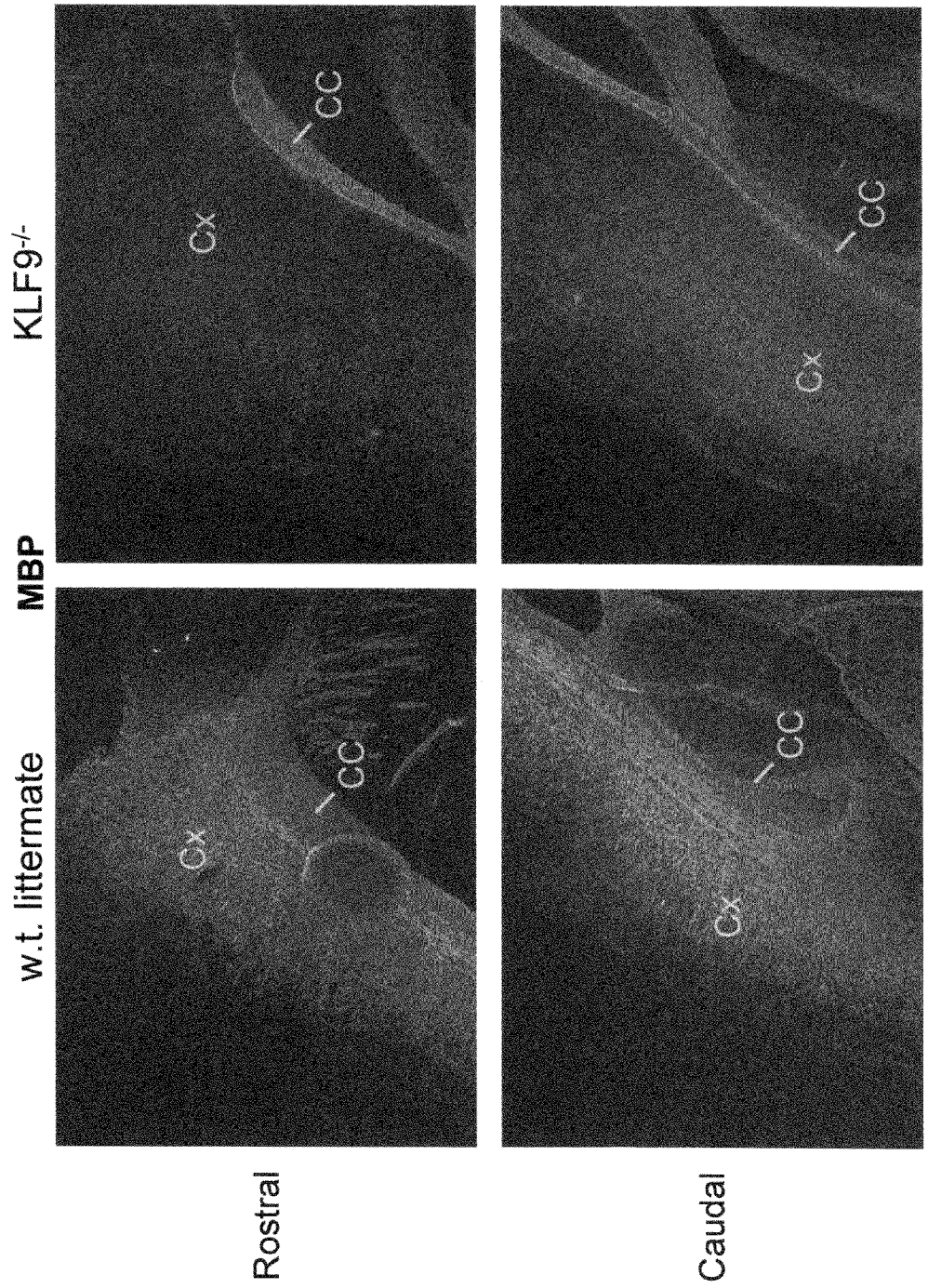

FIG. 66. Shows myelination is delayed in KLF9−/− cortex (P18-sagital). At P18, caudal cortical myelination has commenced in the mutants, but rostral cortical myelination now severely lags behind wild type littermates, indicating a delay in myelination.

Figure 67:
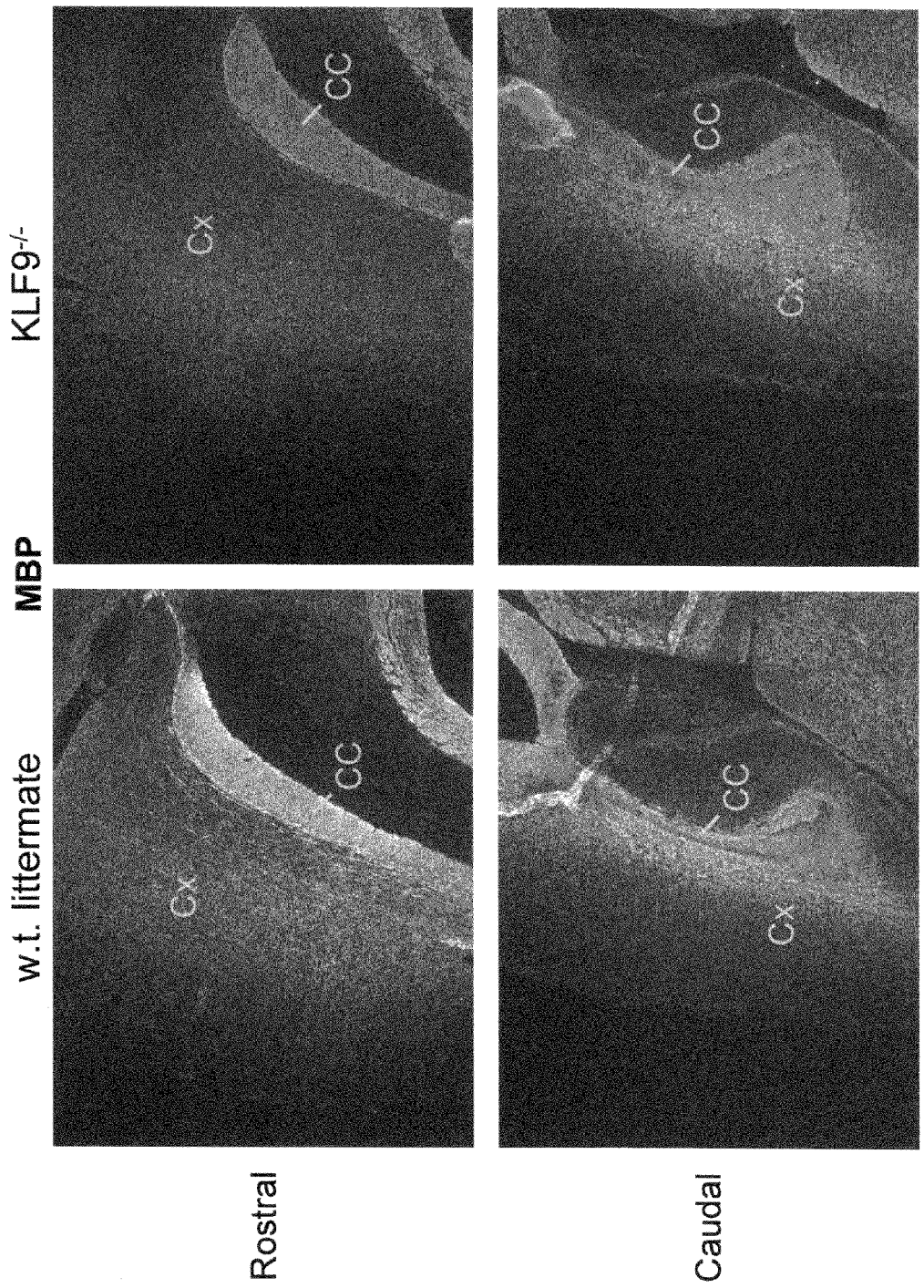

FIG. 67. Shows myelination is delayed in KLF9−/− cortex (P35-sagital). At P35, cortical myelination appears to be catching up in both the caudal and rostral cortex. Myelin formation appears to be delayed but not permanently disrupted in the KLF9 mutant mice. This delay is similar to the delayed myelination observed in mice lacking thyroid hormone, consistent with a proposed role of KLF9 as a downstream effector of T3-promoted myelin formation FIG. 68. Shows myelination is delayed in KLF9−/− cortex.

Figure 69:
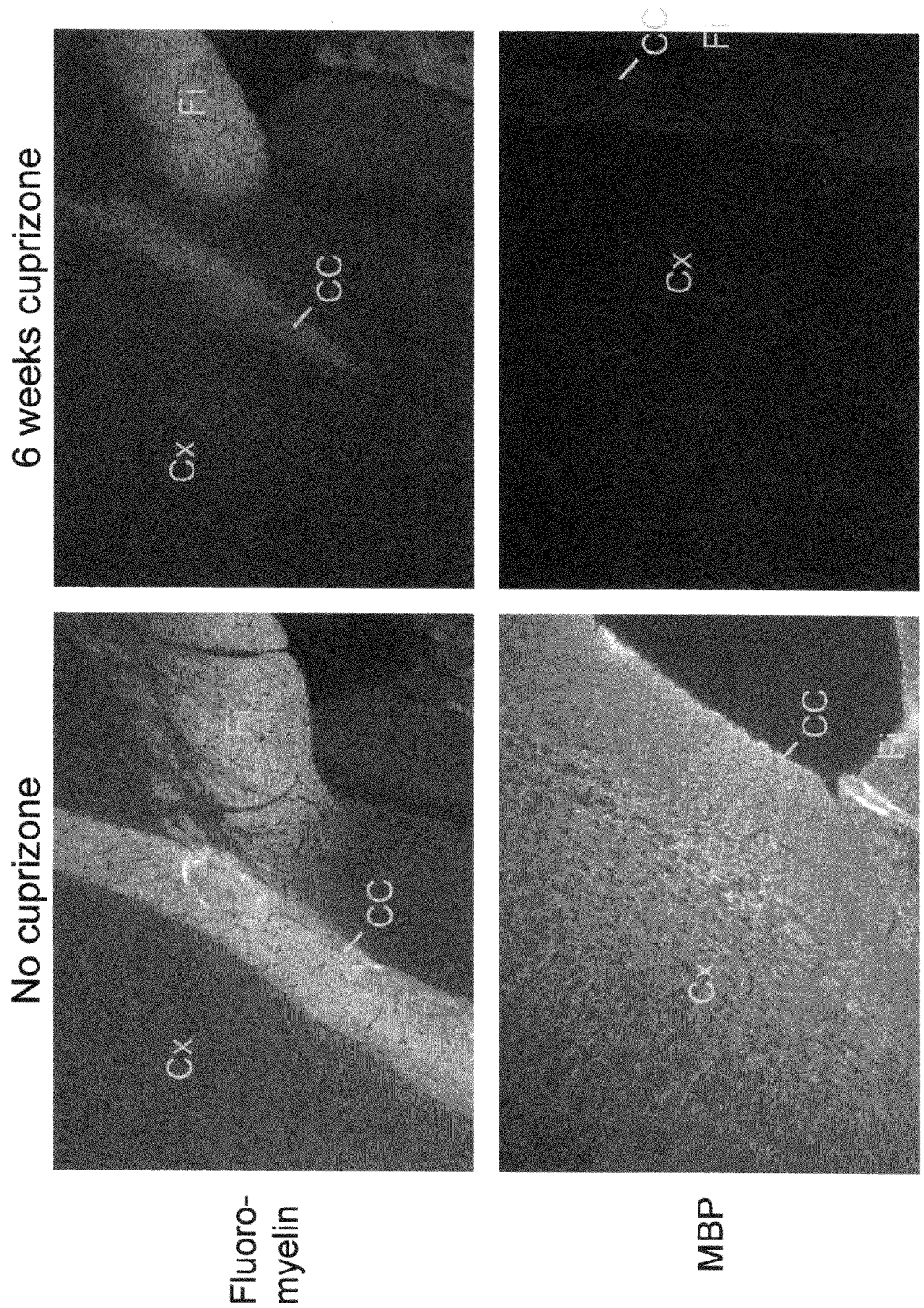

FIG. 69. Shows cuprizone disrupts myelin in the corpus callosum (CC) and cortex. Demyelination in both KLF9 mutant and wild type littermate control animals was induced via cuprizone administration. By removing Cuprizone from the diet at 6 weeks, repair of the damaged myelin can commence. The rate of remyelination following the withdrawal of cuprizone from the diet can then be monitored. Depicted in this figure are examples of the standard demyelination produced by a 6-week diet of Cuprizone (compared to untreated animals) in both the CC (as shown by fluoromyelin staining) and Cortex (as shown by MBP staining) of treated animals.

Figure 70:
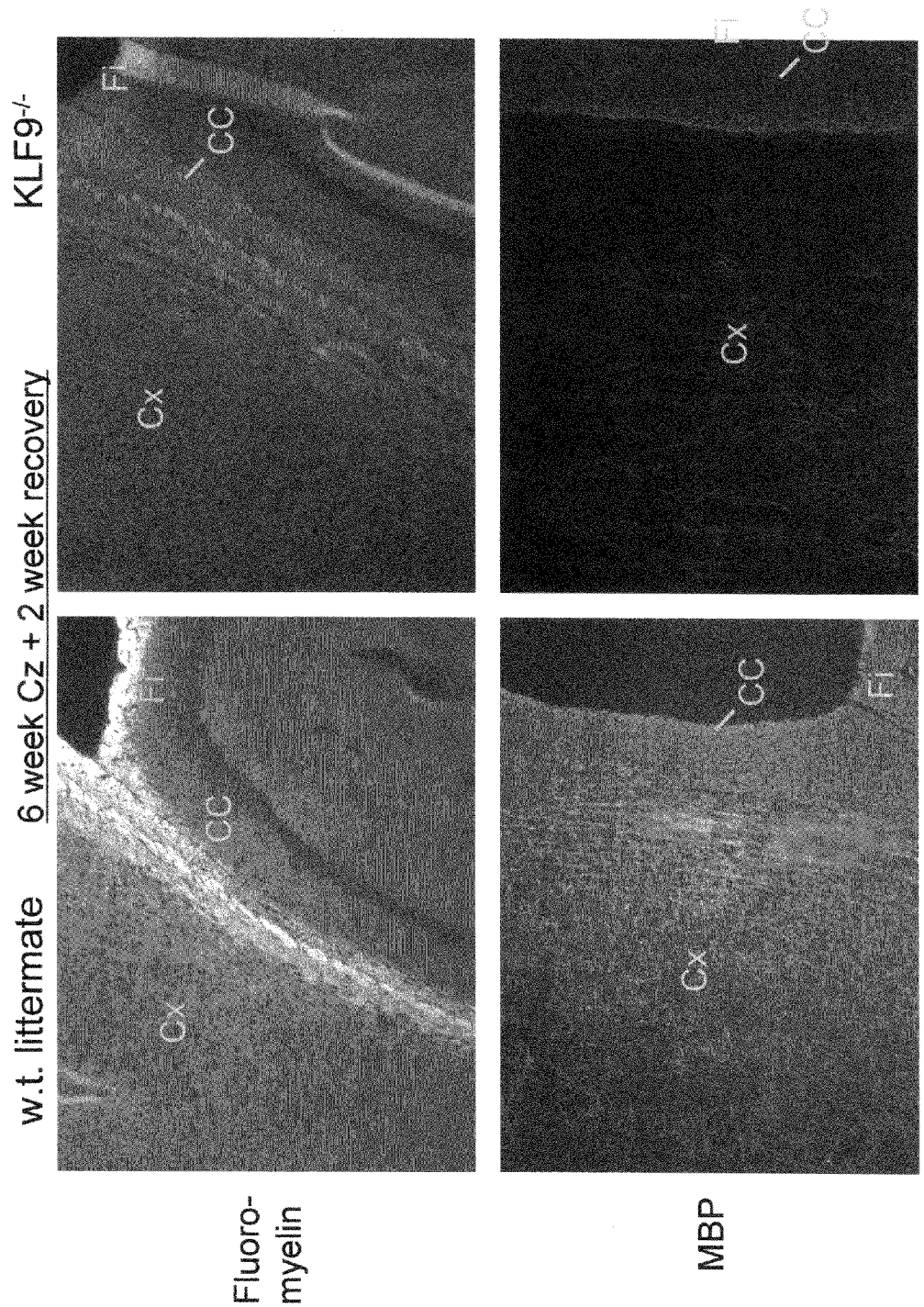

FIG. 70. Shows myelin repair is delayed in KLF9−/− cortex and corpus callosum (CC). Depicted here are mice that have been allowed to regenerate their myelin for 2 weeks. Myelin repair commenced nicely in the wild type littermates, while the KLF9−/− mice did not repair their damaged myelin as robustly.

Figure 71:
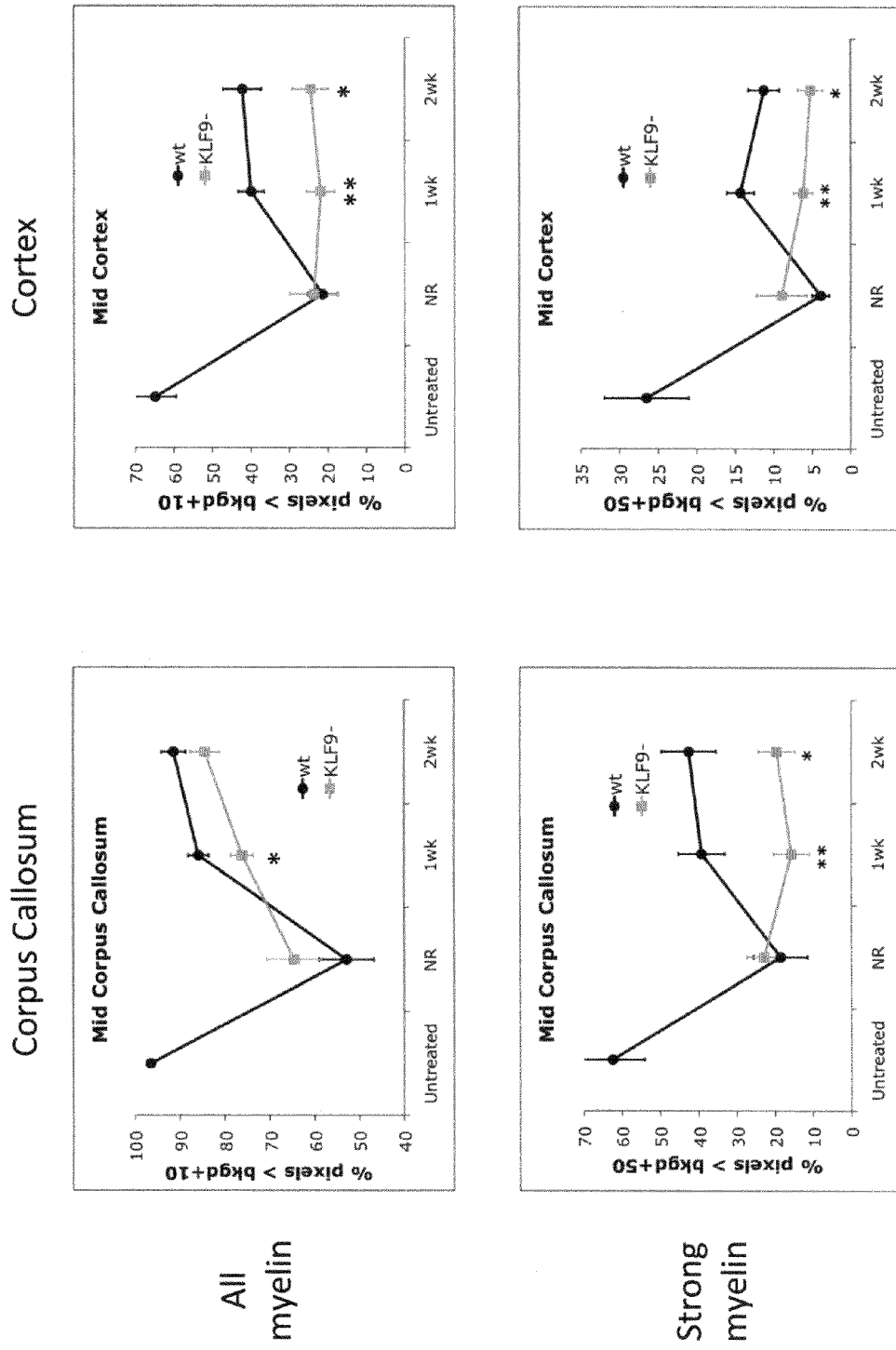

FIG. 71. Shows myelin regeneration is delayed in KLF9−/−cortex and corpus callosum (CC).

Figure 72:
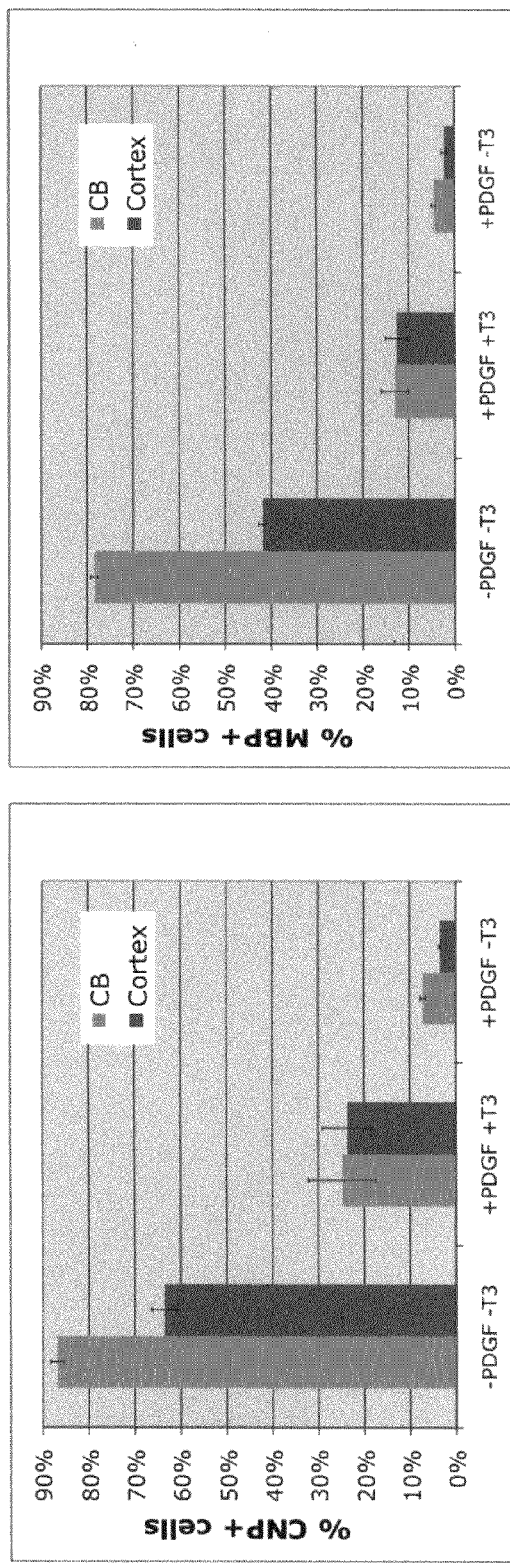

FIG. 72. Shows OPCs from the cortex and cerebellum respond similarly to T3

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

General Techniques

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, $2^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

As used in the specification and claims, the singular form "a", "an" and "the" include plural references unless the context clearly dictates otherwise. For example, the term "a cell" includes a plurality of cells, including mixtures thereof.

Definitions

The term "control" is an alternative subject, cell or sample used in an experiment for comparison purpose. A control can be "positive" or "negative". For example, a control cell can be employed in assaying for differential expression of a gene product in a given cell of interest. The expression of the gene product of the control cell may be compared to that of a test cell, for example a test cell contacted with a bioactive agent. Furthermore, a "control" can also represent the same subject, cell or sample in an experiment for comparison of different time points. In the context for screening bioactive agent, a control cell can be a neural cell that has not been contacted with a test bioactive agent.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein, "expression" refers to the process by which a polynucleotide is transcribed into mRNA and/or the process by which the transcribed mRNA (also referred to as "transcript") is subsequently being translated into peptides, polypeptides, or proteins. The transcripts and the encoded polypeptides are collectedly referred to as "gene product." If the polynucleotide is derived from genomic DNA, expression may include splicing of the mRNA in a eukaryotic cell.

The terms "contact", "delivery" and "administration" are used interchangeably herein to mean an agent enters a subject, tissue or cell. The terms used throughout the disclosure herein also include grammatical variances of a particular term. For example, "delivery" includes "delivering"; "delivered", "deliver", etc. Various methods of delivery or administration of bioactive agents are known in the art. For example, one or more agents described herein can be delivered parenterally, orally, intraperitoneally, intravenously, intraarterially, transdermally, intramuscularly, liposomally, via local delivery by catheter or stent, subcutaneously, intraadiposally, or intrathecally.

The term "differentially expressed" as applied to nucleotide sequence or polypeptide sequence refers to over-expression or under-expression of that sequence when compared to that detected in a control. Under-expression also encompasses absence of expression of a particular sequence as evidenced by the absence of detectable expression in a test subject when compared to a control.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

A "subject," "individual" or "patient" is used interchangeably herein, which refers to a vertebrate, preferably a mammal, more preferably a human. Mammals include, but are not limited to mice, rats, dogs, pigs, monkey (simians) humans, farm animals, sport animals, and pets. Tissues, cells and their progeny of a biological entity obtained in vivo or cultured in vitro are also encompassed.

As used herein, "treatment" or "treating," or "ameliorating" are used interchangeably herein. These terms refers to an approach for obtaining beneficial or desired results including and preferably clinical results. For purposes of this invention, beneficial or desired clinical results include, but are not limited to, one or more of the following: shrinking the size of demyelinating lesions (in the context of demyelination disorder, for example), promoting OPC proliferation and growth or migration to lesion sites, promoting differentiation of oligodendrocytes, delaying the onset of a neuropathy, delaying the development of demyelinating disorder, decreasing symptoms resulting from a neuropathy, increasing the quality of life of those suffering from the disease, decreasing the dose of other medications required to treat the disease, enhancing the effect of another medication such as via targeting and/or internalization, delaying the progression of the disease, and/or prolonging survival of individuals. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance.

The terms "agent", "biologically active agent", "bioactive agent", "bioactive compound" or "biologically active compound" are used interchangeably and also encompass plural references in the context stated. Such compounds utilized in one or more combinatorial treatment methods of the invention described herein, include but are not limited to a biological or chemical compound such as a simple or complex organic or inorganic molecule, peptide, peptide mimetic, protein (e.g. antibody), nucleic acid molecules including DNA, RNA and analogs thereof, carbohydrate-containing molecule, phospholipids, liposome, small interfering RNA, or a polynucleotide (e.g. anti-sense).

Such agents can be agonists or antagonists of components of cell cycle pathways related to neural cell proliferation or differentiation. In some embodiments of the invention, it is envisioned that compounds having the same three dimensional structure at the binding site may be used as antagonists. Three dimensional analysis of chemical structure is used to determine the structure of active sites, including binding sites for polypeptides related to neural cell cycle.

The term "antagonist" as used herein refers to a molecule having the ability to inhibit a biological function of a target polypeptide. Accordingly, the term "antagonist" is defined in the context of the biological role of the target polypeptide. While preferred antagonists herein specifically interact with (e.g. bind to) the target, molecules that inhibit a biological activity of the target polypeptide by interacting with other members of the signal transduction pathway of which the target polypeptide is a member are also specifically included within this definition. A preferred biological activity inhibited by an antagonist is associated with increasing proliferation of OPCs, decreasing proliferation of OPCs, increasing differentiation of OLs, or increasing proliferation of astrocytes, and/or promoting remyelination. For example, an antagonist can interact directly or indirectly with a polypeptide related to neural cell cycle. Antagonists, as defined herein, without limitation, include oligonucleotide decoys, aptamers, antichemokine antibodies and antibody variants, peptides, peptidomimetics, non-peptide small molecules, antisense molecules, and small organic molecules.

The term "agonist" as used herein refers to a molecule having the ability to initiate or enhance a biological function of a target polypeptide. Accordingly, the term "agonist" is defined in the context of the biological role of the target polypeptide. While preferred agonists herein specifically interact with (e.g. bind to) the target, molecules that inhibit a biological activity of the target polypeptide by interacting with other members of the signal transduction pathway of which the target polypeptide is a member are also specifically included within this definition. A preferred biological activity inhibited by an agonist is associated with increasing proliferation of OPCs, decreasing proliferation of OPCs, increasing differentiation of OLs, or astrocytes thereby promoting remyelination. Antagonists, as defined herein, without limitation, include oligonucleotide decoys, aptamers, antichemokine antibodies and antibody variants, peptides, peptidomimetics, non-peptide small molecules, antisense molecules, and small organic molecules.

Agonists, antagonists, and other modulators of a neural cell proliferation/differentiation are expressly included within the scope of this invention. In certain embodiments, the agonists, antagonists, and other modulators are antibodies and immunoglobulin variants that bind to a polypeptide involved in modulating neural cell cycle, i.e., proliferation or differentiation. These agonistic, antagonistic modulatory compounds can be provided in linear or cyclized form, and optionally comprise at least one amino acid residue that is not commonly found in nature or at least one amide isostere. These compounds may be modified by glycosylation, phosphorylation, sulfation, lipidation or other processes.

The term "effective amount" or "therapeutically effective amount" refers to that amount of an antagonist that is sufficient to effect beneficial or desired results, including without limitation, clinical results such as shrinking the size of demyelinating lesions (in the context of demyelination disorder, for example), promoting OPC proliferation and growth, delaying the onset of a neuropathy, delaying the development of demyelinating disorder, decreasing symptoms resulting from a neuropathy, increasing the quality of life of those suffering from the disease, decreasing the dose of other medications required to treat the disease, enhancing the effect of another medication such as via targeting and/or internalization, delaying the progression of the disease, and/or prolonging survival of individuals. The therapeutically effective amount will vary depending upon the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose will vary depending on the particular antagonist chosen, the dosing regimen to be followed, whether it is administered in combination with other compounds, timing of administration, the tissue to be imaged, and the physical delivery system in which it is carried.

The term "antibody" as used herein includes all forms of antibodies such as recombinant antibodies, humanized antibodies, chimeric antibodies, single chain antibodies, humanized antibodies, fusion proteins, monoclonal antibodies etc. The invention is also applicable to antibody functional fragments that are capable of binding to a polypeptide involved in neural cell cycle (e.g., binding a transcription factor or protein involved in regulating neural cell proliferation/differentiation).

In one embodiment, comparatively low doses of an entire, naked antibody or combination of entire, naked antibodies are used. In some embodiments, antibody fragments are utilized, thus less than the complete antibody. In other embodiments, conjugates of antibodies with drugs, toxins or therapeutic radioisotopes are useful. Bispecific antibody fusion proteins which bind to the chemokine antigens can be used according to the present invention, including hybrid antibodies which bind to more than one antigen. Therefore, antibody encompasses naked antibodies and conjugated antibodies and antibody fragments, which may be monospecific or multispecific.

The terms "modulating", "modulated" or "modulation" are used interchangeably and mean a direct or indirect change in a given context. For example, modulation of $p57^{Kip2}$ expression results in altered neural cell proliferation or differentiation. In another example, modulation can be that of a gene/gene product that itself can regulate expression of a gene involved with neural cell cycle. Examples of such agents (e.g., transcription factors) are disclosed herein.

The term "aptamer" as applied to bioactive agent includes DNA, RNA or peptides that are selected based on specific binding properties to a particular molecule. For example, an aptamer(s) can be selected for binding a particular gene or gene product involved in neural cell cycle, as disclosed herein, where selection is made by methods known in the art and familiar to one of skill in the art. Subsequently, said aptamer(s) can be administered to a subject to modulate or regulate an immune response. Some aptamers having affinity to a specific protein, DNA, amino acid and nucleotides have been described (e.g., K. Y. Wang, et al., *Biochemistry* 32:1899-1904 (1993); Pitner et al., U.S. Pat. No. 5,691,145; Gold, et al., *Ann. Rev. Biochem.* 64:763-797 (1995); Szostak et al., U.S. Pat. No. 5,631,146). High affinity and high specificity binding aptamers have been derived from combinatorial libraries (supra, Gold, et al.). Aptamers may have high affinities, with equilibrium dissociation constants ranging from micromolar to sub-nanomolar depending on the selection used. Aptamers may also exhibit high selectivity, for example, showing a thousand fold discrimination between 7-methylG and G (Haller and Sarnow, *Proc. Natl. Acad. Sci. USA* 94:8521-8526 (1997)) or between D and L-tryptophan (supra, Gold et al.).

The term "decoy" as applied to bioactive agent is meant to include a nucleic acid molecule, for example RNA or DNA, or aptamer that is designed to preferentially bind to a predetermined ligand or unknown ligand. Such binding can result in the inhibition or activation of a target molecule. The decoy or aptamer can compete with a naturally occurring binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA (Sullenger et al., *Cell* 63, 601-608 (1990)). This is but a specific example and those in the art will recognize that other embodiments can be readily generated using techniques generally known in the art, see for example Gold et al., *Annu. Rev. Biochem.*, 64, 763-797 (1995); Brody and Gold, *J. Biotechnol.*, 74, 5-13 (2000); Sun, *Curr. Opin. Mol. Ther.*, 2, 100-105 (2000); Kusser, *J. Biotechnol.*, 74, 27-38 (2000); Hermann and Patel, *Science*, 287, 820-825 (2000); and Jayasena, *Clinical Chemistry*, 45, 1628-1650 (1999). Similarly, a decoy can be designed to bind to a target antigen to occupy its active site, or a decoy can be designed to bind to a target molecule to prevent interaction with another ligand protein(s), thus short-circuiting a cell signaling pathway that is involved in cell proliferation or differentiation.

Various aspects of the invention relate to the discovery of the involvement of certain Cdk inhibitors in regulating neural cell proliferation or differentiation. In particular, one aspect relates to the discovery that $p57^{Kip2}$ (Cdkn1c), as an intracellular molecule, synchronously accumulates in each daughter cell and ultimately reaches a level that prohibits further proliferation. The data presented herein indicates that all daughters of a clone of OPCs share the same level of $p57^{Kip2}$ immunoreactivity, that $p57^{Kip2}$ level increases over time in a clone of OPCs, and that p57 levels regulate how many times an OPC can divide before differentiating. These findings reveal a novel part of the mechanism by which OPCs keep time and which mechanism can be extended to similar timers in many other precursor cell types.

In various aspects, bioactive agents are administered which target components of a CDK-mediated signaling cell pathway thus modulating neural cell proliferation and differentiation. In some embodiments such bioactive agents block CDK-inhibitor-mediated signaling thus promoting neural cell proliferation, which enhances or promotes myelination. In some embodiments, such bioactive agents increase CDK-inhibitor-mediated signaling thus promoting neural cell differentiation which enhances myelin repair in the CNS.

One aspect of the invention is that $p57^{Kip2}$ is an integral component for the OPC timer which regulates OPC proliferation and differentiation into OLs. As is described in more detail herein, increasing $p57^{Kip2}$ slows OPC proliferation and accelerates the intrinsic differentiation timer increasing OLs and thus promoting myelination. The following general techniques are useful in utilizing compositions and methods disclosed herein. These and other aspects of the invention may be disclosed in related U.S. Provisional Patent Application No. 60/833,744, which is incorporated by reference herein in its entirety.

$p57^{Kip2}$ is an integral component of the timer that normally regulates OL differentiation. The precise regulation of how many times a precursor cell can divide before differentiating is crucial to the normal development of any complex multicellular organism. OPCs present an excellent model system in which to study the normal timing of vertebrate cell differentiation, due to the fact that OPCs can be highly purified and cultured in defined, serum-free media that either promotes precursor proliferation or OL differentiation (Barres and Raff, *Neuron* 12:935-942 (1994)). Previous studies identified an intrinsic clock that regulates how many times an OPC can divide before it differentiates (Barres et al., *Development* 120:1097-1108 (1994); Temple and Raff, *Cell* 44:773-779 (1986)). To function normally, the clock requires the combined activity of both an effector component, which responds to the presentation of external cues such as triiodothyronine (T3) or retinoic acid (RA), and a timer component, which intracellularly measures the passage of time as an OPC proliferates in the presence of mitogens, independent of T3 stimulation. Any candidate for the timer component of the clock should possess certain characteristics: its level should change synchronously over time within OPC clones in the absence of any differentiation-promoting stimuli, the change that occurs over time should be required for T3 exposure to initiate OL differentiation, and the change that occurs to measure time should be independent of T3 stimulation. Otherwise, early presentation of T3 would accelerate the timer and young proliferating OPCs would rapidly differentiate in response to T3 exposure, similar to the immediate differentiation induced by mitogen withdrawal.

Data presented herein illustrates that $p57^{Kip2}$ is an integral component of the timer that normally regulates OL differentiation. In vivo, it was observed that $p57^{Kip2}$ expression Was transiently upregulated around the age at which myelination is initiated and reduced after the peak of myelination has passed. Early in development, $p57^{Kip2}$ was detected in both OPCs and OLs, whereas later in development the majority of $p57^{Kip2}$-expressing cells were OLs. These data indicate that a rise in $p57^{Kip2}$ expression is likely a very early event in OL differentiation, potentially marking OPCs that are on the verge of differentiating into OLs. In addition, the extinguishing of $p57^{Kip2}$ expression indicates that $p57^{Kip2}$ may be involved in the initiation but not the maintenance of the mature OL phenotype in vivo.

In vitro, it was observed that $p57^{Kip2}$ expression increases intrinsically in purified OPCs over time in the absence of any extrinsic cues, and that this induction occurs synchronously within all the cells of individual OPC clones. This correlates with the synchronous differentiation of OPC clones previously observed in vitro (Barres et al., *Development* 120:1097-1108 (1994); Temple and Raff *Cell* 44:773-779 (1986)). Importantly, exposure to T3 does not alter $p57^{Kip2}$ expression, meaning that $p57^{Kip2}$ increase could measure time independent of environmental T3 levels. Data presented herein indicate that increasing $p57^{Kip2}$ accelerates the intracellular timer that regulates T3-mediated OL differentiation, and that reducing $p57^{Kip2}$ retards this timer. These effects are mediated by altering cell cycle regulation, as these same manipulations respectively increase and reduce OPC cell cycle time in both the presence and absence of T3.

Interestingly, manipulations of p73 activity have similar phenotypic outcomes for OL differentiation (Billon et al., *Development* 131:1211-1220 (2004)) as demonstrated herein with alterations in $p57^{Kip2}$ levels. Induction of $p57^{Kip2}$ expression by p73β (Balint et al., *Proc. Natl. Acad. Sci. USA* 99:3529-3534 (2002); Vaccarello et al., *J. Mol. Biol.* 356:578-588 (2006)) explains this outcome.

OLs are generated from proliferating, immature oligodendrocyte precursor cells (OPCs), which exit the cell cycle and differentiate throughout the CNS at predictable developmental ages (Baumann and Pham-Dinh, *Physiol. Rev.* 81:871-927 (2001)). Therefore by administering bioactive agents that regulate the generation of oligodendrocytes (OLs), the myelin-forming cells of the central nervous system (CNS), remyelination can be enhanced.

Previous experiments have demonstrated that the precise timing of OL generation is regulated in part by an intracellular molecular clock, which intrinsically determines how many times an OPC can divide before differentiating (Barres et al., *Development* 120:1097-1108 (1994); Temple and Raff, *Cell* 44.773-779 (1986)). However, the component regulating the clock was not known.

When stimulated to divide by mitogens, this intracellular OPC clock measures the passage of time independent of additional external cues (Barres et al., *Development* 120: 1097-1108 (1994)). Only once sufficient time has passed do dividing OPCs finally respond to environmental cues such as retinoic acid (RA) and thyroid hormone (T3) by dropping out of the cell cycle and differentiating into mature OLs (Barres et al., *Development* 120:1097-1108 (1994)). These external cues are required to trigger the "effector" component of the clock that promotes differentiation, as in the absence of such external cues OPCs can proliferate indefinitely in the presence of mitogens (Barres et al., Development 120:1097-1108 (1994); Tang et al., *J. Cell Biol.* 148:971-984 (2000)). The clock mechanism also relies on mitogen signaling, as in the absence of mitogen stimulation OPCs immediately initiate OL differentiation regardless of the status of the timer or T3 signaling (Barres et al., *Cell* 70:31-46 (1992); Barres et al., *Development* 118:283-295 (1993); Raff et al., *Nature* 303: 390-396 (1983)). Interestingly, mitogen withdrawal and the clock mechanism do not induce OL maturation via identical pathways, as mitogen withdrawal and T3 exposure differentially alter gene expression in early differentiating OLs, and genes distinctly required for T3-mediated OL differentiation have been identified (Billon et al., *Development* 131:1211-1220 (2004); Tokumoto et al., *EMBO J.* 20:5261-5268 (2001)).

The importance of the clock mechanism in regulating the timing of OL generation in vivo is demonstrated by the fact that hypothyroid animals have delayed myelination, whereas hyperthyroid animals have accelerated myelin formation (Dussault and Ruel, *Ann. Rev. Physiol.* 49:321-334 (1987); Walters and Morell, *J. Neurochemistry* 36:1792-1801 (1981)). While the extrinsic cues that trigger the clock effector have been extensively studied, the components of the intracellular timer that intrinsically regulate when an OPC will differentiate remain largely uncharacterized. Cell cycle arrest is an obligate step in the terminal differentiation of many mammalian cell types, including cells of the nervous system such as OLs (Casaccia-Bonnefil and Liu, *Development* 126:4027-4037 (2003)). Several groups have investigated the links between cell cycle regulation and OL differentiation. During OL differentiation, activity of the G1-S phase checkpoint complex CyclinE—cyclin-dependent kinase 2 (cdk2) decreases (Ghiani and Gallo, *J. Neurosci.* 21:1274-1282 (2001)). CyclinE-cdk2 complex formation is inhibited by members of the Cip/Kip family of cyclin-dependent kinase inhibitor proteins (Cunningham and Roussel, *Cell Growth Differ.* 12:387-396 (2001)), and all three members of this family, $p21^{Cip1}$, $p27^{Kip1}$, and $p57^{Kip2}$, have been implicated in regulating various stages of OL differentiation. $p27^{Kip1}$ appears to be specifically involved in inhibiting OPC proliferation and not induction the OL differentiation program, whereas $p21^{Cip1}$ is required for OL differentiation but not cessation of the cell cycle (Casaccia-Bonnefil et al., *Development* 126:4027-4037 (1999); Tang et al., *J. Cell. Biochem.* 76.270-279 (1999); Zezula et al., *EMBO Rep.* 2:27-34 (2001)). In zebrafish, $p57^{Kip2}$ has been implicated in the specification of OPCs from uncommitted neural precursor cells (Park et al., *J. Neurosci.* 25:6836-6844 (2005)).

As demonstrated herein, $p57^{Kip2}$ is an important component of the OPC timer affecting the mechanism that couples the regulation of OPC proliferation and differentiation. For example, it is demonstrated in vitro that all daughters of a clone of OPCs share the same level of $p57^{Kip2}$ immunoreactivity, that $p57^{Kip2}$ levels increase over time in proliferating OPCs, and that $p57^{Kip2}$ levels regulate how many times a given OPC can divide before differentiating. These findings reveal a novel part of the mechanism by which OPCs keep time and can be applied to similar timers in many other precursor cell types.

Modulation of Neural Cell Cycle and Myelin Repair

According to one or more findings disclosed herein, the present invention provides a method of regulating proliferation or differentiation of a neural cell. Regulation of neural cell proliferation or differentiation is particularly relevant in a variety of CNS and PNS disorders. Such disorder include but are not limited to Multiple Sclerosis (MS), Progressive Multifocal Leukoencephalopathy (PML), Encephalomyelitis, Central Pontine Myelolysis (CPM), Anti-MAG Disease, Leukodystrophies: Adrenoleukodystrophy (ALD), Alexander's Disease, Canavan Disease, Krabbe Disease, Metachromatic Leukodystrophy (MLD), Pelizaeus-Merzbacher Disease, Refsum Disease, Cockayne Syndrome, Van der Knapp Syndrome, Zellweger Syndrome, Guillain-Barre Syndrome (GBS), chronic inflammatory demyelinating polyneuropathy (CIDP), multifocal motor neuropathy (MMN), spinal cord injury (e.g., trauma or severing of), Alzheimer's Disease, Huntington's Disease, Amyotrophic Lateral Sclerosis, Parkinson's Disease, and optic neuritis, which have been linked to the degeneration of neural cells in particular locations of the CNS, leading to the inability of these cells or the brain region to carry out their intended function.

The method of regulating neural cell proliferation or differentiation comprises the steps of contacting said neural cell with a bioactive agent effective in modulating the activity or expression level of $p57^{Kip2}$ in said neural cell, thereby regulating said proliferation or differentiation of said neural cell. The present invention also provides a method of regulating proliferation or differentiation of a neural comprising contacting said neural cell with a bioactive agent effective in modulating the activity or expression level of one or more oligodendrocyte-regulated transcription factors or myelin-enriched genes implicated in a discrete phase of differentiation of said neural cell. A preferred example of an oligodendrocyte-regulated transcription factor is ZFP536.

Exemplary neural cells whose proliferation or differentiation process can be modulated include without limitation glial cells, especially oligodendrocytes (OLs). Oligodendrocytes (OLs) are the myelin forming cells of the CNS, which are generated from proliferating, immature oligodendrocyte precursor cells (OPCs). The present disclosure identifies cell cycle components involved in various stages of OLs' lineage from precursor OPC cells. In addition, the disclosure provides mechanisms by which OPC proliferation and OL differentiation can be modulated, through modulation of activity of such cell cycle components or transcription factors and any other myelin-enriched genes. As such the present invention provides compositions and methods to enhance myelination or remyelination by modulation of OPC proliferation and differentiation. Such modulation is effected by targeting the activity/function of one or more genes or gene products involved in OPCs proliferation and OLs differentiation. For example, bioactive agents can be utilized to modulate the activity/function (e.g., expression levels and or activity) of such cell cycle components. In other words, such cell cycle components involved in OPC proliferation and differentiation (e.g., FIGS. 7, 10 and 21), can be targeted to enhance or slow the intrinsic clocks that regulate cellular differentiation and proliferation.

Modulating the activity or expression level of any exemplary gene implicated in oligodendrocyte proliferation or differentiation can be ascertained by a variety of methods. For example, detection of a change in gene expression level can be conducted in real time in an amplification assay. In one aspect, the amplified products can be directly visualized with fluorescent DNA-binding agents including but not limited to DNA intercalators and DNA groove binders. Because the amount of the intercalators incorporated into the double-stranded DNA molecules is typically proportional to the amount of the amplified DNA products, one can conveniently determine the amount of the amplified products by quantifying the fluorescence of the intercalated dye using conventional optical systems in the art. DNA-binding dye suitable for this application include SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, and the like.

In another aspect, other fluorescent labels such as sequence specific probes can be employed in the amplification reaction to facilitate the detection and quantification of the amplified products. Probe-based quantitative amplification relies on the sequence-specific detection of a desired amplified product. It utilizes fluorescent, target-specific probes (e.g., TaqMan probes) resulting in increased specificity and sensitivity. Methods for performing probe-based quantitative amplification are well established in the art and are taught in U.S. Pat. No. 5,210,015.

In yet another aspect, conventional hybridization assays using hybridization probes that share sequence homology with neural cycle related genes can be performed. Typically, probes are allowed to form stable complexes with the target polynucleotides contained within the biological sample derived from the test subject in a hybridization reaction. It will be appreciated by one of skill in the art that where antisense is used as the probe nucleic acid, the target polynucleotides provided in the sample are chosen to be complementary to sequences of the antisense nucleic acids. Conversely, where the nucleotide probe is a sense nucleic acid, the target polynucleotide is selected to be complementary to sequences of the sense nucleic acid.

As is known to one skilled in the art, hybridization can be performed under conditions of various stringencies. Suitable hybridization conditions for the practice of the present invention are such that the recognition interaction between the probe and target neural cell cycle gene is both sufficiently specific and sufficiently stable. Conditions that increase the stringency of a hybridization reaction are widely known and published in the art. (See, for example, Sambrook, et al., (1989), supra; Nonradioactive In Situ Hybridization Application Manual, Boehringer Mannheim, second edition). The hybridization assay can be formed using probes immobilized on any solid support, including but are not limited to nitrocellulose, glass, silicon, and a variety of gene arrays. A preferred hybridization assay is conducted on high-density gene chips as described in U.S. Pat. No. 5,445,934.

For a convenient detection of the probe-target complexes formed during the hybridization assay, the nucleotide probes are conjugated to a detectable label. Detectable labels suitable for use in the present invention include any composition detectable by photochemical, biochemical, spectroscopic, immunochemical, electrical, optical, or chemical means. A wide variety of appropriate detectable labels are known in the art, which include fluorescent or chemiluminescent labels, radioactive isotope labels, enzymatic or other ligands. In preferred embodiments, one will likely desire to employ a fluorescent label or an enzyme tag, such as digoxigenin, B-galactosidase, urease, alkaline phosphatase or peroxidase, avidin/biotin complex.

The detection methods used to detect or quantify the hybridization intensity will typically depend upon the label selected above. For example, radiolabels may be detected using photographic film or a phosphoimager. Fluorescent markers may be detected and quantified using a photodetector to detect emitted light. Enzymatic labels are typically detected by providing the enzyme with a substrate and measuring the reaction product produced by the action of the enzyme on the substrate; and finally colorimetric labels are detected by simply visualizing the colored label.

An agent-induced change in expression neural cell cycle related genes can also be determined by examining the corresponding gene products. Determining the protein level typically involves a) contacting the protein contained in a biological sample comprising myelinating cells with an agent that specifically bind to the neural cell cycle related gene-encoded protein; and (b) identifying any agent:protein complex so formed. In one aspect of this embodiment, the agent that specifically binds a protein is an antibody, preferably a monoclonal antibody.

The bioactive agents utilized in the subject methods are effective in modulating the activity or expression level of a gene implicated in neural cell proliferation or differentiation. Modulation may involve augmenting or decreasing the activity or expression level of a gene of interest. For example, an agent can be utilized which enhances expression levels of components necessary to enhance proliferation or differentiation, or enhance responsiveness to external cues that enhance proliferation or differentiation. Therefore, bioactive agents can be an agonist or antagonist relative to cell cycle components, transcription factors and myelin-enriched proteins disclosed herein that are implicated in OPC proliferation and differentiation. Non-limiting exemplary categories of such bioactive agents are a peptide, polypeptide, aptamer, siRNA, small organic molecule, pharmaceutical or antibody, or combinations thereof, which can target gene products for any of the genes disclosed herein that are related to neural cell cycle, including proliferation or differentiation.

Depending on the characteristics of the agent, an agent can be delivered via any of the modes of delivery known to one of skill in the art including delivery via systemic or localized delivery, delivery via plasmid vectors, viral vectors or non-viral vector systems, pharmaceutical, including liposome formulations and minicells. The agents can be selected based on whether they affect promote activity (e.g., enhance expression levels) or inhibit activity (e.g., reduce expression levels or block function through binding to the target molecule). In some embodiments, the agent co-administered to effect either immunomodulation, myelin repair/remyelination or axonal protection is expressed from a nucleic acid sequence, which are further described herein below.

In some embodiments, bioactive agents can be expressed in cells or tissues so that such agents are expressed to impart their desired function. Typically, gene expression is placed under the control of certain regulatory elements, including constitutive or inducible promoters, tissue-specific regulatory elements, and enhancers. Such a gene is said to be "operably linked to" the regulatory elements. For example, constitutive, inducible or cell/tissue specific promoters can be incorporated into an expression vector to regulate expression of a gene that is expressed in a host cell. Therefore, depending on the promoter elements utilized, a bioactive agent can be expressed as desired so as to block, enhance or promote the cell cycle components described herein. For example, an agent that blocks function of, or binds to, $p57^{Kip2}$ can be temporally expressed in cells/tissue resulting in enhanced proliferation. In another example, a bioactive agent can temporally express in cells/tissue that itself promotes/enhances expression of $p57^{Kip2}$ thus promoting/enhancing OPC differentiation into OLs, which ultimately results in myelination/remyelination.

Neural cell-specific promoters can be used to regulate expression of bioactive agents. For example, where the bioactive agent is a polypeptide that itself enhances or inhibits cell cycle components related to neural cell proliferation/differentiation, it can be encoded by a nucleic acid sequence which is operably linked to neural cell-specific transcription regulatory elements. Exemplary transcriptional regulatory sequences/elements include transcriptional regulatory sequences/elements selected from the genes encoding the following proteins: the PDGFa receptor, proteolipid protein (PLP), the glial fibrillary acidic gene (GFAP), myelin basic protein (MBP), neuron specific enolase (NSE), oligodendrocyte specific protein (OSP), myelin oligodendrocyte glycoprotein (MOG), microtubule-associated protein 1B (MAP1B), Thy1.2, CC1, ceramide galactosyltransferase (CGT), myelin associated glycoprotein (MAG), oligodendrocyte-myelin glycoprotein (OMG), cyclic nucleotide phosphodiesterase (CNP), NOGO, myelin protein zero (MPZ), peripheral myelin protein 22 (PMP22), protein 2 (P2), Tyrosine hydroxylase, BSF1, dopamine 3-hydroxylase, Serotonin 2 receptor, choline acetyltransferase, galactocerebroside (GalC), and sulfatide. Furthermore, examples of neural cell-specific promoters are known in the art, such as disclosed in U.S. Patent Application Publication No. 2003/0110524; see also the website <chinook.uoregon.edu/promoters.html>. Additionally, cell/tissue specific promoters are also known in the art.

In some embodiments, the transcriptional regulatory elements are inducible. For example, non-limiting examples of inducible promoters include metallothionine promoters and mouse mammary tumor virus promoters. Other examples of promoters and enhancers effective for use in the recombinant vectors of the present invention include, but are not limited to, CMV (cytomegalovirus), SV40 (simian virus 40), HSV (herpes simplex virus), EBV (Epstein-Barr virus), retrovirus, adenoviral promoters and enhancers, and smooth-muscle-specific promoters and enhancers; strong constitutive promoters that: will be suitable for use as the heterologous promoter for expression include the adenovirus major later promoter, the cytomegalovirus immediate early promoter, the .beta. actin promoter, or the .beta. globin promoter. Promoters activated by RNA polymerase III could also be used.

In some embodiments, inducible promoters that have been used to control gene expression include the tetracycline operons, RU 486, heavy metal ion inducible promoters such as the metallothionein promoter; steroid hormone inducible promoters, such as the MMTV promoter, or the growth hormone promoter; promoters which would be inducible by the helper virus such as adenovirus early gene promoter inducible by adenovirus E1 A protein, or the adenovirus major late promoter; herpesvirus promoter inducible by herpesvirus proteins such as VP16 or 1CP4; vaccinia or poxvirus inducible promoters or promoters inducible by a poxvirus RNA polymerase; bacterial promoter such as that from T7 phage which would be inducible by a poxvirus RNA polymerase; or a bacterial promoter such as that from T7 RNA polymerase, or edyasone. In one embodiment, a promoter element is a hypoxic response elements (HRE) recognized by a hypoxia-inducible factor-1 (HIF-1) which is one of the key mammalian transcription factors that exhibit dramatic increases in both protein stability and intrinsic transcriptional potency during low-oxygen stress. HRE has been reported in the 5' or 3' flanking regions of VEGF and Epo and several other genes. The core consensus sequence is (A/G)CGT(G/C)C. HREs isolated from Epo and VEGF genes have been used to regulate several genes, such as suicide and apoptosis gene expression in hypoxic tumors to enhance tumor killing.

Furthermore, where expression of the transgene in particular subcellular location is desired, the transgene can be operably linked to the corresponding subcellular localization sequences by recombinant DNA techniques widely practiced in the art. Exemplary subcellular localization sequences include but are not limited to (a) a signal sequence that directs secretion of the gene product outside of the cell; (b) a membrane anchorage domain that allows attachment of the protein to the plasma membrane or other membraneous compartment of the cell; (c) a nuclear localization sequence that mediates the translocation of the encoded protein to the nucleus; (d) an endoplasmic reticulum retention sequence (e.g. KDEL sequence) that, confines the encoded protein primarily to the ER; (e) proteins can be designed to be farnesylated so as to associate the protein with cell membranes; or (f) any other sequences that play a role in differential subcellular distribution of an encoded protein product.

Vectors utilized in in vivo or in vitro methods can include derivatives of SV-40, adenovirus, retrovirus-derived DNA sequences and shuttle vectors derived from combinations of functional mammalian vectors and functional plasmids and phage DNA. Eukaryotic expression vectors are well known, e.g. such as those described by Southern and Berg, *J. Mol. Appl. Genet.* 1:327-341 (1982); Subramini et al., *Mol. Cell. Biol.* 1:854-864 (1981), Kaufmann and Sharp, I 159:601-621 (1982); Scahill et al., *Proc. Natl. Acad. Sci. USA* 80:4654-4659 (1983) and Urlaub and Chasin, *Proc. Natl. Acad. Sci. USA* 77:4216-4220 (1980), which are hereby incorporated by reference. The vector used in the methods of the present invention may be a viral vector, preferably a retroviral vector. Replication deficient adenoviruses are preferred. For example, a "single gene vector" in which the structural genes of a retrovirus are replaced by a single gene of interest, under the control of the viral regulatory sequences contained in the long terminal repeat, may be used, e.g. Moloney murine leukemia virus (MoMulV), the Harvey murine sarcoma virus (HaMuSV), murine mammary tumor virus (MuMTV) and the murine myeloproliferative sarcoma virus (MuMPSV), and avian retroviruses such as reticuloendotheliosis virus (Rev) and Rous Sarcoma Virus (RSV), as described by Eglitis and Andersen, *BioTechniques* 6(7):608-614 (1988), which is hereby incorporated by reference. Expression constructs may be viral or nonviral vectors. Viral vectors that are considered part of the invention include, but are not limited to, adenovirus, adeno-associated virus, herpesvirus, retrovirus (including lentiviruses), polyoma virus, or vaccinia virus.

Recombinant retroviral vectors into which multiple genes may be introduced may also be used according to the methods of the present invention. Vectors with internal promoters containing a cDNA under the regulation of an independent promoter, e.g. SAX vector derived from N2 vector with a selectable marker (noe.sup.R) into which the cDNA for human adenosine deaminase (hADA) has been inserted with its own regulatory sequences, the early promoter from SV40 virus (SV40), may be designed and used in accordance with the methods of the present invention by methods known in the art.

In mammalian host cells, a number of viral-based expression systems can be utilized. In cases where an adenovirus is used as an expression vector, the nucleotide sequence of interest (e.g., encoding a therapeutic capable agent) can be ligated to an adenovirus transcription or translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the AQP1 gene product in infected hosts. (See e.g., Logan & Shenk, *Proc. Natl. Acad. Sci. USA* 8 1:3655-3659 (1984)).

Specific initiation signals can also be required for efficient translation of inserted therapeutic nucleotide sequences. These signals include the ATG initiation codon and adjacent sequences. In cases where an entire therapeutic gene or cDNA, including its own initiation codon and adjacent sequences, is inserted into the appropriate expression vector, no additional translational control signals can be needed. However, in cases where only a portion of the therapeutic coding sequence is inserted, exogenous translational control signals, including, perhaps, the ATG initiation codon, may be provided. Furthermore, the initiation codon should be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (See e.g., Bittner et al., *Methods in Enzymol.* 153:516-544 (1987)).

In some embodiments, neural cells, such as glial cells are genetically modified by utilization of the foregoing vectors, so as to produce different expression levels of a gene product that results in modulation of neural cell cycle, such as oligodendrocyte differentiation or OPC proliferation. Genetically modifying or transfecting cells either in vitro or in vivo can be conducted utilizing methods known in the art, as described in references noted herein above, and such as disclosed in U.S. Pat. No. 6,998,118, 6,670,147 or 6,465,246.

The bioactive agent can be a peptide, polypeptide, peptidomimetic, antibody, antisense, aptamer, siRNA or small molecule that targets and modulates expression of $p57^{Kip2}$, CSCRP1, TMEM10, UHRF1, ZFP536, HMGa2, MLR1, TCF7L2, SIRt2, CARHSP1, CREB3L2, CHES1, PCAF, LITAF, LRRFIP1, CDY1, NFKBIB, ELF1, PRICKLE1, RNF141, APLP1, APP, KUA, KLF13, ZFP 276, LMO1, EGR1, ETV5, CEBPb, UHFR1, HMGb2, DNMT1, SOX11, HMBb3, TRIP13, LMO4, FOSL2, MYC, CITED2, HMGa1, RUVBL1, TAF9, TSC22d4, KLF9, PBX3, TLE1, CSRP1, NFE2L2, MOG, ABCA8, TTYH2, DIXDC1, TENS1, WIPI49, HYDIN, CRYAB, RICTOR, PRKCA, PITPNC1, DEK, NRP2, HMGa1, BRUNOL5, HN1, TUBB, CDK6, GMNN, CLIC1, or KPNA2, thus altering the corresponding activity of each product relative to neural cell cycle. In preferred embodiments, the gene is HMGa2, $p57^{Kip2}$, ZFP536, KLF13, CEBPb, UHRF1, HMGa1, KLF9, TLE1, or CSRP1. In yet other preferred embodiments, the gene is KLF9, for example, promoting its expression or activity. In one aspect, the biological agent can be a peptide, polypeptide, or peptidomimetic of the above named target genes. For clarity, "targeting" includes binding directly or indirectly to a gene product, or functional site, of such a product (e.g., antibody binding and neutralizing $p57^{Kip2}$, thus modulating its CDK inhibitory activity).

In one aspect, the bioactive agent utilizes "RNA interference (RNAi)" as a mechanism to effect neural cell proliferation or differentiation. RNAi is a process of sequence-specific, post-transcriptional gene silencing initiated by double stranded RNA (dsRNA) or siRNA. RNAi is seen in a number of organisms such as Drosophila, nematodes, fungi and plants, and is believed to be involved in anti-viral defense, modulation of transposon activity, and regulation of gene expression. During RNAi, dsRNA or siRNA induces degradation of target mRNA with consequent sequence-specific inhibition of gene expression.

As used herein, a "small interfering RNA" (siRNA) is a RNA duplex of nucleotides that is targeted to a gene interest. A "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure.

In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' and/or 5' overhang portions. In some embodiments, the overhang is a 3' and/or a 5' overhang 0, 1, 2, 3, 4 or 5 nucleotides in length. The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal In one aspect of the invention, bioactive agents are administered to a cell or subject that modulate activity of two or more Cip/Kip cell cycle inhibitors, myelin-enriched genes, or transcription factors. In some embodiments, the CDKIs include $p21^{Cip1}$, $p18^{INK4c}$, $p27^{Kip1}$, p53, $p57^{Kip2}$, or p73. In preferred embodiments the Cip/Kip cell cycle inhibitor is $p57^{kip2}$, and the myelin-enriched gene and/or transcription factor is OL-regulated, as in FIG. 7, 10, 11, or 21. More preferably, the transcription factor is selected from a highlighted gene in FIG. 30. As such, the combination of such bioactive agents can be administered sequentially over a period of time or administered concurrently for a combined synergistic effect on cell cycle OPC proliferation and differentiation. Therefore, in one embodiment bioactive agents that upregulate activity ("upregulators") of two or more Cip/Kip cell cycle inhibitors is administered to a cell/subject so as to enhance OPC differentiation. In another embodiment, bioactive agents that downregulate activity ("downregulators") of two or more Cip/Kip cell cycle inhibitors are administered to a cell/subject so as to enhance OPC proliferation into OLs thus promoting myelin production. In yet another embodiment, downregulators are administered first to induce proliferation of OPCs so as to increase the baseline number of progenitor cells, followed by administration of upregulators so as to enhance differentiation so as to optimize the promotion of remyelination.

In one embodiment a CDKI upregulator as well as a second component that upregulates genes associated with mature (late-stage) oligodendrocyte cells are administered concurrently or sequentially to cooperatively promote late-stage oligodendrocyte differentiation. Furthermore, promotion of OL differentiation enhances remyelination. In one embodiment bioactive agents are administered to a cell/subject that upregulate $p57^{Kip2}$ and ZFP536 activity. For example, nucleic acid molecules are administered that induce endogenous $p57^{Kip2}$ and ZFP536 activity, or which themselves encode $p57^{Kip2}$ and ZFP536 activity.

In some embodiments, neural cells, particularly glial cells, more particularly, astrocytes, oligodendrocytes, SCs, OPCs or NSCs are cultured in the presence of such bioactive agents. In some embodiments the bioactive agents are specific for HMGa2, $p57^{Kip2}$, ZFP536, KLF13, CEBPb, UHRF1, HMGa1, KLF9, TLE1, or CSRP1. In preferred embodiments, the bioactive agents are specific for KLF9.

In some embodiments, the subject bioactive agents are antibodies targeting one or more of the genes implicated in neural cell proliferation or differentiation. Producing antibodies specific for polypeptides encoded by any of the preceding genes (or specific to active sites of the same) is known to one of skill in the art, such as disclosed in U.S. Pat. Nos. 6,491,916; 6,982,321; 5,585,097; 5,846,534; 6,966,424 and U.S. Patent Application Publication Nos. 2005/0054832; 2004/0006216; 2003/0108548, 2006/002921 and 2004/0166099, each of which is incorporated herein by reference. For example, monoclonal antibodies can be obtained by injecting mice with a composition comprising the antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen that was injected, culturing the clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, for example, Coligan et al., (eds.), CURRENT PROTOCOLS IN IMMUNOLOGY, pages 2.7.1 to 2.7.12 and pages 2.9.1 to 2.9.3 (John Wiley & Sons, Inc. 1991). Also, see Baines et al., "Purification of Immunoglobulin G (IgG)," in METHODS IN MOLECULAR BIOLOGY, VOL. 10, pages 79 to 104 (The Humana Press, Inc. 1992).

Suitable amounts of well-characterized antigen for production of antibodies can be obtained using standard techniques. As an example, $p57^{Kip2}$ antigen can be immunoprecipitated from cells using the deposited antibodies described by Tedder et al., U.S. Pat. No. 5,484,892. Alternatively, such antigens can be obtained from transfected cultured cells that overproduce the antigen of interest. Expression vectors that comprise DNA molecules encoding each of these proteins can be constructed using published nucleotide sequences. See, for example, Wilson et al., *J. Exp. Med.* 173:137-146 (1991); Wilson et al., *J. Immunol.* 150:5013-5024 (1993). As an illustration, DNA molecules encoding CD3 can be obtained by synthesizing DNA molecules using mutually priming long oligonucleotides. See, for example, Ausubel et al., (eds.), CURRENT PROTOCOLS IN MOLECULAR BIOLOGY, pages 8.2.8 to 8.2.13 (1990). Also, see Wosnick et al., *Gene* 60:115-127 (1987); and Ausubel et al. (eds.), SHORT PROTOCOLS IN MOLECULAR BIOLOGY, 3rd Edition, pages 8-8 to 8-9 (John Wiley & Sons, Inc. 1995). Established techniques using the polymerase chain reaction provide the ability to synthesize genes as large as 1.8 kilobases in length. (Adang et al., *Plant Molec. Biol.* 21:1131-1145 (1993); Bambot et al., *PCR Methods and Applications* 2:266-271 (1993); Dillon et al., "Use of the Polymerase Chain Reaction for the Rapid Construction of Synthetic Genes," in METHODS IN MOLECULAR BIOLOGY, Vol. 15: PCR PROTOCOLS: CURRENT METHODS AND APPLICATIONS, White (ed.), pages 263 268, (Humana Press, Inc. 1993)). In a variation, monoclonal antibody can be obtained by fusing myeloma cells with spleen cells from mice immunized with a murine pre-B cell line stably transfected with cDNA which encodes the antigen of interest. See Tedder et al., U.S. Pat. No. 5,484,892.

In some embodiments, an agent is administered to promote differentiation of OPCs into mature oligodendrocytes. Alternatively, such an agent can induce proliferation of cells involved in myelination or cells involved in functional interactions related to myelination, such neural cells include but are not limited to oligodendrocyte progenitor cells (OPC), Schwann cells (SCs), olfactory bulb ensheathing cells, astrocytes, microglia and neural stem cells (NSCs). In another aspect, such neural cells can be administered prior to, concurrent with or subsequent to administration of a bioactive agent. In other embodiments, one or more types of neural cells can be administered with one or more types of bioactive agents. For clarity, type means for example different types of cells (e.g., oligodendrocyte and astrocyte) or different types of bioactive agents (e.g., antibody and antisense).

Neural cell differentiation such as differentiation of OPCs can be ascertained by a variety of methods known in the art. For example, one can test for oligodendrocyte differentiation or maturation by assaying for a panel of markers indicative of myelination. Such markers include without limitation CC1, myelin basic protein (MBP), ceramide galactosyltransferase (CGT), myelin associated glycoprotein (MAG), myelin oligodendrocyte glycoprotein (MOG), oligodendrocyte-myelin glycoprotein (OMG), cyclic nucleotide phosphodiesterase (CNP), NOGO, myelin protein zero (MPZ), peripheral myelin protein 22 (PMP22), protein 2 (P2), galactocerebroside (GalC), sulfatide and proteolipid protein (PLP). MPZ, PMP22 and PO are preferred markers for Schwann cells.

Screening Assays

The present invention provides a method of screening for a candidate bioactive agent effective in regulating proliferation or differentiation of a test neural cell. The method comprises a) contacting said test neural cell with said candidate bioactive agent; b) assaying for a change in $p57^{Kip2}$ activity or $p57^{Kip2}$ expression level in said test neural cell as compared to a control neural cell, wherein said change in $p57^{Kip2}$ activity or $p57^{Kip2}$ expression level is indicative of a bioactive agent effective in regulating proliferation or differentiation of said test neural cell. In a related embodiment, the present invention provides another screening method that involves the steps of a) contacting said test neural cell with said candidate bioactive agent; b) assaying for a change in the activity or expression level of one or more OL-regulated transcription factors or myelin-enriched genes in said test neural cell as compared to a control neural cell; wherein said change in the activity or expression level of one or more OL-regulated transcription factors or myelin-enriched genes is indicative of a bioactive agent effective in regulating proliferation or differentiation of said test neural cell.

In some aspects, the invention is directed to methods of screening candidate agents to determine if such bioactive agents modulate CDK-inhibitor-mediated cell signaling, such as modulation of $p57^{Kip2}$ or other cell cycle arrest genes, as other cell cycle arrest genes could partially compensate for the loss of $p57^{Kip2}$. $p27^{Kip1}$, a second member of the Cip/Kip family of cell cycle inhibitor genes, has been previously implicated in OL differentiation in vitro (Miskimins et al., *J. Neurosci. Res.* 67:100-105 (2002); Tang et al., *J. Cell. Biochem.* 76:270-279 (1999); Wei et al., *Mol. Cell. Biol.* 23:4035-4045 (2003); Wei et al., *J. Neurosci. Res.* 78:796-802 (2004)). For example, $p27^{Kip1-/-}$ mice demonstrate a delay, but not a block, in mature OL generation and an increase in OPC proliferation in vivo (Casaccia-Bonnefil et al., *Development* 126:4027-4037 (1999)).

In another aspect: of the invention, cells are utilized to screen candidate agents to determine if such agents modulate OL-specific or OL-regulated genes (together OL-related genes), thus identifying a candidate agent that either downregulates or upregulates OL-related genes, and thereby an agent that promotes or inhibits OL proliferation or differentiation. Modulation of OL-regulated genes can be assayed by analyzing or comparing gene expression profiles, for example, genes listed in FIG. 7, 10, or 21. In preferred embodiments, the genes to be modulated are HMGa2, $p57^{Kip2}$, ZFP536, KLF13, CEBPb, UHRF1, HMGa1, KLF9, TLE1, or CSRP1. Such a candidate agent can be utilized in methods for inducing neural cell proliferation or differentiation in treating a neuropathy.

In some embodiments, a candidate agent is administered in distinct temporal stages of the precursor cell cycle so as to determine if the agent affects early or late genes thus early or mature differentiated cells. For example, a candidate agent can be screened to determine if genes associated with young or mature OLs are affected, such as those induced early or late (e.g., FIGS. 12, 13, 16, 17, 18, 19). Screening OPCs for early or late gene induction/downregulation deficiency may provide better therapeutic targeting to promote OL differentiation, by selecting agents that modulate activity of genes identified herein to be associated with early and late stage OL differentiation or OPC proliferation. Furthermore, such agents can be administered to a subject to promote normal, complete maturation of OLs from different stages of undifferentiated OPCs or immature OLs. Such agents can also be utilized in reconstructing the genetic program required to produce a myelinating OL from different stages of OL differentiation. In other embodiments, a candidate agent is screened to determine if an agent retards younger or older OPC differentiation (e.g., FIGS. 44-47, 49-55).

In a related but separate embodiment, the present invention provides a method of assessing the ability of a test immature OL or a test OPC to differentiate. The method involves the steps of (a) assaying an expression level of one or more OL-regulated transcription factors or myelin-enriched genes present in said test immature OL or said test OPC, wherein said one or more oligodendrocyte-regulated transcription factors are implicated in a discrete phase of OL differentiation, said phase being selected from an early phase of differentiation and a late phase of differentiation; and (b) comparing said expression level of (a) to that of a control immature OL or a control OPC, wherein a statistically significant increase in expression of said one or more OL-regulated transcription factors or myelin-enriched genes of said early and/or late phase implicates the ability of said test immature OL or said test OPC to differentiate. Such assessment can be indicative of the reparative potential of a MS lesion. For example, an OPC or immature OL may express an OL-specific gene, such as in FIGS. 7, 10, or 21, at a statistically significant increased level compared to a control cell, indicating an ability to differentiate more quickly or robustly than the control cell. Typically, statistical significance may be determined by Student's t-test, ANOVA analysis and/or pattern recognition methods. The capacity to differentiate more robustly may indicate the potential for the cell to remyelinate.

In some aspects, the assaying step is performed in vitro. In another aspect of the method, the assaying step is performed in vivo. A variety of in vitro and in vivo methodologies are available in the art. For example, in vitro assays can be employed to promote OL proliferation or differentiation in cell culture (e.g. FIG. 22). In vivo assays may be performed as described above in transplantation methods, or as described below with animal models. Assay of expression profiles, such as by gene chip or array technology (e.g., gene chips are readily available through multiple commercial vendors, Agilent, Affymetrix, Nanogen, etc.), immunoblot analysis, RT-PCR, and other means is well known to one of ordinary skill in the art.

In another embodiment, one or more candidate bioactive agents is placed in contact with such a culture of cells, and before, concurrent or subsequent to such contact, one or more myelin repair- or axonal protection-inducing agent is also administered to the cells, to determine which combination of bioactive agent and myelin repair or axonal protection agent produces a synergistic effect. For example, a synergistic effect may be observed in culture by utilizing time-lapse microscopy revealing a transition from precursor cell types to myelinating oligodendrocyte. Furthermore, progenitor cells can be transfected with a membrane-targeted form of enhanced green fluorescent protein (EGFP) to facilitate convenient fluorescence microscopy in detection of differentiated cells. Therefore, in various embodiments, cells can be cultured and/or genetically modified to express target polypeptides utilizing techniques that are known in the art, such as disclosed in U.S. Pat. Nos. 7,008,634; 6,972,195; 6,982,168; 6,962,980; 6,902,881; 6,855,504; or 6,846,625.

In one embodiment, OPCs are obtained from a subject and expanded in culture from about 5, 6, 7, 8, 9 to about 14 days. In other embodiments, the cells can be cultured for 1, 2, 3, 4, 5, 6, 7, 8, or 9 days. In some embodiments, such cells can be transfected with one or more vectors during expansion in culture.

Another aspect of the present invention is a system for the screening assays. Accordingly, FIG. 60 is a block diagram showing a representative example logic device through which data relating to the screening assays may be generated. FIG. 60 shows a computer system (or digital device) 800 to receive and store data, such as expression profiles of OL-regulated genes of neural cells contacted with or without a candidate bioactive agent. The computer system may also perform analysis on the data, such as comparing expression profiles between neural cells contacted with a bioactive agent, and neural cells that were not contacted with bioactive agents. The computer system 800 may be understood as a logical apparatus that can read instructions from media 811 and/or network port 805, which can optionally be connected to server 809 having fixed media 812. The system shown in FIG. 60 includes CPU 801, disk drives 803, optional input devices such as keyboard 815 and/or mouse 816 and optional monitor 807. Data communication can be achieved through the indicated communication medium to a server 809 at a local or a remote location.

The communication medium can include any means of transmitting and/or receiving data. For example, the communication medium can be a network connection, a wireless connection or an interne connection. Such a connection can provide for communication over the World Wide Web. It is envisioned that data relating to the present invention can be transmitted over such networks or connections for reception and/or review by a party 822. The receiving party 822 can be but is not limited to an individual. In one embodiment, a computer-readable medium includes a medium suitable for transmission of a result of an analysis of expression profiles resulting from neural cells contacted with a candidate bioactive agent. The medium can include a result, such as if the bioactive agent modulates the expression of an OL-regulated gene, derived using the methods described herein.

In practicing the screening methods of the present invention, any known methods applicable to ascertain oligodendrocyte proliferation or differentiation including those exemplified herein can be utilized.

Microarrays

The subject screening methods can be performed with the use of microarrays or gene chips that are immobilized thereon, a plurality of probes corresponding to OL-regulated genes implicated in regulating OL proliferation or differentiation is provided. Accordingly, the present invention provides compositions comprising such microarrays. In one embodiment, the OL-regulated genes are transcription factors or myelin-enriched genes. In other embodiments, the OL-regulated genes are implicated in a discrete phase of OL differentiation. In preferred embodiments, the plurality of probes may correspond to genes in FIG. 7, 10, 11, or 21. In, other embodiments, the plurality of probes may correspond to one or more of HMGa2, p57$^{Kip2}$, ZFP536, KLF13, CEBPb, UHRF1, HMGa1, KLF9, TLE1, and CSRP1.

The probe refers to a polynucleotide used for detecting or identifying its corresponding target polynucleotide in a hybridization reaction. The term "hybridize" as applied to a polynucleotide refers to the ability of the polynucleotide to form a complex that is stabilized via hydrogen bonding between the bases of the nucleotide residues in a hybridization reaction. Different polynucleotides are said to "correspond" to each other if one is ultimately derived from another. For example, a sense strand corresponds to the anti-sense strand of the same double-stranded sequence. mRNA (also known as gene transcript) corresponds to the gene from which it is transcribed. cDNA corresponds to the RNA from which it has been produced, such as by a reverse transcription reaction, or by chemical synthesis of a DNA based upon knowledge of the RNA sequence. cDNA also corresponds to the gene that encodes the RNA. Polynucleotides may be said to correspond even when one of the pair is derived from only a portion of the other.

The arrays of the present invention may comprise control probes, positive or negative, for comparison purpose. The selection of an appropriate control probe is dependent on the sample probe initially selected and its expression pattern which is under investigation. Control probes of any kind can be localized at any position in the array or at multiple positions throughout the array to control for spatial variation, overall expression level, or non-specific binding in hybridization assays.

The polynucleotide probes embodied in this invention, can be obtained by chemical synthesis, recombinant cloning, e.g. PCR, or any combination thereof. Methods of chemical polynucleotide synthesis are well known in the art and need not be described in detail herein. One of skill in the art can use the sequence data provided herein to obtain a desired polynucleotide by employing a DNA synthesizer, PCR machine, or ordering from a commercial service. Selected probes are immobilized onto predetermined regions of a solid support by any suitable techniques that effect in stable association of the probes with the surface of a solid support. By "stably associated" is meant that the polynucleotides remain localized to the predetermined region under hybridization and washing conditions. As such, the polynucleotides can be covalently associated with or non-covalently attached to the support surface. Examples of non-covalent association include binding as a result of non-specific adsorption, ionic, hydrophobic, or hydrogen bonding interactions. Covalent association involves formation of chemical bond between the polynucleotides and a functional group present on the surface of a support. The functional may be naturally occurring or introduced as a linker. Non-limiting functional groups include but are not limited to hydroxyl, amine, thiol and amide. Exemplary techniques applicable for covalent immobilization of polynucleotide probes include, but are not limited to, UV cross-linking or other light-directed chemical coupling, and mechanically directed coupling (see, e.g. U.S. Pat. Nos. 5,837,832, 5,143,854, 5800992, WO 92/10092, WO 93/09668, and WO 97/10365). A preferred method is to link one of the termini of a polynucleotide probe to the support surface via a single covalent bond. Such configuration permits high hybridization efficiencies as the probes have a greater degree of freedom and are available for complex interactions with complementary targets.

Typically, each array is generated by depositing a plurality of probe samples either manually or more commonly using an automated device, which spots samples onto a number of predefined regions in a serial operation. A variety of automated spotting devices are commonly employed for production of polynucleotide arrays. Such devices include piezo or ink-jet devices, automated micro-pipetters and any of those devices that are commercially available (e.g. Beckman Biomek 2000).

The microarrays of the present invention may be useful in obtaining expression profiles of OL-regulated genes, for example genes in FIGS. 7, 10, 11, or 21, in preferred embodiments, expression profiles for one or more of HMGa2, $p57^{Kip2}$, ZFP536, KLF13, CEBPb, UHRF1, HMGa1, KLF9, TLE1, or CSRP1. The microarrays may be used for the screening assays described above. These microarrays may also be used to assess the differentiation states of oligodendrocyte-lineage cells present in several types of diseased human tissue, for example, multiple sclerosis lesions or oligodendroglioma tumor tissue.

Animal Models. In another aspect of the invention, animal subjects are utilized to screen candidate agents to determine if such agents modulate OL-specific or OL-upregulated genes (together OL-related genes), thus identifying a candidate agent that either downregulate or upregulate OL-related genes, and thereby an agent that promotes or inhibits OL proliferation or differentiation. Assay of expression profiles, such as by gene chip or array technology is well known to one of ordinary skill in the art (e.g., gene chips are readily available through multiple commercial sources).

In some aspects, screening assays for determining a beneficial therapeutically effective combination of bioactive agents directed to immunomodulation and myelin repair/remyelination or axonal protection are conducted utilizing animal models. In preferred embodiments, the animal is a small rodent, or simian species. In more preferred embodiments, the animal is a mouse, rat, guinea pig, or monkey. In some embodiments, such animal models can be utilized to screen candidates to determine if it affects neural cell proliferation or differentiation. In some embodiments, the animal can be modified in any of the genes encoding HMGa2, $p57^{Kip2}$, ZFP536, KLF13, CEBPb, UHRF1, HMGa1, KLF9, TLE1, or CSRP1. For example, a KLF9 mutant or knock-out mouse can be used to screen for agents that promote myelination, either in response to demyelination, or during development. In other embodiments, the animal can be modified for two or more genes described herein disclosing oligodendrocyte-specific genes (i.e., FIGS. 7, 10, and 30 disclosing top 50 OL upregulated genes, top 50 OL-specific expressed genes, OL-regulated genes, highly linked MS loci genes and OL-regulated transcription factors).

In some embodiments, the animal is a transgenic animal that can be a "knock-out" or "knock-in", with one or more desired characteristics. For example, in some embodiments, a transgenic animal can be modified to express or express at altered levels (i.e., up or down) an agent that promotes immunomodulation, myelin repair/remyelination or axonal protection. Therefore, such an animal is utilized to screen a plurality of different bioactive agents also directed to immunomodulation, myelin repair/remyelination or axonal protection, where if the transgenic animal comprises an agent directed to one end point, then the animal is administered an agent directed to a different end point(s), and vice versa, to identify a candidate combination of therapeutic agents that result in a synergistic therapeutic result for a neuropathy or related conditions described herein above.

As noted above, transgenic animals can be broadly categorized into two types: "knockouts" and "knockins". A "knockout" has an alteration in the target gene via the introduction of transgenic sequences that result in a decrease of function of the target gene, preferably such that target gene expression is insignificant or undetectable. A "knockin" is a transgenic animal having an alteration in a host cell genome that results in an augmented expression of a target gene, e.g., by introduction of an additional copy of the target gene, or by operatively inserting a regulatory sequence that provides for enhanced expression of an endogenous copy of the target gene. The knock-in or knock-out transgenic animals can be heterozygous or homozygous with respect to the target genes. Both knockouts and knockins can be "bigenic". Bigenic animals have at least two host cell genes being altered. A preferred bigenic animal carries a transgene encoding a neural cell-specific recombinase and another transgenic sequence that encodes neural cell-specific marker genes. The transgenic animals of the present invention can broadly be classified as Knockins.

In other embodiments, the transgenic model system can also be used for the development of biologically active agents that promote or are beneficial for neural remyelination. For example, a transgenic animal that is modified to express an agent resulting in an immunomodulatory, myelin repair or axonal protection phenotype, can be utilized in methods of screening unknown compounds to determine (1) if a compound enhances immune tolerance, suppresses an inflammatory response, or promotes remyelination and/or (2) if a compound can result in a synergistic therapeutic effect in the animal model. Moreover, neural cells can be isolated from the transgenic animals of the invention for further study or assays conducted in a cell-based or cell culture setting, including ex vivo techniques. Furthermore, the model system can be utilized to assay whether a test agent imparts a detrimental effect or reduces remyelination, e.g., post demyelination insult.

Advances in technologies for embryo micromanipulation now permit introduction of heterologous DNA into fertilized mammalian ova. For instance, totipotent or pluripotent stem cells can be transformed by microinjection, calcium phosphate mediated precipitation, liposome fusion, retroviral infection or other means. The transformed cells are then introduced into the embryo, and the embryo will then develop into a transgenic animal. In a preferred embodiment, developing embryos are infected with a viral vector containing a desired transgene so that the transgenic animals expressing the transgene can be produced from the infected embryo. In another preferred embodiment, a desired transgene is coinjected into the pronucleus or cytoplasm of the embryo, preferably at the single cell stage, and the embryo is allowed to develop into a mature transgenic animal. These and other variant methods for generating transgenic animals are well established in the art and hence are not detailed herein. See, for example, U.S. Pat. Nos. 5,175,385 and 5,175,384.

Accordingly, in some embodiments the present invention provides a method of using animal models for detecting and quantifying synergistic combinatorial treatment. In one embodiment, the method comprises the steps of: (a) inducing demyelination insult in the transgenic animal of the invention expressing an immunotolerance-inducing agent; (b) administering a candidate agent and allowing time for myelin repair to occur if it is to occur; (c) detecting and/or quantifying expression of cell-specific marker gene(s) (d) determining if and how much remyelination has occurred and if such remyelination is enhanced as compared to a control. In such an example, the control could be wild-type in which a disease model is induced, or a transgenic to which the candidate agent is not administered.

A number of methods for inducing demyelination in a test animal have been established. For instance, neural demyelination may be inflicted by pathogens or physical injuries, agents that induce inflammation and/or autoimmune responses in the test animal. A preferred method employs demyelination-induced agents including but not limited to IFN-γ and cuprizone (bis-cyclohexanone oxaldihydrazone). The cuprizone-induced demyelination model is described in Matsushima et al., *Brain Pathol.* 11:107-116 (2001). In this method, the test animals are typically fed with a diet containing cuprizone for a few weeks ranging from about 1 to about 10 weeks.

After induction of a demyelination condition by an appropriate method, the animal is allowed to recover for a sufficient amount of time to allow remyelination at or near the previously demyelinated lesions. While the amount of time required for developing remyelinated axons varies among different animals, it generally requires at least about 1 week, more often requires at least about 2 to 10 weeks, and even more often requires about 4 to about 10 weeks. Remeylination can be ascertained by observing an increase in myelinated axons in the nervous systems (e.g., in the central or peripheral nervous system), or by detecting an increase in the levels of marker proteins of a myelinating cell. The same methods of detecting demyelination can be employed to determine whether remyelination has occurred.

Candidate bioactive agents useful for the subject screening methods can comprise peptide, polypeptide, peptidomimetic, antibody, antisense, aptamer, siRNA and/or small molecule. Any agents suspected to have the ability to regulate neural cell proliferation or differentiation can be subject to the screening methods disclosed herein.

Therapeutics

Remyelination. In various embodiments, bioactive agents described herein are administered to a subject to enhance neural cell proliferation and/or differentiation. As described herein, the bioactive agent can affect a neural cell cycle by modulating expression of a neural cell cycle related gene. Alternatively, the bioactive agent itself is a product from a neural cell cycle related gene. In other words, by either means the amount of an effector of neural cell proliferation or differentiation is increased thus enhancing myelination in the CNS. Administration of such an effector can be achieved by exogenous administration of the agent itself or by providing a nucleic acid vector that encodes and expresses the agent constitutively, inducibly or in a cell specific manner, via the appropriate transcription regulatory elements described herein and known to one of ordinary skill in the art. As such the bioactive agent thus expressed can promote neural cell differentiation or proliferation. Such neural cells include OLs, OPCs, SCs, NSCs, astroctyes and microglial cells. In preferred embodiments nucleic acid vectors encode products of genes regulated during OL differentiation, genes linked to MS loci or genes encoding transcription factors that intrinsically direct OL differentiation, which include without limitation $p57^{Kip2}$, CSCRP1, TMEM10, UHRF1, ZFP536, HMGa2, MLR1, TCF7L2, SIRt2, CARHSP1, CREB3L2, CHES1, PCAF, LITAF, LRRFIP1, CDY1, NFKBIB, ELF1, PRICKLE1, RNF141, APLP1, APP, KUA, KLF13, ZFP 276, LMO1, EGR1, ETV5, CEBPb, UHFR1, HMGb2, DNMT1, SOX11, HMBb3, TRIP13, LMO4, FOSL2, MYC, CITED2, HMGa1, RUVBL1, TAF9, TSC22d4, KLF9, PBX3, TLE1, CSRP1, NFE2L2, ABCA8, TTYH2, DIXDC1, TENS1, WIPI49, HYDIN, CRYAB, RICTOR, PRKCA, PITPNC1, DEK, NRP2, HMGa1, BRUNOL5, HN1, TUBB, CDK6, GMNN, CLIC1, or KPNA2.

In some embodiments, concurrent to, before or subsequent to administration of any bioactive agent disclosed herein, a growth factor or hormone can also be administered to a cell or subject to promote neural cell differentiation or proliferation. Examples of such growth factors or hormones include thyroid hormone T3, insulin like growth factor-1, fibroblast growth factor-2, platelet-derived growth factor (PDGF), nerve growth factor, neurotrophins, neuregulins, or a combination thereof. Alternatively, such bioactive agents can also be encoded by nucleic acid vectors that are provided concurrently, before or subsequent to any other bioactive agent disclosed herein.

In one embodiment, a bioactive agent is administered that increases expression of a CDK inhibitor which results in neural cell proliferation or differentiation. In other embodiments the bioactive agent administered is a CDK inhibitor. In yet other embodiments, the bioactive agent administered is a nucleic acid vector encoding a modulator of CDK inhibitor expression or encoding a CDK inhibitor itself. In preferred embodiments, such CDK inhibitors include $p57^{Kip2}$. It will be evident to one of ordinary skill that nucleic acid vectors can contain constitutive, inducible or cell-specific transcription regulatory elements thus providing continuous expression of a desired bioactive agent or temporally distinct expression. For example, $p57^{Kip2}$ expression can be induced in cells with doxycycline using the tetracycline repressor system. Alternatively, an expression vector can comprise a neural specific promoter, as described herein or as familiar to one of skill in the art. Therefore, in a method of treating a subject in need thereof, expression of a neural cell bioactive agent can be regulated if need be to alternate between OPC proliferation and OL differentiation to enhance remyelination.

In various embodiments, bioactive agents that induce endogenous $p57^{Kip2}$ expression are administered to a cell/subject so as to promote neural cell differentiation and/or remyelination. In some embodiments, $p57^{Kip2}$ expression is modulated to enhance OL differentiation by administering polypeptides or nucleic acids encoding polypeptides which include p73. In another embodiment, green tea polyphenols or green tea can be administered to induce $p57^{Kip2}$ expression thus promoting OL differentiation (Hsu et al., *J. Pharmacol. Exp. Ther.* 306:29-34 (2003)).

In another embodiment, diethylstilbestrol (DES) can be administered to a cell to induce $p57^{Kip2}$ expression (Salleh et al., *Toxicology* 185:49-57 (2003)). Another embodiment is directed to administering GUT-70, isolated from the stem bark of *Calophyllum brasiliense* collected in Brazil, to induce $p57^{Kip2}$ and enhance OL differentiation (Kimura et al., *Int J Cancer* 113:158-165 (2005)).

In yet another embodiment, glucocorticoids are known regulators of the cell cycle, normally exerting an anti-proliferative effect (i.e., cell arrest into cell differentiation). Glucocorticoids stimulate expression of $p57^{Kip2}$, which involves primary transcriptional effects where no de novo protein synthesis is necessary, suggesting a direct interaction of the glucocorticoid receptor with the $p57^{Kip2}$ gene. Indeed, a functional glucocorticoid response element (GRE), is located 5 kilo bases (kb) upstream of the transcription start site in the human $p57^{Kip2}$ promoter (Alheim et al., *J. Mol. Endocrinol.* 30:359-368 (2003)). This GRE was functional also when isolated, suggesting a direct transcriptional effect of the glucocorticoid receptor.

In another embodiment, TGF beta can be administered or expressed from an expression vector to induce $p57^{Kip2}$ expression, thus promoting OL differentiation and/or remyelination (Scandura et al., *Proc. Natl. Acad. Sci. USA* 101:15231-15236 (2004)).

In other embodiments, cells are genetically modified to express HMGa2, $p57^{Kip2}$, ZFP536, KLF13, CEBPb, UHFR1, HMGa1, KLF9, TLE1, or CSRP1 to promote myelination. In some embodiments neural cells are genetically modified to express one or more transcription factors including ZFP536, HMGa2, MLR1, TCF7L2, SIRt2, CARHSP1, CREB3L2, CHES1, PCAF, LITAF, LRRFIP1, CDY1, NFKBIB, ELF1, PRICKLE1, RNF141, APLP1, APP, KUA, KLF13, ZFP 276, LMO1, EGR1, ETV5, CEBPb, UHFR1, HMGb2, DNMT1, SOX11, HMBb3, TRIP13, LMO4, FOSL2, MYC, CITED2, HMGa1, RUVBL1, TAF9, TSC22d4, KLF9, PBX3, TLE1, CSRP1 or NFE2L2. In yet other embodiments, neural cells are transformed to express one or more polypeptides encoded by genes including SEPP1, ABCA8, TTYH2, DIXDC1, TENS1, WIPI49, HYDIN, CRYAB, RICTOR, PRKCA, PITPNC1, DEK, NRP2, HMGa1, BRUNOL5, HN1, TUBB, CDK6, GMNN, CLIC1, or KPNA2.

Nucleic acids encoding a desired polypeptide can be transformed into target cells by homologous recombination, integration or by utilization of plasmid or viral vectors utilizing components and methods described herein and familiar to those of ordinary skill in the art. Neural cells that can be transfected include OLs, OPCS, SCs, NSCs, astocytes or microglial cells. In some embodiments, such neural cells can be transfected with more than one vector, either concurrently or at different time points. Furthermore, nucleic acids encoding any of the polypeptides disclosed herein can be operably linked to constitutive, inducible or cell-specific promoters disclosed herein, and recognized by those of ordinary skill in the art.

In another embodiment, cells in culture can be co-transfected with a vector comprising a gene of interest, for example, the gene to be modulated by a bioactive agent, and a vector encoding a detectable marker. In some embodiments, a detectable marker can be a fluorescent protein, which is described herein. The gene of interest can encode a peptide, polypeptide, antisense, siRNA aptamer or peptidomimetic, each which can modulate neural cell proliferation or differentiation by targeting neural cell cycle related genes including but not limited to $p57^{Kip2}$, CSCRP1, TMEM10, UHRF1, ZFP5:36, HMGa2, MLR1, TCF7L2, SIRt2, CARHSPL1, CREB3L2, CHES1, PCAF, LITAF, LRRFIP1, CDY1, NFKBIB, ELF1, PRICKLE1, RNF141, APLP1, APP, KUA, KLF13, ZFP 276, LMO1, EGR1, ETV5, CEBPb, UHFR1, HMGb2, DNMT1, SOX11, HMBb3, TRIP13, LMO4, FOSL2, MYC, CITED2, HMGa1, RUVBL1, TAF9, TSC22d4, KLF9, PBX3, TLE1, CSRP1, NFE2L2, ABCA8, TTYH2, DIXDC1, TENS1, WIPI49, HYDIN, CRYAB, RICTOR, PRKCA, PITPNC1, DEK, NRP2, HMGa1, BRUNOL5, HN1, TUBB, CDK6, GMNN, CLIC1, or KPNA2. In preferred embodiments, the gene may be HMGa2, $p57^{Kip2}$, ZFP536, KLF13, CEBPb, UHRF1, HMGa1, KLF9, TLE1, or CSRP1.

In some embodiments, neural cells are transfected (genetically modified) with a nucleic acid molecule that is operably linked to a constitutive, inducible or neural-cell-specific promoter and encodes a polypeptide involved in neural cell differentiation/proliferation. In some embodiments, such cells can be transformed to express a CDK inhibitor at altered expression levels thus modulating neural cell proliferation/differentiation. For example, the polypeptide can be $p57^{Kip2}$. Therefore, the polypeptide can be a component of cell cycle mechanism as identified herein or a polypeptide that itself blocks the activity, function or expression of said component.

It should be understood, that the foregoing is also applicable to formulation of nucleic acid vectors that can be utilized to effect transfection of target cells. Such vectors are described herein and recognized by those of ordinary skill in the art as being capable of transfecting a target cell and expressing a desired polypeptide. In sum, such vectors can also be utilized in pharmaceutical formulations or therapeutics as described herein.

Transplantation of remyelinating cells. Remyelination of CNS axons has been demonstrated in various animal models.

Many recent studies have since demonstrated new techniques and novel mechanisms associated with the use of cell transplantation in demyelinating disease. Human OP cells isolated from adult brains were able to myelinate naked axons when transplanted into a dysmyelinating mouse mutant. Importantly, the use of adult progenitor cells avoids ethical concerns. While OP cells are responsible for endogenous remyelination, NSCs are an alternative source of cells to promote myelin repair. NSCs are found in the adult CNS, can be expanded extensively in vitro, and can differentiate to form OLs, astrocytes, or neurons. When transplanted into rodents with relapsing or chronic forms of experimental autoimmune encephalomyelitis (EAE), NSCs have been shown to migrate to areas of CNS inflammation and demyelination and to preferentially adopt a glial cell-fate. Furthermore, attenuation of clinical disease in transplanted mice was associated with repair of demyelinating lesions and decreased axonal injury. Histological analysis confirmed that transplanted NSCs differentiated predominantly into PDGFR$^+$OP cells.

In an aspect of the invention, the subject bioactive agents can comprise cells involved in myelin repair or remyelination of denuded axons administered to a subject, wherein said cells are modified to over-express a chemokine-signaling antigen. Such cells can be cultured and transfected with an appropriate vector to express a polypeptide that leads to enhanced cell proliferation or migration to an injury or insult site (e.g., demyelinated site). In some embodiments, cells involved in remyelination or myelin repair are modified to express a polypeptide involved in oligodendrocyte proliferation or differentiation so as to enhance myelination, wherein such polypeptides include but are not limited to HMGa2, p57$^{Kip2}$, ZFP536, KLF13, CEBPb, UHRF1, HMGa1, KLF9, TLE1, or CSRP1.

In various embodiments, the cells ("cell types") are oligodendrocyte progenitor cells (OPC), Schwann cells (SCs), olfactory bulb ensheathing cells, astrocytes, microglia, or neural stem cells (NSCs), which can be administered prior to, concurrent with or subsequent to administration of a bioactive agent. In some embodiments, such cells can be administered to an animal subject to enhance neural cell proliferation and/ or migration.

In some embodiments, one or more cell types are modified to overexpress a chemokine and administered to a subject to treat a neuropathy. In one embodiment, two cell types are administered including OPCs and astrocytes. In some embodiments, the myelin producing cells or progenitor cells thereof include but are not limited to fetal or adult OPCs. In one embodiment the OPC has a A2B5$^+$PSA$^-$NCAM$^-$ phenotype (positive for the early oligodendrocyte marker A2B5 and negative for polysialylated neural cell adhesion molecule).

In one embodiment, the cells are glial cells that express the NG2 proteoglycan (NG2(+) cells), which are considered to be oligodendrocyte progenitors (OPCs) in the central nervous system (CNS), based on their ability to give rise to mature oligodendrocytes. In some embodiments, oligodendrocyte progenitor cells (OPC), Schwann cells (SC), olfactory bulb ensheathing cells, astrocytes, microglia or neural stem cells (NSC) are cultured, transformed with a vector encoding a chemokine, and expanded in vitro prior to transplantation. In other embodiments, the cells may be transfected or genetically modified in vivo to express a protein encoded by a neural cell cycle related gene, which are disclosed herein.

In some embodiments, oligodendrocyte progenitor cells (OPC), Schwann cells (SCs), olfactory bulb ensheathing cells, and neural stem cells (NSCs) are transfected with one or more expression vectors, using methods known in the art or disclosed herein, so as to enable expression of one or more desired bioactive agent. Such bioactive agents can modulate CDK-inhibitor-mediated signaling, including but not limited to HMGa2, p57$^{Kip2}$, ZFP536, KLF13, CEBPb, UHRF1, HMGa1, KLF9, TLE1, or CSRP1.

In another embodiment, such agents can promote oligodendrocyte proliferation at, or migration to, a lesion site. In yet another embodiment, such agents can promote OPC differentiation into mature oligodendrocytes, and/or proliferation or migration to lesion sites. In various embodiments, the cells are transfected before, concurrent or subsequent to expansion in culture. In preferred embodiments, such cells are transfected with vectors encoding HMGa2, p57$^{Kip2}$, ZFP536, KLF13, CEBPb, UHRF1, HMGa1, KLF9, TLE1, or CSRP1.

In other embodiments, such neural cells are genetically modified to alter expression for HMGa2, p57$^{Kip2}$, ZFP536, KLF13, CEBPb, UHRF1, HMGa1, KLF9, TLE1, or CSRP1 polypeptides. In yet other embodiments, such neural cells are genetically modified for two or more genes encoding HMGa2, p57$^{Kip2}$, ZFP536, KLF13, CEBPb, UHRF1, HMGa1, KLF9, TLE1, or CSRP1. In yet further embodiments, such neural cells are genetically modified for any of the genes disclosed herein (i.e., FIGS. 7, 10, 30 disclosing the top 50 OL upregulated genes, top 50 OL-specific expressed genes, OL-regulated genes, highly linked MS loci genes and OL-regulated transcription factors).

It will be appreciated that transplantation is conducted using methods known in the art, including invasive, surgical, minimally invasive and non-surgical procedures. Depending on the subject, target sites, and agent(s) to be the delivered, the type and number of cells can be selected as desired using methods known in the art.

Pharmaceutical Compositions

Pharmaceutical compositions are contemplated wherein a agent or agents is comprised of a peptide, polypeptide, aptamer, siRNA or antisense, nucleic acid expression vectors, antibody or antibody fragment of the present invention and one or more therapeutically active agents are formulated. Such compositions can target (i.e., bind directly/indirectly) CDK-inhibitors, including but not limited to p57$^{Kip2}$ thus inhibiting cell cycle arrest and promoting neural cell proliferation. In some embodiments, such compositions are antagonists or allosteric inhibitors of HMGa2, p57$^{Kip2}$, ZFP536, KLF13, CEBPb, UHRF1, HMGa1, KLF9, TLE1, or CSRP1.

Formulations of such agents are prepared for storage by mixing such agents having the desired degree of purity with optional pharmaceutically acceptable carriers, excipients or stabilizers. (Remington's Pharmaceutical Sciences 16th edition, Osol, A. Ed., 1980), in the form of lyophilized formulations or aqueous solutions. Acceptable carriers, excipients, or stabilizers are nontoxic to recipients at the dosages and concentrations employed, and include buffers such as phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches; binding agents; additives; coloring agents; salt-forming counter-ions such as sodium; metal complexes (e.g. Zn-protein complexes); and/or non-ionic surfactants such as TWEEN™, PLURONICS™, or polyethylene glycol (PEG).

In a preferred embodiment, the pharmaceutical composition that comprises the bioactive agents of the present invention is in a water-soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine; tripropylamine, and ethanolamine. The formulations to be used for in vivo administration are preferably sterile. This is readily accomplished by filtration through sterile filtration membranes or other methods known in the art.

The agents targeting HMGa2, $p57^{Kip2}$, ZFP536, KLF13, CEBPb, UHRF1, HMGa1, KLF9, TLE1, or CSRP1 may also be formulated as immunoliposomes. A liposome is a small vesicle comprising various types of lipids, phospholipids and/or surfactant that is useful for delivery of a therapeutic agent to a mammal. Liposomes containing bioactive agents are prepared by methods known in the art, such as described in Eppstein et al., Proc. Natl. Acad. Sci. USA 82:3688-3692 (1985); Hwang et al., Proc. Natl. Acad. Sci. USA 77:4030-4034 (1990); U.S. Pat. Nos. 4,485,045; 4,544,545; and PCT WO 97/38731. Liposomes with enhanced circulation time are disclosed in U.S. Pat. No. 5,013,556. The components of the liposome are commonly arranged in a bilayer formation, similar to the lipid arrangement of biological membranes. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. A chemotherapeutic agent or other therapeutically active agent is optionally contained within the liposome (Gabizon et al., J. National Cancer Inst 81:1484-1488 (1989)).

EXAMPLES

Example 1

Expression Profiles of OPCs and OLs

Figure 5:
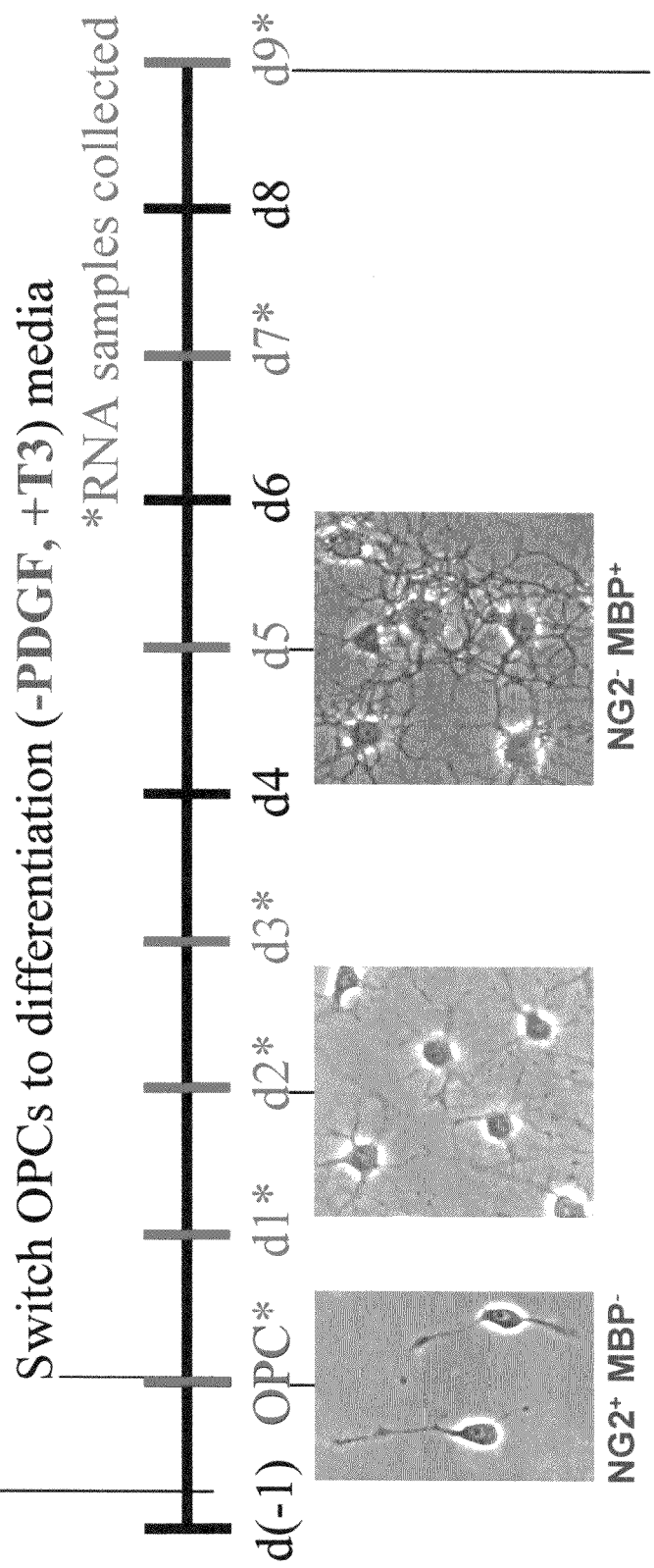
FIG. 5. Provides a time line of culturing OPCs during which RNA samples were collected to assess OL-specific gene expression profiles. Cells were purified in proliferation media and switched to differentiation media and cultured for 9 days. RNA samples were collected on days 0, 1, 2, 3, 5, 7 and 9.
Figure 6:
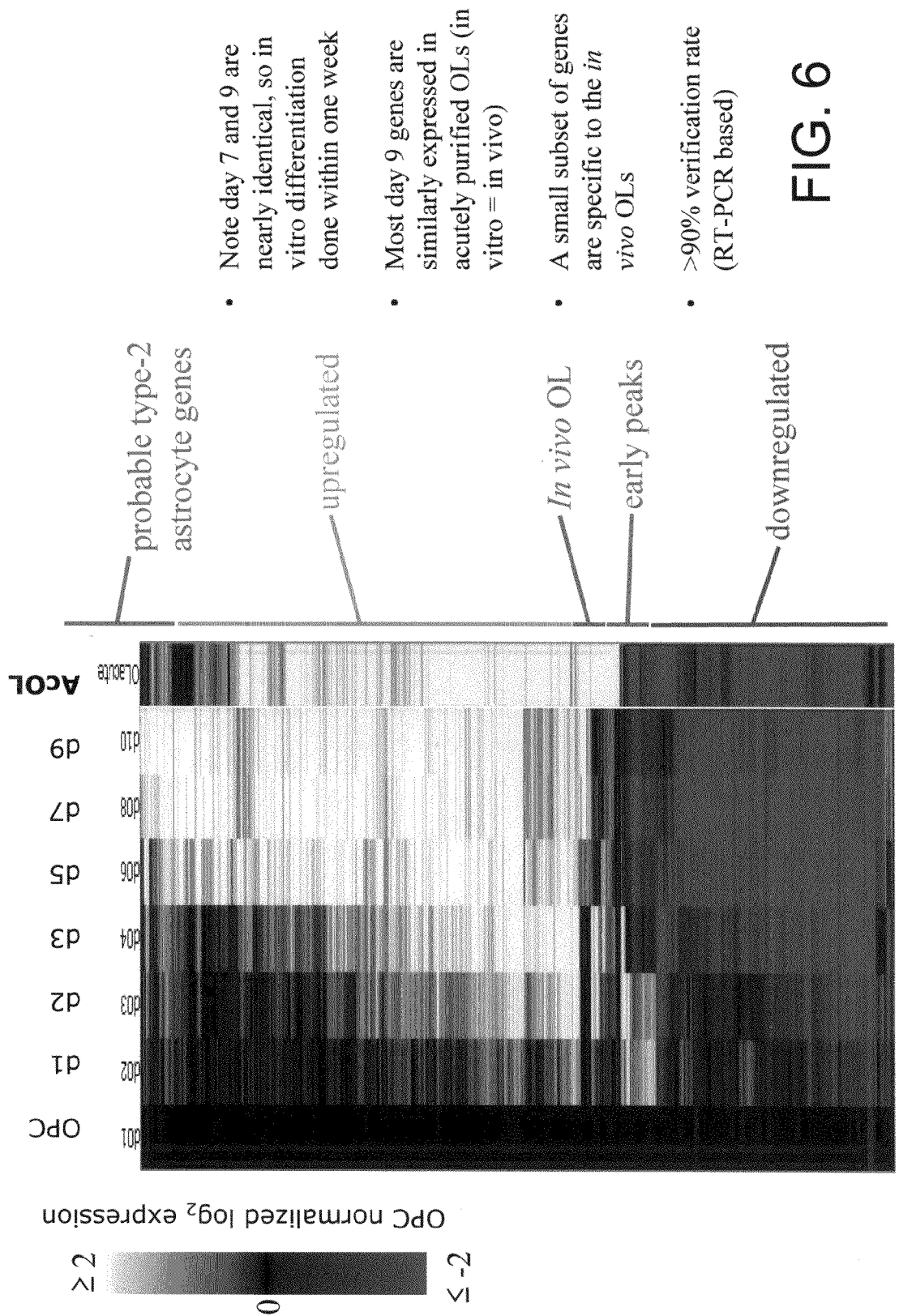
FIG. 6. Presents gene expression profiles observed during OPC maturation differentiation.

Expression profiles for undifferentiated OPCs and differentiating OLs in culture were obtained at various time points (FIG. 5). Highly regulated genes recapitulated in vivo expression (FIG. 6). Based on the expression profiles obtained from OPCs differentiating into OLs, two tables were compiled depicting the top 50 OL upregulated and top 50 OL-specific genes (FIG. 7). In comparison of the two lists, it was observed that 16 genes occur in both lists (FIG. 7) and a total of 52 genes were identified as not previously known to be expressed in OLs (FIG. 7). Furthermore, from these 52 genes, 13 were identified as demonstrating white-matter enriched expression patterns (FIG. 7). Moreover, 22 genes were identified as both OL-regulated and highly linked to MS loci (FIGS. 9, 10). Of these SEPP1 was one of the most strongly induced OL genes that also demonstrated white matter specific expression. SEPP1 maintains normal $Se^+$ levels including in the CNS, and low $Se^+$ levels have been implicated as a potential MS risk factor. Furthermore, deficiencies in SEPP1 lead to ataxia.

Figure 13:
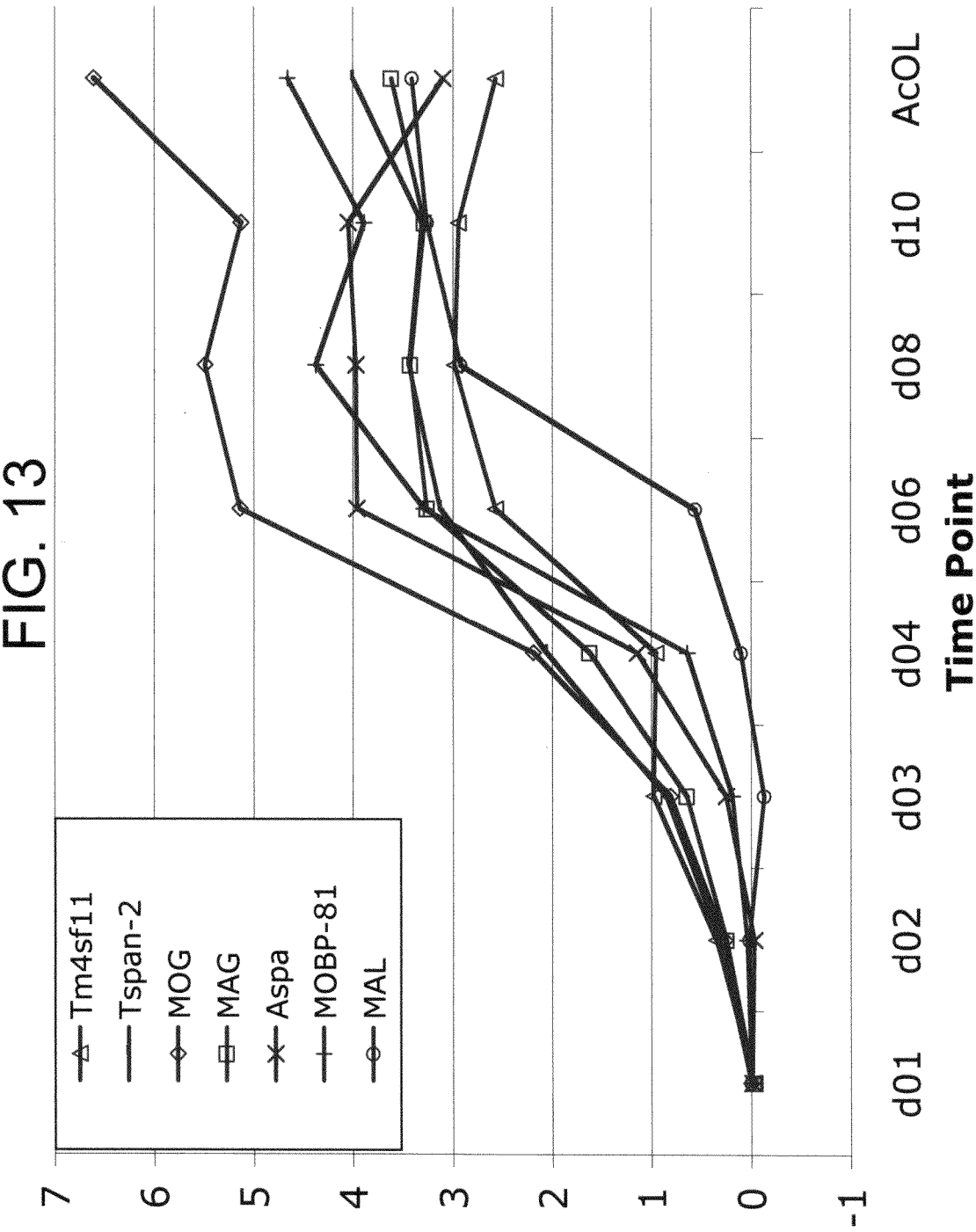
FIG. 13. Depicts myelin-enriched genes that are induced with a delay after initiation of differentiation.
Figure 14:
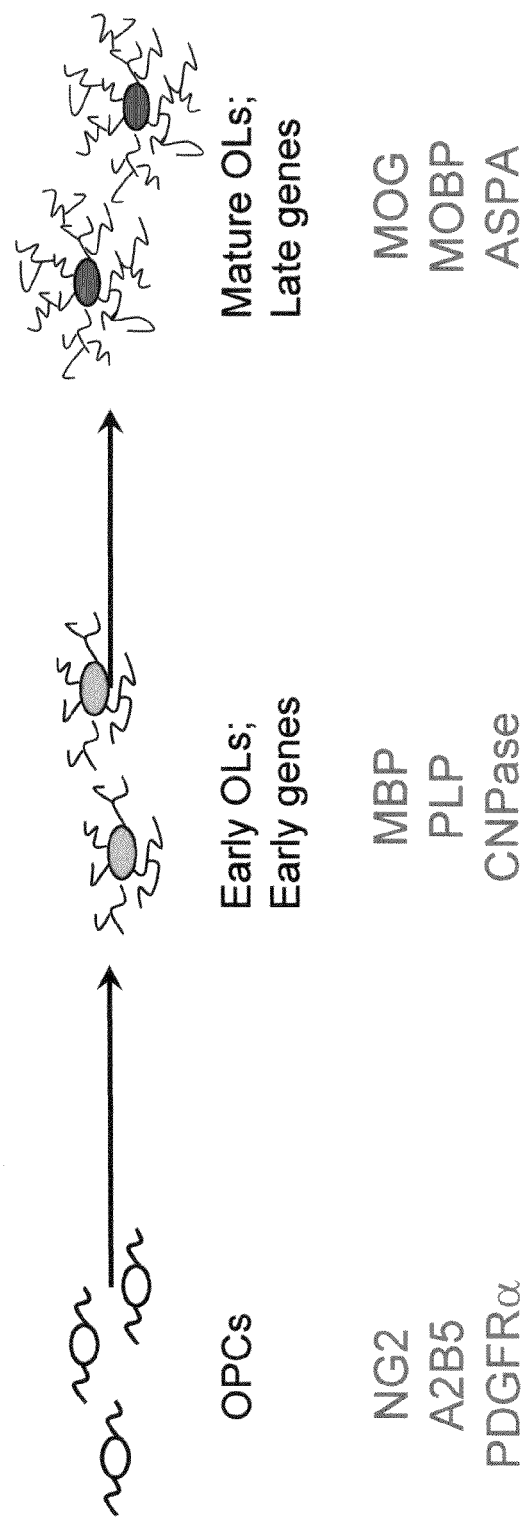
FIG. 14. Depicts a schematic representation of OL progression from OPCs to mature OLs in distinct temporal stages, with exemplary early genes and late genes observed respectively.
Figure 15:
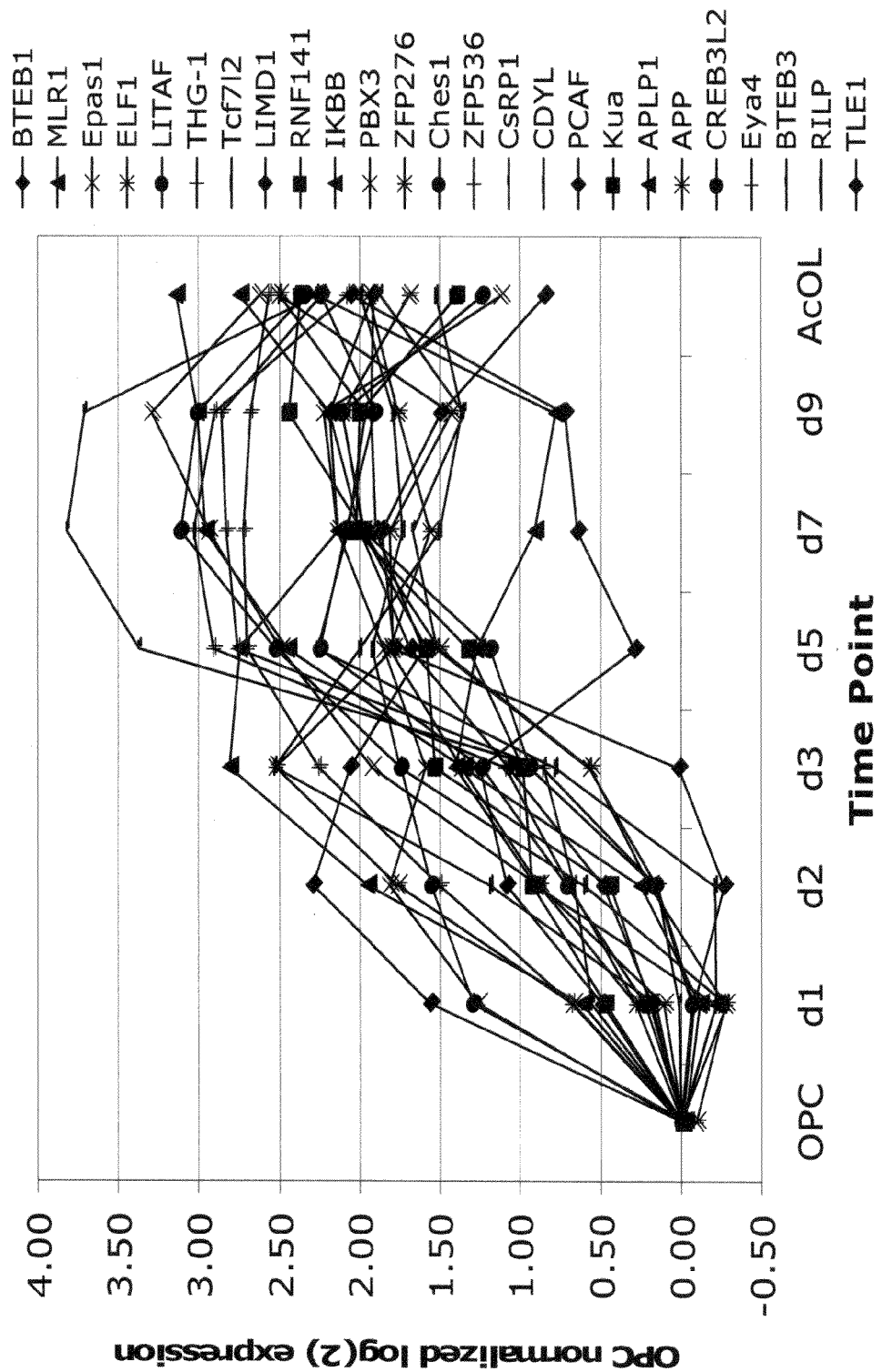
FIG. 15. Depicts a graph of transcription factors that are up-regulated during OL differentiation.
Figure 16:
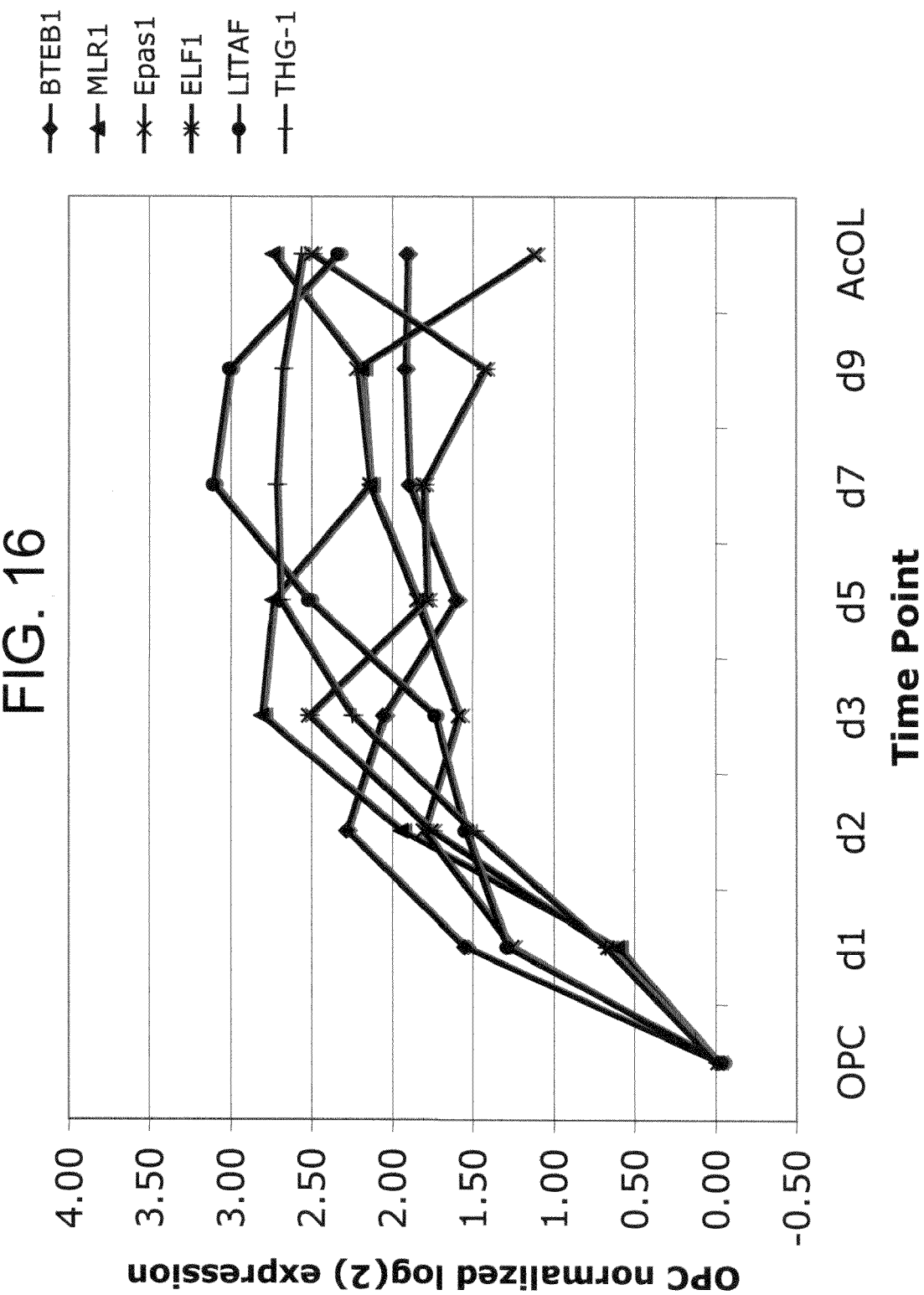
FIG. 16. Depicts a graph of transcription factors that are induced immediately upon initiation of differentiation.

The analysis for the gene expression profiles further demonstrated that myelin-enriched genes are upregulated in OLs (FIG. 11), and both immediately (FIG. 12) and with a delay after initiation of OL differentiation (FIG. 13). Therefore, it is clear that OL differentiation proceeds in distinct temporal stages (FIG. 14).

Figure 17:
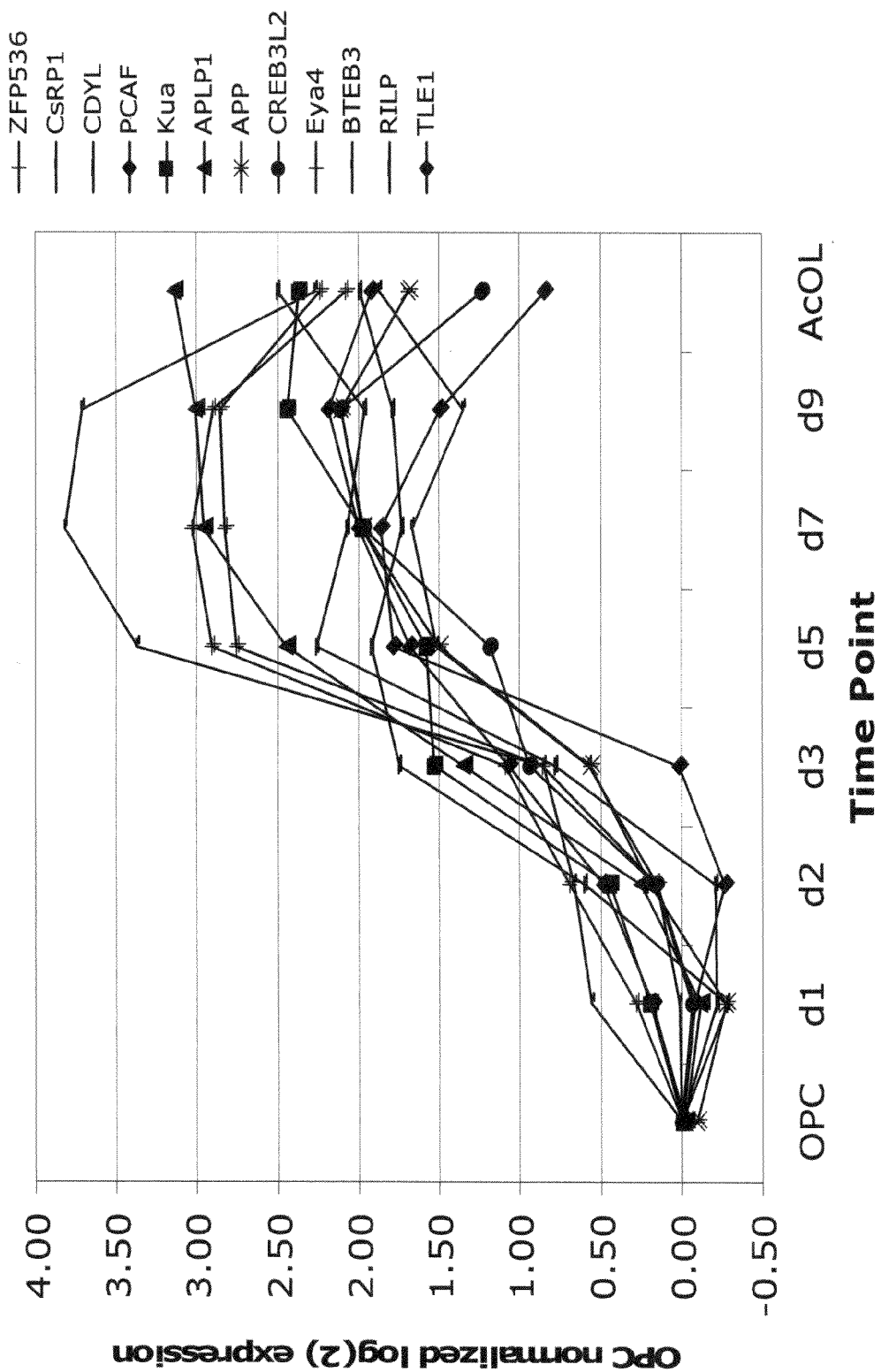
FIG. 17. Depicts a graph of transcription factors that are induced with a delay after initiation of differentiation.
Figure 18:
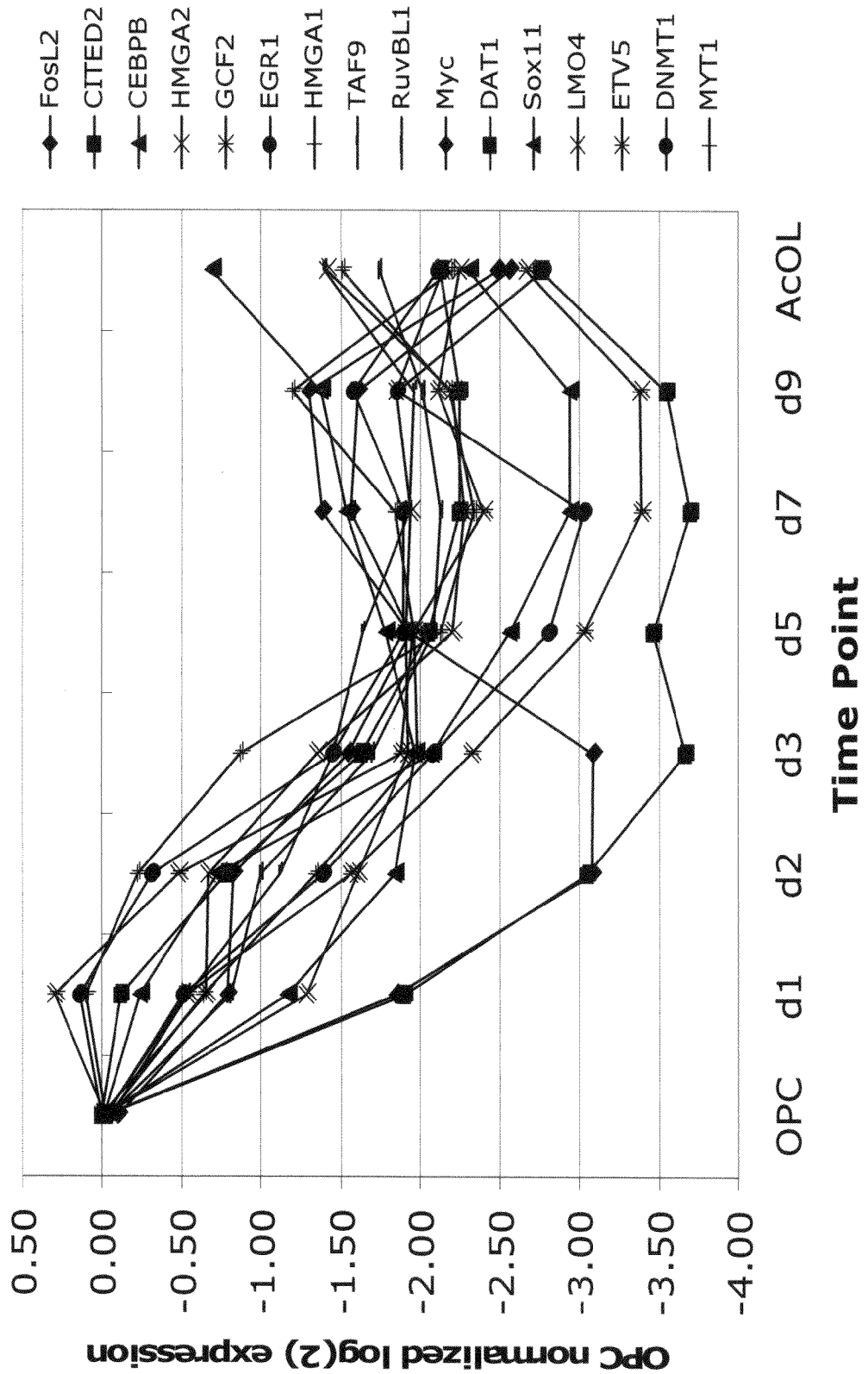
FIG. 18. Depicts a graph of transcription factors that are downregulated during OL differentiation.
Figure 19:
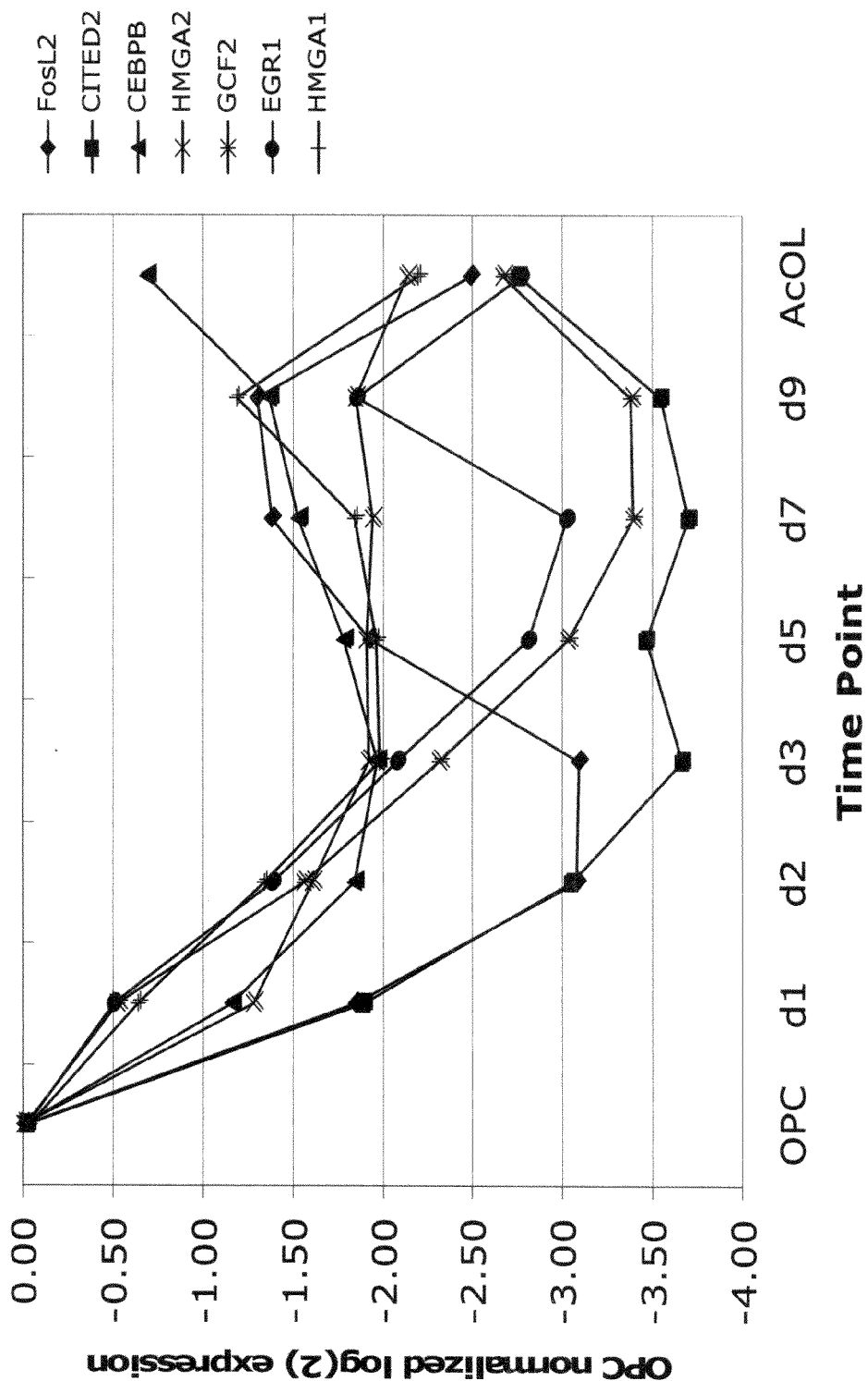
FIG. 19. Depicts a graph of transcription factors that are downregulated immediately upon initiation of differentiation.
Figure 23:
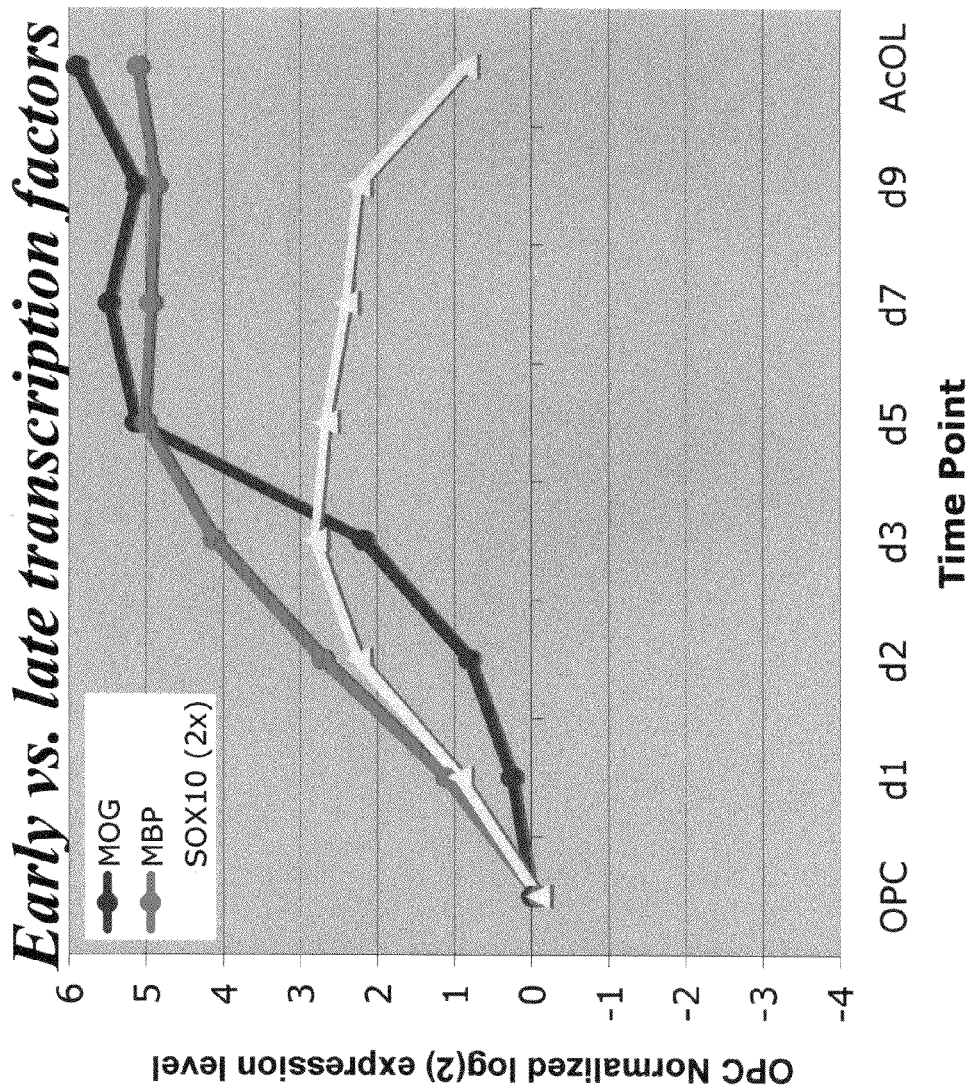
FIG. 23. Depicts a graph comparing early versus late myelin-enriched genes, MBP and MOG, respectively.
Figure 24:
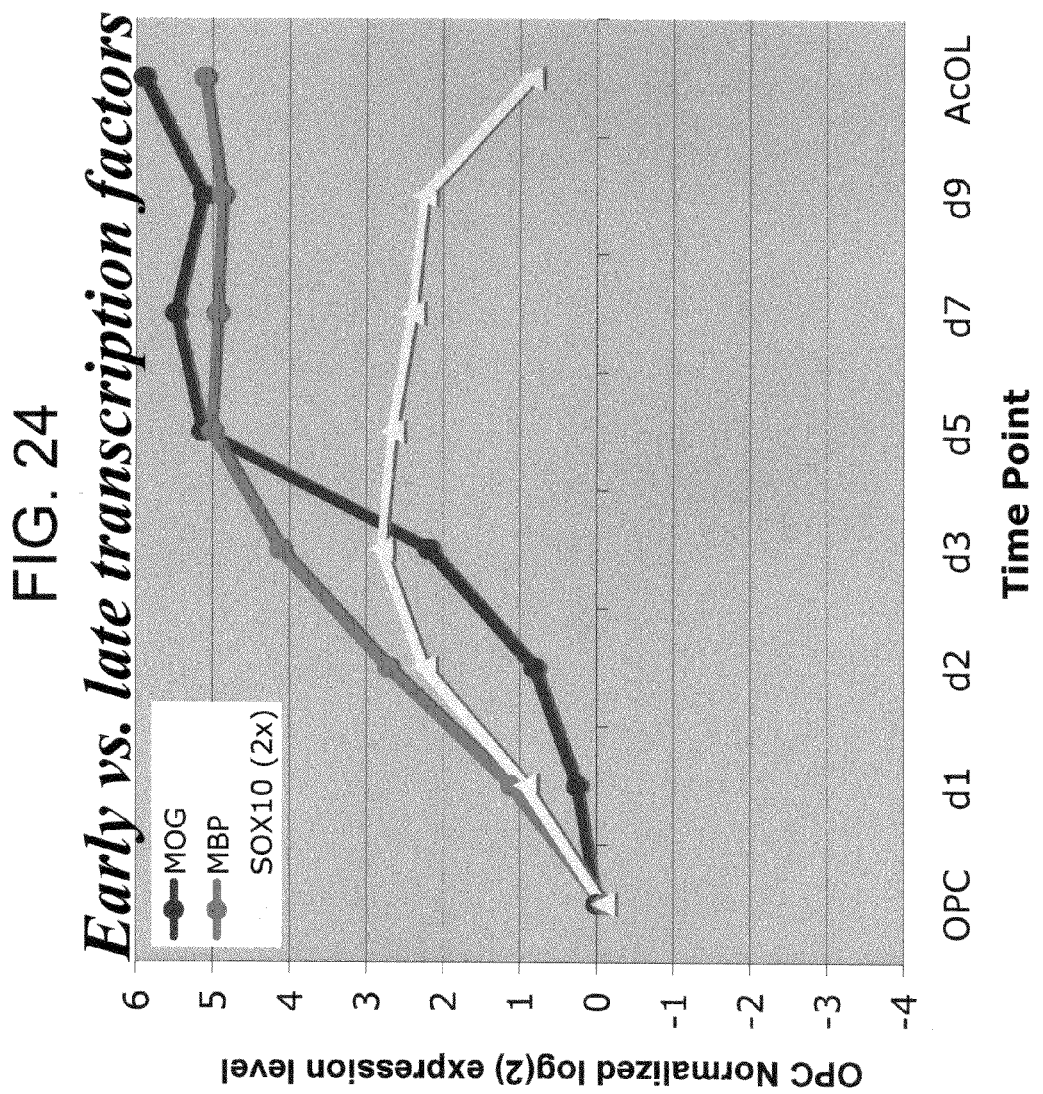
FIG. 24. Same as in FIG. 23, but also depicts transcription factor SOX10.
Figure 25:
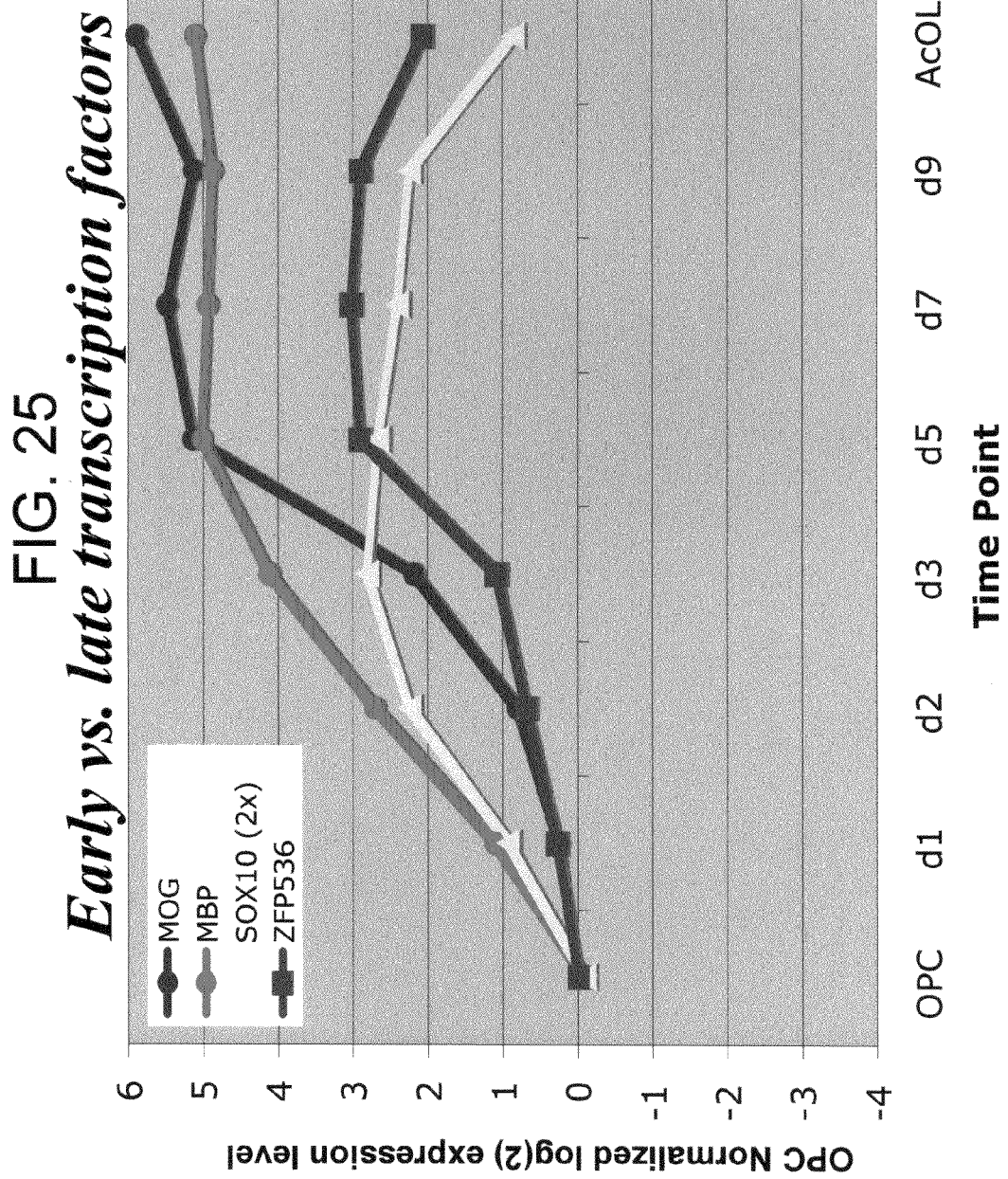
FIG. 25. Same as in FIG. 24, but also depicts transcription factor ZFP536.
Figure 26:
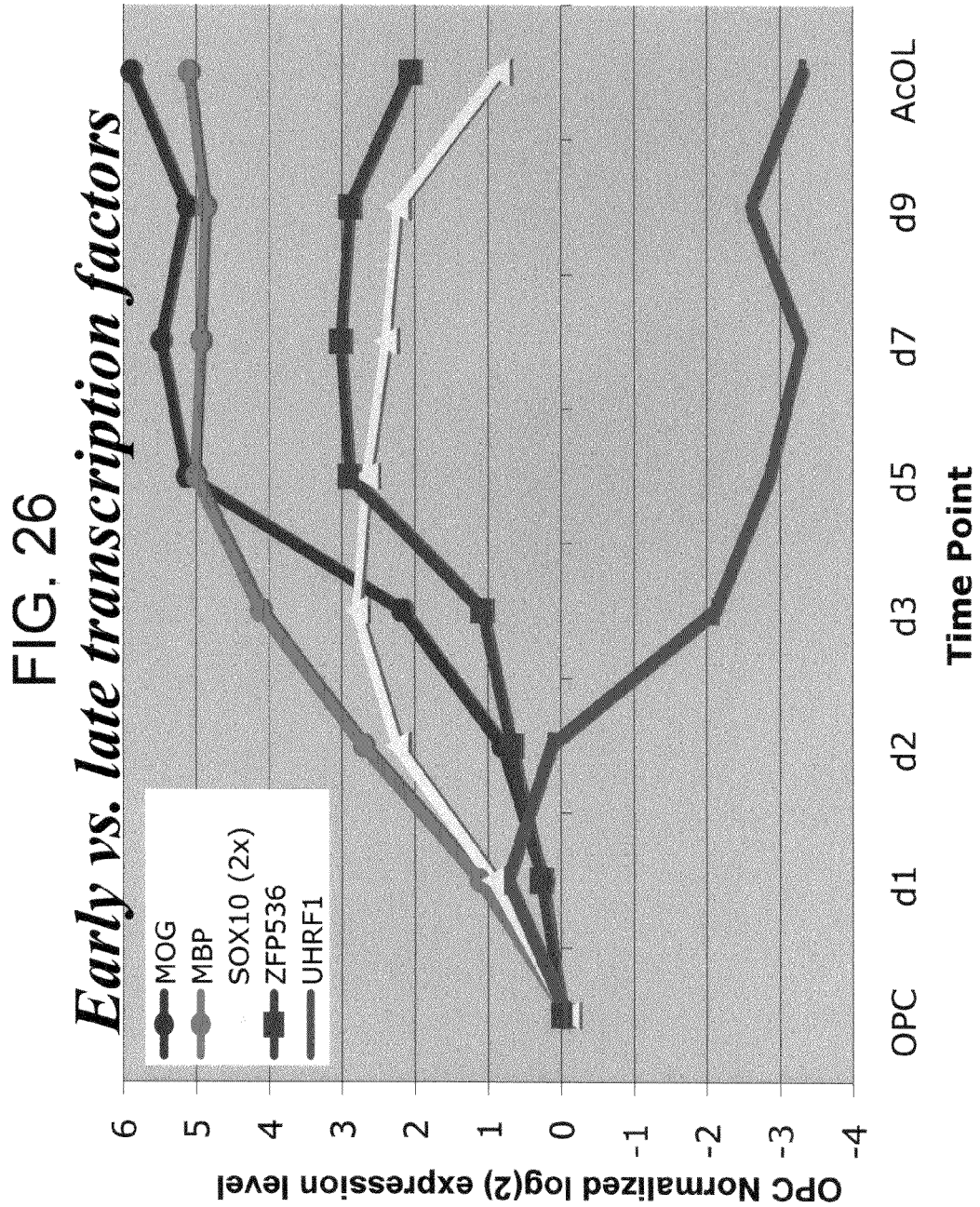
FIG. 26. Same as in FIG. 25, but also depicts transcription factor UHRF1.

In additional gene expression analysis, it was observed that certain transcription factors are induced both immediately (FIG. 16) and with a delay after initiation of OL differentiation (FIG. 17). In addition, transcription factors are repressed in distinct phases (FIGS. 19 and 20). Based on these results a list of transcription factors were compiled and indexed based on a particular type of neural cell (FIG. 21).

Example 2

Screening Assay: Transcription Factors

In a screening assay to determine the role of transcription factors in OL differentiation, OPCs in culture were co-transfected with expression vectors that encoded a marker (e.g., GFP) and transcription factors identified above, or pools of siRNA designed to reduce expression of targeted transcription factors. Cells were plated in differentiation or proliferation medium (i.e., +/−PDGF:+/−T3). Cells were incubated for several days and subsequently stained for early and late myelin markers, e.g., MBP and MOG respectively. PDGF promotes proliferation while T3 promotes differentiation (FIG. 22).

Figure 27:
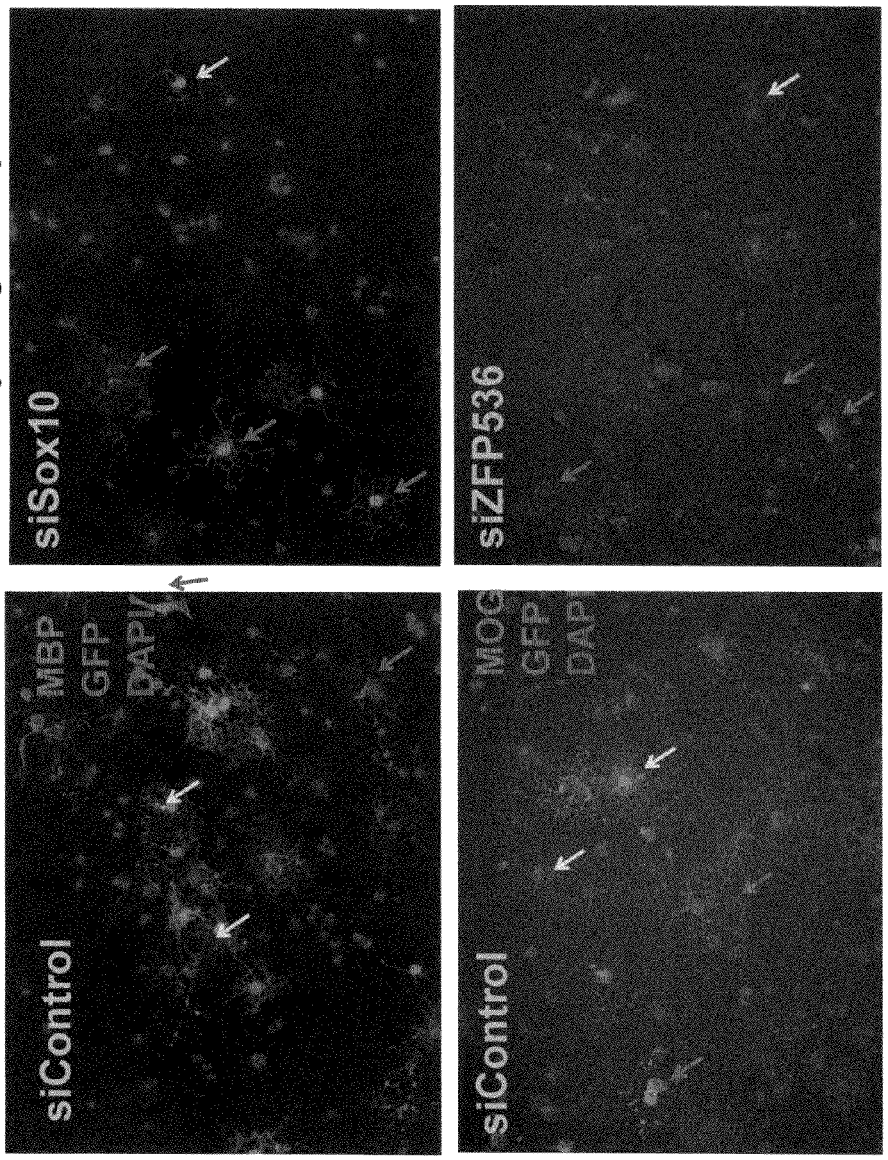
FIG. 27. Presents an image for knockdown experiments using siRNA for SOX10 and ZFP536, and compares MBP (early) and MOG (late) stages.
Figure 28:
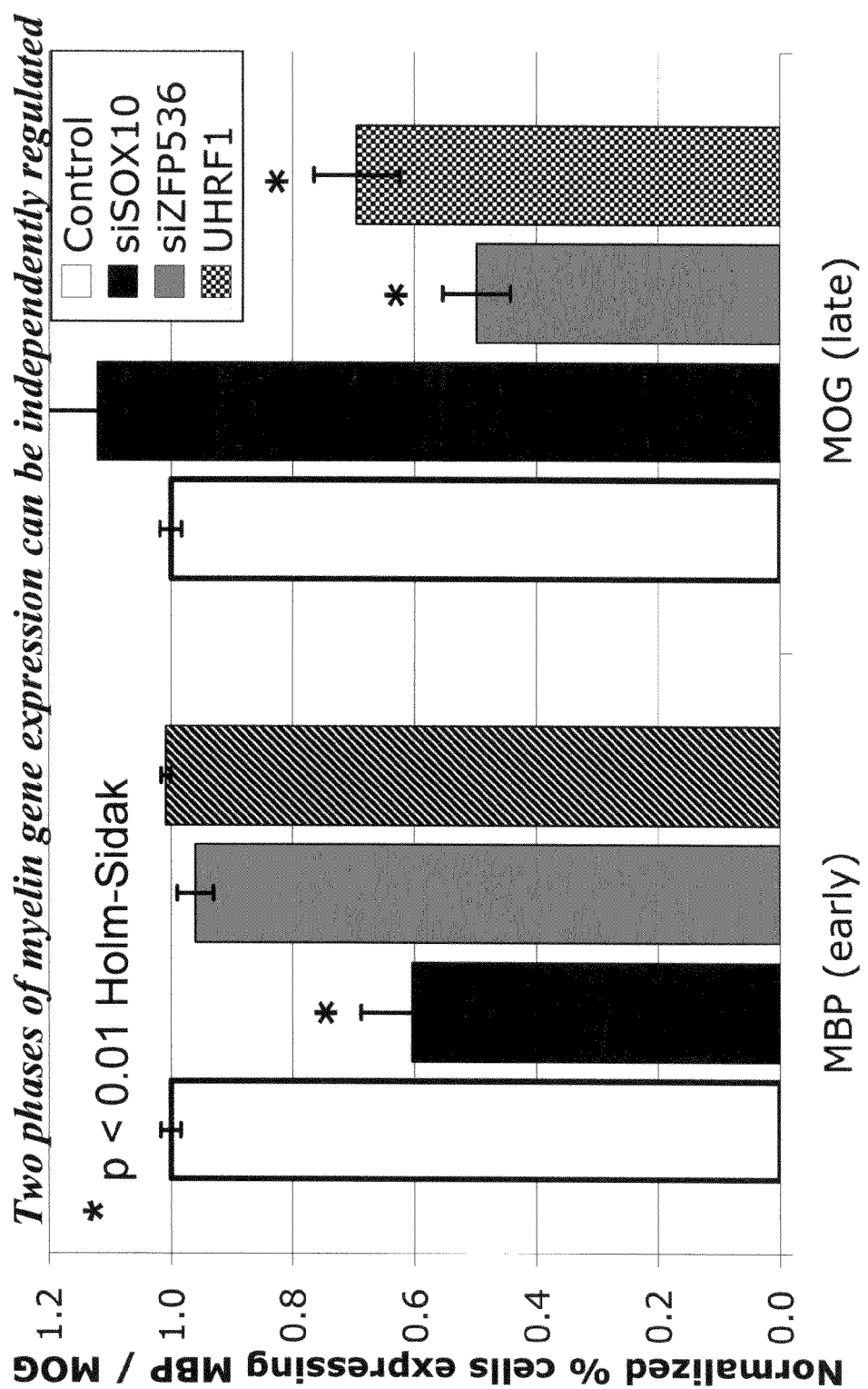
FIG. 28. Illustrates that two phases (early/late) of myelin gene expression can be independently regulated.

Various transcription factors tested, included early versus late transcription factors, such as SOX10, ZFP536 and UHRF1 (FIGS. 23-26). Knock down of SOX10 and ZFP536 reduced myelin gene expression, while overexpression of UHRF1 also reduced myelin gene expression, as demonstrated by MBP and MOG staining (FIG. 27, 28). Also, knockdowns for SOX10 and ZFP536 and overexpression of UHRF1 results demonstrated that during OL differentiation late and early genes are regulated independently (FIGS. 28, 29). Thus, SOX10 induces early genes while ZFP536 induces late genes and UHFRF1 downregulates late genes.

Figure 34:
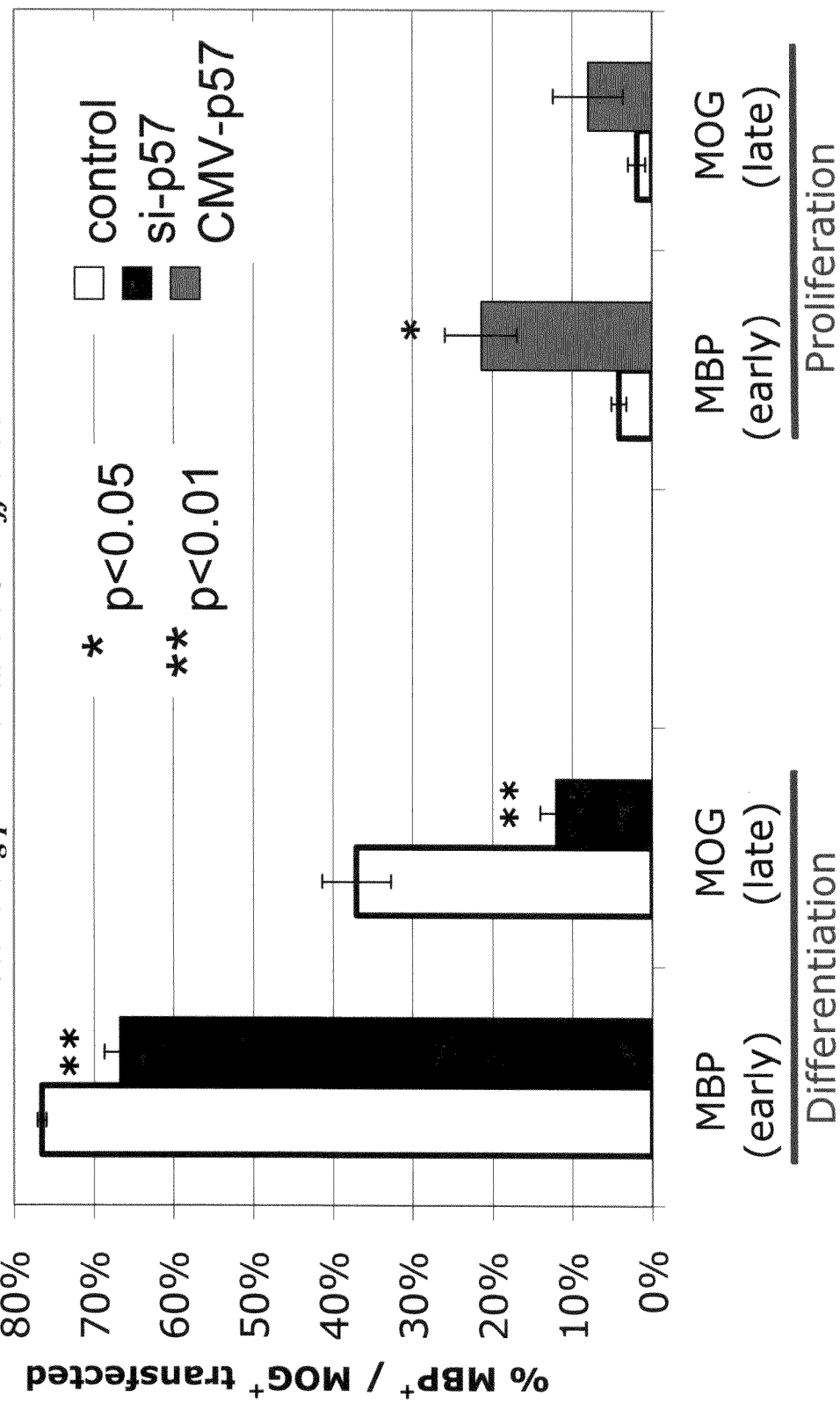
FIG. 34. Depicts a graph illustrating that reducing $p57^{kip2}$ levels retards OL differentiation while increased $p57^{kip2}$ levels enhance OL differentiation.
Figure 35:
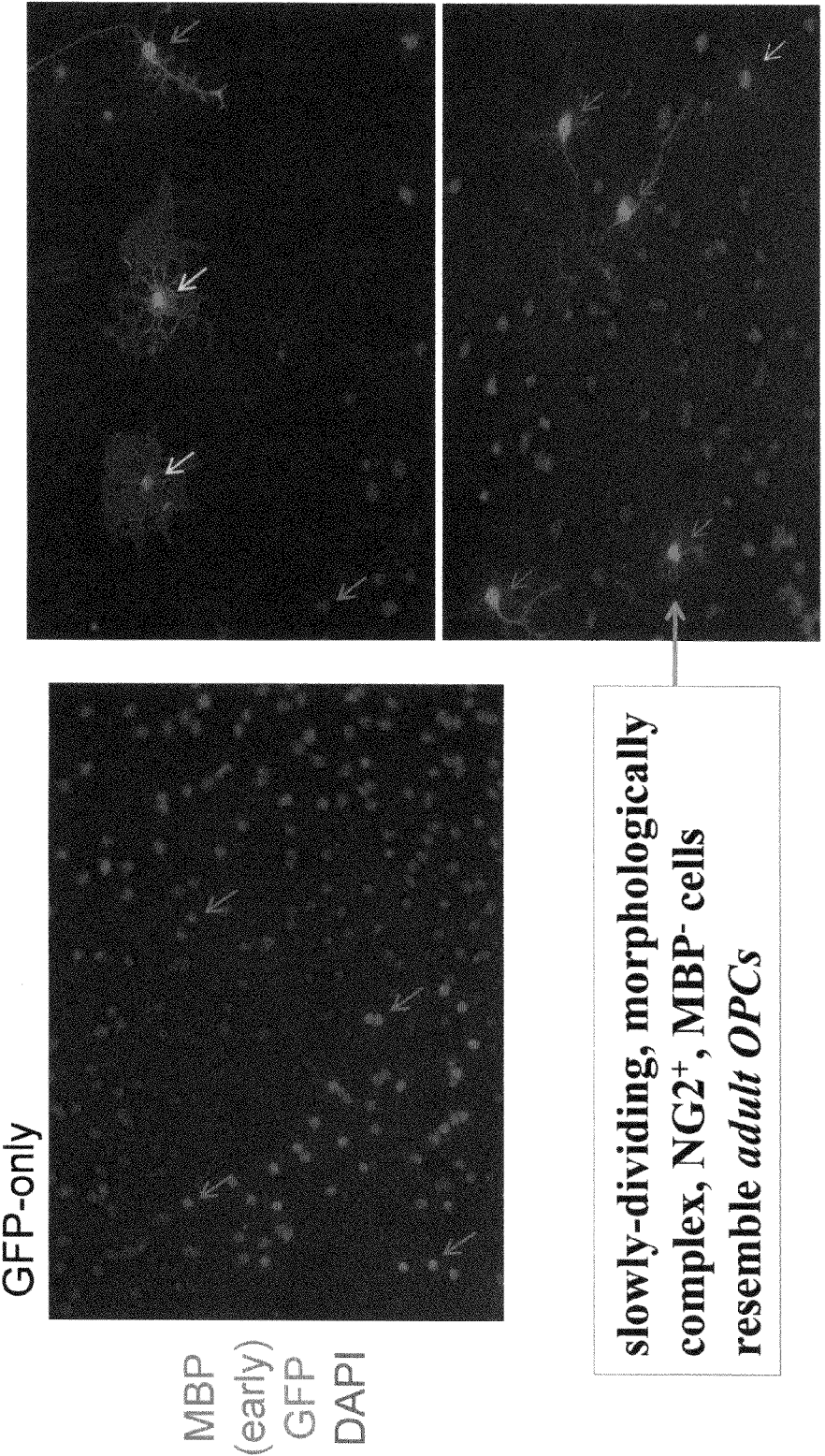
FIG. 35. Depicts an image showing increased $p57^{kip2}$ accelerates OL differentiation and slows OPC proliferation.
Figure 36:
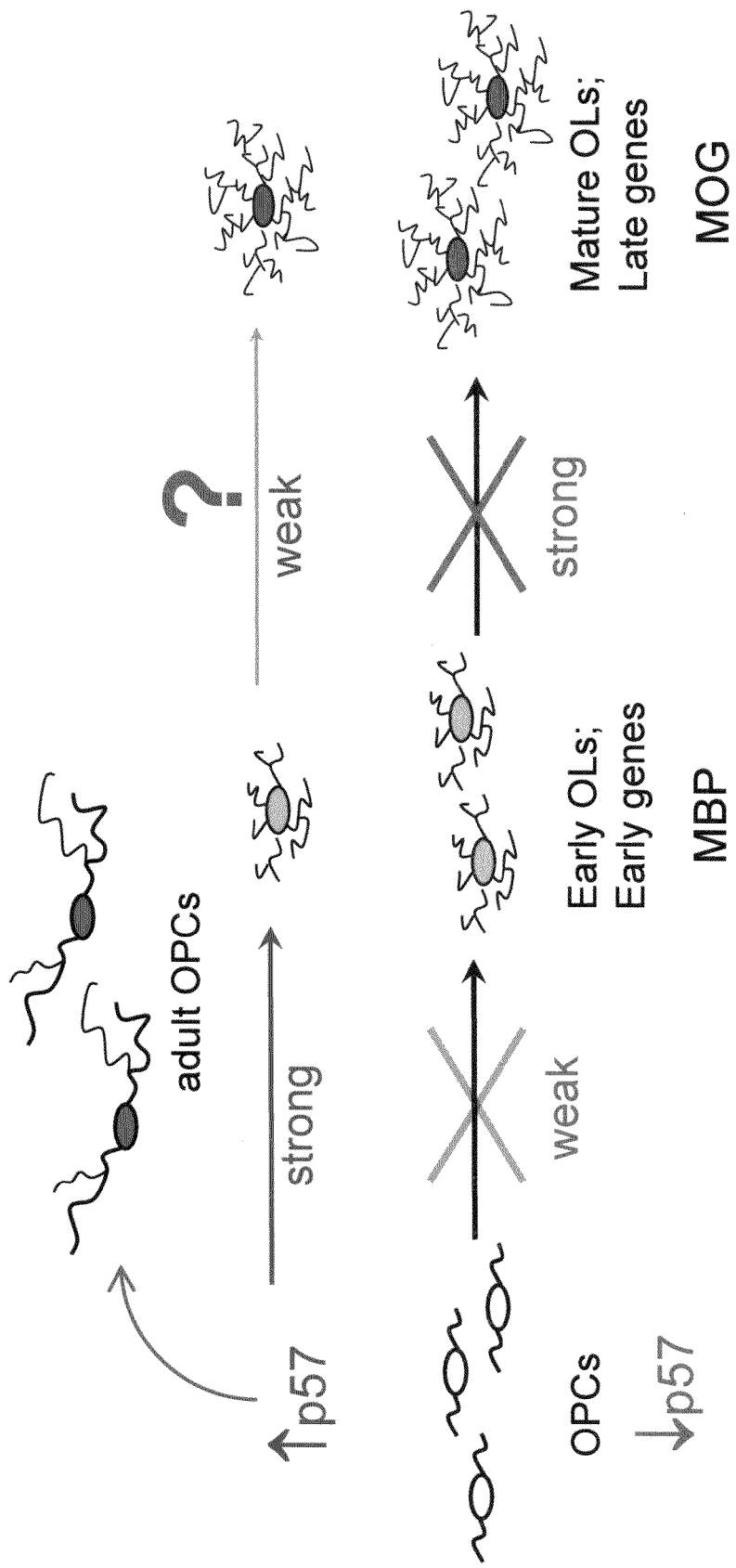
FIG. 36. Depicts a schematic representation outlining effects of $p57^{kip2}$ on OL differentiation.
Figure 37:
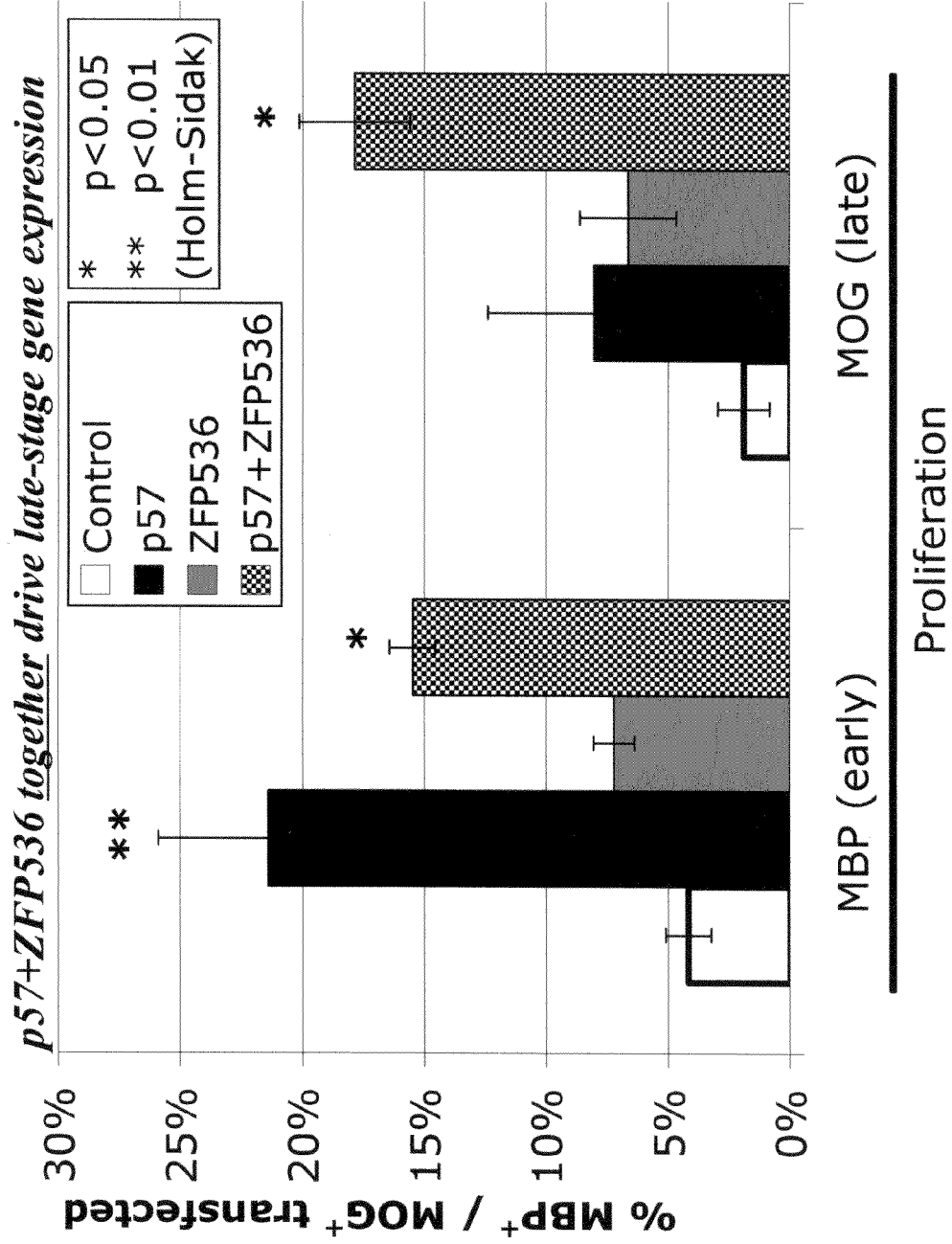
FIG. 37. Depicts a graph illustrating that $p57^{kip2}$ and ZFP536 together drive late-stage gene expression.
Figure 38:
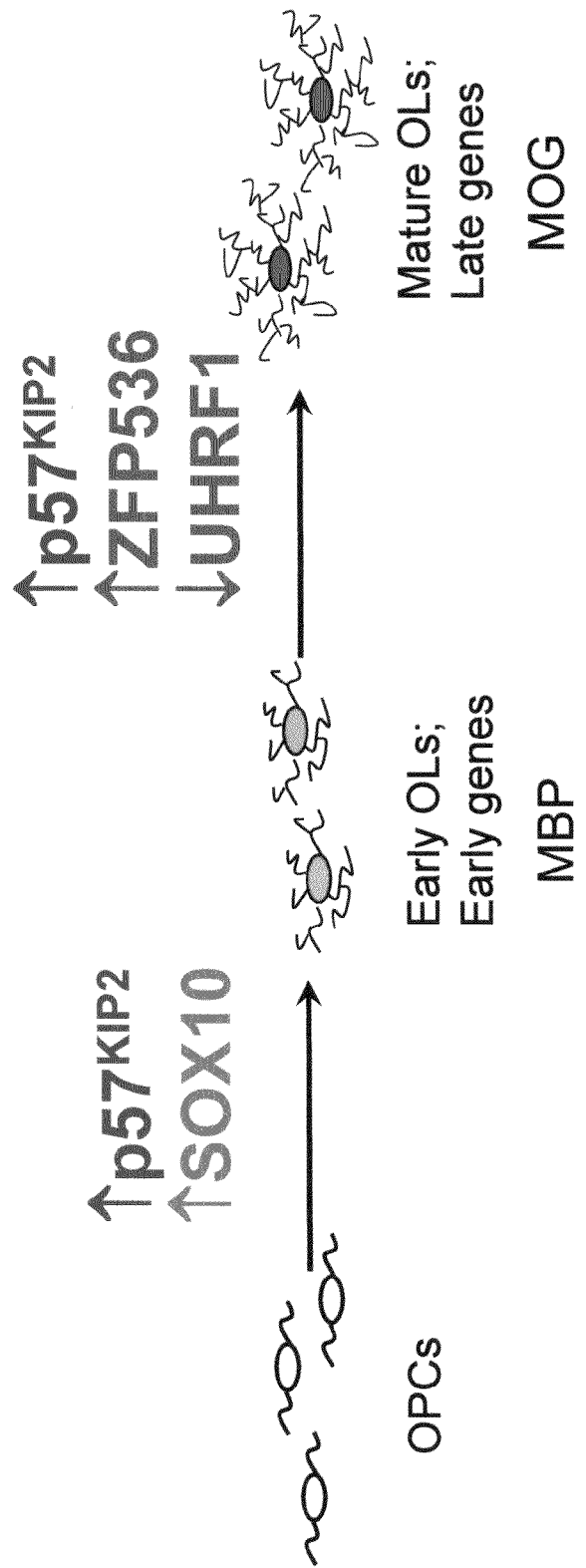
FIG. 38. Depicts a schematic representation for OL differentiation as affected by p57, SOX10, ZFP536 and UHRF1, during early and rate phases.
Figure 39:
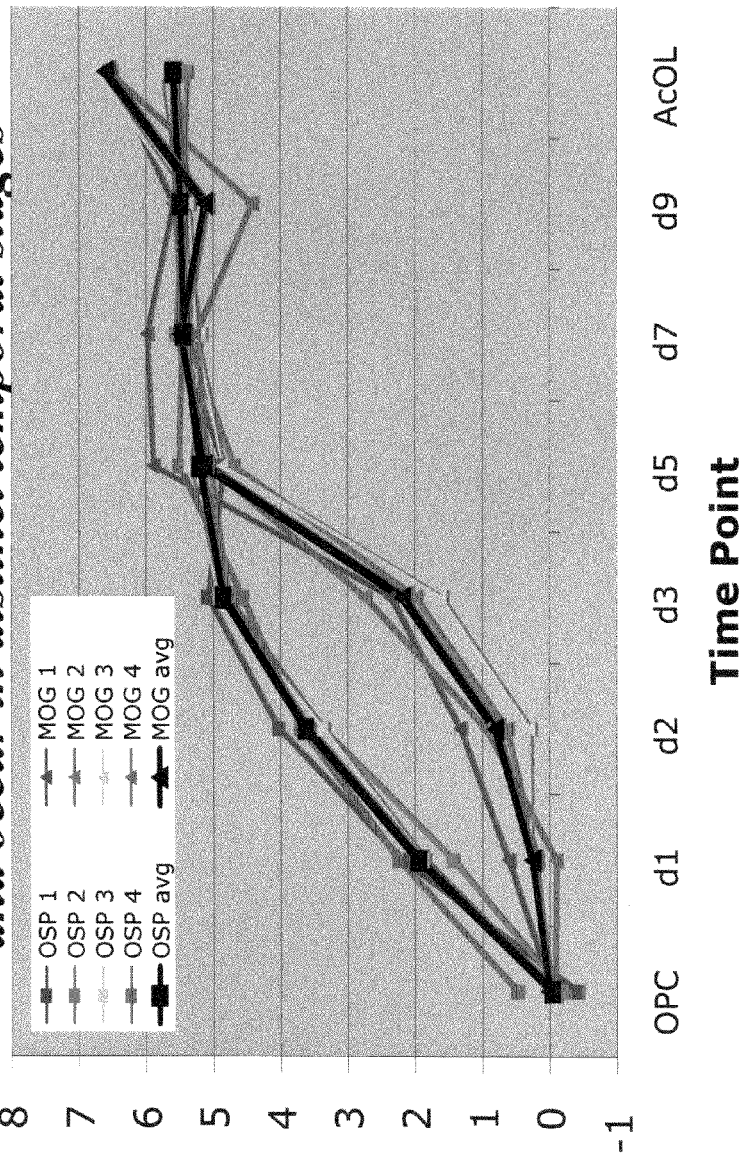
FIG. 39. Depicts a graph illustrating that gene expression changes are highly reproducible and occur in distinct stages.

The CKDI $p57^{Kip2}$ is induced early robustly during the course of OL differentiation (FIG. 30) and in adult white matter in vivo (FIG. 31). Additional studies with $p57^{Kip2}$ under control of a constitutive promoter (CMV) and knockdown experiments demonstrated that reducing $p57^{Kip2}$ retards OL differentiation and increasing $p57^{Kip2}$ enhances differentiation, which demonstrates the role of $p57^{Kip2}$ as a cell cycle arrest component resulting in modulation of proliferation downward while modulation of differentiation upward (FIGS. 34, 35, 36). Furthermore, ZFP536 and p57$^{Kip2}$ cooperatively increased late stage gene expression (FIG. 37)

Example 3 p57$^{Kip2}$'s Role in OL Differentiation

Figure 32:
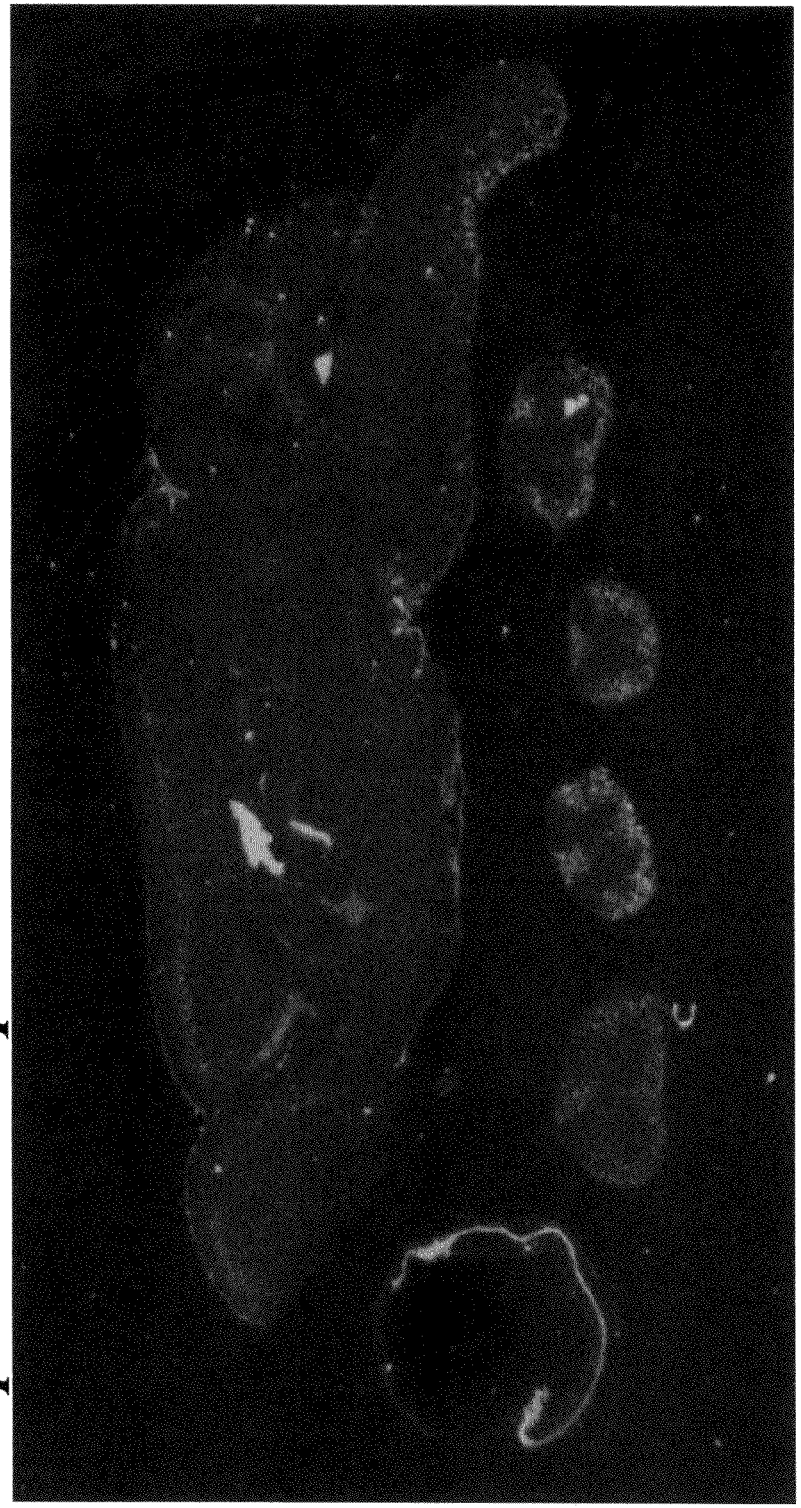
FIG. 32. Presents a photograph illustrating in situ expression pattern of $p57^{kip2}$ in adult mouse CNS (from GENSAT; NCBI).
Figure 33:
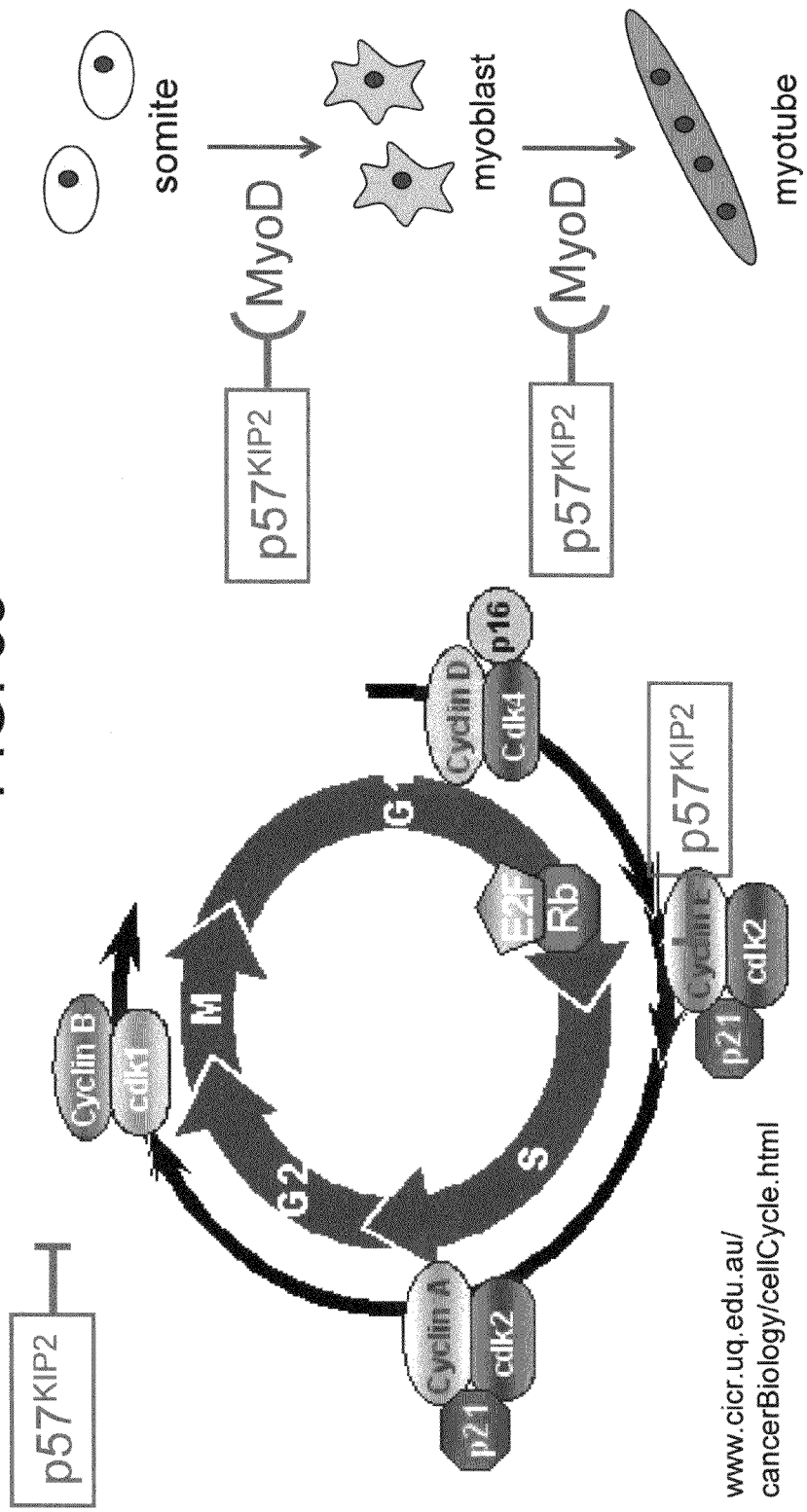
FIG. 33. Depicts a schematic representation for $p57^{kip2}$ and its role in cyclin/cdk cell cycling and myotube formation.
Figure 40:
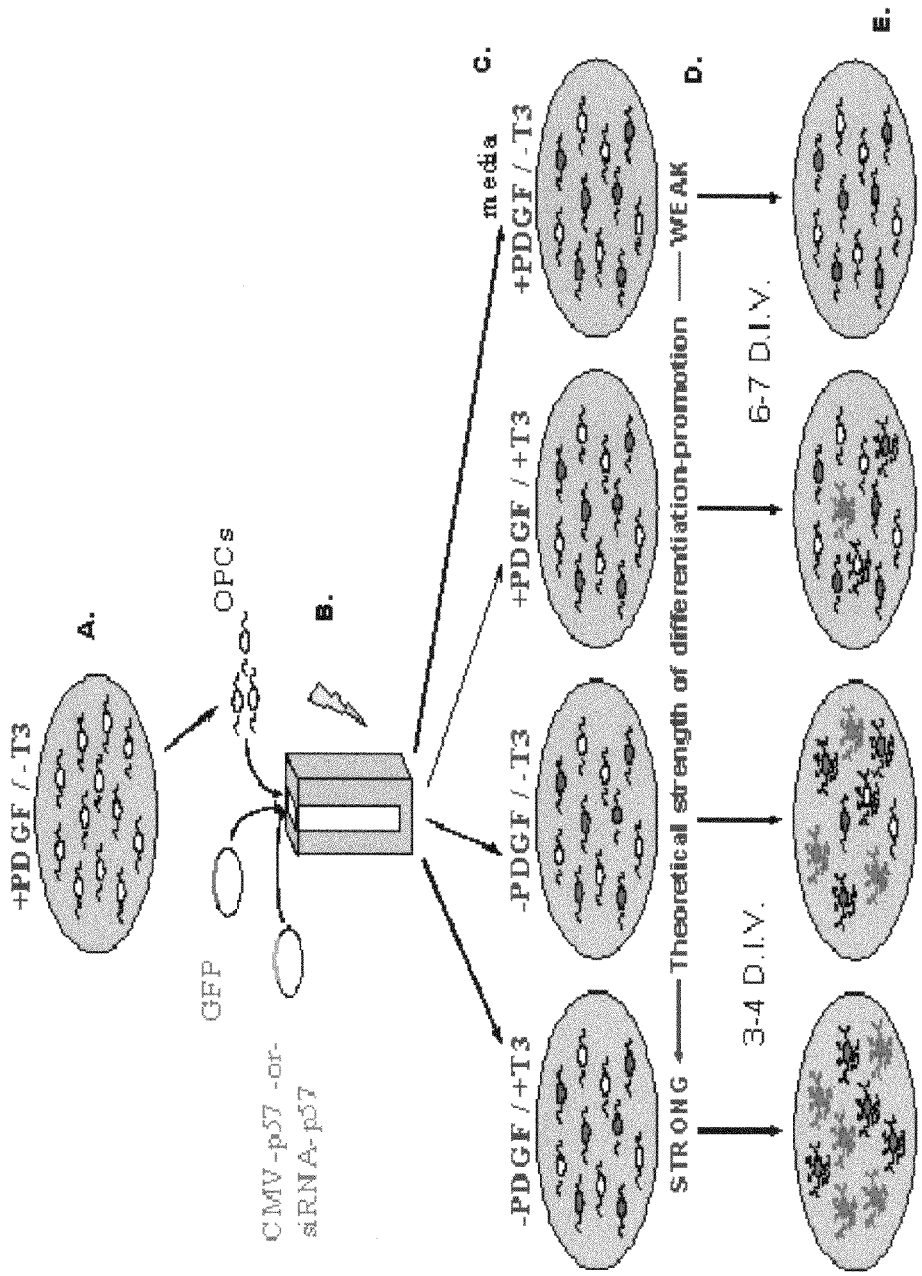
FIG. 40. Depicts a schematic representation of the screening procedure. A. Immunopan-purify P7 rat OPCs and expand in proliferation media for 6-7 days in vitro. Gently lift cells for transfection. B. Co-transfect GFP and pSPORT6-p57 expression vector or Dharmacon p57 siRNA pool into OPCs (AMAXA); negative control siRNA-firefly luciferase. C. Plate in +/−PDGF and T3. D. Incubate for several days and stain for mature OL marker. E. Determine % transfected cells (GFP) stained with mature OL marker (MBP/MOG) for each condition, and compare to control GFP-only level.
Figure 41B:
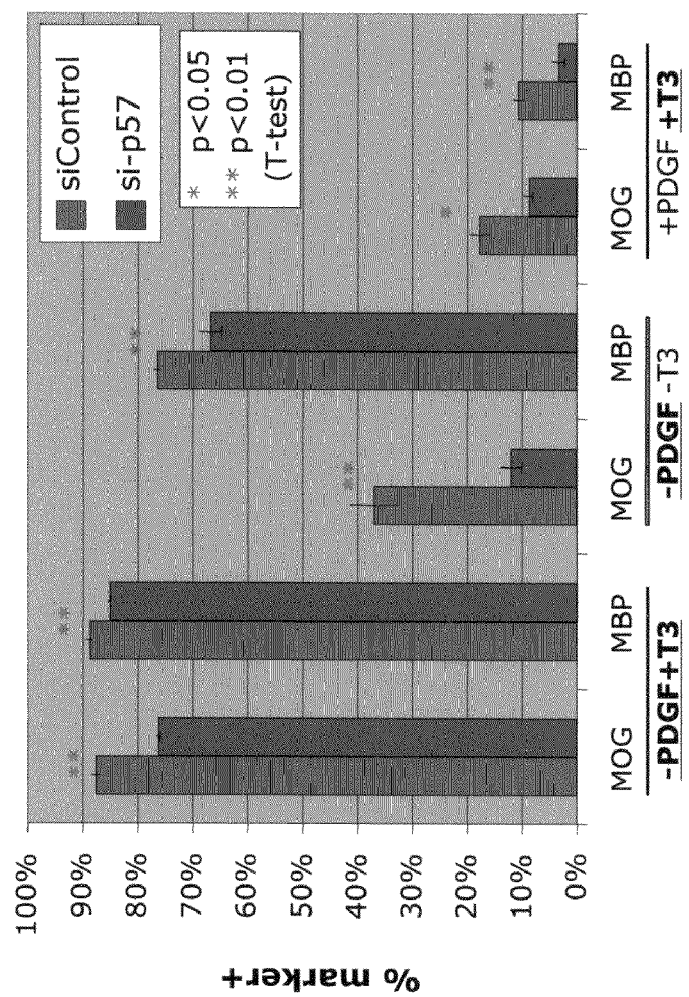
FIG. 41. Depicts reducing $p57^{kip2}$ retards OL differentiation. A. Reduction of p57 levels in transfected OPCs/OLs. OPCs transfected with firefly luciferase- (cont) or $p57^{kip2}$-targeting siRNA pools (Dharmacon), cultured for 4 D.I.V. in −PDGF +T3 or +PDGF +T3 media. $p57^{kip2}$ levels assayed by RT-PCR (27 cycles). B. Reducing $p57^{kip2}$ retards OL differentiation. Transfected cells (GFP+) were scored blind for MBP or MOG marker expression (+ or −). All ±S.E.M., n=3. C. Examples of MBP staining ±$p57^{kip2}$ siRNA. Green arrows denote GFP+ MBP− cells, red arrows denote GFP− MBP+ cells, and yellow arrows denote GFP+ MBP+ cells. GFP expression identifies transfected cells.
Figure 41A:
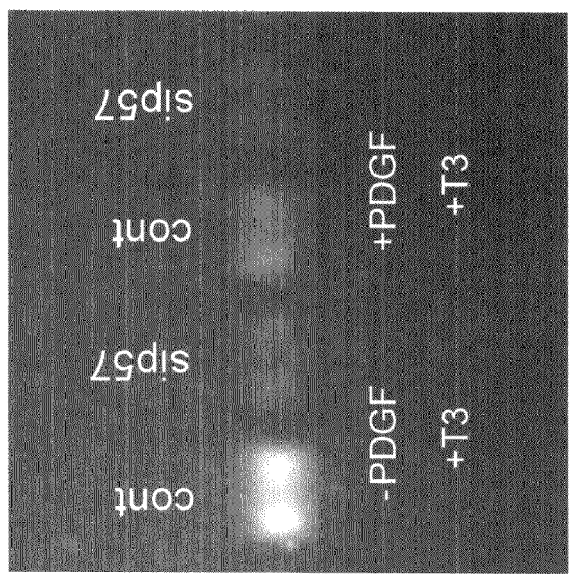

Oligodendrocyte development is a key aspect for any method of treating a myelin disorder, because oligodendrocyte cells are the primary cells responsible for myelin repair in the CNS. In an in vitro model system of OL differentiation, where OL differentiation from a pure population of committed, proliferating oligodendrocyte precursor cells (OPCs) was monitored, p57$^{Kip2}$ was one of the most rapidly induced genes upon initiation of OL differentiation from OPCs (FIG. 31). This induction was also observed in vivo by comparing p57$^{Kip2}$ expression levels in acutely purified OPCs and newly formed OLs. In addition, p57$^{Kip2}$ is expressed in myelinated, white matter areas of the central nervous system (FIG. 32). P73 which promotes OL differentiation also induces p57$^{Kip2}$ expression and p57$^{Kip2}$ is a known inhibitor of the cell cycle, inhibiting formation of Cdk/cyclin complexes (FIG. 33). Furthermore, p57$^{Kip2}$ mutants display several cell cycle exit related defects, similar to human Beckwith-Weidemann syndrome, which has a mutation in the area of p57$^{Kip2}$. In addition, p57$^{Kip2}$ stabilizes transcription factor MyoD thus affecting myeogenesis. Also, p57$^{Kip2}$ promotes domaminergic neuron differentiation through interaction with nuclear receptor Nurr1. All of these data indicated that p57 plays a key a role in moderating OL differentiation.

p57$^{Kip2}$ was either over-expressed or reduced in levels in pure OPCs, and normal OL differentiation and OPC proliferation was observed. To test the necessity of p57$^{Kip2}$ in OL differentiation, knockdowns for p57$^{Kip2}$ were used to reduce p57$^{Kip2}$ levels in OPCs. p57$^{Kip2}$ levels were reduced by transfecting OPCs with siRNA directed against the p57$^{Kip2}$ transcript, and then cultured the transfected OPCs in media that stimulated OL differentiation. Cells transfected with CMV-p57$^{Kip2}$ or siRNA p57$^{Kip2}$ pool were cultured in −PDGF +T3, −PDGF−T3 and +PDGF+/−T3 (FIG. 40), The sip57 knockdowns resulted in reduced p57$^{Kip2}$ expression (FIG. 41A). OPCs transfected with firefly luciferase- (cont) or p57$^{Kip2}$-targeting siRNA pools (Dharmacon) were cultured for 4 D.I.V. in −PDGF +T3 or +PDGF +T3 media and reduction in p57$^{Kip2}$ transcript levels by this method was confirmed by RT-PCR (27 cycles).

Figure 41C:
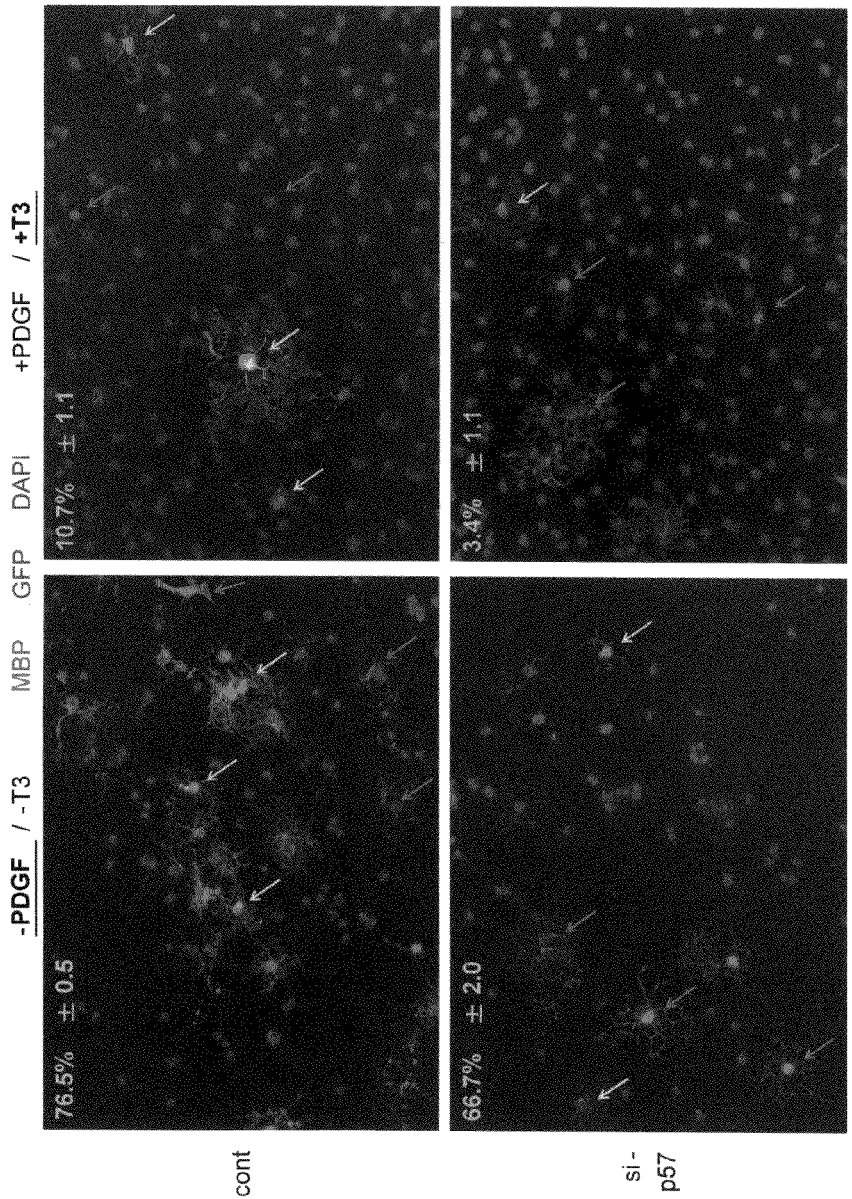
Figure 42:
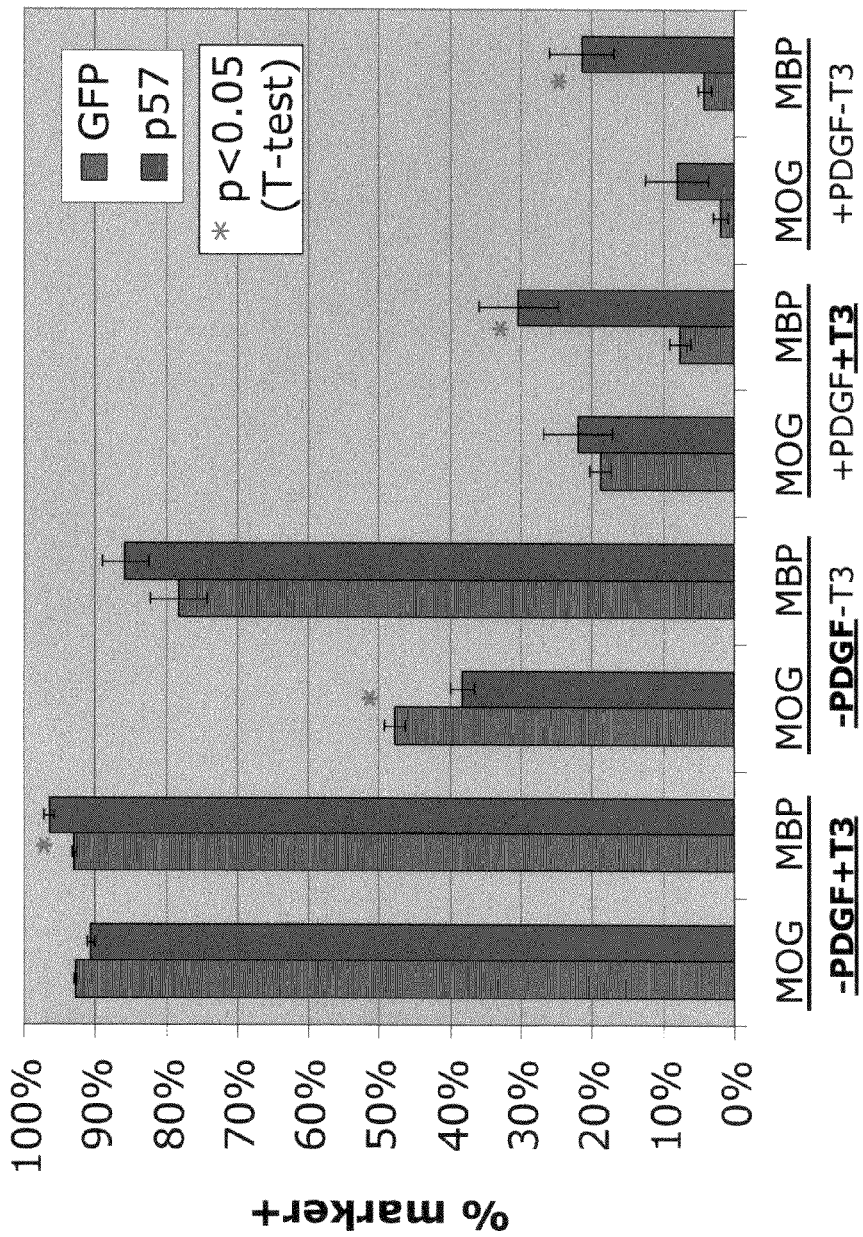
FIG. 42. Shows increasing p57$^{kip2}$ accelerates OL differentiation. p57$^{kip2}$ overexpression accelerates OL differentiation in the presence of PDGF. OPCs transfected with GFP±pSPORT– p57$^{kip2}$ were cultured in ±PDGF±T3 media, then GFP+ cells were scored blind for marker expression (±S.E.M., n=3). Effects most prominent in OPCs cultured in the presence of PDGF; T3 enhances this effect.

Reduction of p57$^{Kip2}$ levels retarded normal OL differentiation when compared to control, non-targeting siRNA transfected OPCs cultured in identical conditions. Levels of differentiation were assayed by observing expression levels of mature OL marker genes (myelin basic protein, MBP and myelin oligodendrocyte glycoprotein, MOG) in transfected cells by immunostaining; transfected cells were identified by expression of co-transfected green fluorescent protein. (FIG. 41). Transfected cells (GFP+) were scored blind for MBP or MOG marker expression (+ or −) (all ±S.E.M., n=3) (FIG. 41B), and examples of MBP staining ±p57$^{Kip2}$ siRNA are shown in FIG. 41C, where green arrows denote GFP+MBP−cells, red arrows denote GFP− MBP+ cells, and yellow arrows denote GFP+MBP+ cells, GFP expression identifies transfected cells. To test the sufficiency of p57$^{Kip2}$ in promoting OL differentiation, OPCs were transfected with a construct that expressed high levels of mammalian p57$^{Kip2}$, and then cultured the OPCs in media that maintains OPCs as immature, proliferating cells. Overexpression of p57$^{Kip2}$ increased levels of inappropriate OL differentiation in proliferation-promoting media compared to control transfected cells (FIG. 42). Together, these findings illustrate that plays an important role in regulating OL differentiation.

Figure 43:
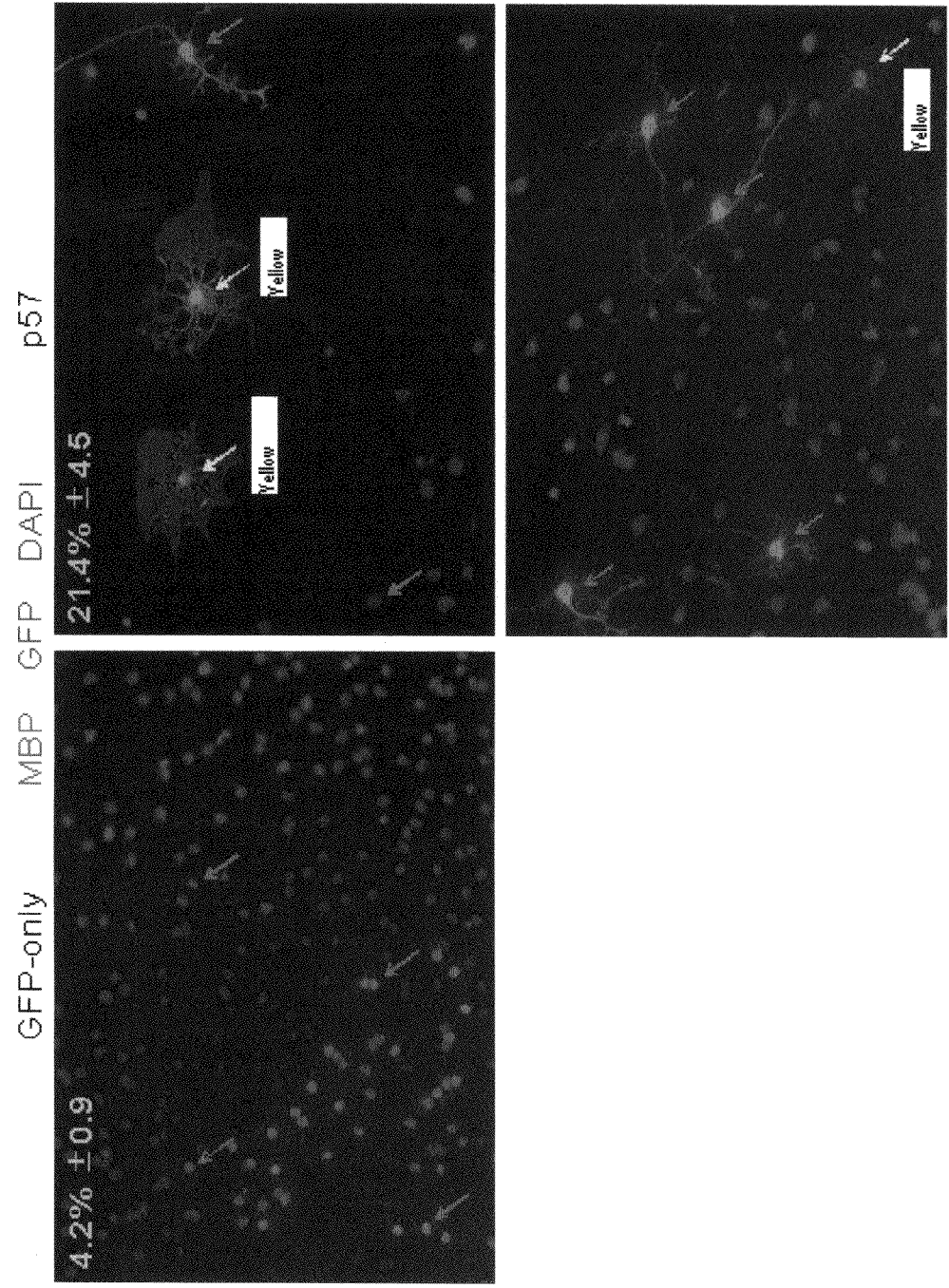
FIG. 43. Shows increasing p57$^{kip2}$ slows OPC proliferation. Some p57$^{kip2}$-overexpressing OPCs cultured in proliferation media (+PDGF−T3) differentiate early (yellow arrows), while others do not differentiate, but divide more slowly and are more morphologically complex than control transfections (green arrows).
Figure 44C:
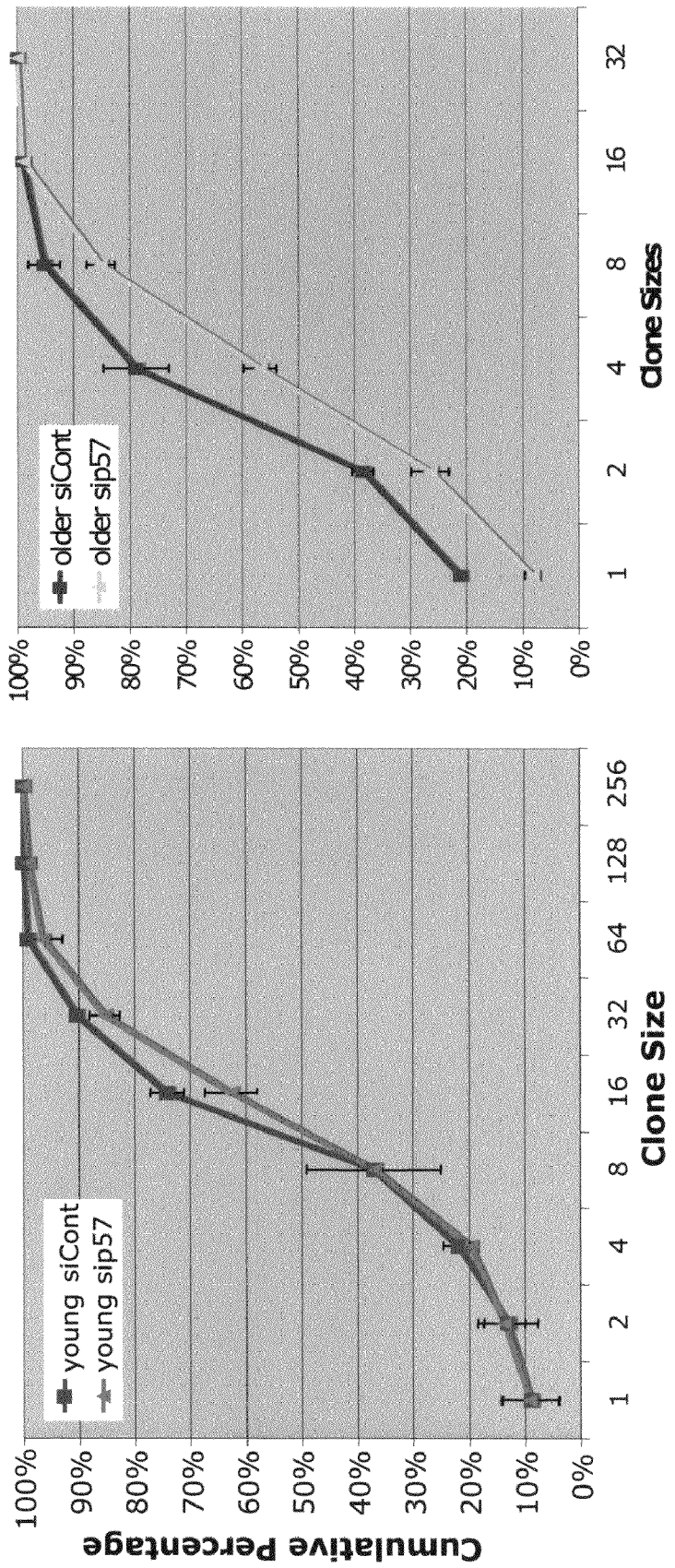
FIG. 44. Shows p57$^{kip2}$ slows OPC proliferation in older OPCs. A. OPC proliferation slows after ~2 weeks in vitro in absence of differentiation-promoting stimuli (initial purification at P7). B. p57$^{kip2}$ levels increase in both differentiated OLs and in slower-dividing OPCs. RT-PCR with p57$^{kip2}$ or actin primers, 27 cycles. C. p57$^{kip2}$ reduction increases older OPC proliferation rate. OPCs passaged for 1 week (young) or 4 weeks (older) in +PDGF−T3 media were transfected with si-control or si-p57$^{kip2}$ and plated at clonal density in +PDGF−T3 media. Clone sizes were analyzed at 4 D.I.V., cumulative clone sizes are plotted as percentage of total number of clones counted (50-100/condition, all points ±S.E.M., n=2). Younger OPCs divide more rapidly than older. OPCs, and p57$^{kip2}$ reduction increases proliferation rate more strongly in older OPCs.

Surprisingly, overexpression of p57$^{Kip2}$ not only promoted early differentiation in a percentage of transfected cells, but also promoted an "adult OPC" like phenotype in undifferentiated transfected cells. OPCs transfected with the p57$^{Kip2}$ expression construct cultured in proliferation-promoting media that did not differentiate into mature OLs did not resemble normal, rapidly proliferating immature OPCs (FIG. 43). Instead, the p57$^{Kip2}$-expressing OPCs divided much more slowly and were more morphologically complex than control transfected OPCs, even though both control and p57$^{Kip2}$-expressing OPCs still expressed OPC markers such as NG2. Therefore, the phenotype of the p57$^{Kip2}$-expressing, undifferentiated OPCs resembled that of OPCs found in adult brains (as compared to young developing brains), where a small pool of undifferentiated, slowly dividing OPCs are retained.

p57$^{Kip2}$ knockdown experiments were also utilized to reduce p57$^{Kip2}$ in cultures grown −PDGF +T3, −PDGF−T3 and +PDGF+/−T3. In culture conditions tested (e.g., differentiation, proliferation, control) OL differentiation was reduced. (FIG. 41). In addition OPC proliferation slows after about 2 weeks in the absence of differentiation promoting stimuli (FIG. 44A). Furthermore, p57$^{Kip2}$ levels increase in both differentiated OLs and in slower-dividing OPCs. RT-PCR with p57$^{Kip2}$ or actin primers confirmed this result. (FIG. 44). In addition, in comparing older OPCs versus younger OPCs, the latter divide more rapidly, but the proliferation rate in older OPCs increased more rapidly where p57$^{Kip2}$ is knockdown. (FIG. 44C).

Figure 45:
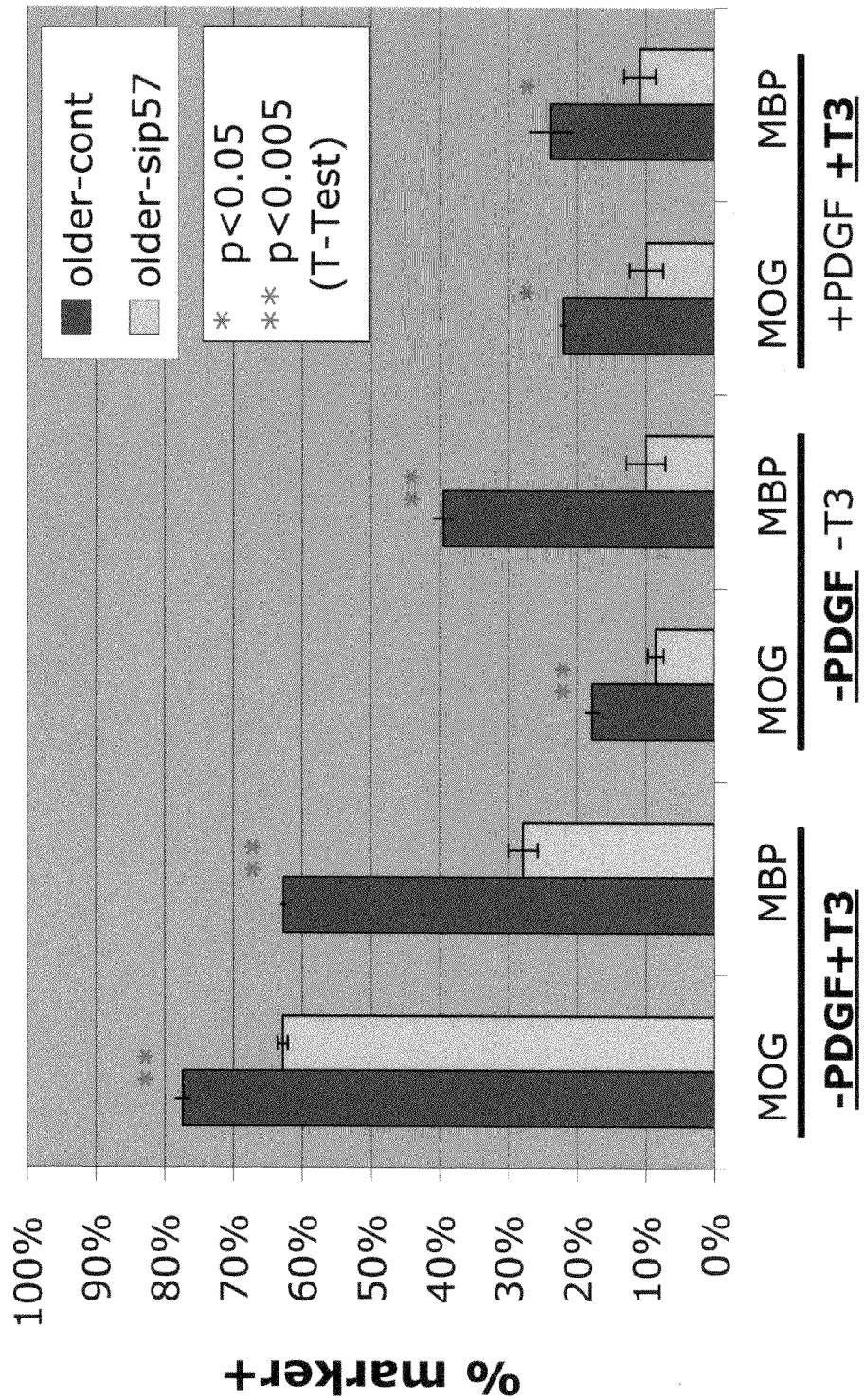
FIG. 45. Shows reducing p57$^{kip2}$ retards older OPC differentiation into OLs. p57$^{kip2}$ knockdown retards OL differentiation from older, slower-dividing OPCs in all conditions tested. Older OPCs were transfected with si-Control or si-p57 and cultured in indicated media, then transfected cells were scored blind for marker expression (±S.E.M., n=3). Note that these effects are generally more pronounced than in younger OPCs.

To determine whether p57$^{Kip2}$ may normally be playing a role in promoting the "adult OPC" like phenotype, young OPC were cultured in vitro for several weeks, under which conditions OPCs innately slow their division rates. p57$^{Kip2}$ levels increased autonomously in OPCs whose division rates had slowed. Knocking down p57$^{Kip2}$ levels in these slowly-dividing OPCs by siRNA transfection, resulted in an increase the cell division rates (FIG. 44C). In addition, in older, slowly-dividing OPCs, reduced p57$^{Kip2}$ levels inhibited their differentiation even though cells were cultured in media that normally promotes OL differentiation (FIG. 45).

Figure 46A:
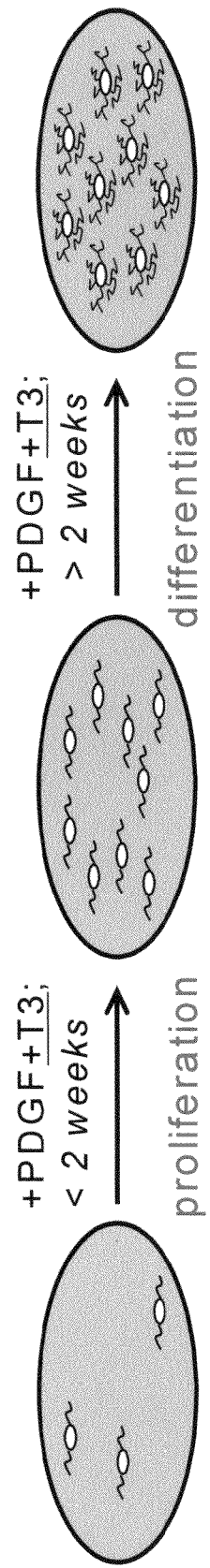
FIG. 46. Shows T3 promotes differentiation robustly in older OPCs; mitogen withdrawal promotes differentiation robustly in younger OPCs. A. OPCs cultured in +PDGF +T3 media proliferate for ~2 weeks before differentiation is induced. B. Younger OPCs differentiate more quickly than older OPCs in response to mitogen withdrawal; older OPCs differentiate more quickly than younger OPCs in response to T3 in PDGF. All scored blind; ±S.E.M., n=3.
Figure 46B:
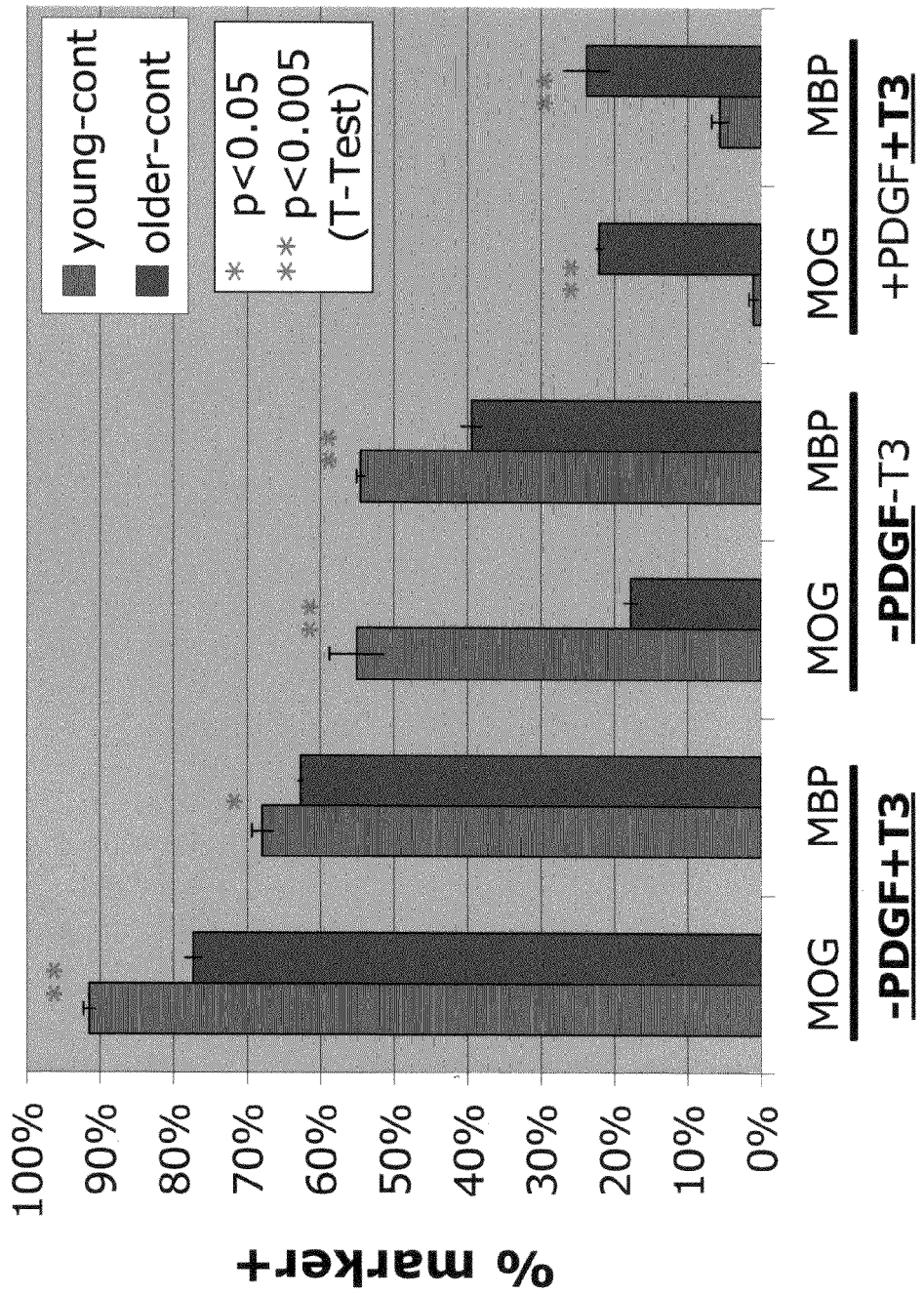

OL differentiation can be extrinsically promoted in a number of ways. Differentiation can be promoted immediately by withdrawing the mitogenic factor PDGFa from the media, which is required to promote OPC proliferation. Alternatively, OPC exposure to thyroid hormone T3 triggers differentiation even in the presence of PDGFa, but only after OPCs have undergone a sufficient number of divisions. Interestingly, the amount of time required to pass before OPCs begin responding to T3 closely resembles the amount of time in culture that passes before rapidly dividing OPCs begin to intrinsically slow their division rates (FIG. 46). In older OPCs that both divide slowly and differentiate robustly in response to T3, p57$^{Kip2}$ knock down reduces differentiation in response to T3 hormone (FIG. 45).

Figure 47:
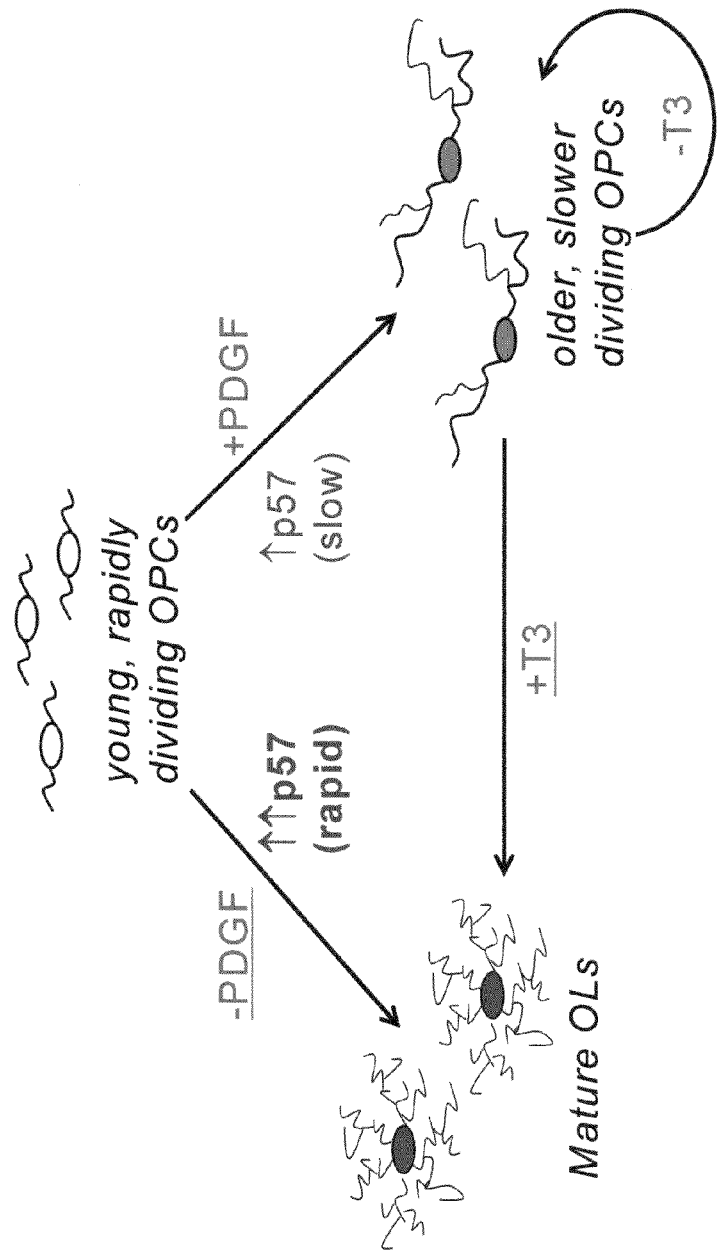
FIG. 47. Depicts a schematic that p57$^{kip2}$ increase promotes differentiation. Mitogen withdrawal can trigger rapid p57 increase in young OPCs, which promotes OL differentiation. This differentiation is enhanced in the presence of T3. In the presence of PDGF, young OPCs proliferate and gradually accumulate p57$^{kip2}$. Once p57$^{kip2}$ levels rise in OPCs, the cells divide more slowly, resembling "adult" OPCs. At this stage, T3 can promote OL differentiation by overriding the proliferation-promoting signals from mitogens.

In addition, p57$^{Kip2}$ expression is immediately increased in OPCs in response to mitogen withdrawal, but that T3 exposure does not, on its own, promote an increase in p57$^{Kip2}$ expression. Taken together, these data illustrate that p57$^{Kip2}$ is immediately induced in OPCs in response to mitogen withdrawal, and that this acute increase in p57$^{Kip2}$ promotes OL differentiation. In addition, p57$^{Kip2}$ can gradually increase over time in undifferentiated, dividing OPCs, and that this increase in p57$^{Kip2}$ can lead to a reduction in proliferation rate, producing a population of slowly dividing precursors maintained into adulthood. This increase in p57$^{Kip2}$ levels also makes the undifferentiated older OPCs more sensitive to thyroid hormone, such that the older OPCs can now respond to T3 by differentiating into mature OLs (FIG. 47).

As a therapeutic target, if $p57^{Kip2}$ is in fact keeping adult OPC proliferation rates very low, temporary disruption of $p57^{Kip2}$ activity can promote the expansion of the population of OPCs present in the adult brain. This expanded population of OPCs may then be able to more readily remyelinate demyelinated plaques in the multiple sclerosis affected brain. In addition, since $p57^{Kip2}$ activity is crucial to promote normal OL differentiation, and therefore myelination, modulation of $p57^{Kip2}$ activity serves to promote the formation of myelin from OPCs that are inhibited from differentiating in demyelinated plaques.

Figure 48A:
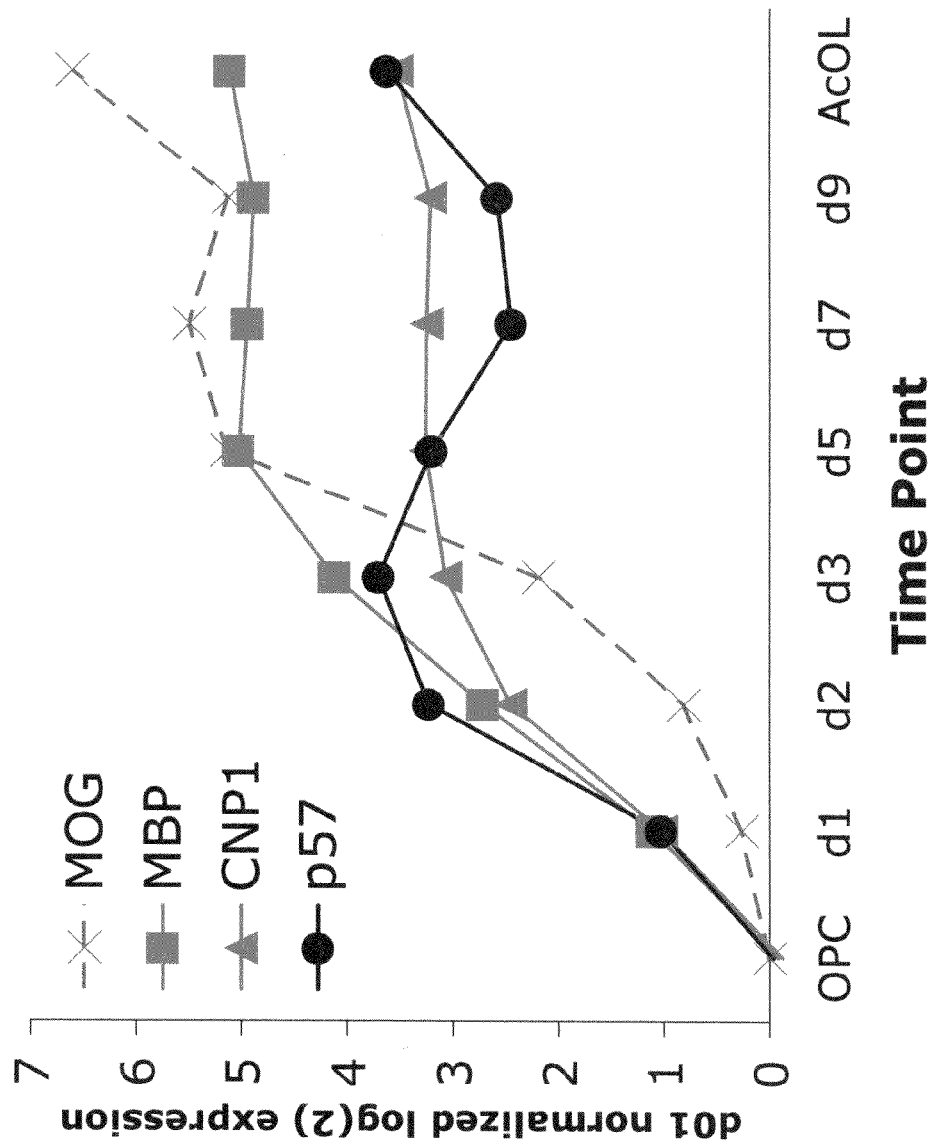
FIG. 48. Shows regulation of p57$^{Kip2}$ expression and p57$^{Kip2}$ is expressed in differentiating OLs. A. p57$^{kip2}$ is induced in differentiating OLs in vitro. Expression levels of p57$^{Kip2}$ (black circles, rc_AA998565_at probe set), early induced myelin genes CNP (grey triangles, L16532_at) and MBP (grey squares, average K00512_at, rc_AI044093_at, rc_AI145512_at), and late induced myelin gene MOG (grey dashed Xs, M99485_at) as assayed on Affymetrix U34A-C gene chips (Dugas et al., J. Neurosci. 26:10967-10983 (2006)). OPC-purified OPCs, d1-d9—days following induction of OL differentiation in vitro by mitogen withdrawal and T3 exposure, AcOL—acutely purified P12 OLs. All p57$^{Kip2}$ expression values normalized to OPC expression level, expressed on a log$^2$ scale. B. In situ expression of p57$^{Kip2}$ in sagital sections of P7 (B1) and P42 (B2) mouse brain, obtained from St. Jude's BGEM website (www.stjudebgem.org). C-F. Immunostaining of P7 (C-D) and P24 (E-F) optic nerve sections. Sections were co-stained for CC-1 (red) and p57$^{Kip2}$ (white) expression (C, E) or NG2 (red) and p57$^{Kip2}$ (white) expression (D, F); blue—DAPI nuclear stain. Green arrows indicate cells expressing only p57$^{Kip2}$, red arrows indicate cells only expressing CC-1 (C, E) or NG2 (D, F), and yellow arrows indicate cells co-expressing p57$^{Kip2}$ and either CC-1 or NG2. G. Proportion of NG2+ OPCs (grey bars) and CC1+ OLs (black bars) that were positive for p57$^{Kip2}$ expression in the optic nerve at various developmental ages, as assayed by immunostaining. H. Proportion of p57$^{Kip2}$-positive cells that were NG2+ OPCs (grey bars) or CC-1+ OLs (black bars) in the optic nerve at various developmental ages. In G-H, for each age-staining (p57$^{Kip2}$+ NG2 and p57$^{Kip2}$+ CC-1), >100 cells were scored from two distinct optic nerves, except P24-NG2 and P40-NG2 (48 and 23 cells respectively) due to paucity of NG2+ and p57$^{Kip2}$+ cells at those ages. I. RTPCR to assay p57$^{Kip2}$ (23 and 25 cycles) and beta-actin (control, 23 cycles) expression levels in purified P8 OPCs incubated for 6 DIV in medium containing or lacking PDGF/NT3 (±P), containing or lacking T3 (±T).

As mentioned above, to investigate how cell cycle regulation is linked to OL differentiation, gene chip technology was utilized to identify the cell cycle control genes that are strongly regulated as OPCs differentiate into OLs in vitro (Dugas et al., *J. Neurosci.* 26:10967-10983 (2006)). In particular, the cell cycle inhibitor gene $p57^{Kip2}$ (a.k.a. cdkn1c) was strongly upregulated immediately following the initiation of OL differentiation (FIG. 48A). In fact, $p57^{Kip2}$ is one of the earliest induced genes in purified OPCs following coupled mitogen withdrawal (removal of platelet derived growth factor-AA (PDGF) and neurotrophin-3 (NT3); "-PDGF") and thyroid hormone triiodothyronine exposure ("+T3") to induce differentiation. Indeed, $p57^{Kip2}$ demonstrated a strong change in expression level. The induction of $p57^{Kip2}$ expression in OLs was confirmed in vivo by comparing $p57^{Kip2}$ levels in total RNA obtained from acutely-purified postnatal day 7 (P7) OPCs and P12 OLs, both on Affymetrix gene chips (FIG. 48A, "AcOL"=acutely purified OLs) and by RT-PCR on independently-obtained samples.

Figure 48B:
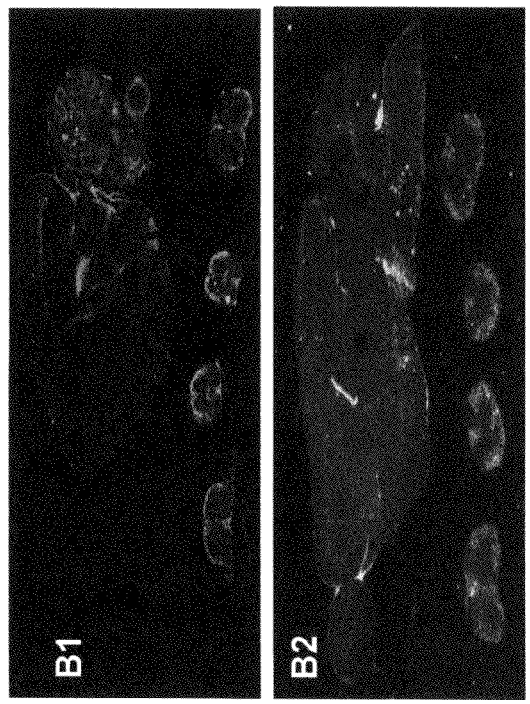
Figure 48D:
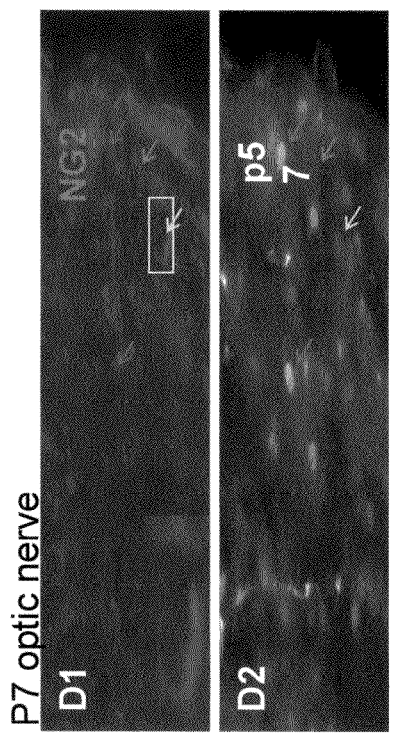
Figure 48F:
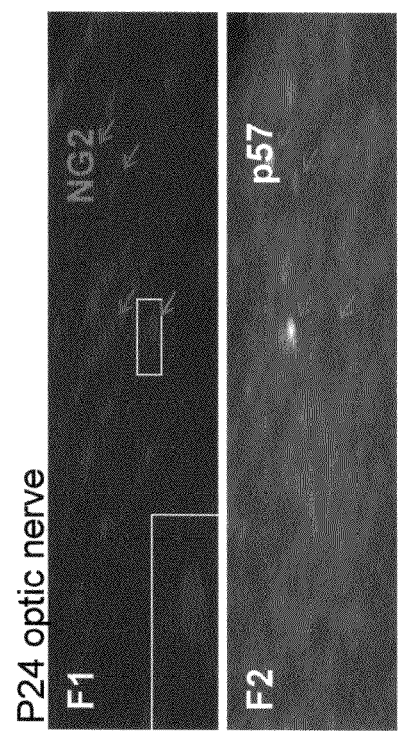
Figure 48C:
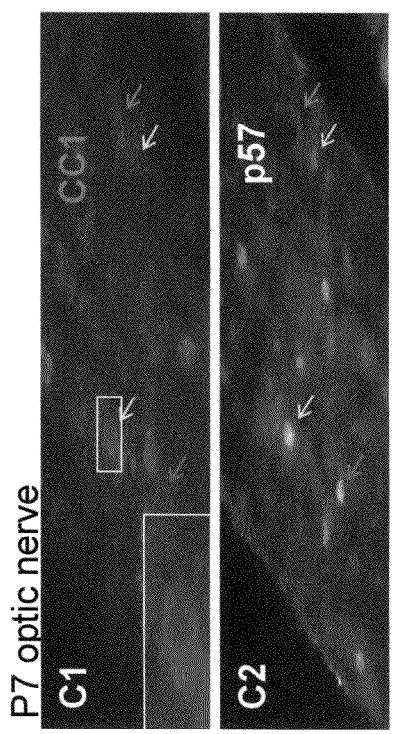
Figure 48E:
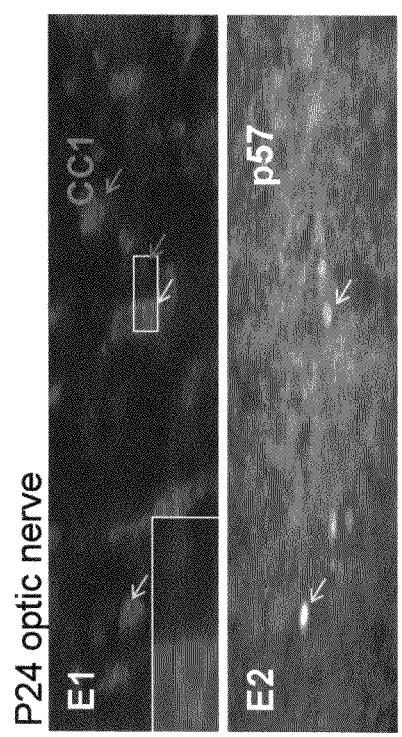

To more closely examine/expression in vivo, the in situ RNA expression patterns in P7 and adult mice were analyzed, as determined by the St. Jude Children's Research Hospital Brain Gene Expression Map (BGEM) (FIG. 48B). At P7, $p57^{Kip2}$ expression is detected in the white matter areas of the spinal cord and corpus callosum. Interestingly, by adulthood (P42) $p57^{Kip2}$ expression was still present in white matter regions of the spinal cord, but no longer detected in the corpus callosum. To more precisely resolve the in vivo cellular time course of $p57^{Kip2}$ expression, rat optic nerves were co-stained at various developmental ages (P2, P7, P24, P40) for $p57^{Kip2}$ and markers of immature OPCs (NG2) and mature OLs (CC1). Expression was detected in the nuclei of both OLs and OPCs at P2, P7 (FIG. 48C-D), and P24 (FIG. 48E-F), and almost entirely extinguished by P40 (FIG. 48G). By determining how many OPCs or OLs were co-expressing $p57^{Kip2}$ at each age, it was determined that $p57^{Kip2}$ expression peaked at P7 (FIG. 48G), the time at which myelination is initiated in the optic nerve. After determining the phenotype of cells expressing $p57^{Kip2}$ at various ages, it was observed that an equal proportion of $p57^{Kip2}$-expressing cells are OPCs and OLs early in development (P2), and that the majority of $p57^{Kip2}$-expressing cells are OLs at later time points (FIG. 48H).

Figure 48I:
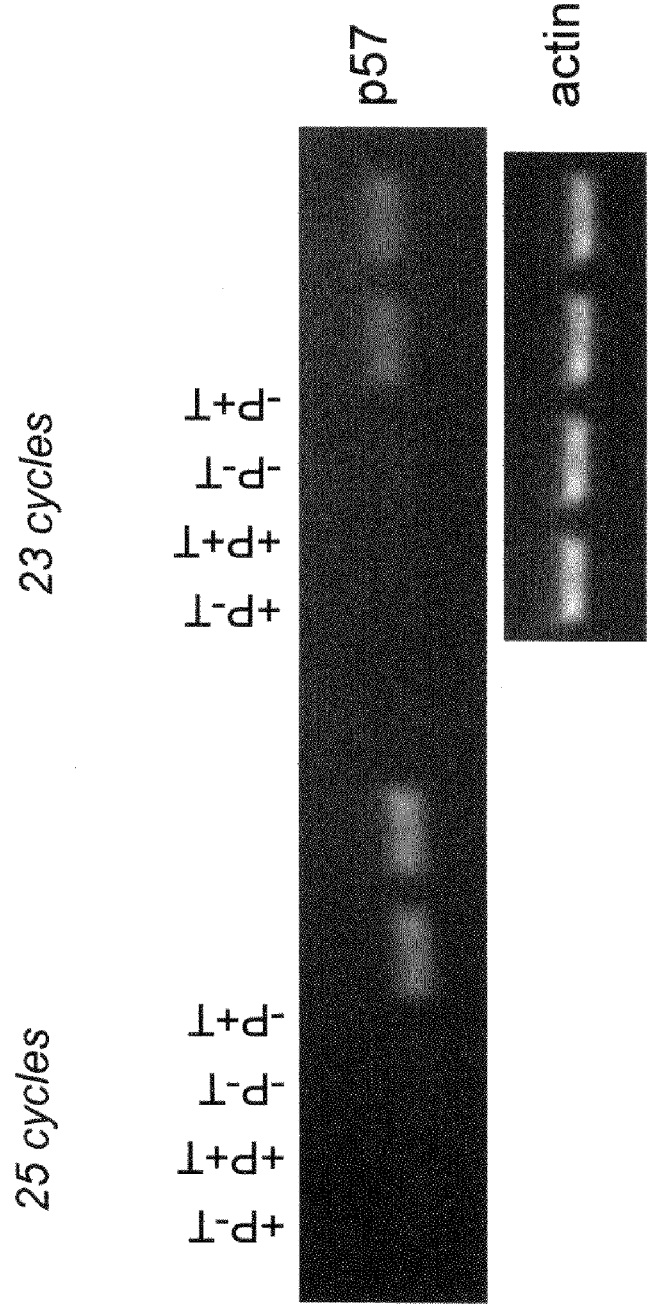

These results indicate that $p57^{Kip2}$ expression peaks during the initiation of myelination in OL-lineage cells, and is extinguished in established, stably mature OLs in vivo, at least in the optic nerve and corpus callosum. OL differentiation can be triggered by either by mitogen withdrawal or by the intrinsic timer coupled with exposure to T3 (Barres and Raff, *Neuron* 12:935-942 (1994)). Whereas either of these conditions will produce mature OLs, the initial genetic programs triggered by these two stimuli are not identical (Tokumoto et al., *EMBO J.* 20:5261-5268 (2001)). To more precisely determine how $p57^{Kip2}$ expression is induced, purified P8 OPCs were subjected to either mitogen withdrawal, T3 exposure, or both differentiation-promoting stimuli simultaneously (FIG. 48I). By semi-quantitative RT-PCR, it was found that mitogen withdrawal strongly induced $p57^{Kip2}$ expression after 6 days in vitro (DIV), in either the presence or absence of T3; induction of $p57^{Kip2}$ expression was seen as early as 3 DIV after mitogen withdrawal (data not shown). Conversely, it was found that T3 exposure did not induce $p57^{Kip2}$ expression after 6 DIV. Therefore, mitogen withdrawal is the stimulus responsible for the rapid induction of $p57^{Kip2}$ that was observed in the genomics experiments (FIG. 48A).

The previous studies have indicated that $p57^{Kip2}$ expression is robustly upregulated in OPCs induced to differentiate specifically by mitogen withdrawal in vitro, but also that $p57^{Kip2}$ expression is detected in undifferentiated OPCs in vivo (FIG. 48). To investigate the regulation of $p57^{Kip2}$ expression in undifferentiated OPCs, we cultured purified P8 OPCs for 28 days consistently in proliferation-promoting (+PDGF -T3) medium. To maintain the OPCs at a density that would minimize their spontaneous differentiation into OLs, the OPCs were passaged every 4-7 days by gentle trypsinization, followed by re-plating at lower densities. Cultures were checked at various times, and at no point were greater than 2-4% of the cells present OLs by morphology. By RT-PCR, it was found that OPCs increased their $p57^{Kip2}$ expression over time, such that after 28 DIV in the absence of any differentiation-promoting stimuli, these OPCs expressed $p57^{Kip2}$ at a level higher than the original population of purified P8 OPCs, and at a level similar to OLs generated in vitro by mitogen withdrawal (FIG. 49A). Interestingly, this intrinsic rise in $p57^{Kip2}$ expression correlates with a reduction in OPC division rate (FIG. 50A and FIG. 51A, C), and can account for the slowing in passaged OPC cell division rate previously reported (Tang et al., *J. Cell. Biol.* 148:971-984 (2000)). When a single OPC is plated at clonal density in the presence of PDGF, all of the cells derived from that single proliferating OPC tend to differentiate synchronously in response to T3 exposure (Barres et al., *Development* 120: 1097-1108 (1994); Temple and Raff, *Cell* 44.773-779 (1986)). Therefore, any molecule involved in controlling the intracellular timer that regulates the sensitivity of OPCs to T3 would be expected to simultaneously change in all of the cells belonging to a single OPC clone.

To determine whether $p57^{Kip2}$ levels rise synchronously within proliferating OPC siblings, the expression levels of $p57^{Kip2}$ within individual clones of OPCs were examined. Proliferating OPCs were plated at clonal density in the presence of mitogens with or without T3 for 4 or 7 DIV and then immunostained for $p57^{Kip2}$ expression. With rare exception, by examining staining intensity it was evident $p57^{Kip2}$ was expressed uniformly in every cell belonging to a single clone (FIG. 49B). At 4 days post-plating, we found only 1 of 27 clones where individual cells expressed different levels of $p57^{Kip2}$, and only 3 mixed out of 47 total clones at 7 days post plating (FIG. 49H). Much more common were clones expressing uniformly high (FIG. 49C, F) or low (FIG. 49D, G) levels of $p57^{Kip2}$. Consistent with observations that $p57^{Kip2}$ expression increases in cultured, proliferating OPCs over time in the absence of any T3 stimulation (+PDGF -T3 medium), an increase is observed in the number of clones expressing higher levels of $p57^{Kip2}$ from day 4 to day 7: 5 of 27 clones uniformly expressed high levels of $p57^{Kip2}$ at day 4, which increased to 16 of 24 at day 7. Interestingly, T3 exposure does not increase the rate of clonal $p57^{Kip2}$ induction (15 out of 23 total clones expressed uniformly high levels of $p57^{Kip2}$ after 7 days in +PDGF +T3 medium), reinforcing the finding that T3 does not regulate p57$^{Kip2}$ expression. The finding that p57$^{Kip2}$ expression increases over time in proliferating OPCs, but that clones of OPCs rarely contain cells expressing both high and low levels of p57$^{Kip2}$, indicates that induction of p57$^{Kip2}$ expression occurs about simultaneously in all the cells belonging to a single clone.

Figure 50A:
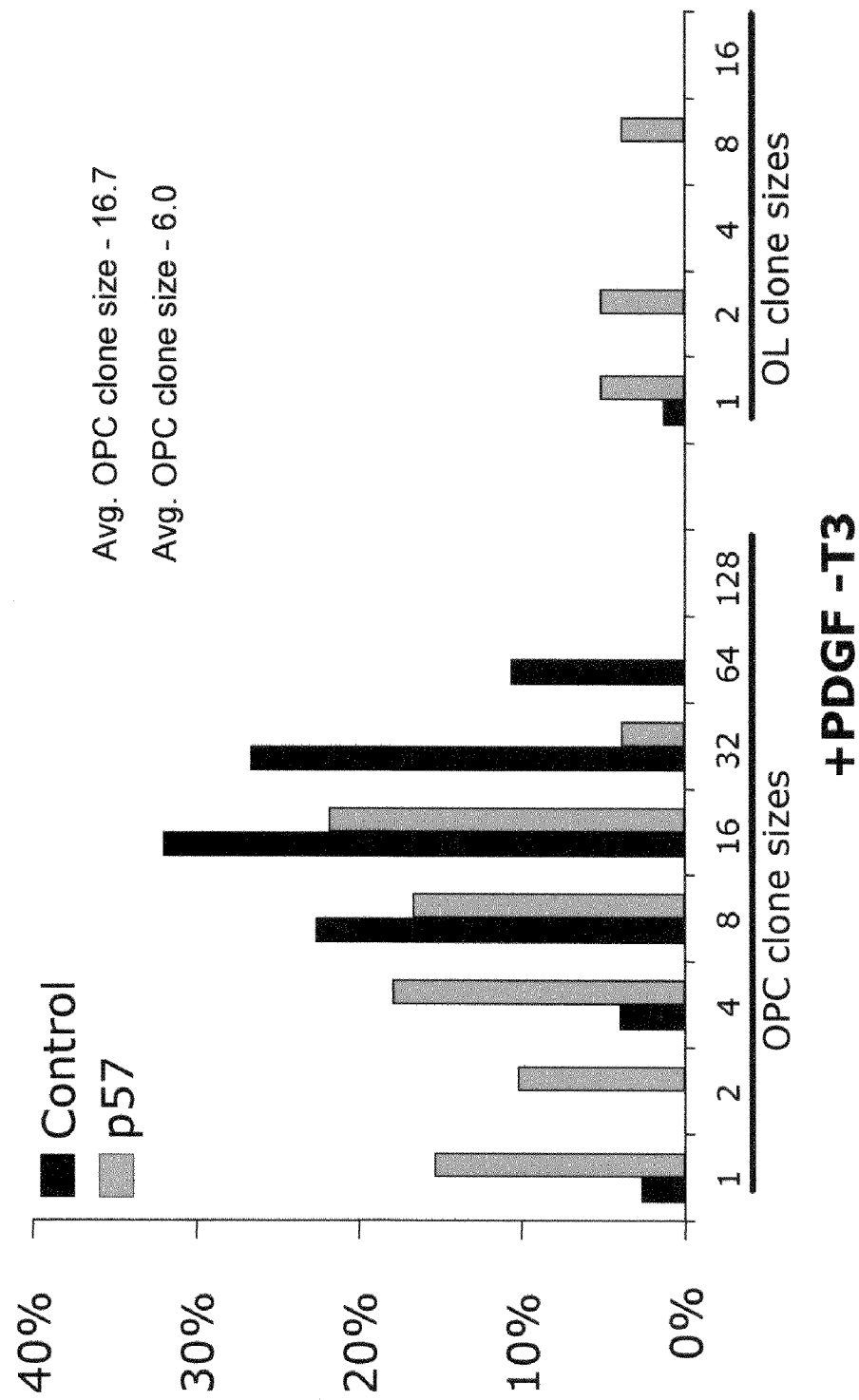
FIG. 50. Shows increasing p57$^{Kip2}$ slows OPC proliferation and accelerates OPC responsiveness to T3. A-B. Purified OPCs transfected with a CMV-GFP vector alone (black bars) or CMV-GFP+CMV-p57$^{Kip2}$ vectors (grey bars), then plated at clonal density (250 cells/well) and cultured for 4 DIV in PDGF/NT3 containing medium without (A) or with (B) added T3 (+PDGF ±T3). Only clones containing GFP+ cells were scored. Clones containing ≧50% OLs (by morphology) were scored as OL clones, <50% OLs as OPC clones, and both OPC and OL clone sizes were binned and plotted as histograms (1, 2, 3-4, 5-8 cells, etc.). In each condition >70 clones were scored. In both A and B OPC clone sizes are significantly decreased by p57$^{Kip2}$ overexpression (p<0.0001 Student's t-test). C-E. In each experiment, the proportions of transfected (GFP+) cells expressing CNP, MBP, or MOG were determined by immunostaining after culturing as described; ±S.E.M., n=3 each condition. C. Purified OPCs transfected with CMVGFP (black bars) or CMV-GFP+CMV-p57$^{Kip2}$ (grey bars) were cultured for 7 DIV in +PDGF +T3 medium before immunostaining; *=p<0.01, **=p<0.001
Figure 50B:
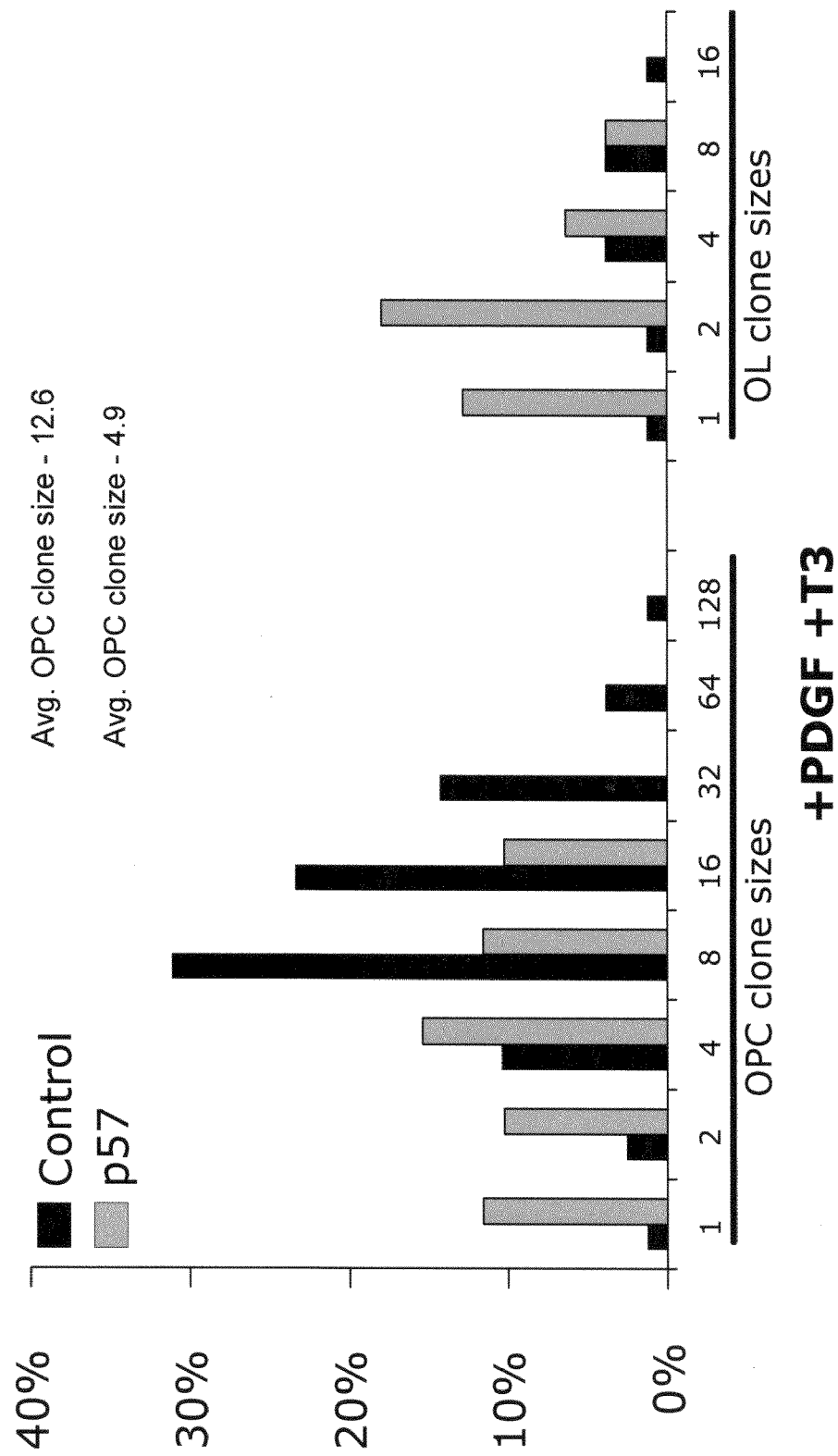

The fact that p57$^{Kip2}$ expression increases synchronously in clones of proliferating OPCs, independent of T3 stimulation, indicates that p57$^{Kip2}$ is a component of the intrinsic timer that limits the number of divisions OPCs can undergo in the presence of T3 (Barres et al., *Development* 120:1097-1108 (1994)). To investigate this further, effects of increasing p57$^{Kip2}$ levels on OPC proliferation rate and responsiveness to T3 were examined. Purified OPCs were co-transfected with plasmids expressing GFP (to identify transfected cells) and p57$^{Kip2}$ from constitutive CMV promoters, and then plated at clonal density in mitogen-containing media that either contained or lacked T3 for 4 DIV. In pure proliferation-promoting medium (+PDGF −T3), p57$^{Kip2}$ overexpression significantly reduced OPC proliferation rate when compared to control, GFP-only transfected OPCs (FIG. 50A, and Table 1). In addition, the percentage of clones containing >50% OLs (by morphology) is slightly increased, corresponding to the low level of spontaneous differentiation previously observed in OPCs after proliferation for an extended period of time (Barres and Raff, *Neuron* 12:935-942 (1994)). When OPCs were cultured in mitogens in the presence of T3 (FIG. 50B), a slight reduction in division rate in response to T3 alone (control transfections) and a stronger reduction in division rate when p57$^{Kip2}$ overexpression was coupled with T3 exposure (Table 1) resulted. p57$^{Kip2}$ overexpression also greatly increased the number of clones that differentiated in response to T3, raising the percentage of OL-majority clones from 11.7% to 41%. p57$^{Kip2}$-transfected clones also differentiated earlier in response to T3, as indicated by the average clone sizes of the OL-morphology clones (control =4.3 versus p57$^{Kip2}$=2.1). The role of p57$^{Kip2}$ in regulating the timer that controls OL differentiation was established in greater detail by determining the effect of p57$^{Kip2}$ overexpression on T3-induced myelin gene expression. As previously determined that OL differentiation occurs in multiple distinct stages (Dugas et al., *J. Neurosci.* 26:10967-10983 (2006)), the data herein indicates the effects of increasing p57$^{Kip2}$ on markers of both early (cyclic nucleotide phosphodiesterase 1 (CNP); myelin basic protein (MBP)) and late (myelin oligodendrocyte glycoprotein (MOG)) stage OL differentiation (FIG. 48A). Transfected OPCs were cultured for 7 DIV in the presence of both mitogens and T3, and then immunostained for CNP, MBP, or MOG expression (FIG. 50C). When compared with GFP-only transfected control cells, p57$^{Kip2}$ overexpression greatly enhanced the percentages of transfected cells expressing early markers of OL differentiation (CNP and MBP) in the presence of T3, resembling the increase in OL-majority clones observed previously. Interestingly, the acceleration of the OPC differentiation timer induced by p57$^{Kip2}$ expression only augmented the early phase of OL maturation; expression of the late-phase marker MOG was not altered by overexpression of p57$^{Kip2}$. Since OPCs aged in culture intrinsically increased their p57$^{Kip2}$ expression levels, these older OPCs were examined to determine if they were also more responsive to T3. Similar to previously published observations (Barres et al., *Development* 120:1097-1108 (1994)), when purified P8 OPCs were initially aged in culture for 28 DIV in +PDGF −T3 medium, a much higher percentage of these older OPCs differentiated in response to T3 exposure relative to younger purified OPCs (FIG. 50D). In contrast to the p57$^{Kip2}$-overexpressing younger OPCs, these older OPCs generated OLs that robustly expressed not only the early OL differentiation markers CNP and MBP, but also the later marker MOG in response to T3.

Figure 50E:
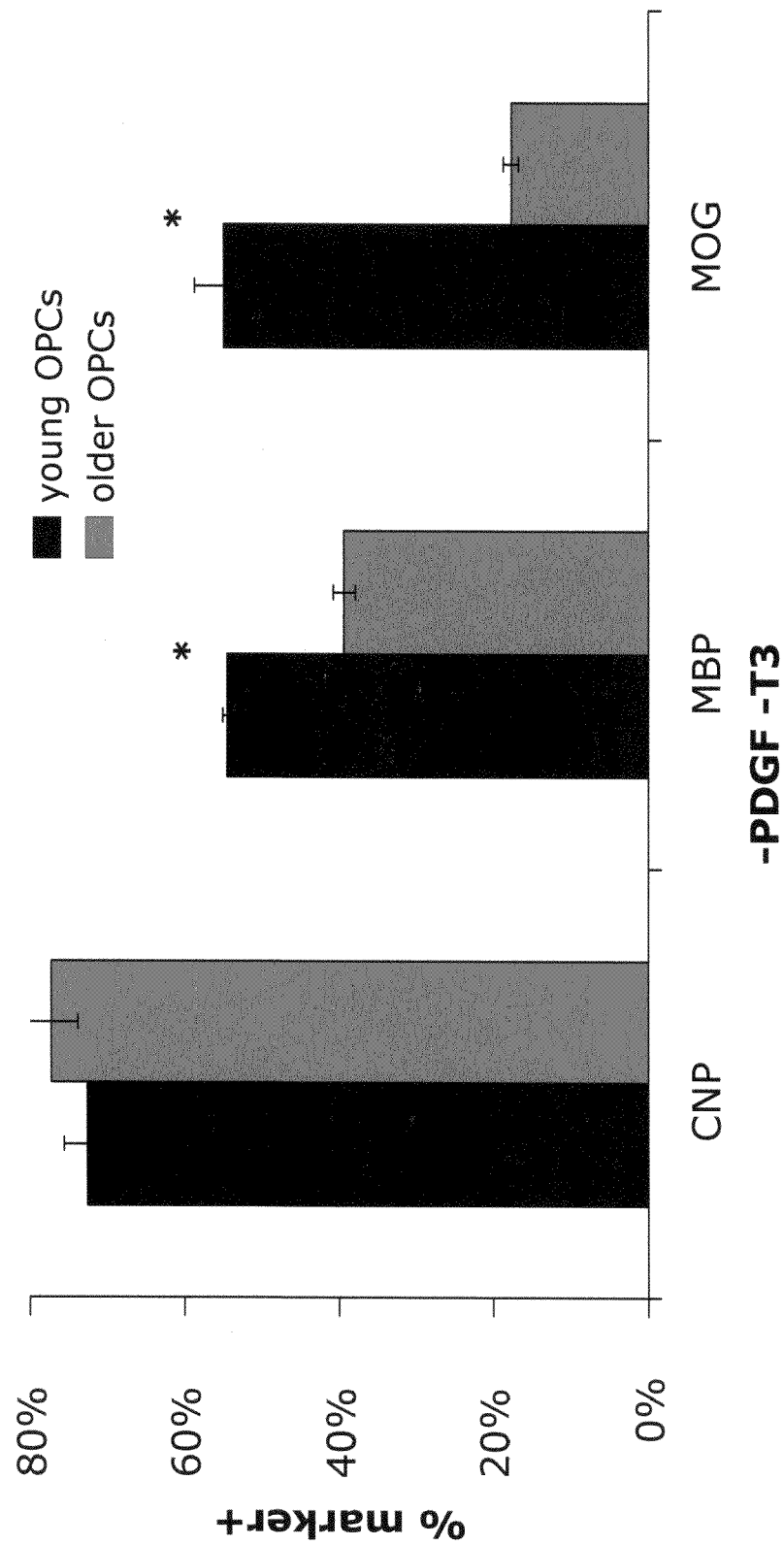

These data indicate that genes in addition to p57$^{Kip2}$ may be intrinsically induced in older OPCs that promote rapid late-phase differentiation in response to T3. In order to determine whether the enhanced differentiation capacity observed in older OPCs is specific to T3-triggered timer, or are older OPCs simply more prone to rapidly mature into OLs, OPCs initially cultured for 7 or 28 DIV in +PDGF −T3 medium were stimulated into differentiation by subsequent mitogen withdrawal (FIG. 50E). The data clearly demonstrate that whereas older OPCs differentiate more rapidly in response to T3 exposure, younger OPCs differentiate more rapidly in response to mitogen withdrawal. These data indicate that in older OPCs, which intrinsically express higher levels of p57$^{Kip2}$, only differentiation mediated by the clock mechanism is accelerated.

Figure 56A:
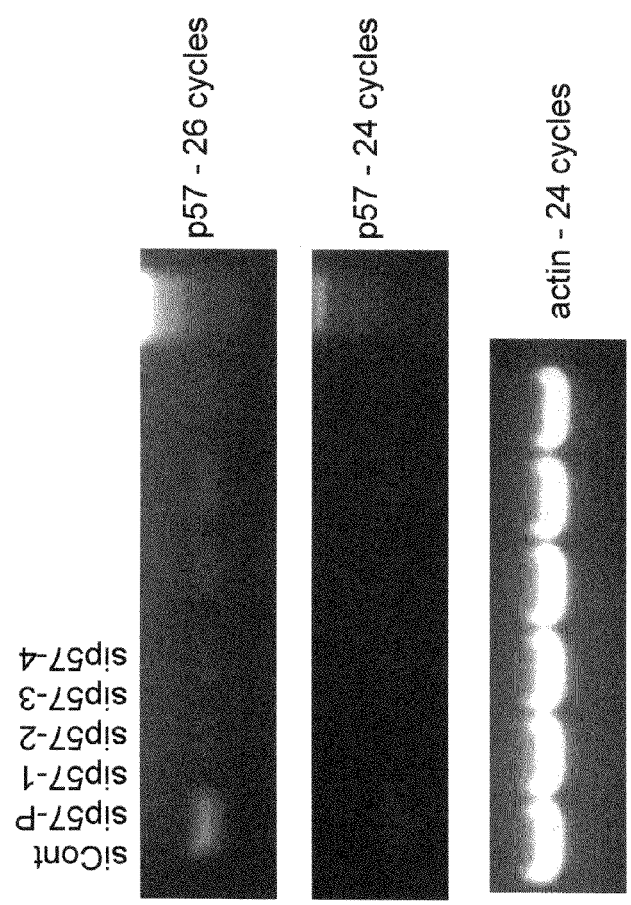

Having demonstrated that increased p57$^{Kip2}$ levels were sufficient to both increase OPC cell cycle time and to accelerate the intrinsic timer that allows T3 to induce OL differentiation, it was next determined whether p57$^{Kip2}$ was necessary for normal timing of differentiation and cell cycle regulation in OPCs. First, it was determined whether OPC proliferation rates were normally regulated by p57$^{Kip2}$ by reducing p57$^{Kip2}$ levels in both younger, rapidly dividing, and older, more slowly dividing OPCs. After either 7 or 28 days in proliferation-promoting (+PDGF −T3) medium, cultured OPCs were transfected with an siRNA pool targeting p57$^{Kip2}$ (sip57 pool) to reduce intrinsic p57$^{Kip2}$ levels, and then plated at clonal density. Knockdown of p57$^{Kip2}$ expression was confirmed by semiquantitative RT-PCR (FIG. 56A).

When compared to controls transfected with a nontargeting siRNA pool, clones of OPCs in which p57$^{Kip2}$ expression had been knocked down were notably larger when assayed after 4 days in +PDGF −T3 medium (FIG. 51A, C, Table 1). Significantly, the proliferation rate observed for the older OPCs, in which p57$^{Kip2}$ levels were initially intrinsically higher, increased from one division per 62.5 hours to one division per 36.8 hours when p57$^{Kip2}$ levels were reduced. In addition, the low level of spontaneous OL differentiation normally seen in +PDGF −T3 medium was almost completely abolished in both younger and older OPCs when p57$^{Kip2}$ levels were reduced. To next determine whether p57$^{Kip2}$ was required for controlling the timing of T3-stimulated OL differentiation, the same siRNA-transfected sets of OPCs described above were cultured at clonal density in medium containing mitogen and T3 for 4 DIV (FIG. 51B,D). With younger OPCs that had only been proliferating for 7 DIV prior to transfection, the reduction in division rate normally induced by T3 exposure was completely abolished when p57$^{Kip2}$ levels were reduced (Table 1). There was also a large decrease in the number clones that differentiated in response to T3 (from 25.5 to 7.4%). Similarly, when p57$^{Kip2}$ levels were reduced in older OPCs that had initially been proliferating for 28 DIV prior to transfection and T3 exposure, a strong reduction in the number of clones that differentiated in response to T3 was observed (from 54.7% to 23.1%).

Figure 51E:
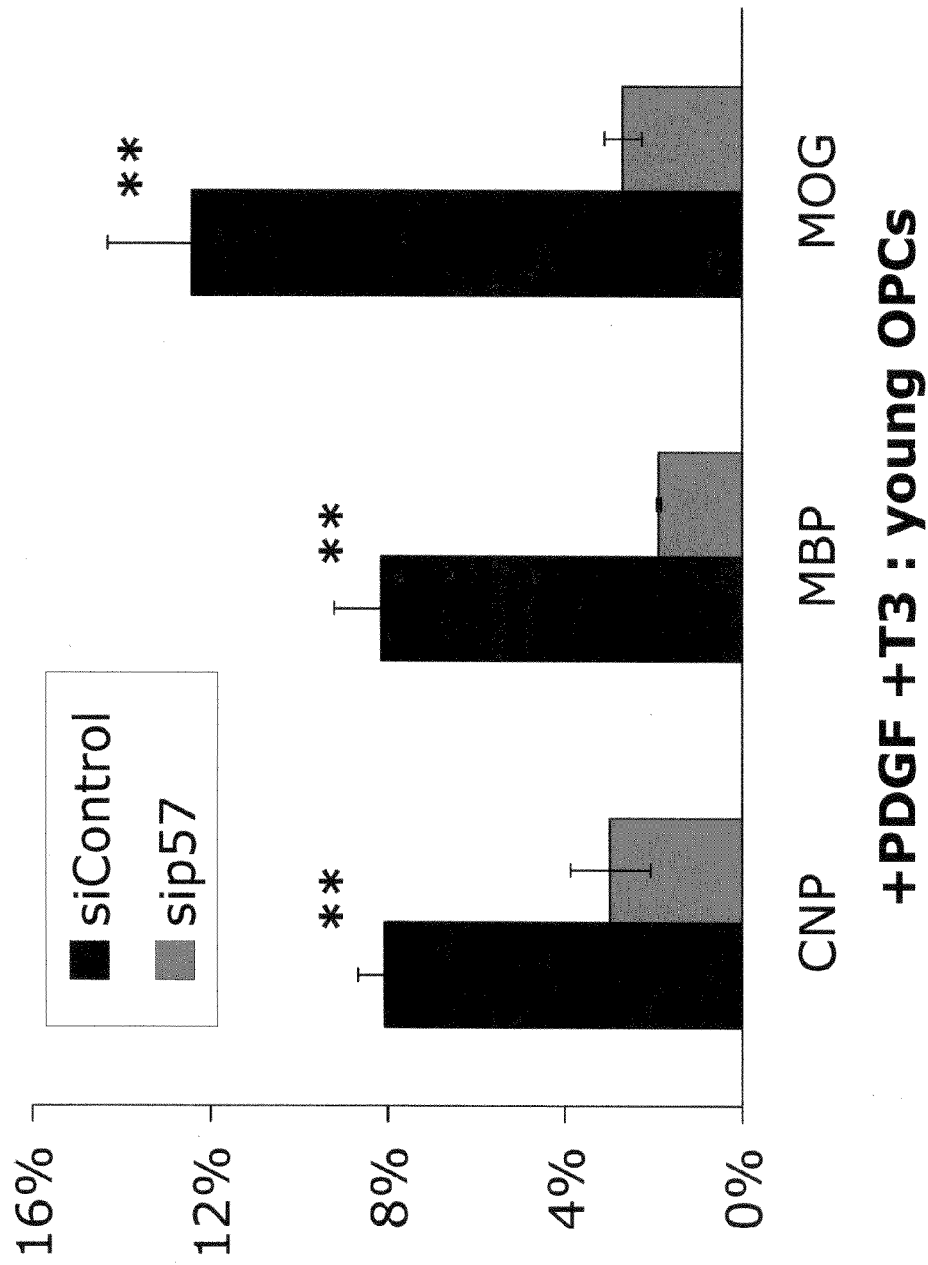
Figure 51F:
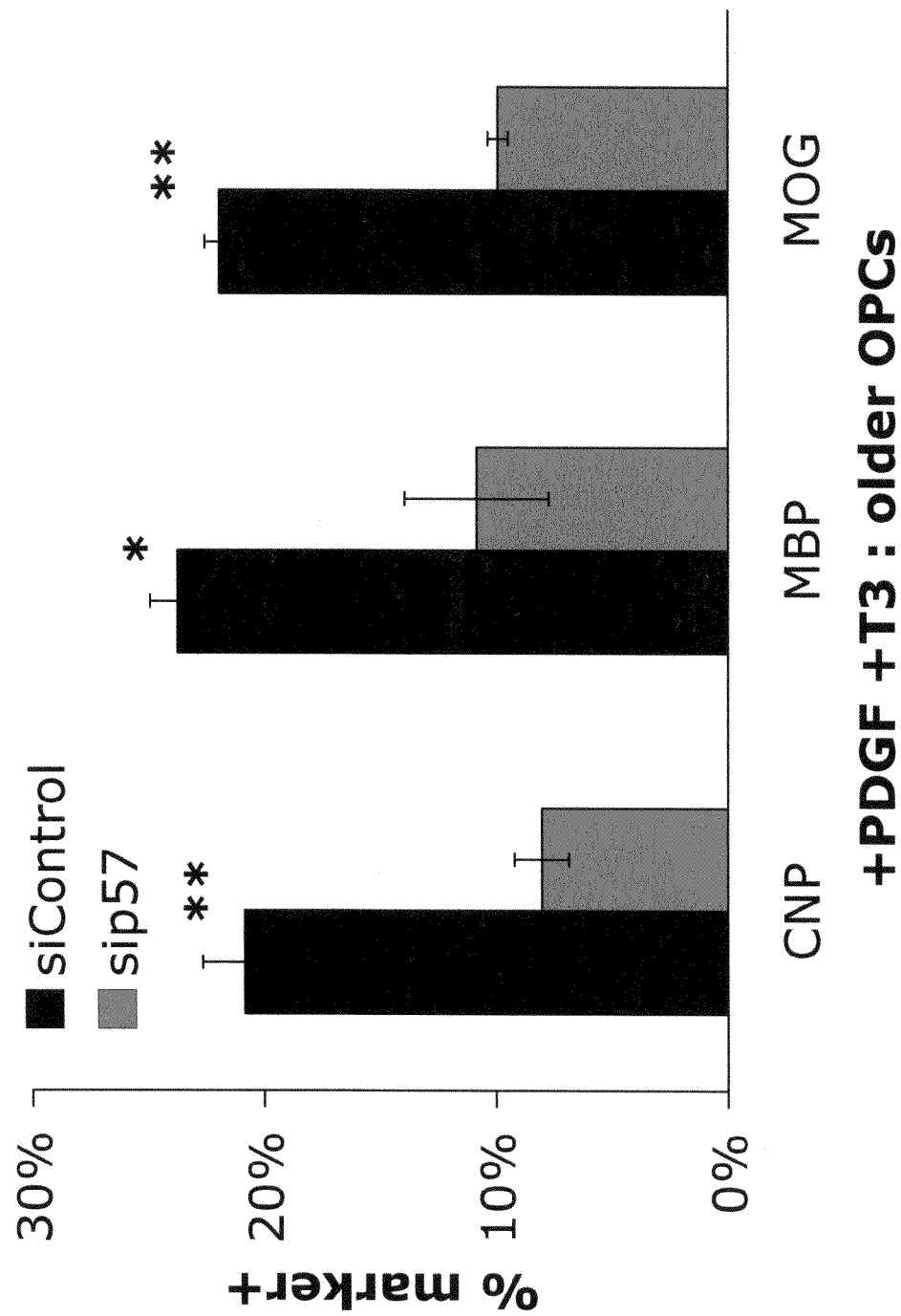
Figure 56B:
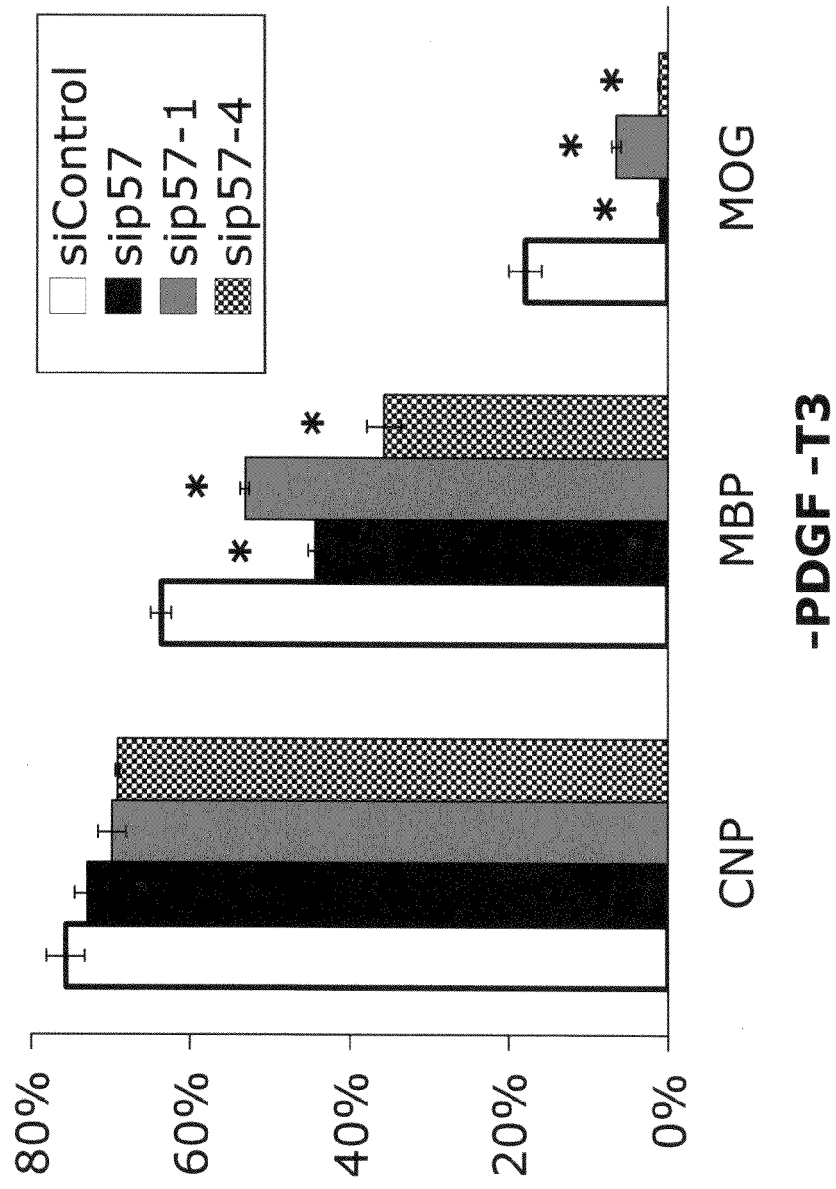
Figure 56C:
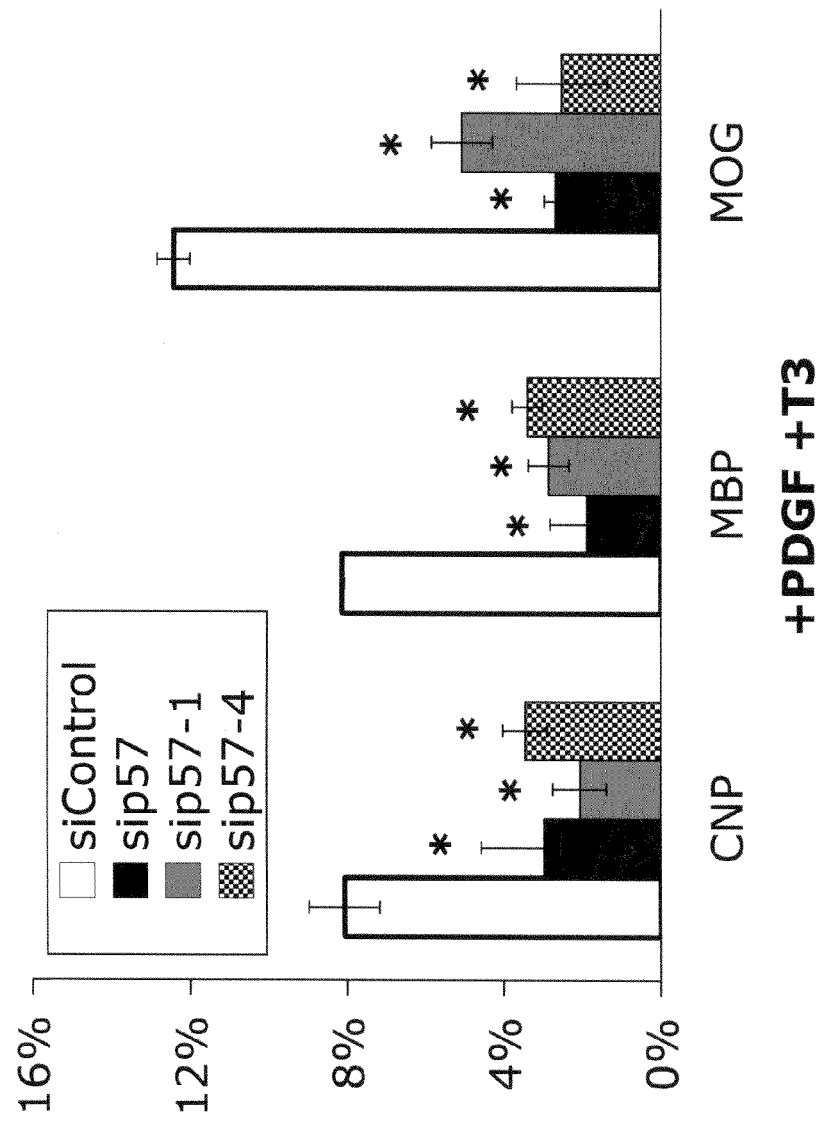

To determine the extent to which myelin gene expression induced by T3 exposure relied on p57$^{Kip2}$ expression, purified P8 OPCs were transfected with sip57 pool, plated for 7 DIV in mitogens in the presence of T3, and then in for CNP, MBP, and MOG expression. Knockdown of p57$^{Kip2}$ expression in OPCs reduced the numbers of cells that expressed both early and late OL differentiation markers in response to T3 exposure (FIG. 51E). When this experiment was repeated with OPCs initially proliferated for 28 DIV, in which intrinsic $p57^{Kip2}$ levels are higher, similar results were obtained (FIG. 51F). Whereas it is possible that the sip57 pool could have offtarget effects by directly silencing genes other than $p57^{Kip2}$, similar reductions in myelin gene expression were observed with two distinct individual siRNAs targeting non-overlapping regions of $p57^{Kip2}$ (FIG. 56B-C). Since it is unlikely that two distinct siRNA sequences would silence the same off-target genes, the effects observed reflect the direct result of a reduction in $p57^{Kip2}$ expression. Thus, while overexpression of $p57^{Kip2}$ is sufficient only to accelerate the early stage of OL differentiation, $p57^{Kip2}$ appears to be required in the timer for the normal promotion of all OL differentiation stages. Cumulatively, these data indicate that $p57^{Kip2}$ normally plays an important role in regulating the timing of OL differentiation.

The previous data have indicated that the gradual increase in $p57^{Kip2}$ expression observed in proliferating OPCs intrinsically regulates the normal timing of OL differentiation. However, initial findings were that the withdrawal of mitogens from proliferating OPCs produced a rapid increase in $p57^{Kip2}$ expression. Next it was determined whether $p57^{Kip2}$ is required in the differentiation program triggered immediately in OPCs by mitogen withdrawal, by examining the effects of $p57^{Kip2}$ knockdown on the expression of the OL differentiation markers CNP, MBP, and MOG 3-4 days after the removal of mitogens from purified OPCs. Results indicated that purified OPCs transfected with sip57 pool generated fewer mature OLs than control siRNA transfected OPCs in response to mitogen withdrawal (FIG. 52). Specifically, the numbers of MBP+ (FIG. 52A-B) and MOG+ (FIG. 52C-D) OLs were significantly reduced by $p57^{Kip2}$ knockdown (FIG. 52E). Interestingly, expression of the early differentiation marker CNP was not significantly altered by $p57^{Kip2}$ reduction during mitogen withdrawal (FIG. 52E).

Together, these results indicate that the disruption of the timer and immediate induction of OL differentiation triggered by mitogen withdrawal do not initially require $p57^{Kip2}$, but that increasing $p57^{Kip2}$ levels promotes the completion of OL differentiation when mitogens are limiting.

When $p57^{Kip2}$ and $p27^{Kip1}$ are simultaneously knocked down by siRNA transfections, the reductions in myelin gene expression observed following mitogen withdrawal are significantly stronger than those seen in individual knockdowns (FIG. 52E). In addition, while $p57^{Kip2}$−/− knockout mice die around the time of birth before most myelination has commenced in the CNS (Takahashi et al., *J. Biochem.* 127:73-83 (2000)), OPC proliferation rates can be assessed in the spinal cord, where OL-lineage cell generation begins at embryonic ages (Casaccia-Bonnefil et al., *Development* 126:4027-4037 (1999); Hardy, *J. Neurosci. Res.* 50:139-145 (1997)). $p57^{Kip2-/-}$ mice did not show significant increases in OPC levels early in the embryonic spinal cord, but $p57^{Kip2-/-}$ $p27^{Kip1-/-}$ double mutants had more proliferating OL-lineage cells than either single mutant mouse, indicating that $p27^{Kip1}$ may compensate for $p57^{Kip2}$ loss in regulating the OPC cell cycle in vivo. These results indicate that $p57^{Kip2}$ and $p27^{Kip1}$ may synergistically contribute to the immediate cessation of the cell cycle and program of OL differentiation triggered by mitogen withdrawal.

Figure 53B:
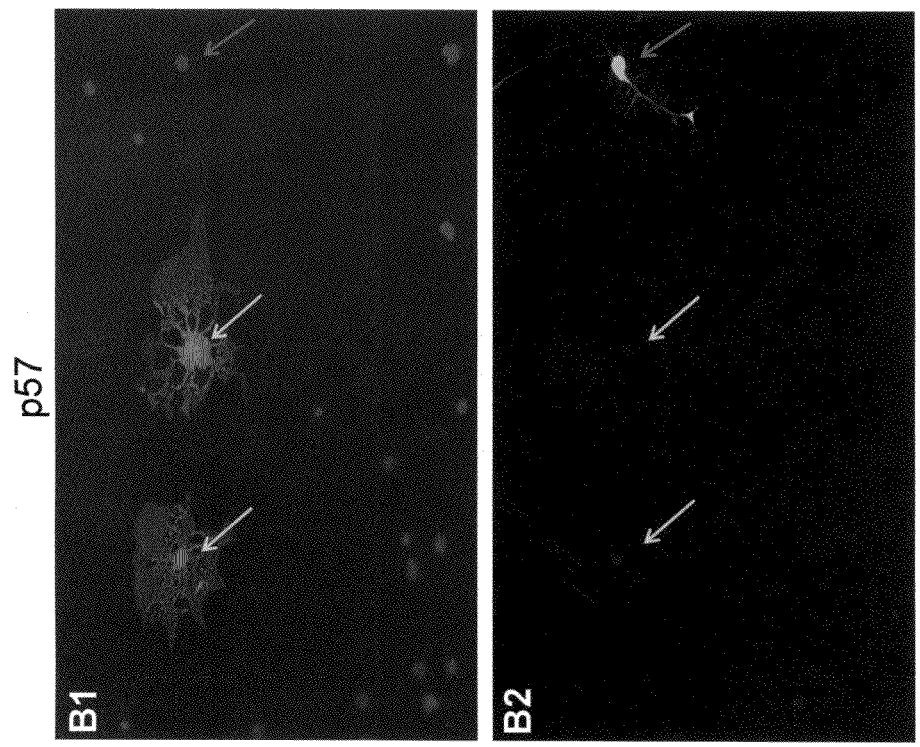
Figure 53A:
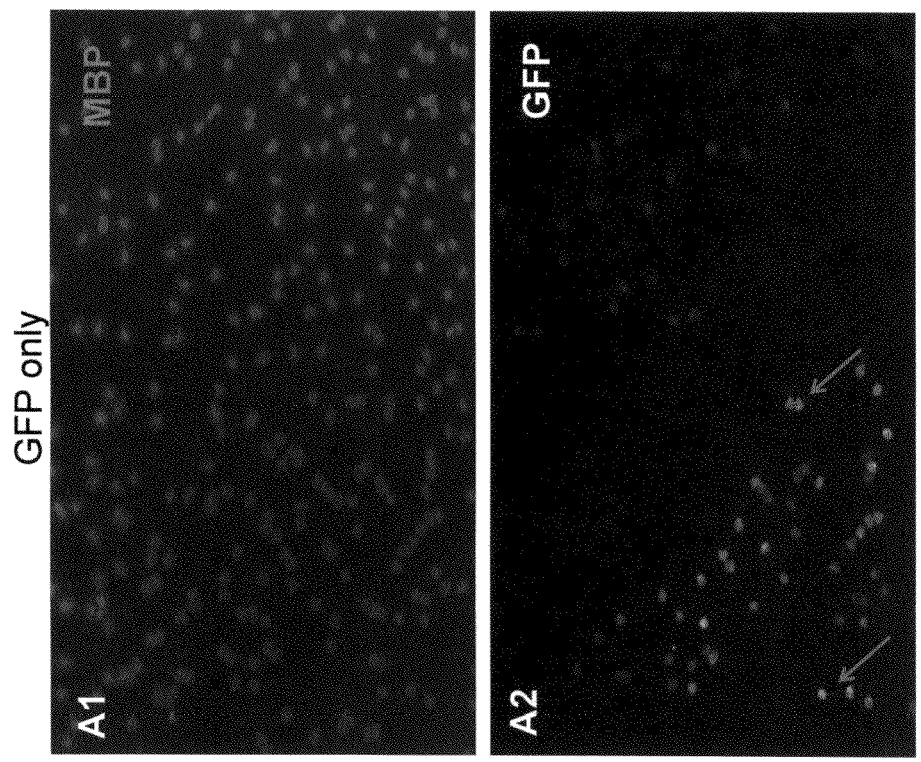
Figure 53F:
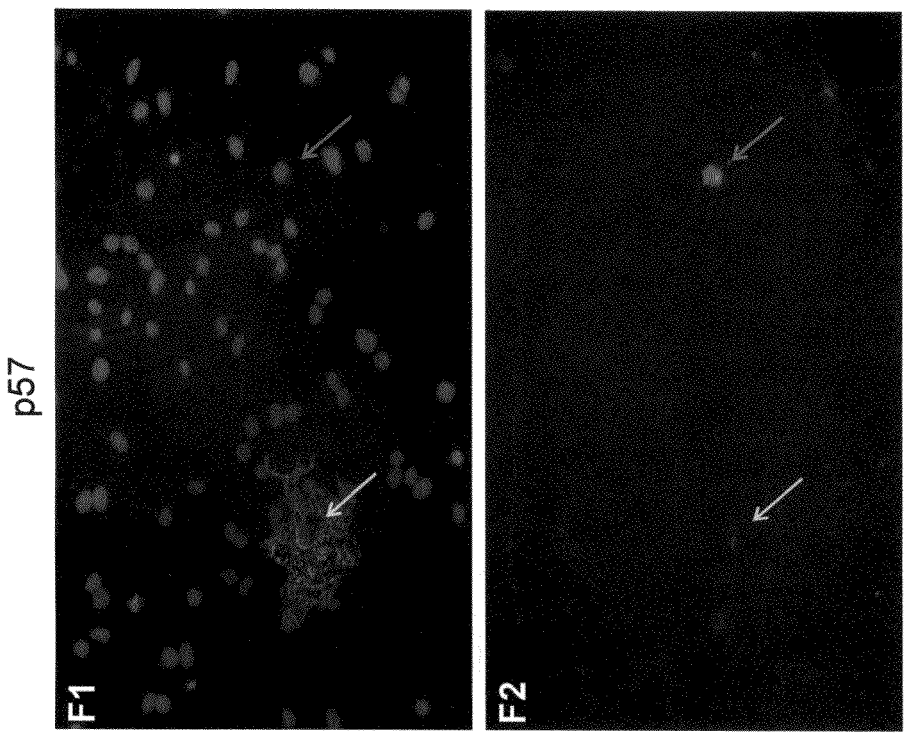
Figure 53E:
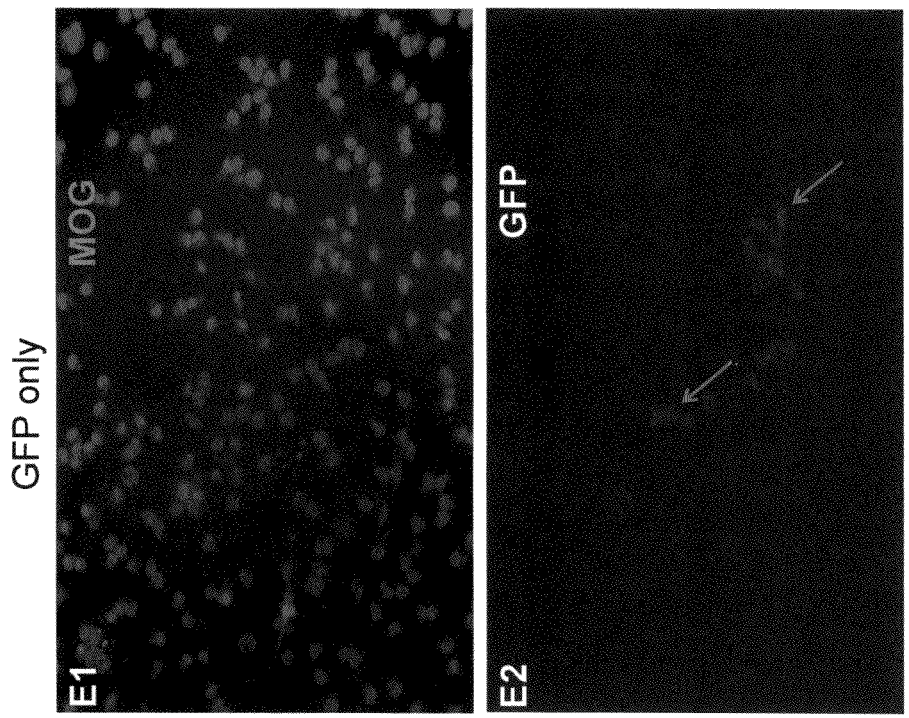

As disclosed herein, the rapid induction of $p57^{Kip2}$ expression triggered by mitogen withdrawal contributes to the disruption of the OPC differentiation timer. Therefore increasing $p57^{Kip2}$ levels in proliferating OPCs should promote OL differentiation in the absence of T3. $p57^{Kip2}$ was overexpressed in transfected OPCs and cells were then cultured for 7 DIV in +PDGF −T3 medium. When compared to control, GFP-only transfected OPCs, a significant increase was seen in the number of morphologically OL-appearing cells expressing CNP and MBP, early markers of OL differentiation (FIG. 53A, B and 54). A smaller but still significant increase in the number of transfected cells expressing the late-stage differentiation marker MOG was also detected (FIG. 53E, F and 54). However, by comparing this data with FIG. 50C, it is evident that $p57^{Kip2}$ overexpression and T3 exposure act cooperatively to provide a much greater enhancement of OL differentiation. Cumulatively, these data indicate that $p57^{Kip2}$ is an important component in the regulation of the intracellular OPC differentiation timer. Furthermore, the data indicate that a rapid increase in $p57^{Kip2}$ may only partially contribute to the ability of mitogen withdrawal to short circuit this intrinsic timer.

Results herein consistently demonstrate that $p57^{Kip2}$ is required, both as a component of the timer and in limiting mitogen conditions, for robust induction of both the early and late stages of OL differentiation. However, increasing $p57^{Kip2}$ appears to be sufficient to accelerate the early stage of OL differentiation (as measured by increases in CNP and MBP expression, but not MOG expression). Additional genes not induced by $p57^{Kip2}$ may be required to fully promote the final stage of OL differentiation.

One such candidate gene is ZFP536, a recently identified transcription factor that is both induced late in the normal time course of OL differentiation, and required specifically to induce the later stage of OL differentiation (Dugas et al., *J. Neurosci.* 26:10967-10983 (2006)). To investigate whether $p57^{Kip2}$ and ZFP536 can combine to robustly promote full OL differentiation, we compared the effects of overexpressing $p57^{Kip2}$ and ZFP536 alone to the effects of coexpressing both $p57^{Kip2}$ and ZFP536 in OPCs. After culturing transfected OPCs for 7 days in +PDGF −T3 medium, we observed that ZFP536 alone was not able to enhance OL differentiation, as assayed by either change in morphology or by measure of early and late marker gene expression (FIGS. 53C, G and 54). In addition, expression of ZFP536 combined with $p57^{Kip2}$ did not further enhance the ability of $p57^{Kip2}$ to promote the early phase of OL differentiation (FIGS. 53D and 54). However, the combination of ZFP536 and $p57^{Kip2}$ was able to significantly increase the number of cells expressing the late-phase marker gene MOG over the level of either ZFP536 or $p57^{Kip2}$ alone (FIGS. 53H and 54). In fact, ZFP536 and $p57^{Kip2}$ act cooperatively, since the increase in MOG+ cells observed with ZFP536-$p57^{Kip2}$ cotransfections is greater than the sum of the effect seen for ZFP536 and $p57^{Kip2}$ single gene transfections. Similar results were observed in the presence of T3 (+PDGF +T3 medium). These results indicate that proteins involved in regulating the intracellular timer of OL differentiation, such as $p57^{Kip2}$, are involved in not just initiating, but also promoting all stages of OL differentiation.

Figure 55B:
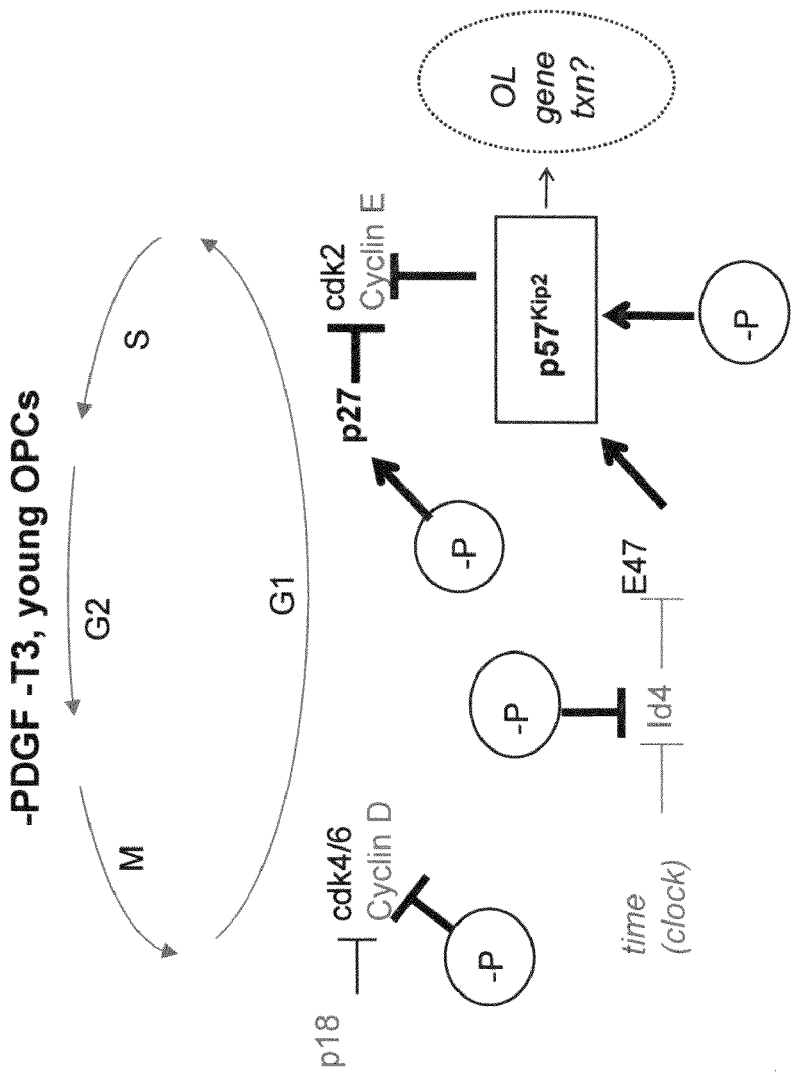

In recently generated, rapidly proliferating OPCs (FIG. 55A), $p57^{Kip2}$ expression levels are low. Weak expression of $p57^{Kip2}$ is likely a result of observed high levels of Id2 and Id4 in OPCs, which are known inhibitors of OL differentiation (Kondo and Raff, *EMBO J.* 19:1998-2007 (2000); Wang et al., Neuron 29:603-614 (2001)). Id2 and Id4 can both dimerize with and inhibit the activity of the class I bHLH protein E47 (Riechmann et al., *Nucl. Acids Res.* 22:749:755 (1994); Sun et al., *Mol. Cell. Biol.* 11:5603-5611 (1991)), thereby blocking E47-driven transcription of $p57^{Kip2}$ (Rothschild et al., *Mol. Cell. Biol.* 2:4351-4361 (2006)). In addition, in the presence of high levels of free Cyclin D and cdk4/6, low levels of $p57^{Kip2}$ are titrated away from stoichiometric inhibition of Cyclin E-cdk2 complexes and towards formation of Cyclin D-cdk4/6 complexes, producing a positive, rather than a negative, regulation of the cell cycle (Cunningham and Roussel, *Cell Growth Differ.* 12:387-396 (2001)). Mitogens are required for the normal operation of the OPC differentiation timer, as when mitogens become limiting OPCs immediately cease dividing and differentiate regardless of age or T3 levels. Mitogen withdrawal may short circuit the timer in part by triggering a rapid increase in $p57^{Kip2}$ expression (FIG. 55B). When mitogens are withdrawn from OPCs, CyclinD levels rapidly drop, and the CyclinD-cdk4/6 complex inhibitor $p19^{INK4d}$ is somewhat induced (Tokumoto et al., *EMBO J.* 20:5261-5268 (2001)). In the absence of CyclinD-cdk4/6 complexes, Retinoblastoma-1 (Rb) is no longer phosphorylated, whereupon it binds to and inhibits both E2F1 and Id2. Loss of E2F1 activity leads to loss of CyclinE production (Cunningham and Roussel, *Cell Growth Differ.* 12:387-396 (2001)), and loss of Id2 activity leads to activation of E47-mediated $p57^{Kip2}$ transcription (Rothschild et al., *Mol. Cell. Biol.* 2:4351-4361 (2006)). In addition, mitogen withdrawal has been shown to produce a rapid reduction in Id4 levels (Kondo and Raff, *EMBO J.* 19:1998-2007 (2000)). Together, these conditions can swiftly produce higher levels of $p57^{Kip2}$ that inhibit CyclinE-cdk2 complex formation, blocking progression of the cell cycle. Discoveries disclosed herein indicate that $p27^{Kip2}$ may also contribute to inhibition CyclinE-cdk2 complex formation. Supporting this model is the fact that inhibition of CyclinE-cdk2 complex formation has been previously implicated in withdrawal of OPCs from the cell cycle (Ghiani and Gallo, *J. Neurosci.* 21:1274-1282 (2001)).

Figure 55C:
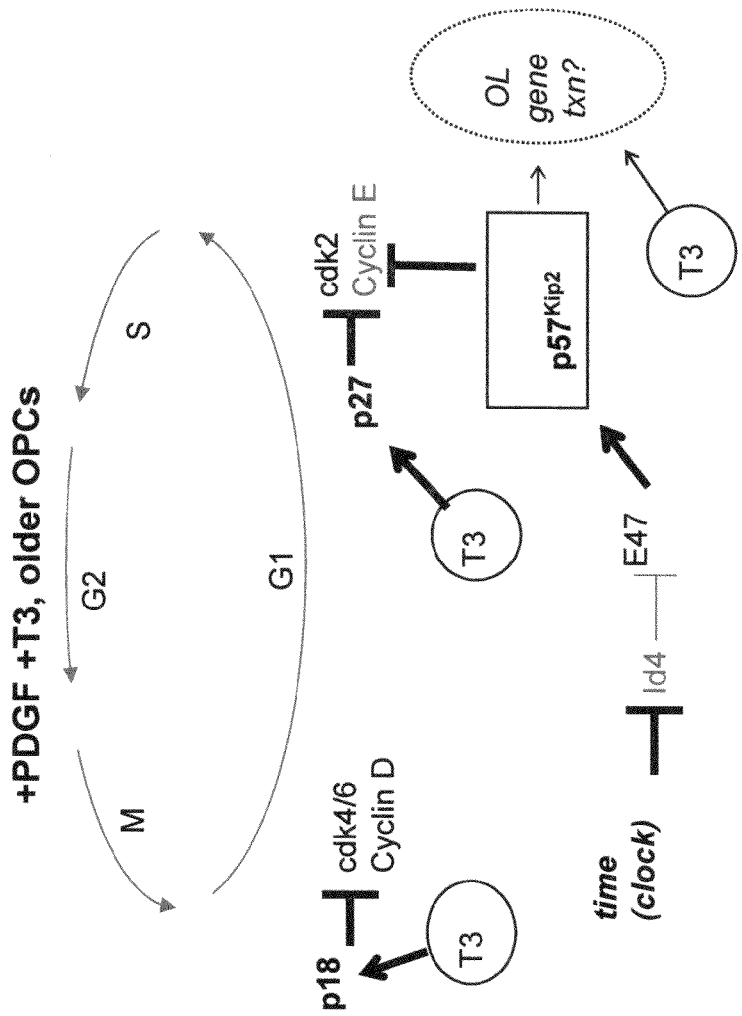

When mitogens and T3 are both present, $p57^{Kip2}$ intrinsically accumulates more gradually as the timer component of the clock to eventually promote OL differentiation in response to T3 (FIG. 55C). T3, the effector component of the clock mechanism, may encourage OL differentiation in a number of ways. T3 can slow the cell cycle by lowering E2F1 levels (Nygard et al., *Mol. Endocrin.* 17:79-92 (2003)), which leads to reduced production of CyclinE. T3 exposure also promotes an increase in several Ink4 family proteins, and may also induce a rise in $p21^{Cip1}$ and $p27^{Kip1}$ levels (Tokumoto et al., *EMBO J.* 20:5261-5268 (2001)). Cumulatively, this would serve to decrease CyclinD-cdk4/6 and CyclinE-cdk2 complex formation. However, the reduction in CyclinE and CyclinD stimulated by T3 exposure is not as strong as that observed for mitogen withdrawal (Tokumoto et al., *EMBO J.* 20:5261-5268 (2001)). This could lead to an incomplete block of Rb phosphorylation, and therefore an incomplete sequestration of Id2.

In addition, high levels of Id4 in young OPCs would serve to further inhibit E47-promoted transcription of $p57^{Kip2}$. The low levels of $p57^{Kip2}$ coupled with an incomplete suppression of Cyclins likely produces the slowing but not cessation of the cell cycle observed in young OPCs exposed to T3. Over time, $p57^{Kip2}$ expression increases in proliferating OPCs due to a gradual loss of Id4 (Kondo and Raff, *EMBO J.* 19:1998-2007 (2000)): loss of Id4 results in a dis-inhibition of E47, which drives $p57^{Kip2}$ transcription. Similar increases in $p21^{Cip1}$ and $p27^{Kip1}$ expression would not be observed as a result of falling Id4 levels because E47 specifically induces $p57^{Kip2}$ (Rothschild et al., *Mol. Cell. Biol.* 2:4351-4361 (2006)). In the absence of T3 stimulation, the $p57^{Kip2}$ produced in older OPCs may both inhibit CyclinE-cdk2 complex formation and promote CyclinD-cdk4/6 complex formation, failing to completely inhibit the cell cycle. Finally, once the cell cycle has stopped, both $p57^{Kip2}$ and T3 may further induce OL differentiation by independent stimulation of other OL genetic programs (Baas et al., *Glia* 19:324-332 (1997)).

While increases in $p57^{Kip2}$ levels alone were sufficient to initiate OL differentiation (FIGS. 53 and 54), increases in $p27^{Kip1}$ levels or other means of arresting the cell cycle were not (Casaccia-Bonnefil and Liu, 2003; Tang et al., *J. Cell. Biochem.* 76:270-279 (1999)). A related Cip/Kip family member, $p27^{Kip1}$, has been shown to directly influence transcription from the mbp promoter in conjunction With the transcription factors Sp1 and Sox10 (Miskimins et al., *J. Neurosci. Res.* 67:100-105 (2002); Wei et al., *Mol. Cell. Biol.* 23:4035-4045 (2003); Wei et al., *J. Neurosci. Res.* 78:796-802 (2004)). $P57^{Kip2}$ may similarly directly promote myelin gene transcription independent of its interactions with Cyclin-cdk complexes.

Among members of the Cip/Kip family, only deficiencies in $p57^{Kip2}$ result in developmental lethality (Takahashi et al., *J. Biochem.* 127:73-83 (2000)). In fact, $p57^{Kip2}$ has been previously implicated in regulating the differentiation of various tissues, such as the lens, pancreas, blood, chondrocytes, muscle, and dopaminergic neurons (Georgia et al., *Dev. Biol.* 298:22-31 (2006); Joseph et al., *Proc. Natl. Acad. Sci. USA* 100:15619-15624 (2003); MacLean et al., *J. Clin. Investig.* 113:1334-1343 (2004); Scandura et al., *Proc. Natl. Acad. Sci. USA*, 101:15231-15236 (2004); Zhang et al., *Genes & Dev.* 12:3162-3167 (1998); Zhang et al., *Genes & Dev.* 13:213-224 (1999)). As indicated by data presented herein, OLs are cell types whose maturation is regulated by $p57^{Kip2}$.

TABLE 1

Effects of $p57^{Kip2}$ induction/repression on OPC cell cycle and differentiation.

| | Avg. OPC clone size | hours/ division | % OL clones | Avg. OL clone sizes |
|---|---|---|---|---|
| Young OPCs-$p57^{Kip2}$ increase | | | | |
| −T3 GFP only | 16.7 | 23.6 | 1.3% | 1.0 |
| −T3 CMV-$p57^{Kip2}$ | 6.0 | 37.1 | 14.1% | 3.1 |
| +T3 GFP only | 12.6 | 26.3 | 11.7% | 4.3 |
| +T3 CMV-$p57^{Kip2}$ | 4.9 | 41.9 | 41.0% | 2.1 |
| Young OPCs-$p57^{Kip2}$ k.d. −T3 siControl | 13.9 | 25.3 | 11.1% | 3.7 |
| −T3 sip57 | 21.9 | 21.6 | 0.0% | — |
| +T3 siControl | 7.1 | 33.9 | 25.5% | 1.8 |
| +T3 sip57 | 17.8 | 23.1 | 7.4% | 1.0 |
| Older OPCs-$p57^{Kip2}$ k.d. | | | | |
| −T3 siControl | 2.9 | 62.5 | 15.4% | 3.4 |
| −T3 sip57 | 6.1 | 36.8 | 1.9% | 3.3 |
| +T3 siControl | 2.8 | 64.6 | 54.7% | 1.6 |
| +T3 sip57 | 4.0 | 48.0 | 23.1% | 2.3 |

Tabulated results of clonal size and differentiation assays described in FIG. 50A-B and 51A-D. In all conditions, only clones containing transfected (GFP+) cells were counted; 50-80 clones were counted per condition.
Young OPCs were transfected after 7 DIV in +PDGF −T3 medium; older OPCs were transfected after 28 DIV in +PDGF −T3 medium, then cultured 4 DIV +PDGF ±T3.
OPC clones contain <50% OLs (by morphology); OL clones contain ≧50% OLs. Hours per division calculated as 96 hours/log$^2$(average OPC clone size).

Example 4

KLF9, BHLHB5, Hr, and DBP as a Regulators of T3-Mediated Oligodendrocyte Differentiation In OPCs cultured in saturating amounts of mitogens and T3, a small number of transcription factors are rapidly and robustly regulated in response to T3 presentation (as compared to control cultures maintained in mitogens in the absence of T3). These four genes are 1) Kruppel-Like Factor 9 (KLF9), also known as Basic Transcription Element Binding protein 1(BTEB1), 2) basic helix-loop-helix domain containing, class B5 (BHLHB5), also known as Beta3, 3) Hairless, (Hr), or ALUNC, AU, N, ba, bldy, hr, rh, rh-bmh, rhino, and 4) D site albumin promoter binding protein (DBP). KLF9, Hr, and DBP are all induced (2-6 fold) rapidly in OPCs in response to T3, before the OPCs initiate differentiation in response to T3 presentation (FIG. 57). Interestingly, BHLHB5 is induced rapidly only in older OPCs that respond to T3 by initiating differentiation, and therefore may represent a gene whose induction more directly stimulates OL differentiation.

KLF9 is the gene most rapidly and robustly induced by T3 in OPCs (4-fold induction within 3 hours of T3 exposure). Overexpression and siRNA knockdown experiments were performed to test the sufficiency and necessity of KLF9 in regulating OL myelin gene expression in vitro. To test the sufficiency of KLF9 in promoting OL differentiation, OPCs were transfected with an expression plasmid that constitutively expresses KLF9 from a CMV promoter. These transfected OPCs were then cultured in media that supports their survival in the presence or absence of mitogens (±PDGF) and in the presence or absence of T3 (±T3). KLF9 overexpression could reliably induce myelin basic protein (MBP) expression (FIG. 58, see also FIG. 62), could variably induce cyclic nucleotide phosphodiesterase 1 (CNP1) expression, and could not induce myelin oligodendrocyte glycoprotein (MOG) expression when OPCs were cultured in +PDGF −T3 media (i.e. media in which OPCs should not be induced to differentiate). These data indicate that KLF9 is sufficient to promote some aspects of OL differentiation, but cannot fully promote OL differentiation on its own.

To test the necessity of KLF9 in promoting OL differentiation, we have transfected OPCs with small interfering RNA (siRNA) to reduce KLF9 gene expression (FIG. 59, see also FIG. 63). Transfected OPCs were then stimulated to differentiate either by mitogen withdrawal (−PDGF −T3) or T3 presentation (+PDGF +T3). Reducing KLF9 expression reduced the expression of every myelin gene tested (CNP1, MBP, MOG) when OPCs were induced to differentiate in response to T3, indicating that KLF9 is necessary for most aspects of T3-mediated OL differentiation. In contrast, in OPCs stimulated to differentiate by mitogen withdrawal, KLF9 reduction did not affect MOG expression, and only modestly reduced MBP and CNP expression, indicating that KLF9 loss can affect mitogen withdrawal mediated OL differentiation, but that KLF9 is not as strongly required for this process.

In all, these data likely indicate a crucial role for KLF9 in regulating T3-mediated OL differentiation, and also identify three additional candidate transcription factors to be contributing to the regulation of this process.

Example 5

Genomic Analysis of OL Gene Expression

Genomic analyses of gene expression changes induced by OL differentiation were performed as described previously (Dugas et al., *J. Neurosci.* 26:10967-10983 (2006)). Briefly, P7 OPCs purified by immunopanning were induced to differentiate by mitogen withdrawal and T3 exposure, and RNA samples obtained every 1-2 days following the induction of differentiation were labeled and hybridized to Affymetrix U34A-C chips. RNA from acutely purified P12 OLs was also applied to Affymetrix chips. Data from four independent experiments were averaged to obtain the probe set expression values depicted.

Example 6

Purification and Culture of OL-Lineage Cells

Purification and culturing of OPCs and OLs were performed as described previously (Dugas et al., *J. Neurosci.* 26:10967-10983 (2006)). Briefly, OPCs were purified from enzymatically-dissociated P7-P8 Sprague-Dawley rat brains by immunopanning: following removal of potential contaminating OLs and other cells by Ran-2 and GC antibody binding, OPCs were selected by O4 antibody binding. Non-adherent cells were washed away and purified OPCs recovered by trypsinization. Acutely purified OLs were similarly obtained from enzymatically-dissociated P12 rat brains: positive selection by GC antibody binding followed negative selection by Ran-2 and A2B5 antibody binding. Purified OPCs were cultured on poly-D-lysine (pDL) coated tissue culture plastic or glass coverslips in DMEM-Sato based medium containing N-acetyl-L-cysteine (5 µg/ml), forskolin (4.2 µg/ml), bovine insulin (5 µg/ml), and ciliary neurotrophic factor (10 ng/ml). OPC proliferation was induced by addition of mitogenic PDGF-AA (10 ng/ml) and neurotrophin-3 (NT3, 1 ng/ml) ("+PDGF") (Barres et al., 1994b; Barres et al., 1993). Differentiation of pure OPCs into OLs was stimulated either by removal of PDGF and NT3 from the medium ("-PDGF"), or by addition of T3 ("+T3") (40 ng/ml) to the culture medium as noted. All cultures were maintained at 37° C. in 10% $CO_2$.

Example 7

Immunostaining

Immunostaining of OPC and OL cultures for CNP, MBP, MOG, and GFP expression was performed as described previously (Dugas et al., *J. Neurosci.* 26:10967-10983 (2006)). To stain for $p57^{Kip2}$ expression, purified cells cultured on glass coverslips were fixed in 4% paraformaldehyde for 10' at 25° C. and then incubated for 1 hr in a 50% donkey serum, 1% bovine serum albumin (BSA) and 100 mM L-lysine solution to block nonspecific binding and 0.4% Triton X-100 to permeabilize the cells. Coverslips were then incubated overnight at 4° C. in 10% donkey serum, 1% BSA, 100 mM L-lysine solution containing 1/50 goat anti-$p57^{Kip2}$ (Santa Cruz SC-1039). Finally, coverslips were incubated for 1 hr at 25° C. in 1% BSA, 100 mM L-lysine solution containing 1/1000 Alexa Fluor-488 donkey anti-goat (Invitrogen A-11055) secondary antibody. To stain for $p57^{Kip2}$ expression in vivo, optic nerves were dissected from rats at various ages and fixed by immersion in 4% paraformaldehyde for 2-3 hours at 4° C. Nerves were then equilibrated in 30% sucrose solution overnight at 4° C., mounted in OCT, and 10 µm thick sections were generated on a cryostat. Sections mounted onto silane-prep slides (Sigma-Aldrich S4651) were then blocked and stained as described above for $p57^{Kip2}$ expression. Slides were co-stained with either 1/100 mouse anti-CC1 (Calibochem OP80) or 1/400 mouse anti-NG2 (Chemicon MAB5384) primary antibody, and 1/1000 Alexa Fluor-594 donkey anti-mouse secondary antibody. All staining was mounted in Vectashield anti-fade medium plus 4',6'-diamidino-2-phenylindole (DAPI) to allow identification of healthy cell nuclei.

Example 8

RT-PCR

Total RNA was isolated from cells with the RNeasy mini kit (Qiagen), utilizing Qiashredder columns for cell lysis, and inserting Qiagen on-column DNase steps to remove any contaminating genomic DNA. Equivalent amounts of RNA from each sample were reverse transcribed with Superscript III (Invitrogen 18080-044) according to manufacturer protocols. PCR reactions were then set up with equivalent volumes of completed RT reactions, using Platinum Taq DNA polymerase (Invitrogen 10966-026) according to manufacturer protocols. PCR reactions: 94° C. 30", 55° C. 30", 68° C. 45" cycles, cycle numbers as indicated in figures. Primers for PCR reactions are as follows: $p57^{Kip2}$ —5'TGTCCCTCTC-CTAACGTGGCTC (SEQ ID NO: 1) and 5'CATTGCA-CAGTTTTCAGATTTCCAC (SEQ ID NO: 2) (234 bp product); beta-actin—5'GCATTGTCACCAACTGGGACG (SEQ ID NO: 3) and 5'ACCGCTCATTGCCGATAGTG (SEQ ID NO: 4) (543 bp product).

Example 9

OPC Transfection and Differentiation Assay

OPC transfections were performed as described previously (Dugas et al., *J. Neurosci.* 26:10967-10983 (2006)). Briefly, purified P8 OPCs were cultured in proliferation-promoting medium for 7 DIV (unless otherwise noted), then enzymatically lifted by gentle trypsinization. Rinsed 2×106-3×106 aliquots of OPCs were resuspended in 100 μl Amaxa OPC nucleofection reagent (Amaxa VPG-100) plus: 1.5-3.0 μg pC1-eGFP (CMV-promoter driven eGFP expression; Clontech 6084-1); 2.5 μg pSPORT6-$p57^{Kip2}$ (CMV-$p57^{Kip2}$; Open Biosystems MMM1013-63856); 2.5 μg pSPORT6-ZFP536 (CMV-ZFP536; Open Biosystems MMM1013-7513950); 100-200 pmol siGenome SMARTpool siRNA targeting rat ZFP536 (Dharmacon M-082235-00); 100-200 pmol siGenome SMARTpool siRNA targeting rat $p27^{Kip1}$ (Dharmacon M-090938-00); 100-200 pmol siGenome SMARTpool siRNA targeting rat $p57^{Kip2}$ (Dharmacon M-098880-00); 100 pmol siGenome individual siRNA duplexes targeting rat $p57^{Kip2}$ (Dharmacon M-098880-01, -02, -03, -04); 100-200 siControl non-targeting siRNA pool (Dharmacon D-001206-13). Note that, unless otherwise noted, knockdown of $p57^{Kip2}$ expression was performed with the siRNA pool targeting $p57^{Kip2}$. OPC-plasmid/siRNA mixes were then electroporated with the Amaxa nucleofection apparatus, 0-17 program. For clonal assays, 250-500 cells were added into medium in pDL-coated 6-well tissue culture plates or 40 cells were added to pDL-coated glass coverslips. OLs were identified by their characteristic complex, thin, multi-branched morphology, as compared to the simpler, thicker processes of OPCs. For myelin gene expression assays, transfected OPCs were plated at either 30,000 cells/pDL-coated glass coverslip in 24-well plates and incubated for 3-4 days in medium lacking PDGF and NT3, or plated at 1000 cells/coverslip and incubated for 7 days in medium containing PDGF and NT3 in the presence or absence of T3. Coverslips were then stained for GFP and either CNP, MBP or MOG expression as described above. Myelin gene expression was scored as the percentage of transfected (GFP+) cells positive for CNP, MBP, or MOG expression. All experiments were scored blind, 100-300 cells counted per coverslip, ≧3 coverslips scored per data point. All experiments were repeated at least twice with similar results obtained.

Example 10

KLF9 is Expressed in OLs In Vivo (P17 KLF9$^{+/-}$)

P17 mice that were heterozygous for the LacZ knock-in to the KLF9 locus (in which LacZ is expressed in place of functional KLF9; Morita et al., *Mol Cell Biology* 23:2489-2500 (2003)) were collected, anesthetized, and perfusion fixed with 4% PFA. Brains and optic nerves were collected, fixed, equilibrated in 30% sucrose, mounted in OCT mounting medium, and sectioned in the sagital plane from the midline (brains) or longitudinally (nerves) as shown in FIG. 64. 10 μm thick sections were immunostained for LacZ ((β-galactosidase, red) to identify cells expressing KLF9 and either a marker for mature myelin (MBP, green) or mature OLs (CC-1, green). Colocalization of LacZ expression in myelinated areas and within CC-1$^+$ cells is shown (yellow arrows). Additional LacZ$^+$ cells not expressing CC-1 are also observed (red arrows).

Example 11

Myelination is Delayed in KLF9$^{-/-}$ Cortex

P12, P18, or P35 KLF9$^{-/-}$ or wild type littermate control mice were collected, anesthetized, and perfusion fixed with 4% PFA (see FIGS. 65, 66, and 67 respectively). Brains were collected, fixed, equilibrated in 30% sucrose, mounted in OCT mounting medium, and sectioned in the sagital plane from the midline (brains) as described above. 10 μm thick sections were immunostained for MBP to reveal the presence of myelin. Structures shown are the cortex (Cx) and corpus callosum (CC). Myelination is most prominently delayed in the cortex, and not significantly delayed in the corpus callosum.

Example 12

Myelination is Delayed in KLF9$^{-/-}$ Cortex

Figure 68:
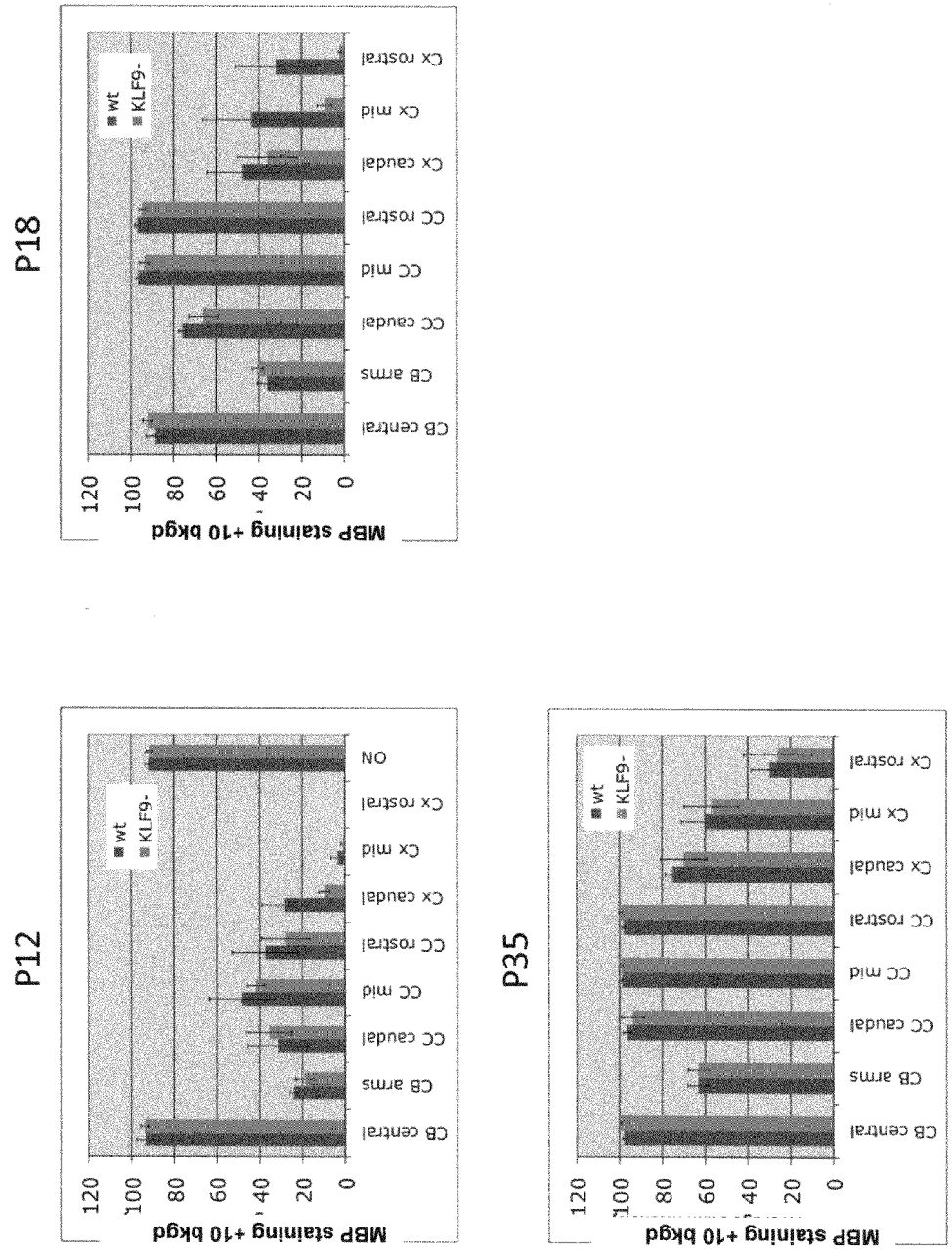

Quantification of the presence of myelin in various CNS structures: CB—cerebellum arms and central myelinated regions, CC—caudal, central, and rostral corpus callosum, Cx—caudal, central, and rostral cortex; all quantified at P12, P18, and P35 as shown in FIG. 68. Sagital sections from KLF9$^{-/-}$ and wt littermate control mice were stained for MBP as described above. To quantify the presence of myelin, 8-bit pictures were taken on a fluorescence microscope with a digital CCD camera at a fixed exposure time, and the boundaries of assayed structures were identified and outlined in Photoshop. For quantification of cortical myelination, 500 μm×500 μm boxes placed directly above the corpus callosum were analyzed. In the images, intensity of staining was on a 0-255 scale. After the intensity of background staining was determined, myelinated areas were defined as pixels that were ≧10 units brighter than the background intensity. The percentages of pixels within a denied structure that were ≧10 units brighter than the background intensity were then quantified. For each data point, 2 separate slides separated by ≧150 μm from 4-5 animals were analyzed. Error bars ±S.E.M.

Example 13

Cuprizone Disrupts Myelin in the Corpus Callosum and Cortex and Myelin Repair is Delayed in KLF9$^{-/-}$ Cortex and Corpus Callosum KLF9$^{-/-}$ or wild type littermate controls aged at least 8 weeks were fed chow containing 0.2% cuprizone for 6 weeks (no cuprizone animals were similarly aged but never fed cuprizone). Mice were sacrificed at the end of the 6 week cuprizone feeding period, or 1-2 weeks following the cessation of the cuprizone feeding. Mice were fixed and brains were collected and sectioned as described above. Sagital sections were stained for MBP expression to analyze myelin levels in the cortex (Cx), or stained with fluoromyelin to analyze myelin levels in the corpus callosum (CC); Fi—fimbra, shown to orient relative location of the image in the mid-region of the sagital corical sections. Images were taken. The images demonstrate that cuprizone administration in the diet is able to disrupt myelination in both the corpus callosum and overlying cortex (FIG. 69: wt mice shown in all images), and that the regeneration of myelination in these structures following the cessation of cuprizone feeding is delayed in KLF9$^{-/-}$ animals (6 wk cuprizone+2 wk recovery; FIG. 70)

Example 14

Myelin Regeneration is Delayed in KLF9$^{-/-}$ Cortex and Corpus Callosum (CC)

Images were taken and quantified as described above. For corpus callosum, fluoromyelin staining levels were quantified; for cortex, MBP staining levels were quantified (see FIG. 71). For untreated animals, only wt mice were quantified. NR—no recovery (immediately following 6 wk cuprizone administration); 1 wk and 2 wk-1 and 2 weeks following cessation of cuprizone administration. All myelin—% pixels in analyzed regions that are 10 units brighter than background; strong myelin—% pixels in analyzed regions that are 50 units brighter than background. For each data point, 2 separate slides separated by $\geq$150 μm from 4-9 animals were analyzed. Error bars ±S.E.M.

Example 15

OPCs from the Cortex and Cerebellum Respond Similarly to T3

OPCs were purified via immunopanning specifically from the cortices or cerebellums of P7 Sprague-Dawley rats. These cells were then plated onto glass coverslips in the presence or absence of mitogens PDGF and NT3 (±PDGF) and presence or absence of thyroid hormone (±T3) and cultured for 3 (−PDGF) or 7 (+PDGF ±T3) days in vitro, with fresh media being supplied every 2-3 days. At the end of this time, cultures were stained for either CNPase expression (less mature) or MBP expression (more mature) as markers of OL differentiation. Percentages of healthy cells (as assessed by healthy nuclei visualized by DAPI staining) expressing indicated markers were quantified for each condition. The data indicates that OPCs from the cerebellum and cortex initiate the expression of mature OL proteins similarly in response to T3, illustrating that cerebellar OPCs are capable of initiating differentiation in response to T3. Perhaps surprisingly, cerebellar OPCs differentiate more rapidly than cortical OPCs in response to mitogen withdrawal (−PDGF −T3 condition). All experiments analyzed in triplicate, ±S.E.M.

Summary of In Vivo Data

The analysis of the development of myelin in vivo in the KLF9$^{-/-}$ and paired wild type littermate controls indicates that, in the KLF9$^{-/-}$ mice, the initial development of myelin is delayed in the cortex, but proceeds normally in other, more densely myelinated structures such as the corpus callosum, cerebellum, and optic nerve. In vitro data has indicated that KLF9 is a transcription factor specifically induced in response to T3 in OPCs, and that KLF9 expression is required for normal T3-induced differentiation in OPCs.

Therefore, analysis of the KLF9$^{-/-}$ phenotype may be a proxy for studying the effects of loss of T3 signaling in promoting the development of myelin. To determine whether OPCs from brain regions unaffected by the loss of KLF9 or T3 are able to respond to T3, OPCs were isolated from unaffected regions (cerebellum) and affected regions (cortex) of the brain, and assessed their ability to differentiate in response to T3 in vitro. Cerebellar OPCs were as response to T3 as cortical OPCs. Cumulatively, these data indicate that OPCs throughout the brain are capable of differentiating in response to T3, but that during normal development only OPCs in more sparse regions, such as the cortex, rely on T3 to drive the normal timing of their differentiation. One potential explanation is that OPCs located in regions of denser myelin formation expand to the point where they exhaust the local supply of mitogens, and therefore differentiate normally irrespective of T3 signaling. Remyelination was delayed both in areas affected by KLF9 loss during development (cortex), and also areas unaffected by KLF9 loss during development (corpus callosum). These data indicate a more widespread role for KLF9, and by extension potentially T3 signaling, in promoting OL differentiation and myelination in the repair of damaged CNS myelin relative to during the normal development of myelin.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the claims herein define the scope of the invention and that methods and structures within the scope of these claims and their equivalents be covered thereby.

What is claimed:

1. A method of regulating proliferation or differentiation of a neural cell comprising contacting said neural cell with a bioactive agent effective in modulating the activity or expression level of transcription factor ZFP536, thereby regulating said proliferation or differentiation of said neural cell.

2. The method of claim 1, wherein said neural cell is a glial cell.

3. The method of claim 2, wherein said glial cell has undergone no more than four divisions.

4. The method of claim 2, wherein said glial cell is an immature oligodendrocyte (OL) or an oligodendrocyte precursor cell (OPC).

5. The method of claim 1, wherein said regulation reduces proliferation or promotes differentiation of said neural cell.

6. The method of claim 1, wherein said regulation promotes proliferation or reduces differentiation of said neural cell.

* * * * *

SEQUENCE LISTING

<160> NUMBER OF SEQ ID NOS: 4

<210> SEQ ID NO 1
<211> LENGTH: 22
<212> TYPE: DNA
<213> ORGANISM: Artificial sequence
<220> FEATURE:
<223> OTHER INFORMATION: Primer

<400> SEQUENCE: 1
tgtccctctc ctaacgtggc tc                                            22

```
<210> SEQ ID NO 2
<211> LENGTH: 25
<212> TYPE: DNA
<213> ORGANISM: Artificial sequence
<220> FEATURE:
<223> OTHER INFORMATION: Primer

<400> SEQUENCE: 2
cattgcacag ttttcagatt tccac                                    25

<210> SEQ ID NO 3
<211> LENGTH: 21
<212> TYPE: DNA
<213> ORGANISM: Artificial sequence
<220> FEATURE:
<223> OTHER INFORMATION: Primer

<400> SEQUENCE: 3
gcattgtcac caactgggac g                                        21

<210> SEQ ID NO 4
<211> LENGTH: 20
<212> TYPE: DNA
<213> ORGANISM: Artificial sequence
<220> FEATURE:
<223> OTHER INFORMATION: Primer

<400> SEQUENCE: 4
accgctcatt gccgatagtg                                          20
```